US010947242B2

(12) United States Patent
Van Roosbroeck et al.

(10) Patent No.: US 10,947,242 B2
(45) Date of Patent: Mar. 16, 2021

(54) [1,2,4]TRIAZOLO[1,5AND#8208;A]PYRIMIDINE COMPOUNDS AS PDE2 INHIBITORS

(71) Applicant: Janssen Pharmaceutica NV, Beerse (BE)

(72) Inventors: Yves Emiel Maria Van Roosbroeck, Antwerp (BE); Frans Alfons Maria Van den Keybus, Essen (BE); Gary John Tresadern, Toledo (ES); Petrus Jacobus Johannes Antonius Buijnsters, Etten-Leur (NL); Adriana Ingrid Velter, Antwerp (BE); Edgar Jacoby, Vosselaar (BE); Gregor James Macdonald, Kent (GB); Henricus Jacobus Maria Gijsen, Breda (NL); Abdellah Ahnaou, Sint-Lambrechts-Woluwe (BE); Wilhelmus Helena Ignatius Maria Drinkenburg, Molenschot (NL)

(73) Assignee: Janssen Pharmaceutica, NV, Beerse (BE)

(*) Notice: Subject to any disclaimer, the term of this patent is extended or adjusted under 35 U.S.C. 154(b) by 0 days.

(21) Appl. No.: 16/346,730

(22) PCT Filed: Oct. 31, 2017

(86) PCT No.: PCT/EP2017/077910
§ 371 (c)(1),
(2) Date: May 1, 2019

(87) PCT Pub. No.: WO2018/083098
PCT Pub. Date: May 11, 2018

(65) Prior Publication Data
US 2019/0276462 A1    Sep. 12, 2019

(30) Foreign Application Priority Data

Nov. 2, 2016   (EP) .................................... 16196924

(51) Int. Cl.
| C07D 487/04 | (2006.01) |
| A61P 25/28 | (2006.01) |
| C07D 513/08 | (2006.01) |
| C07D 519/00 | (2006.01) |

(52) U.S. Cl.
CPC ............ *C07D 487/04* (2013.01); *A61P 25/28* (2018.01); *C07D 513/08* (2013.01); *C07D 519/00* (2013.01)

(58) Field of Classification Search
CPC .................................................. C07D 487/04
USPC .................................................. 514/259.31
See application file for complete search history.

(56) References Cited

U.S. PATENT DOCUMENTS

| 7,449,465 B2 | 11/2008 | Freyne et al. |
| 8,138,168 B1 | 3/2012 | Jones et al. |
| 8,946,415 B2 | 2/2015 | Bi et al. |
| 9,682,953 B2 | 6/2017 | Kharul et al. |
| 2004/0014744 A1 | 1/2004 | Haviv et al. |
| 2009/0259044 A1 | 10/2009 | Kazantsev |
| 2014/0031547 A1 | 1/2014 | Sheridan et al. |

FOREIGN PATENT DOCUMENTS

| CA | 2979222 | 9/2016 |
| CN | 1938308 | 3/2007 |
| CN | 103958473 | 7/2014 |
| CN | 104302649 | 1/2015 |
| CN | 105566321 | 11/2016 |
| EP | 0941994 | 9/1999 |
| JP | 2007332061 | 12/2007 |
| JP | 2014503528 | 2/2014 |
| WO | WO 93/00313 | 7/1993 |
| WO | WO 99/37304 | 7/1999 |
| WO | WO 2004/031148 | 4/2004 |
| WO | WO 2004108136 | 12/2004 |
| WO | WO 2005/063738 | 7/2005 |
| WO | WO 2006/034341 | 3/2006 |
| WO | WO 2006/034440 | 3/2006 |
| WO | WO 2006044687 | 4/2006 |
| WO | WO 2007/022225 | 2/2007 |
| WO | WO 2007113136 | 10/2007 |
| WO | WO 2008/048914 | 4/2008 |
| WO | WO 2009047514 | 4/2009 |
| WO | WO 2012/114222 | 8/2012 |
| WO | WO 2013/000924 | 1/2013 |
| WO | WO 2013134113 | 9/2013 |
| WO | WO 2015/130905 | 9/2015 |
| WO | WO 2015140055 | 9/2015 |
| WO | WO 2015/164508 | 10/2015 |
| WO | WO 2016/107602 | 7/2016 |
| WO | WO 2017/003894 | 1/2017 |

(Continued)

OTHER PUBLICATIONS

Albensi et al. Exp Neurol. 2007, vol. 204A, pp. 1-13.
Alzheimer's Association. "Huntington's Disease." (2012). Accessed Mar. 29, 2019. Available from:< https://www.alz.org/alzheimers-dementia/what-is-dementia/types-of-dementia/huntington-s-disease >. (Year: 2012).
Alzheimer's Association. "What Is Alzheimer's?" (Jan. 2007). Accessed Mar. 29, 2019. Available from:< https://www.alz.org/alzheimers-dementia/what-is-alzheimers >. (Year: 2007).
Barco et al., Expert Opin Ther Targets 2003, vol. 7, pp. 101-114.
Bergado and Almaguer Neural Plast. 2002, vol. 9, No. 4, pp. 217-232.

(Continued)

*Primary Examiner* — Kahsay Habte
(74) *Attorney, Agent, or Firm* — Yuriy P. Stercho

(57) ABSTRACT

The present invention relates to novel [1,2,4]triazolo[1,5-a]pyrimidin-yl derivatives as inhibitors of phosphodiesterase 2 (PDE2). The invention is also directed to pharmaceutical compositions comprising the compounds, to processes for preparing such compounds and compositions, and to the use of such compounds and compositions for the prevention and treatment of disorders in which PDE2 is involved, such as neurological and psychiatric disorders.

13 Claims, 17 Drawing Sheets

(56) References Cited

FOREIGN PATENT DOCUMENTS

| WO | WO 2017/003895 | 1/2017 |
|---|---|---|
| WO | WO 2017/066705 | 4/2017 |
| WO | WO 2017157882 | 9/2017 |
| WO | WO 2017/076900 | 11/2017 |
| WO | WO 2018/083098 | 5/2018 |
| WO | WO 2018/083101 | 5/2018 |
| WO | WO 2018/083103 | 5/2018 |
| WO | WO 2018109198 | 6/2018 |

OTHER PUBLICATIONS

Buijnsters et al. "Structure-Based Design of a Potent, Selective, and Brain Penetrating PDE2 Inhibitor with Demonstrated Target Engagement" ACS Med Chem Lett. 2014, vol. 5(9), pp. 1049-1053.
Cooke and Bliss, Curr Opin Investig Drugs. 2005, vol. 6, No. 1, pp. 25-34.
Dyatkin A.B. et. al, Chirality 2002, vol. 14, pp. 215-219.
Francis et al. Physiol Rev. 2011, vol. 9, pp. 651-690.
Gomez Laurent et al. "PDE2 inhibition: Potential for the treatment of cognitive disorders" Bioorganic & Medicinal Chemistry Letters 2013, vol. 3, No. 24, pp. 6522-6527.
Knott, E.P., et al. "Phosphodiesterase Inhibitors as a Therapeutic Approach to Neuroprotection and Repair." International Journal of Molecular Sciences. (2017), vol. 18, Issue 696, pp. 1-38 of 38. (Year: 2017).
Lakics, V. et al. "Quantitative comparison of phosphodiesterase mRNA distribution in human brain and peripheral tissues" 2010 Neuropharmacol. vol. 59, pp. 367-374.
Muller, N., et al. "Tourette's syndrome: clinical features, pathophysiology, and therapeutic approaches." Dialogues Clin Neurosci. (2007), vol. 9, pp. 161-171. (Year: 2007).
National Institute of Environmental Health Sciences. "Parkinson's Disease." (Feb. 2014). Accessed Mar. 29, 2019. Available from:<https://www.niehs.nih.gov/health/topics/conditions/parkinson/index.cfm >. (Year: 2014).
Omori and Kotera Circ Res. 2007, vol. 100, pp. 309-327.
Perugi, G., et al. "Diagnosis and Treatment of Agoraphobia with Panic Disorder." CNS Drugs. (2007), 21 (9), pp. 741-764. (Year:2007).
Reisman, M. "PTSD Treatment for Veterans: What's Working, What's New, and What's Next." P&T. (Oct. 2016), vol. 41, No. 10 , pp. 623-634. (Year: 2016).
Rowan et al. Biochem Soc Trans. 2005, vol. 33, pp. 563-567.
"Schizophrenia." (Mar. 2015). Accessed Mar. 29, 2019. Available from: < https://www.nami.org/NAMI/media/NAMI-Media/Images/FactSheets/Schizophrenia-FS.pdf >. (Year: 2015).
"Substance-induced psychotic disorder." (Oct. 2005). Accessed Mar. 29, 2019. Available from: < http://www.minddisorders.com/Py-Z/Substance-induced-psychotic-disorder.html > . (Year: 2005).
Su et al. Angew. Chem. Int. Ed. 2015, vol. 54, pp. 12942-12946.
Sweeney, P. "Parkinson's disease." Cleveland Clinic. (May 2013). Accessed Mar. 29, 2019. Available from:< http://www .clevelandclinicmeded.com/medicalpubs/diseasemanagement/neurology/parkinsons-disease/ >. (Year: 2013).
Van Duinen et al., Curr Pharm Des. 2015, vol. 21, pp. 3813-3828.
Xu et al., Neurobiol Aging. 2015, vol. 36, pp. 955-970.
International Search Report and Written Opinion—PCT/EP2016/076420—dated Dec. 15, 2016.
International Search Report and Written Opinion—PCT/EP2017/077910—dated Dec. 12, 2017.
International Search Report and Written Opinion—PCT/EP2017/077918—dated Dec. 18, 2017.
International Search Report and Written Opinion—PCT/EP2017/077920—dated Dec. 15, 2017.
CAS 1240215-31-9, Sep. 8, 2010, Methanone, [5-[(diethylamino)methyl]-2-furanyl][3-[6-(methylsulfonyl)[1,2,4]triazolo[1,5-a]pyrimidin-7-yl]-1-piperidinyl].
CAS 1240208-98-3, Sep. 8, 2010, Methanone, (1,2-dimethyl-1H-benzimidazol-5-yl)[3-[6-(methylsulfonyl)[1,2,4]triazolo [1,5-a]pyrimidin-7-yl]-1-piperidinyl.
CAS 1240206-26-1, 08 Set 2010, 1-Piperidinecarboxylic acid, 3-[3-methyl-2-(3-methylphenyl)pyrazolo[1,5-a]pyrimidin-7-yl]-, 1,1-dimethylethyl ester.
CAS 1240201-99-3, Sep. 7, 2010, Benzoic acid, 4-[[3-[6-(methylsulfonyl)[1,2,4]triazolo[1,5-a]pyrimidin-7-yl]-1-piperidinyl]carbonyl]-, methyl ester.
CAS 1240195-90-7, Sep. 7, 2010, Methanone, (1,5-dimethyl-1H-pyrazol-4-yl)[3-[6-(methylsulfonyl)[1,2,4]triazolo[1,5-a]pyrimidin-7-yl]-1-piperidinyl].
CAS 1240195-65-6, Sep. 7, 2010, Methanone, [3-[6-(methylsulfonyl)[1,2,4]triazolo[1,5-a]pyrimidin-7-yl]-1-piperidinyl]-1H-pyrazol-3-yl.
CAS 1240193-46-7, Sep. 7, 2010, Methanone, [1-(4-methoxyphenyl)cyclopropyl][3-[6-(methylsulfonyl)[1,2,4]triazolo [1,5-a]pyrimidin-7-yl]-1-piperidinyl].
CAS 1240193-08-1, Sep. 7, 2010, 1-Piperidinecarboxylic acid, 3-[2-(3-methylphenyl)pyrazolo[1,5-a]pyrimidin-7-yl]-, 1,1-dimethylethyl ester.
CAS 1240192-13-5, Sep. 7, 2010, 1-Propanone, 3-(5-methyl-1H-pyrazol-1-yl)-1-[3-[6-(methylsulfonyl)[1,2,4]triazolo[1,5-a]pyrimidin-7-yl]-1-piperidinyl].
CAS 1240186-67-7, Sep. 7, 2010, 1-Propanone, 3-(1-ethyl-3,5-dimethyl-1H-pyrazol-4-yl)-1-[3-[6-(methylsulfonyl)[1,2,4]triazolo [1,5-a]pyrimidin-7-yl]-1-piperidinyl].
CAS 1240181-24-1, Sep. 7, 2010, Methanone, (5-methyl-1-propyl-1H-pyrazol-4-yl)[3-[6-(methylsulfonyl)[1,2,4]triazolo[1,5-a]pyrimidin-7-yl]-1-piperidinyl].
CAS 1240176-67-3, Sep. 7, 2010, 1-Butanone, 4-(1H-indol-3-yl)-1-[3-[6-(methylsulfonyl)[1,2,4]triazolo[1,5-a]pyrimidin-7-yl]-1-piperidinyl].
CAS 1240169-61-2, Sep. 7, 2010, Methanone, (1-ethyl-5-methyl-1H-pyrazol-4-yl)[3-[6-(methylsulfonyl)[1,2,4]triazolo[1,5-a]pyrimidin-7-yl]-1-piperidinyl].
CAS 1240169-40-7, Sep. 7, 2010, Ethanone, 2-(3,4-dimethoxyphenyl)-1-[3[6-(methylsulfonyl)[1,2,4]triazolo[1,5-a]pyrimidin-7-yl]-1-piperidinyl].
CAS 1240166-99-7, Sep. 7, 2010, Methanone, [3-(1,1-dimethylethyl)-1-methyl-1H-pyrazol-5-yl][3-[6-(methylsulfonyl)[1,2,4]triazolo[1,5-a]pyrimidin-7-yl]-1-piperidinyl].
CAS 1240166-22-6, Sep. 7, 2010, Methanone, (2-methyl-1H-benzimidazol-6-yl)[346-(methylsulfonyl)[1,2,4]triazolo[1,5-a]pyrimidin-7-yl]-1-piperidinyl].
CAS 1240165-13-2, Sep. 7, 2010, Methanone, [1-(4-chlorophenyl)cyclobutyl][3-[6-(methylsulfonyl)[1,2,4]triazolo[1,5-a]pyrimidin-7-yl]-1-piperidinyl].
CAS 1240153-22-3, Sep. 7, 2010, Methanone, (1-ethyl-3-methyl-1H-pyrazol-4-yl)[3-[6-(methylsulfonyl)[1,2,4]triazolo[1,5-a]pyrimidin-7-yl]-1-piperidinyl].
CAS 1240147-20-9, Sep. 7, 2010, 1-Piperidineacetamide, N-(3-ethoxypropyl)-3-[2-methyl-6-(3-methyl-5-isoxazolyl)pyrazolo[1,5-a]pyrimidin-7-yl].
CAS 1240146-72-8, Sep. 7, 2010, Pyrimido[1,2-a]benzimidazole, 4-[1-[[1-(2-propyn-1-yl)-1H-indol-3-yl]methyl]-3-piperidinyl].
CAS 1240140-89-9, Sep. 7, 2010, 1-Piperidinecarboxylic acid, 3-[2-(4-methylphenyl)pyrazolo[1,5-a]pyrimidin-7-yl]-, 1,1-dimethylethyl ester.
CAS 1240128-18-0, Sep. 7, 2010, Methanone, (3,4-dimethoxyphenyl)[3-[6-(methylsulfonyl)[1,2,4]triazolo[1,5-a]pyrimidin-7-yl]-1-piperidinyl].
CAS 1240127-92-7, Sep. 7, 2010, 1-Piperidinecarboxylic acid, 3-[2-(3-fluorophenyl)pyrazolo[1,5-a]pyrimidin-7-yl]-, 1,1-dimethylethyl ester.
CAS 1240115-42-7, Sep. 7, 2010, Methanone, (1-ethy1-1H-pyrazol-4-y1)[346-(methylsulfony1)[1,2,4]triazolo[1,5-a]pyrimidin-7-y1]-1-piperidinyl].
CAS 1240104-61-3, Sep. 7, 2010, 1-Piperidinecarboxylic acid, 3-(2-phenylpyrazolo[1,5-a]pyrimidin-7-yl)-,1,1-dimethylethyl ester.
CAS 1240102-95-7, Sep. 7, 2010, Methanone, [3-[6-(methylsulfonyl)[1,2,4]triazolo[1,5-a]pyrimidin-7-yl]-1-piperidinyl](4,5,6,7-tetrahydro-1H-indazol-3-yl).

(56) References Cited

OTHER PUBLICATIONS

CAS 1240096-26-7, Sep. 7, 2010, Ethanone, 2-(2,5-dimethoxyphenyl)-1-[3-[6-(methylsulfonyl)[1,2,4]triazolo[1,5-a]pyrimidin-7-yl]-1-piperidinyl].
CAS 1240096-02-9, Sep. 7, 2010, 1-Piperidinecarboxylic acid, 3-[3-(4-fluorophenyl)-2-methylpyrazolo[1,5-a]pyrimidin-7-y]-, 1,1-dimethylethyl ester.
CAS 1240093-87-1, Sep. 7, 2010, Methanone, (2,3-dihydro-1,4-benzodioxin-6-yl[3-[6-(methylsulfonyl)[1,2,4]triazolo[1,5-a]pyrimidin-7-yl]-1-piperidinyl].
CAS 1240091-60-4, Sep. 7, 2010, Methanone, (4-amino-5-chloro-2-methoxyphenyl)[3-[6-(methylsulfonyl)[1,2,4]triazolo[1,5-a]pyrimidin-7-yl]-1-piperidinyl].
CAS 1214610-92-0, Mar. 25, 2010, Methanone, (3-methyl-2-benzofuranyl)[3-[6-(methylsulfonyl)[1,2,4]triazolo[1,5-a]pyrimidin-7-yl]-1-piperidinyl].
CAS 1214601-85-0, Mar. 25, 2010, Methanone, [3-[6-(methylsulfonyl)[1,2,4]triazolo[1,5-a]pyrimidin-7-yl]-1-piperidinyl](4-methyl-5-thiazolyl).
CAS 1214591-56-6, Mar. 25, 2010, Methanone, [3-[6-(methylsulfonyl)[1,2,4]triazolo[1,5-a]pyrimidin-7-yl]-1-piperidinyl](1,4,5,6-tetrahydro-3-cyclopentapyrazolyl).
CAS 1214520-74-7, Mar. 25, 2010, 1-Piperidineacetamide, N,N-bis(1-methylethyl)-3-[2-methyl-6-(3-methyl-5-isoxazolyppyrazolo[1,5-a]pyrimidin-7-yl].
CAS 1214496-02-2, Mar. 25, 2010, 1-Propanone, 3-(5-methyl-1H-pyrazol-1-yl)-1-[3-[2-(trifluoromethyl)[1,2,4]triazolo[1,5-a]pyrimidin-7-yl]-1-piperidinyl].
CAS 1214486-88-0, Mar. 25, 2010, Methanone, (3,5-dimethyl-4-isoxazolyl)[3-[6-(methylsulfonyl)[1,2,4]triazolo[1,5-a]pyrimidin-7-yl]-1-piperidinyl].
CAS 1214449-93-0, Mar. 25, 2010, 1-Propanone, 3-(5-methyl-2-furanyl)-1-[3-(2-methylpyrazolo[1,5-a]pyrimidin-7-yl)-1-piperidinyl].
CAS 1214427-36-7, Mar. 25, 2010, Methanone, 5-isoxazolyl[3-[6-(methylsulfonyl)[1,2,4]triazolo[1,5-a]pyrimidin-7-yl]-1-piperidinyl].
CAS 1184920-74-8, Sep. 16, 2009, 1-Piperidinecarboxylic acid, 3-(6-cyano-2-methylpyrazolo[1,5-a]pyrimidin-7-yl)-, 1,1-dimethylethyl ester.
CAS 960201-98-3, Jan. 9, 2008, 1-Piperidinecarboxylic acid, 3-(2-methylpyrazolo[1,5-a]pyrimidin-7-yl)-,1,1-dimethylethyl ester.
CAS 960201-89-2, Jan. 9, 2008, 1-Piperidinecarboxylic acid, 3-[2-(1,1-dimethylethyl)pyrazolo[1,5-a]pyrimidin-7-yl]-, 1,1-dimethylethyl ester.
CAS 958718-11-1, Dec. 19, 2007, Ethanone, 2-(4-methoxyphenyl)-1-[3-[6-(methylsulfonyl)[1,2,4]triazolo[1,5-a]pyrimidin-7-yl]-1-piperidinyl].
CAS 958715-94-1, Dec. 19, 2007, 1-Piperidinecarboxylic acid, 3-[3-(4-methoxyphenyl)-2-methylpyrazolo[1,5-a]pyrimidin-7-yl], 1,1-dimethylethyl ester.
CAS 958709-70-1, Dec. 19, 2007, Ethanone, 2-(4-fluorophenyl)-1-[3-[6-(methylsulfonyl)[1,2,4]triazolo[1,5-a]pyrimidin-7-yl]-1-piperidinyl].
CAS 958707-04-5, Dec. 19, 2007, Methanone, (3,5-difluorophenyl)[3-[6-(methylsulfonyl)[1,2,4]triazolo[1,5-a]pyrimidin-7-yl]-1-piperidinyl].
CAS 958706-09-7, Dec. 19, 2007, Methanone, [3-[6-(methylsulfonyl)[1,2,4]triazolo[1,5-a]pyrimidin-7-yl]-1-piperidinyl][4-(2-propen-1-yloxy)phenyl].
CAS 958706-04-2, Dec. 19, 2007, Methanone, cyclopentyl[3-[6-(methylsulfonyl)[1,2,4]triazolo[1,5-a]pyrimidin-7-yl]-1-piperidinyl].
CAS 958699-24-6, Dec. 19, 2007, Methanone, [3-(1,1-dimethylethyl)-1-methyl-1H-pyrazol-5-yl][3-[2-(trifluoromethyl)[1,2,4]triazolo[1,5-a]pyrimidin-7-yl]-1-piperidinyl].

CAS 958618-14-9, Dec. 18, 2007, Methanone, [3-[6-(methylsulfonyl)[1,2,4]triazolo[1,5-a]pyrimidin-7-yl]-1-piperidinyl](4,5,6,7-tetrahydrobenzo[b]thien-3-yl).
CAS 958615-91-3, Dec. 18, 2007, Ethanone, 2-(3-methoxyphenyl)-1-[3-[6-(methylsulfonyl)[1,2,4]triazolo[1,5-a]pyrimidin-7-yl]-1-piperidinyl].
CAS 958615-85-5, Dec. 18, 2007, Ethanone, 2-(2-methoxyphenyl)-1-[3-[6-(methylsulfonyl)[1,2,4]triazolo[1,5-a]pyrimidin-7-yl]-1-piperidinyl].
CAS 958606-22-9, Dec. 18, 2007, 1-Propanone, 1-[3-[6-(methylsulfonyl[1,2,4]triazolo[1,5-a]pyrimidin-7-yl]-1-piperidinyl]-2-phenyl-.
CAS 958606-21-8, Dec. 18, 2007, 1-Butanone, 1-[3-[6-(methylsulfonyl)[1,2,4]triazolo[1,5-a]pyrimidin-7-yl]-1-piperidinyl]-2-phenyl-.
CAS 958606-01-4, Dec. 18, 2007, Methanone, 4-thiazolyl(3-[1,2,4]triazolo[1,5-a]pyrimidin-7-yl-1-piperidinyl).
CAS 958605-43-1, Dec. 18, 2007, 1-Piperidinecarboxylic acid, 3-[2-(3,4-dimethoxyphenyl)pyrazolo[1,5-a]pyrimidin-7-yl]-, 1,1-dimethylethyl ester.
CAS 958603-00-4, Dec. 18, 2007, 1-Propanone, 3-(2-furanyl)-1-[3-[6-(methylsulfonyl)[1,2,4]triazolo[1,5-a]pyrimidin-7-yl]-1-piperidinyl].
CAS 958596-76-4, Dec. 18, 2007, Methanone, (3-[1,2,4]triazolo[1,5-a]pyrimidin-7-yl-1-piperidinyl)(3,4,5-trimethoxyphenyl).
CAS 958596-27-5, Dec. 18, 2007, Methanone, [3-[6-(methylsulfonyl)[1,2,4]triazolo[1,5-a]pyrimidin-7-yl]-1-piperidinyl]-2-pyridinyl.
CAS 958587-78-5, Dec. 18, 2007, Methanone, [4-methoxy-3-(1H-pyrazol-1-ylmethyl)phenyl](3-[1,2,4]triazolo[1,5-a]pyrimidin-7-yl-1-piperidinyl).
CAS 958586-33-9, Dec. 18, 2007, Ethanone, 2-(3-fluorophenyl)-1-[3-[6-(methylsulfonyl)[1,2,4]triazolo[1,5-a]pyrimidin-7-yl]-1-piperidinyl].
CAS 958586-25-9, Dec. 18, 2007, Methanone, [3-[6-(methylsulfonyl)[1,2,4]triazolo[1,5-a]pyrimidin-7-yl]-1-piperidinyl]-3-pyridinyl-.
CAS 958585-88-1, Dec. 18, 2007, Methanone, [5-(1,1-dimethylethyl)-3-methyl-2-furanyl][3-[6-(methylsulfonyl)[1,2,4]triazolo[1,5-a]pyrimidin-7-yl]-1-piperidinyl].
CAS 958585-13-2, Dec. 18, 2007, Methanone, (3,4-dimethoxyphenyl)[3-(2-methylpyrazolo[1,5-a]pyrimidin-7-yl)-1-piperidinyl].
CAS 958583-88-5, Dec. 18, 2007, Ethanone, 2-cyclopentyl-1-[3-[6-(methylsulfonyl)[1,2,4]triazolo[1,5-a]pyrimidin-7-yl]-1-piperidinyl].
CAS 958583-87-4, Dec. 18, 2007, 1-Propanone, 1-[3-[6-(methylsulfonyl)[1,2,4]triazolo[1,5-a]pyrimidin-7-yl]-1-piperidinyl]-3-phenyl-.
CAS 958583-82-9, Dec. 18, 2007, Methanone, cyclohexyl[3-[6-(methylsulfonyl)[1,2,4]triazolo[1,5-a]pyrimidin-7-yl]-1-piperidinyl].
CAS 958583-78-3, Dec. 18, 2007, Methanone, (2-fluorophenyl)[3-[6-(methylsulfonyl)[1,2,4]triazolo[1,5-a]pyrimidin-7-yl]-1-piperidinyl].
CAS 958573-20-1, Dec. 18, 2007, 1-Piperidinecarboxylic acid, 3-[2-methyl-3-(2-thienyl)pyrazolo[1,5-a]pyrimidin-7-yl], 1,1-dimethylethyl ester.
CAS 878693-18-6, Mar. 31, 2006, 1-Piperidinecarboxylic acid, 3-[2-(4-methoxyphenyl)pyrazolo[1,5-a]pyrimidin-7-yl]-, 1,1-dimethylethyl ester.
Cheng Qiong, Studies on synthesis and bioactivity of novel triazolopyrimidine derivatives, Chinese Doctoral Dissertations Full-text Database, Engineering Science and Technology I, vol. 04, pp. B014-196, 2009 (see English Abstract).
Tu Wen-long, Studies on structure-activity relationship of phosphodiesterase 2 inhibitors, Chinese Master's Theses Full-text Database, Engineering Science and Technology I, vol. 8, pp. B016-19, 2014 (see English Abstract).

[1,2,4]TRIAZOLO[1,5AND#8208;A]PYRIMIDINE COMPOUNDS AS PDE2 INHIBITORS

CROSS REFERENCE TO RELATED APPLICATIONS

This application is the national stage of PCT Application No. PCT/EP2017/077910, filed Oct. 31, 2017, which claims priority from European Patent Application No. 16196924.1 filed Nov. 2, 2016, the entire disclosures of which are hereby incorporated by reference in their entirety.

FIELD OF THE INVENTION

The present invention relates to novel [1,2,4]triazolo[1,5-a]pyrimidin-yl derivatives as inhibitors of phosphodiesterase 2 (PDE2). The invention is also directed to pharmaceutical compositions comprising the compounds, to processes for preparing such compounds and compositions, and to the use of such compounds and compositions for the prevention and treatment of disorders in which PDE2 is involved, such as neurological and psychiatric disorders.

BACKGROUND OF THE INVENTION

Phosphodiesterases (PDEs) are a family of enzymes encoded by 21 genes and subdivided into 11 distinct families according to structural and functional properties. These enzymes metabolically inactivate widely occurring intracellular second messengers, 3',5'-cyclic adenosine monophosphate (cAMP) and 3',5'-cyclic guanosine monophosphate (cGMP). These two messengers regulate a wide variety of biological processes, including pro-inflammatory mediator production and action, ion channel function, muscle contraction, learning, differentiation, apoptosis, lipogenesis, glycogenolysis, and gluconeogenesis. They do this by activation of protein kinase A (PKA) and protein kinase G (PKG), which in turn phosphorylate a wide variety of substrates including transcription factors and ion channels that regulate innumerable physiological responses. In neurons, this includes the activation of cAMP and cGMP-dependent kinases and subsequent phosphorylation of proteins involved in acute regulation of synaptic transmission as well as in neuronal differentiation and survival. Intracellular concentrations of cAMP and cGMP are strictly regulated by the rate of biosynthesis by cyclases and by the rate of degradation by PDEs. PDEs are hydrolases that inactivate cAMP and cGMP by catalytic hydrolysis of the 3'-ester bond, forming the inactive 5'-monophosphate (Scheme A).

Scheme A

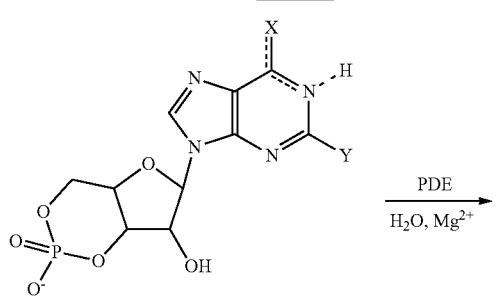

cAMP X = NH$_2$, Y = H
cGMP X = O, Y = NH$_2$

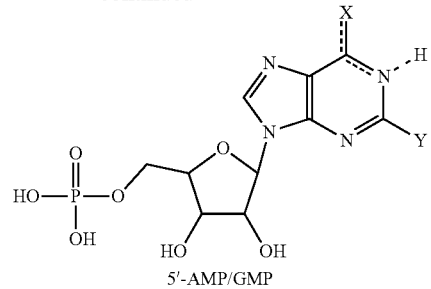

5'-AMP/GMP

On the basis of substrate specificity, the PDE families can be divided into three groups: i) the cAMP-specific PDEs, which include PDE4, 7 and 8; ii) the cGMP-selective enzymes PDE5, 6 and 9; and iii) the dual-substrate PDEs, PDE1, 2 and 3, as well as PDE10 and 11. Furthermore, PDEs are expressed differentially throughout the organism, including the central nervous system. Different PDE isozymes therefore may have different physiological functions. Compounds that inhibit selectively PDE families or isozymes may display particular therapeutic activity, fewer side effects, or both.

Phosphodiesterase 2A (PDE2A) inactivates intracellular signalling mechanisms reliant on cyclic nucleotide signalling mediated by cAMP and cGMP via their degradation (by hydrolizing the biologically relevant second messengers cAMP and cGMP into nonsignalling AMP and GMP, respectively). Such signalling pathways are known to play a role in the regulation of genes involved in the induction of synaptic plasticity.

The pharmacological inhibition of PDE2 therefore causes increased levels of synaptic plasticity (an underlying correlate of learning and memory), suggesting that PDE2A modulation may be a target for alleviating cognitive deficits seen in people suffering from disorders such as for example, schizophrenia, Alzheimer's disease, Parkinson's disease and other CNS disorders associated with cognitive dysfunction.

Phosphodiesterase 2A (PDE2A) is more abundantly expressed in the brain relative to peripheral tissues. The high expression of PDE2 in the limbic system (isocortex, hippocampus, amygdala, habenula, basal ganglia) suggests that PDE2 may modulate neuronal signalling involved in emotion, perception, concentration, learning and memory. Additionally, PDE2 is expressed in the nucleus accumbens, the olfactory bulb, the olfactory tubercle and the amygdala, supporting the suggestion that PDE2 may also be involved in anxiety and depression. (see for instance, Lakics, V. et al. (2010) Quantitative comparison of phosphodiesterase mRNA distribution in human brain and peripheral tissues. Neuropharmacol. 59, 367-374).

Additionally, PDE2 inhibitors have been shown to be beneficial in the reduction of oxidative stress-induced anxiety, supporting their use in the treatment of anxiety in neuropsychiatric and neurodegenerative disorders that involve oxidative stress, such as Alzheimer's disease, Parkinson's disease and multiple sclerosis.

PDE2 inhibitors have been shown to enhance long term potentiation of synaptic transmission and to improve memory acquisition and consolidation in the object recognition and in the social recognition tests in rats. Furthermore, PDE2 inhibitors have been shown to reverse the MK-801 induced working memory deficit in the T-maze in mice. PDE2 inhibitors have also been shown to display activity in forced swim test and light/dark box models; and to show anxiolytic-like effects in elevated plus-maze, hole-board and open-field tests and to prevent stress-induced changes in apoptosis and behaviour.

Thus, PDE2 inhibitors may be useful in the treatment of memory deficiency, cognitive disorders, anxiety, bipolar disorder and depression.

WO2015/164508 (Dart Neuroscience, LLC) discloses substituted [1,2,4]triazolo[1,5-a]pyrimidin-yl compounds as PDE2 inhibitors. WO2017/076900 (Janssen Pharmaceutica NV) discloses [(3S,4R)-3-[5-(difluoromethyl)-[1,2,4]triazolo[1,5-a]pyrimidin-7-yl]-4-methyl-1-piperidyl]-(2,6-dimethyl-4-pyridyl)methanone.

There is still a need for PDE2 inhibitor compounds with an advantageous balance of properties, for example with improved potency, better selectivity against PDE3 and/or PDE10, and/or better chemical or metabolic stability.

SUMMARY OF THE INVENTION

It is the object of the present invention to provide novel inhibitors of PDE2 that may be potentially useful in the treatment of diseases related to PDE2 enzyme activity.

Thus, the present invention is directed to compounds of Formula (I)

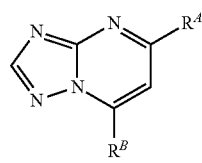

(I)

and the stereoisomeric forms thereof, wherein
$R^A$ is selected from the group consisting of H, $CH_3$, CN, and $CHF_2$;
$R^B$ is a radical selected from the group consisting of (a), (b) and (c):

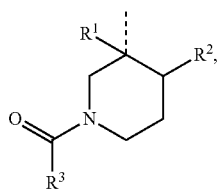

(a)

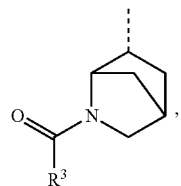

(b)

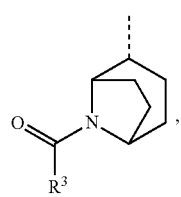

(c)

wherein
$R^1$ is H, F or $CH_3$;
$R^2$ is H or $C_{1-4}$alkyl, in particular methyl or n-butyl; with the proviso that when $R^2$ is H,
then $R^1$ is F or $CH_3$;
$R^3$ is Ar, Het, or Ar—$C_{2-4}$alkenyl; wherein
Ar represents phenyl or naphthyl, each optionally substituted with 1, 2 or 3 substituents, each independently selected from the group consisting of halo; CN; $NR^{2A}R^{2B}$ wherein $R^{2A}$ and $R^{2B}$ are each independently selected from H and $CH_3$; OH; $C_{1-6}$alkyl optionally substituted with 1, 2 or 3 independently selected halo substituents; $C_{1-6}$alkyl substituted with CN; $C_{3-6}$cycloalkyl; $C_{1-6}$alkyloxy optionally substituted with 1, 2 or 3 independently selected halo substituents; and pyrazolyl;
Het represents
(i) a 5-membered heteroaryl selected from the group consisting of 1H-pyrrolyl; thienyl; furanyl; 1H-pyrazolyl; 1H-imidazolyl; 1,2-oxazolyl; 1,3-oxazolyl; and thiazolyl; each of which may be optionally substituted with 1, 2 or 3 substituents each independently selected from the group consisting of halo; $C_{1-4}$alkyl optionally substituted with 1, 2, or 3 independently selected halo substituents; $NR^{3A}R^{3B}$ wherein $R^{3A}$ and $R^{3B}$ are each independently selected from H and $CH_3$; and furan-2-yl; or
(ii) a 6-membered heteroaryl selected from the group consisting of pyridyl, pyrimidinyl, pyrazinyl, and pyridazinyl; each of which may be optionally substituted with 1, 2 or 3 substituents each independently selected from the group consisting of halo; OH; CN; $NR^{4A}R^{4B}$ wherein $R^{4A}$ and $R^{4B}$ are each independently selected from H and $CH_3$; $C_{1-4}$alkyl optionally substituted with 1, 2 or 3 independently selected halo substituents; $C_{1-4}$alkyl substituted with OH; $C_{3-6}$cycloalkyl; $C_{3-6}$cycloalkyloxy; $C_{1-4}$alkyloxy optionally substituted with 1, 2 or 3 independently selected halo substituents; and $C_{1-4}$alkyloxy$C_{1-4}$alkyl; or
(iii) a 8- to 10-membered bicyclic partially unsaturated heterocyclyl selected from the group consisting of 2,3-dihydro-1-benzofuranyl; 2H-chromenyl; 3,4-dihydro-2H-chromenyl; 2,3-dihydro-1H-indolyl optionally substituted at the 1-position with $C_{1-4}$alkyl, methylsulfonyl, 1-acetyl, or fluoroacetyl; 2,2-difluoro-1,3-benzodioxolyl; 1,3-benzodioxolyl optionally substituted with a methyl substituent; 3,4-dihydro-2H-1,4-benzoxazinyl optionally substituted with $C_{1-4}$alkyl; 5,6,7,8-tetrahydroimidazo[1,2-a]pyridinyl; 5,6,7,8-tetrahydroquinolinyl optionally substituted with a halo substituent; and 2,3-dihydropyrazolo[5,1-b][1,3]oxazolyl; or
(iv) a 9- to 10-membered bicyclic heteroaryl selected from the group consisting of 1-benzofuranyl; 1-benzothiophenyl; 1H-indolyl; 1,3-benzoxazolyl; 1,3-benzothiazolyl; indolizinyl; 1H-benzimidazolyl; imidazo[1,2-a]pyridinyl; pyrazolo[1,5-a]pyridinyl; 1H-thieno[2,3-c]pyrazolyl; imidazo[2,1-b]thiazolyl; pyrrolo[2,3-c]pyridinyl; thieno[3,2-b]pyridinyl; quinolinyl; isoquinolinyl; quinoxalinyl; 1,8-naphthyridinyl; and 1,6-naphthyridinyl; each of which may be optionally substituted with 1 or 2 substituents each independently selected from the group consisting of halo; OH; $NR^{5A}R^{5B}$ wherein $R^{5A}$ and $R^{5B}$ are each independently selected from H and $CH_3$;
$C_{1-4}$alkyl optionally substituted with 1, 2 or 3 independently selected halo substituents; and
$C_{1-4}$alkyloxy optionally substituted with 1, 2 or 3 independently selected halo substituents; with the proviso that the compound is not

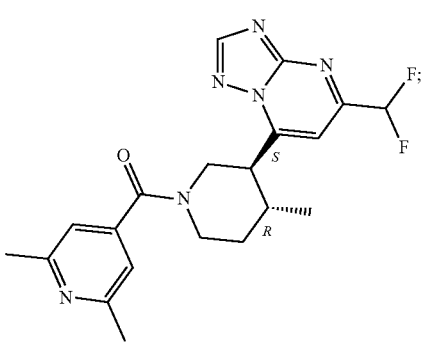

and the N-oxides, and the pharmaceutically acceptable salts and the solvates thereof.

Illustrative of the invention is a pharmaceutical composition comprising a pharmaceutically acceptable carrier and a compound of Formula (I) as described herein, or a pharmaceutically acceptable salt or a solvate thereof. An illustration of the invention is a pharmaceutical composition made by mixing a compound of Formula (I) as described herein, or a pharmaceutically acceptable salt or a solvate thereof, and a pharmaceutically acceptable carrier. Illustrating the invention is a process for making a pharmaceutical composition comprising mixing a compound of Formula (I) as described herein, or a pharmaceutically acceptable salt or a solvate thereof, and a pharmaceutically acceptable carrier.

Further illustrative of the invention are methods to enhance neuronal plasticity comprising administering to a subject in need thereof a therapeutically effective amount of a compound of Formula (I) as described herein, or a pharmaceutically acceptable salt or a solvate thereof, or pharmaceutical compositions described herein.

Exemplifying the invention are methods of treating a disorder mediated by the PDE2 enzyme, comprising administering to a subject in need thereof a therapeutically effective amount of a compound of Formula (I) as described herein, or a pharmaceutically acceptable salt or a solvate thereof, or pharmaceutical compositions described herein.

Further exemplifying the invention are methods of inhibiting the PDE2 enzyme, comprising administering to a subject in need thereof a therapeutically effective amount of a compound of Formula (I) as described herein, or a pharmaceutically acceptable salt or a solvate thereof, or pharmaceutical compositions described herein.

An example of the invention is a method of treating a disorder selected from the group consisting of neurological and psychiatric disorders, comprising administering to a subject in need thereof, a therapeutically effective amount of a compound of Formula (I) as described herein, or a pharmaceutically acceptable salt or a solvate thereof, or pharmaceutical compositions described herein.

An example of the invention is a method of treating a disorder selected from the group of neurological and psychiatric disorders selected from psychotic disorders and conditions; anxiety disorders; movement disorders; drug abuse; mood disorders; neurodegenerative disorders; disorders or conditions comprising as a symptom a deficiency in attention and/or cognition; stroke; and autistic disorders, comprising administering to a subject in need thereof, a therapeutically effective amount of a compound of Formula (I) as described herein, or a pharmaceutically acceptable salt or a solvate thereof, or a pharmaceutically acceptable salt or a solvate thereof or pharmaceutical compositions described herein.

An example of the invention is a method of treating a disorder selected from the group consisting of neurological and psychiatric disorders comprising administering to a subject in need thereof, a therapeutically effective amount of a compound of Formula (I) as described herein or a pharmaceutically acceptable salt or a solvate thereof, or pharmaceutical compositions described herein.

An example of the invention is a method of treating a disorder selected from the group of neurological and psychiatric disorders selected from psychotic disorders and conditions; anxiety disorders; movement disorders; drug abuse; mood disorders; neurodegenerative disorders; disorders or conditions comprising as a symptom a deficiency in attention and/or cognition; disorders related to memory acquisition and consolidation; stroke; and autistic disorders, comprising administering to a subject in need thereof, a therapeutically effective amount of a compound of Formula (I) or a salt or a solvate thereof, or pharmaceutical compositions described herein.

Also exemplifying the invention is a compound of Formula (I) or a salt or a solvate thereof, or a pharmaceutical composition described herein, for use as a medicament.

Further exemplifying the invention is a compound of Formula (I) or a salt or a solvate thereof, or a pharmaceutical composition according to the invention for use in the treatment, prevention, amelioration, control or reduction of the risk of various neurological and psychiatric disorders associated with phosphodiesterase 2 dysfunction in a mammal, including a human, the treatment or prevention of which is affected or facilitated by the inhibition of phosphodiesterase 2.

An example of the invention is a compound of Formula (I) or a pharmaceutically acceptable salt or a solvate thereof according to the present invention or a pharmaceutical composition according to the invention for use in the treatment, prevention, amelioration, control or reduction of the risk of various disorders selected from psychotic disorders and conditions; anxiety disorders; movement disorders; drug abuse; mood disorders; neurodegenerative disorders; disorders or conditions comprising as a symptom a deficiency in attention and/or cognition; disorders related to memory acquisition and consolidation; stroke; and autistic disorder.

An example of the invention is a method of treating a disorder selected from the group consisting of Alzheimer's disease, mild cognitive impairment, senility, dementia, dementia with Lewy bodies, Down's syndrome, dementia associated with stroke, dementia associated with Parkinson's disease and dementia associated with beta-amyloid, preferably Alzheimer's disease, comprising administering to a subject in need thereof, a therapeutically effective amount of a compound of Formula (I) or a pharmaceutically acceptable salt or a solvate thereof, or pharmaceutical compositions described herein.

Another example of the invention is a compound of Formula (I) or a pharmaceutically acceptable salt or a solvate thereof described herein for use in treating: (a) Alzheimer's Disease, (b) mild cognitive impairment, (c) senility, (d) dementia, (e) dementia with Lewy bodies, (f) Down's syndrome, (g) dementia associated with stroke, (h) dementia associated with Parkinson's disease, (i) dementia associated with beta-amyloid, (j) depressive disorders and (k) anxiety disorders, in a subject in need thereof.

DESCRIPTION OF THE FIGURES

In FIGS. 6 to 15, the different doses of the test compounds are represented as follows: ■ 0 mg/kg; ● 0.5 mg/kg; ♦ 0.75 mg/kg ▲ 1 mg/kg; ▼ 1.25 mg/kg; ✹ 1.5 mg/kg; ▽ 2.5 mg/kg.

FIG. 16c shows response morphologies during baseline, 30 min post-treatment and 30 min post-tetanic HFS protocol. Note similarity in the magnitude of fEPSP responses during baseline recordings between treatment groups, which increased above baseline and vehicle condition in the compound 110-treated group.

In FIGS. 16b and c the patterns have the following meanings: ▩ Vehicle (n=10); ▬ compound 110 (mg/kg) (20) n=9; ▬ compound 110 (mg/kg) (40) n=8; in FIGS. 16d and 16e the patterns have the following meanings: ■ vehicle (n=10); ▨ compound 110 (mg/kg), (20) n=9; ■ compound 110 (mg/kg) (40) n=8

DETAILED DESCRIPTION OF THE INVENTION

Definitions

Figure 1A:
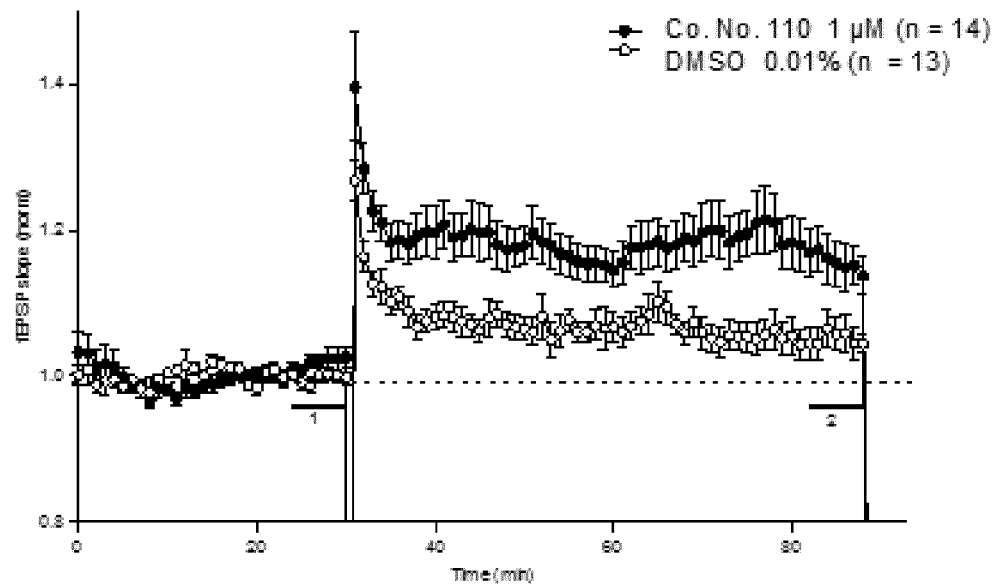
FIG. 1 shows the effect of compound 110 on weak HFS-induction of long term potentiation (LTP) at the mossy fiber synapse.

"$C_{1-4}$alkyl" as used herein alone or as part of another group, defines a saturated, straight or branched, hydrocarbon radical having, 1, 2, 3 or 4 carbon atoms, such as methyl, ethyl, 1-propyl, 1-methyl, butyl, 1-methyl-propyl, 2-methyl-1-propyl, 1,1-dimethylethyl and the like. The term "$C_{1-6}$ alkyl" as used herein as a group or part of a group represents a straight or branched chain saturated hydrocarbon radical having from 1 to 6 carbon atoms such as the groups defined for $C_{1-4}$alkyl and n-pentyl, n-hexyl, 2-methylbutyl and the like. "$C_{1-4}$alkyloxy" shall denote an ether radical wherein $C_{1-4}$alkyl is as defined herein. "$C_{1-6}$alkyloxy" shall denote an ether radical wherein $C_{1-6}$alkyl is as defined herein. "Halo" shall denote fluoro, chloro and bromo. "$C_{3-6}$cycloalkyl" shall denote cyclopropyl, cyclobutyl, cyclopentyl, and cyclohexyl. "$C_{3-6}$cycloalkyloxy" shall denote an ether radical wherein $C_{3-6}$cycloalkyl is as defined herein.

Whenever the term "substituted" is used in the present invention, it is meant, unless otherwise indicated or is clear from the context, to indicate that one or more hydrogens, preferably from 1 to 3 hydrogens, or from 1 to 2 hydrogens, or 1 hydrogen, on the atom or radical indicated in the expression using "substituted" is replaced with a selection from the indicated group, provided that the normal valency is not exceeded, and that the substitution results in a chemically stable compound, i.e. a compound that is sufficiently robust to survive isolation to a useful degree of purity from a reaction mixture, and formulation into a therapeutic agent.

The N-oxide forms of the compounds according to Formula (I) are meant to comprise those compounds of Formula (I) wherein one or several nitrogen atoms are oxidized to the so called N-oxide, particularly those N-oxides wherein a nitrogen atom in a pyridinyl radical is oxidized. N-oxides can be formed following procedures known to the skilled person. The N-oxidation reaction may generally be carried out by reacting the starting material of Formula (I) with an appropriate organic or inorganic peroxide. Appropriate inorganic peroxides comprise, for example, hydrogen peroxide, alkali metal or alkaline metal peroxides, e.g. sodium peroxide, potassium peroxide; appropriate organic peroxides may comprise peroxy acids such as, for example, benzenecarboperoxoic acid or halo substituted benzenecarboperoxoic acid, e.g. 3-chloroperoxybenzoic acid (or 3-chloroperbenzoic acid), peroxoalkanoic acids, e.g. peroxoacetic acid, alkylhydroperoxides, e.g. tert-butyl hydroperoxide. Suitable solvents, e.g are for example, water, lower alkanols, e.g. ethanol and the like, hydrocarbons, e.g. toluene, ketones, e.g. 2-butanone, halogenated hydrocarbons, e.g. dichloromethane, and mixtures of such solvents.

Thus, in a particular embodiment, the invention relates to a compound of Formula (I) wherein $R^3$ is Het, and Het is an oxide of an optionally substituted pyridyl radical as described herein, i.e. an optionally substituted pyridiniumyl oxide radical.

The term "subject" as used herein, refers to an animal, preferably a mammal, most preferably a human, who is or has been the object of treatment, observation or experiment.

The term "therapeutically effective amount" as used herein, means that amount of active compound or pharmaceutical agent that elicits the biological or medicinal response in a tissue system, animal or human that is being sought by a researcher, veterinarian, medical doctor or other clinician, which includes alleviation of the symptoms of the disease or disorder being treated.

As used herein, the term "composition" is intended to encompass a product comprising the specified ingredients in the specified amounts, as well as any product which results, directly or indirectly, from combinations of the specified ingredients in the specified amounts.

Hereinbefore and hereinafter, the term "compound of formula (I)" is meant to include the addition salts, the solvates and the stereoisomers thereof.

The terms "stereoisomers" or "stereochemically isomeric forms" hereinbefore or hereinafter are used interchangeably.

The invention includes all stereoisomers of the compound of Formula (I) either as a pure stereoisomer or as a mixture of two or more stereoisomers.

Enantiomers are stereoisomers that are non-superimposable mirror images of each other. A 1:1 mixture of a pair of enantiomers is a racemate or racemic mixture. Diastereomers (or diastereoisomers) are stereoisomers that are not enantiomers, i.e. they are not related as mirror images. Therefore, the invention includes enantiomers, diastereomers, racemates. In the compounds according to the invention, bonds shown with a wedge of parallel lines ( ··· ''' ) represent bonds projected below the plane of the drawing, while bonds shown with a bold wedge ( ➔ ) represent bonds projected above the plane of the drawing.

The absolute configuration is specified according to the Cahn-Ingold-Prelog system. The configuration at an asymmetric atom is specified by either R or S. Resolved compounds whose absolute configuration is not known can be designated by (+) or (-) depending on the direction in which they rotate plane polarized light.

When a specific stereoisomer is identified, this means that said stereoisomer is substantially free, i.e. associated with less than 50%, preferably less than 20%, more preferably less than 10%, even more preferably less than 5%, in particular less than 2% and most preferably less than 1%, of the other isomers. Thus, when a compound of formula (I) is for instance specified as (R), this means that the compound is substantially free of the (S) isomer.

Furthermore, some of the crystalline forms for the compounds of the present invention may exist as polymorphs and as such are intended to be included in the present invention. In addition, some of the compounds of the present invention may form solvates with water (i.e., hydrates) or common organic solvents, and such solvates are also intended to be encompassed within the scope of this invention.

For use in medicine, the salts of the compounds of this invention refer to non-toxic "pharmaceutically acceptable salts". Other salts may, however, be useful in the preparation of compounds according to this invention or of their pharmaceutically acceptable salts. Suitable pharmaceutically acceptable salts of the compounds include acid addition salts which may, for example, be formed by mixing a solution of the compound with a solution of a pharmaceutically acceptable acid such as hydrochloric acid, sulfuric acid, fumaric acid, maleic acid, succinic acid, acetic acid, benzoic acid, citric acid, tartaric acid, carbonic acid or phosphoric acid. Furthermore, where the compounds of the invention carry an acidic moiety, suitable pharmaceutically acceptable salts thereof may include alkali metal salts, e.g., sodium or potassium salts; alkaline earth metal salts, e.g., calcium or magnesium salts; and salts formed with suitable organic ligands, e.g., quaternary ammonium salts.

Representative acids which may be used in the preparation of pharmaceutically acceptable salts include, but are not limited to, the following: acetic acid, 2,2-dichloro-acetic acid, acylated amino acids, adipic acid, alginic acid, ascorbic acid, L-aspartic acid, benzenesulfonic acid, benzoic acid, 4-acetamidobenzoic acid, (+)-camphoric acid, camphorsulfonic acid, capric acid, caproic acid, caprylic acid, cinnamic acid, citric acid, cyclamic acid, ethane-1,2-disulfonic acid, ethanesulfonic acid, 2-hydroxy-ethanesulfonic acid, formic acid, fumaric acid, galactaric acid, gentisic acid, glucoheptonic acid, D-gluconic acid, D-glucoronic acid, L-glutamic acid, beta-oxo-glutaric acid, glycolic acid, hippuric acid, hydrobromic acid, hydrochloric acid, (+)-L-lactic acid, (±)-DL-lactic acid, lactobionic acid, maleic acid, (-)-L-malic acid, malonic acid, (±)-DL-mandelic acid, methanesulfonic acid, naphthalene-2-sulfonic acid, naphthalene-1,5-disulfonic acid, 1-hydroxy-2-naphthoic acid, nicotinic acid, nitric acid, oleic acid, orotic acid, oxalic acid, palmitic acid, pamoic acid, phosphoric acid, L-pyroglutamic acid, salicylic acid, 4-amino-salicylic acid, sebacic acid, stearic acid, succinic acid, sulfuric acid, tannic acid, (+)-L-tartaric acid, thiocyanic acid, p-toluenesulfonic acid, trifluoromethylsulfonic acid, and undecylenic acid. Representative bases which may be used in the preparation of pharmaceutically acceptable salts include, but are not limited to, the following: ammonia, L-arginine, benethamine, benzathine, calcium hydroxide, choline, dimethylethanolamine, diethanolamine, diethylamine, 2-(diethylamino)-ethanol, ethanolamine, ethylene-diamine, N-methyl-glucamine, hydrabamine, 1H-imidazole, L-lysine, magnesium hydroxide, 4-(2-hydroxyethyl)-morpholine, piperazine, potassium hydroxide, 1-(2-hydroxyethyl)-pyrrolidine, secondary amine, sodium hydroxide, triethanolamine, tromethamine and zinc hydroxide.

The names of the compounds of the present invention were generated according to the nomenclature rules agreed upon by the Chemical Abstracts Service (CAS) using Advanced Chemical Development, Inc., software (ACD/Name product version 10.01; Build 15494, 1 Dec. 2006 or ACD/ChemSketch product version 12.5; Build 47877, 20 Apr. 2011) or according to the nomenclature rules agreed upon by the International Union of Pure and Applied Chemistry (IUPAC) using Advanced Chemical Development, Inc., software (ACD/Name product version 10.01.0.14105, October 2006). In case of tautomeric forms, the name of the depicted tautomeric form of the structure was generated. The other non-depicted tautomeric form is also included within the scope of the present invention.

The present invention is directed to compounds of Formula (I) as defined hereinbefore and pharmaceutically acceptable salts and solvates thereof.

In an embodiment, the present invention is directed to compounds of Formula (I)

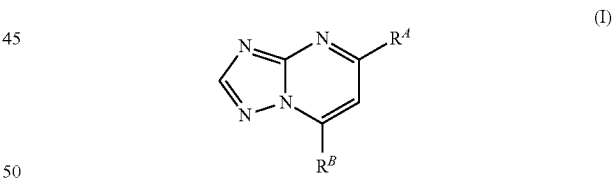

(I)

and the stereoisomeric forms thereof, wherein
$R^A$ is selected from the group consisting of H, $CH_3$, CN, and $CHF_2$;
$R^B$ is a radical selected from the group consisting of (a), (b) and (c):

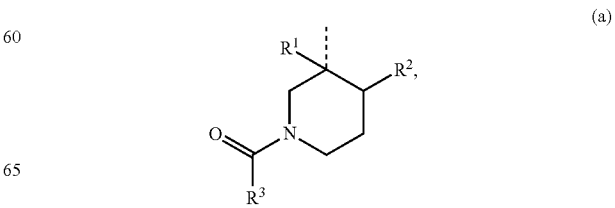

(a)

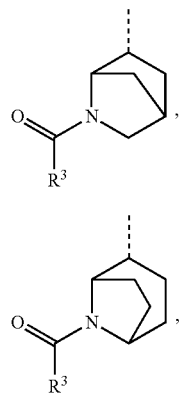

wherein
R¹ is H, F or CH₃;
R² is H or $C_{1-4}$alkyl, in particular methyl or n-butyl; with the proviso that when R² is H,
then R¹ is F or CH₃;
R³ is Ar or Het; wherein
Ar represents phenyl optionally substituted with 1, 2 or 3 substituents, each independently selected from the group consisting of halo; CN; OH; $C_{1-6}$alkyl optionally substituted with 1, 2 or 3 independently selected halo substituents; $C_{1-6}$alkyl substituted with CN; $C_{3-6}$cycloalkyl; and $C_{1-6}$alkyloxy optionally substituted with 1, 2 or 3 independently selected halo substituents;
Het represents
(i) a 5-membered heteroaryl selected from the group consisting of 1H-pyrrolyl; thienyl; furanyl; 1H-pyrazolyl; 1H-imidazolyl; 1,2-oxazolyl; 1,3-oxazolyl; and thiazolyl; each of which may be optionally substituted with 1, 2 or 3 substituents each independently selected from the group consisting of halo; $C_{1-4}$alkyl optionally substituted with 1, 2, or 3 independently selected halo substituents; $NR^{3A}R^{3B}$ wherein $R^{3A}$ and $R^{3B}$ are each independently selected from H and CH₃; and furan-2-yl; or
(ii) a 6-membered heteroaryl selected from the group consisting of pyridyl, pyrimidinyl, pyrazinyl, and pyridazinyl; each of which may be optionally substituted with 1, 2 or 3 substituents each independently selected from the group consisting of halo; OH; CN; $NR^{4A}R^{4B}$ wherein $R^{4A}$ and $R^{4B}$ are each independently selected from H and CH₃; $C_{1-4}$alkyl optionally substituted with 1, 2 or 3 independently selected halo substituents; $C_{3-6}$cycloalkyl; $C_{3-6}$cycloalkyloxy; and $C_{1-4}$alkyloxy optionally substituted with 1, 2 or 3 independently selected halo substituents; or
(iii) a 8- to 10-membered bicyclic partially unsaturated heterocyclyl selected from the group consisting of 2,3-dihydro-1-benzofuranyl; 2H-chromenyl; 3,4-dihydro-2H-chromenyl; 2,3-dihydro-1H-indolyl optionally substituted at the 1-position with $C_{1-4}$alkyl, methylsulfonyl, 1-acetyl, or fluoroacetyl; 2,2-difluoro-1,3-benzodioxolyl; 1,3-benzodioxolyl optionally substituted with a methyl substituent; 5,6,7,8-tetrahydroimidazo[1,2-a]pyridinyl; 5,6,7,8-tetrahydroquinolinyl optionally substituted with a halo substituent; and 2,3-dihydropyrazolo[5,1-b][1,3]oxazolyl; or
(iv) a 9- to 10-membered bicyclic heteroaryl selected from the group consisting of 1-benzofuranyl; 1-benzothiophenyl; 1H-indolyl; 1,3-benzoxazolyl; 1,3-benzothiazolyl; indolizinyl; 1H-benzimidazolyl; imidazo[1,2-a]pyridinyl; pyrazolo[1,5-a]pyridinyl; 1H-thieno[2,3-c]pyrazolyl; thieno[3,2-b]pyridinyl; quinolinyl; 1,8-naphthyridinyl; and 1,6-naphthyridinyl; each of which may be optionally substituted with 1 or 2 substituents each independently selected from the group consisting of halo; OH; $NR^{5A}R^{5B}$ wherein $R^{5A}$ and $R^{5B}$ are each independently selected from H and CH₃; $C_{1-4}$alkyl optionally substituted with 1, 2 or 3 independently selected halo substituents; and $C_{1-4}$alkyloxy optionally substituted with 1, 2 or 3 independently selected halo substituents; with the proviso that the compound is not

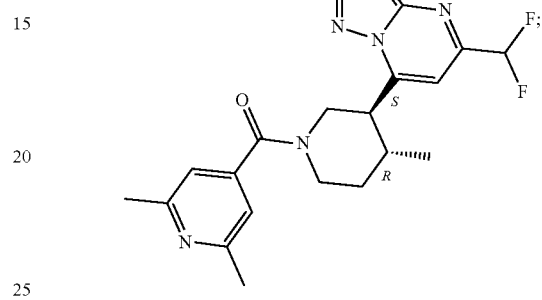

and the pharmaceutically acceptable salts and the solvates thereof.

In a particular embodiment, $R^A$ is CH₃ or CHF₂; and the rest of variables are as defined herein.

In a particular embodiment, $R^B$ is selected from the group consisting of (a) and (c) and the rest of variables are as defined herein.

In a particular embodiment, $R^A$ is CH₃ or CHF₂; $R^B$ is selected from the group consisting of (a) and (c) and the rest of variables are as defined herein.

In a particular embodiment, R¹ is H and R² is $C_{1-4}$alkyl, in particular methyl or n-butyl; and the rest of variables are as defined herein.

In a particular embodiment, R³ is Het and the rest of variables are as defined herein.

In a particular embodiment, R³ is
(i) a 6-membered heteroaryl selected from the group consisting of pyridyl, pyrimidinyl, pyrazinyl, and pyridazinyl; each of which may be optionally substituted with 1, 2 or 3 substituents each independently selected from the group consisting of halo; OH; CN; $NR^{4A}R^{4B}$ wherein $R^{4A}$ and $R^{4B}$ are each independently selected from H and CH₃; $C_{1-4}$alkyl optionally substituted with 1, 2 or 3 independently selected halo substituents; $C_{3-6}$cycloalkyl; $C_{3-6}$cycloalkyloxy; and $C_{1-4}$alkyloxy optionally substituted with 1, 2 or 3 independently selected halo substituents; or
(ii) a 9- to 10-membered bicyclic heteroaryl selected from the group consisting of 1-benzofuranyl; 1-benzothiophenyl; 1H-indolyl; 1,3-benzoxazolyl; 1,3-benzothiazolyl; indolizinyl; 1H-benzimidazolyl; imidazo[1,2-a]pyridinyl; pyrazolo[1,5-a]pyridinyl; 1H-thieno[2,3-c]pyrazolyl; thieno[3,2-b]pyridinyl; quinolinyl; 1,8-naphthyridinyl; and 1,6-naphthyridinyl; each of which may be optionally substituted with 1 or 2 substituents each independently selected from the group consisting of halo; OH; $NR^{5A}R^{5B}$ wherein $R^{5A}$ and $R^{5B}$ are each independently selected from H and CH₃; $C_{1-4}$alkyl optionally substituted with 1, 2 or 3 independently selected halo substituents; and $C_{1-4}$alkyloxy optionally substituted with 1, 2 or 3 independently selected halo substituents; and the rest of variables are as defined herein.

In a further embodiment, $R^3$ is (i) a 6-membered heteroaryl selected from the group consisting of pyridyl, pyrimidinyl, pyrazinyl, and pyridazinyl; each of which may be optionally substituted with 1, 2 or 3 substituents each independently selected from the group consisting of halo; $NR^{4A}R^{4B}$ wherein $R^{4A}$ and $R^{4B}$ are each independently selected from H and $CH_3$; $C_{1-4}$alkyl optionally substituted with 1, 2 or 3 independently selected halo substituents; $C_{3-6}$cycloalkyl; $C_{3-6}$cycloalkyloxy; and $C_{1-4}$alkyloxy optionally substituted with 1, 2 or 3 independently selected halo substituents; or (ii) a 9- to 10-membered bicyclic heteroaryl selected from the group consisting of 1-benzofuranyl; 1-benzothiophenyl; 1H-indolyl; 1,3-benzoxazolyl; 1,3-benzothiazolyl; indolizinyl; 1H-benzimidazolyl; imidazo[1,2-a]pyridinyl; pyrazolo[1,5-a]pyridinyl; 1H-thieno[2,3-c]pyrazolyl; thieno[3,2-b]pyridinyl; quinolinyl; 1,8-naphthyridinyl; and 1,6-naphthyridinyl; each of which may be optionally substituted with 1 or 2 substituents each independently selected from the group consisting of halo; $NR^{5A}R^{5B}$ wherein $R^{5A}$ and $R^{5B}$ are each independently selected from H and $CH_3$;

$C_{1-4}$alkyl optionally substituted with 1, 2 or 3 independently selected halo substituents; and $C_{1-4}$alkyloxy optionally substituted with 1, 2 or 3 independently selected halo substituents;

and the rest of variables are as defined herein.

In an embodiment, the compound of Formula (I) as defined herein, is in particular a compound of Formula (I-a) or (I-b)

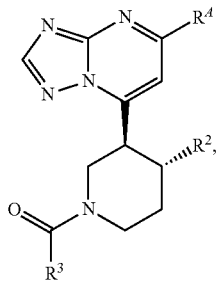

(I-a)

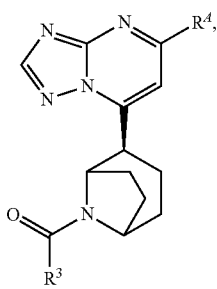

(I-b)

wherein all variables are as defined herein.

More in particular, the compound of Formula (I) as defined herein, has the Formula (I-b1)

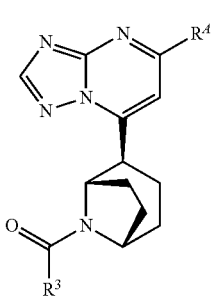

(I-b1)

wherein all variables are as defined herein.

In a particular embodiment, $R^3$ is a radical selected from the group consisting of (3-a), (3-b) and (3-c)

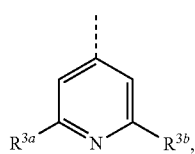

(3-a)

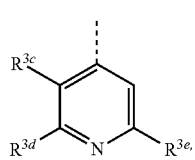

(3-b)

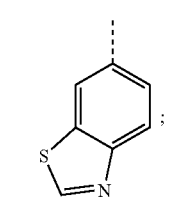

(3-c)

wherein $R^{3a}$ and $R^{3b}$ are each independently selected from the group consisting of hydrogen; halo; CN; $NR^{4a}R^{4b}$ wherein $R^{4a}$ and $R^{4b}$ are each independently selected from H and $CH_3$; $C_{1-4}$alkyl optionally substituted with 1, 2 or 3 independently selected halo substituents; $C_{3-6}$cycloalkyl; and $C_{1-4}$alkyloxy optionally substituted with 1, 2 or 3 independently selected halo substituents; and $R^{3c}$ is selected from the group consisting of F, Cl, $C_{1-3}$alkyl, cyclopropyl, $C_{1-3}$alkyloxy, cyclopropyloxy, and $CF_3$; and $R^{3d}$ and $R^{3e}$ are each independently selected from the group consisting of hydrogen, Cl, CN, $C_{1-3}$alkyl, cyclopropyl, $C_{1-3}$alkyloxy, cyclopropyloxy, $CHF_2$, $CF_3$, $OCHF_2$, and $OCF_3$; with the proviso that $R^{3d}$ and $R^{3e}$ are not simultaneously hydrogen.

In particular, $R^{3a}$ are $R^{3b}$ are each independently selected from the group consisting of hydrogen; chloro; $-NH_2$; $C_{1-4}$alkyl; $-CF_3$; cyclopropyl; $-OCH_3$; $-OCH(CH_3)_2$; $-OCHF_2$; and $-OCF_3$.

More in particular, $R^{3a}$ are $R^{3b}$ are each independently selected from the group consisting of chloro; $C_{1-4}$alkyl; $-CF_3$; cyclopropyl; $-OCH_3$; $-OCH(CH_3)_2$; $-OCHF_2$; and $-OCF_3$.

In particular, $R^{3a}$ is Cl or $CH_3$ and $R^{3b}$ is selected from the group consisting of $CH_3$, $-OCH_3$, $-CF_3$, and cyclopropyl.

In an additional embodiment, $R^{3a}$ is Cl or $CH_3$ and $R^{3b}$ is $CH_3$ or $-OCH_3$.

In particular $R^{3c}$ is selected from the group consisting of F, $CH_3$, and $-OCH_3$; $R^{3d}$ is selected from the group consisting of hydrogen, $CH_3$, cyclopropyl, and $-OCH_3$; and $R^{3e}$ is selected from the group consisting of Cl, $CH_3$, cyclopropyl, $-OCH_3$; $-OCH(CH_3)_2$; cyclopropyloxy; $CHF_2$, and $OCHF_2$. In an additional embodiment $R^{3c}$ is F.

In an additional embodiment, the compound according to the invention is a compound having Formula (I-a), wherein $R^2$ is $C_{1-4}$alkyl, in particular methyl or n-butyl.

Preparation of the Compounds

Experimental Procedure 1

Formula (I-A) and Formula (I-BC) wherein ---- represents $CH_2$ or $CH_2CH_2$, respectively, may be conveniently prepared by reaction with an appropriate carboxylic acid (III) following art-known coupling procedures (reaction step A). Said conversion may conveniently be conducted by treatment of the piperidine type functionality in the intermediates of Formula (II-a) or (II-b) with a coupling agent, such as HBTU or EDCI, in the presence of a base, such as DIPEA and triethylamine in a suitable reaction-inert solvent such as, for example DCM or DMF and the like, at a suitable temperature, for example, at room temperature; alternatively, the intermediates of Formula (II-a) or (II-b) may be reacted with a phosphonic anhydride, such as 1-propane phosphonic anhydride, in the presence of an appropriate base, such as triethylamine, in a suitable reaction-inert solvent, such as, for example, dry ACN. Carboxylic acids of Formula (III) are either commercially available or can be prepared according to art-known procedures.

Experimental Procedure 2

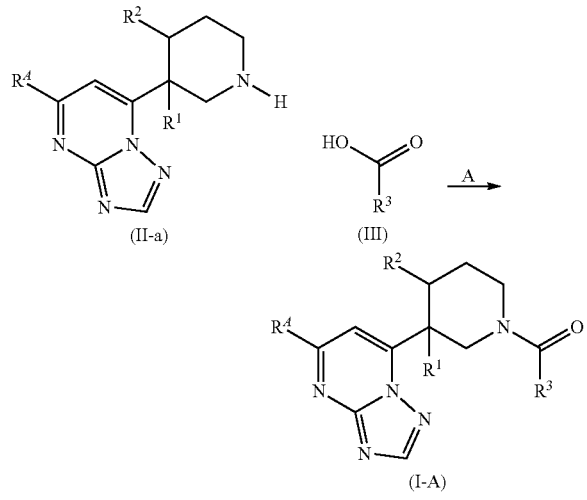

Reaction Scheme 1a

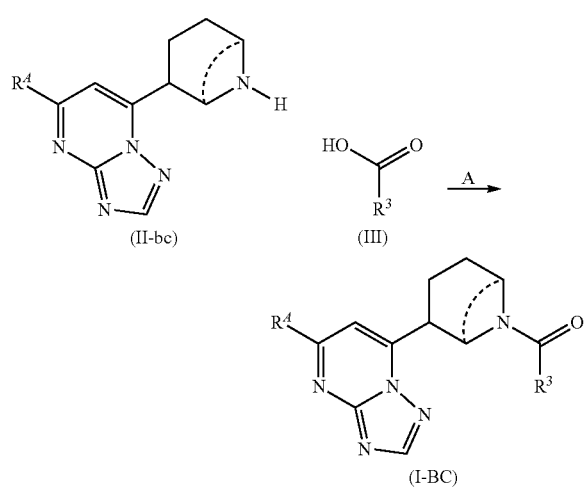

Reaction Scheme 1b

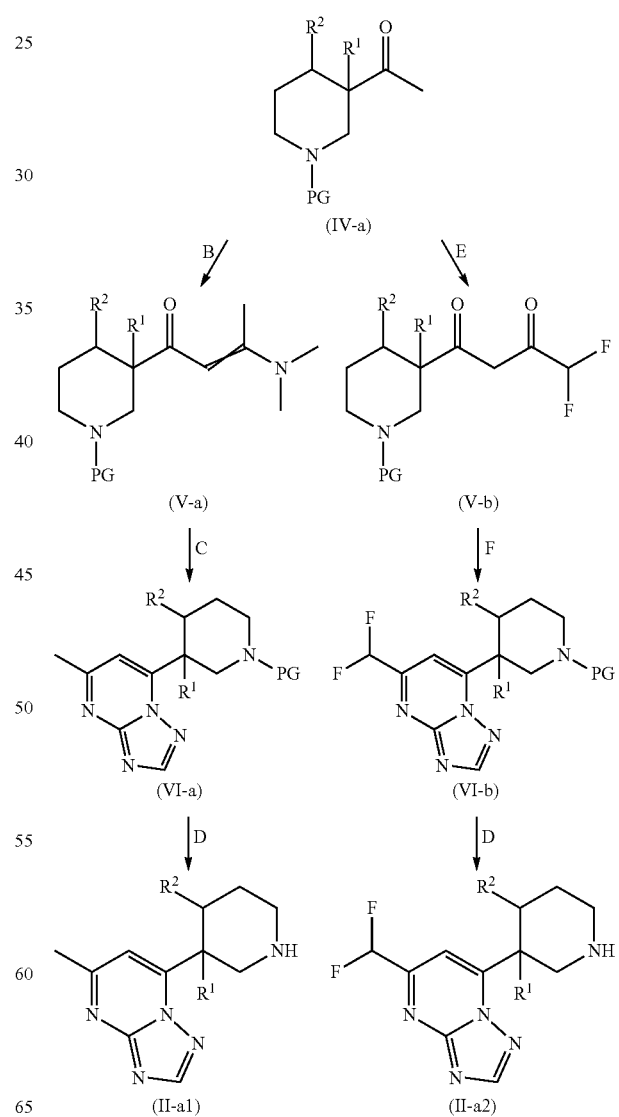

Reaction Scheme 2

A: amide coupling

Final compounds wherein $R^B$ is a radical of Formula (a) or of Formulae (b) or (c) herein referred to as compounds of B: reaction with N,N-dimethylacetamide dimethyl acetal
C, F: reaction with 1H-1,2,4-triazol-3-amine hydrochloride
D: protecting group cleavage
E: reaction with 2,2-difluoro-acetic acid ethyl ester Formation of intermediates of Formula (II-a), for instance wherein $R^A$ is methyl or $CHF_2$, herein referred to as intermediates of Formula (II-a1) and (II-a2), respectively can be prepared from intermediates of Formula (IV-a), wherein PG is a suitable amino protecting group, such as for example, tert-butyloxycarbonyl (Boc).

The reaction with N,N-dimethylacetamide dimethyl acetal can be performed neat, under thermal conditions, such as for example, heating at 100° C.

The reaction with 2,2-difluoroacetic acid ethyl ester can be performed in the presence of a base, such as KO$^t$Bu, in a reaction-inert solvent, such as toluene, at an appropriate temperature, such as 0-5° C., then at RT.

The bicyclic core can be formed by reaction of intermediates (V-a) or (V-b) with 1H-1,2,4-triazol-3-amine hydrochloride in a reaction-inert solvent, such as for example DMF, under thermal conditions, such as for example, heating at 80° C. In the case of (V-b) to (VI-b), the protecting group may be labile and a subsequent protection step may be required. The cleavage of the protecting group in intermediates (VI-a) or (VI-b) can be performed according to art-known procedures, for instance, when the protecting group is Boc, the cleavage can be performed under acidic conditions, such as for example HCl in MeOH at RT, or TFA in DCM.

Experimental Procedure 3

Reaction Scheme 3

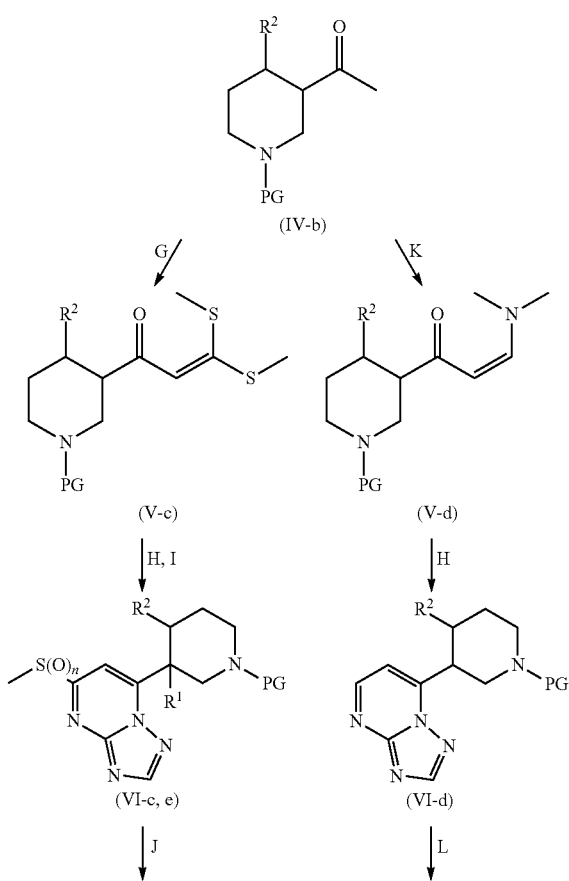

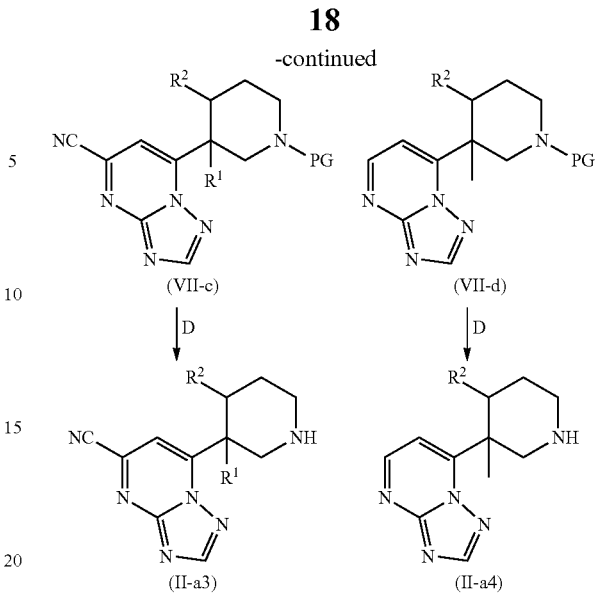

G: reaction with carbon disulphide and methyl iodide

H, L: reaction with 1H-1,2,4-triazol-3-amine hydrochloride

I: oxidation

J: reaction with NaCN

K: reaction with N,N-dimethylformamide dimethyl acetal

L: methylation

D: protecting group cleavage

Intermediates of Formula (II-a), wherein $R^A$ is cyano herein referred to as (II-a3) or wherein $R^A$ is hydrogen and $R^1$ is methyl, herein referred to as (II-a4), can be made according to a series of synthetic steps from intermediates of Formula (IV-b), which are either commercially available or made according to art-known procedures (e.g. $R^2$=H or methyl, PG=Boc)

Thus, reaction with carbon disulphide followed by methyl iodide in the presence of a base such as NaH and a reaction-inert solvent such as THF at 0° C. provides (V-c), which can then be reacted with 1H-1,2,4-triazol-5-amine hydrochloride under conditions described herein thereby providing (VI-c, n=0), followed by oxidation with an appropriate peroxiacid, such as for example mCPBA, in the presence of a reaction-inert solvent, such as for example DCM or CHCl$_3$, to yield (VI-e, n=2). Displacement of the methylsulfone group with a source of cyanide, such as for example NaCN in DMSO, affords (VII-c), which can be subjected to cleavage of the protecting group under conditions as described herein.

The reaction of (IV-b) with N,N-dimethylformamide dimethyl acetal can be performed neat under thermal conditions, such as heating at reflux. Reaction with 1H-1,2,4-triazol-3-amine hydrochloride under conditions described herein affords (VI-d), which can be methylated under art-known conditions, such as for example by reacting it with methyl iodide in the presence of a base such as NaH in a reaction-inert solvent such as DMF. Subsequent protecting group cleavage under conditions as described herein, afford intermediate (II-a4).

Experimental Procedure 4

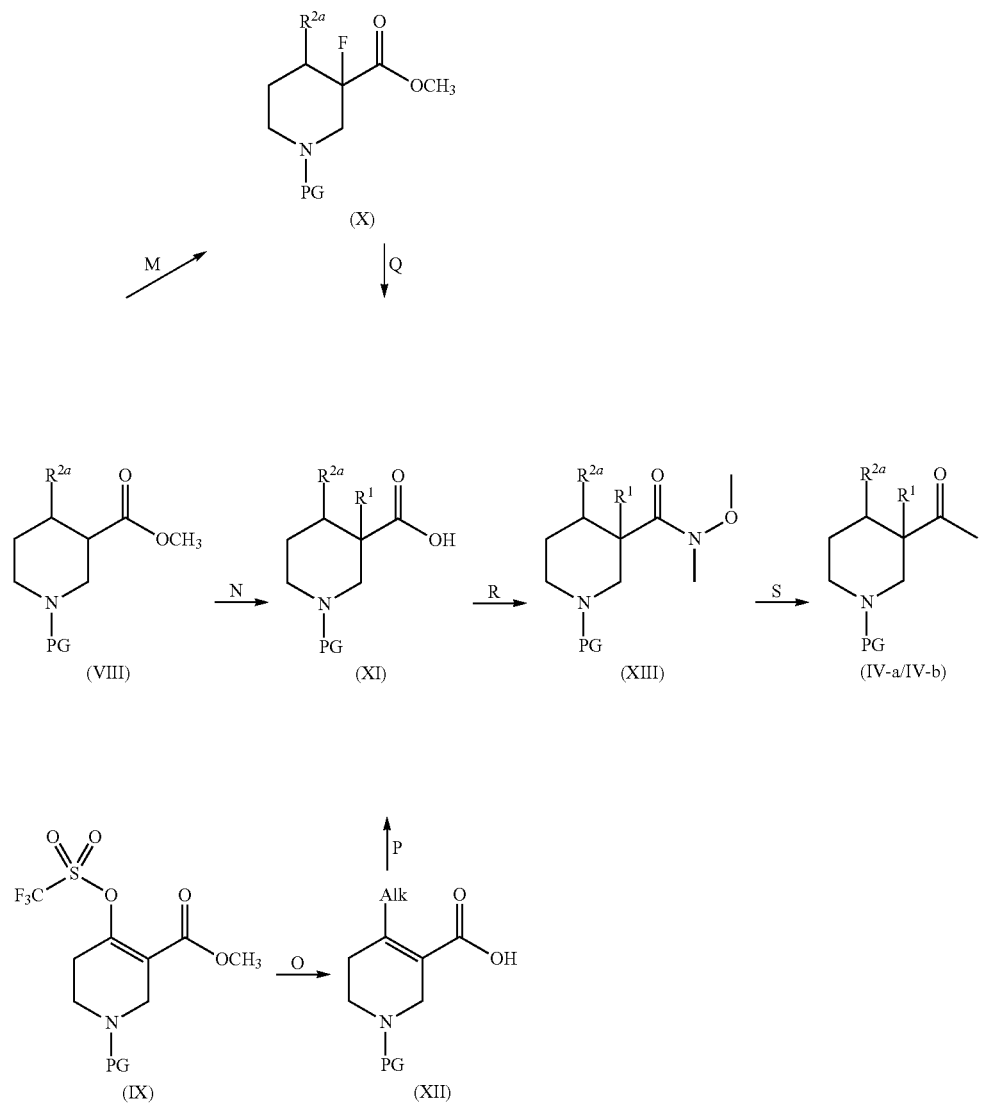

Reaction Scheme 4

M: fluorination
N: methylation and/or saponification
X: reduction
O: Suzuki (alkylation) and saponification
P: hydrogenation
Q: saponification
R: Weinreb amide formation
S: amide to ketone conversion (e.g. Grignard)

The formation of intermediates (IV-a) or (IV-b) can be performed by a series of functional group interconversions, starting from intermediates (VIII), (IX) or (X) which are either commercially available, or can be prepared for example, according to procedures such as those described herein.

Compounds of Formula (VIII), wherein $R^{2a}$ is hydrogen or methyl, and PG is Boc are either commercially available or made according to a series of known procedures, such as those described herein. They can be fluorinated or alkylated according to art-known procedures, such as by reaction with N-fluorobenzenesulfonimide in the presence of a base such as LDA in a reaction-inert solvent such as THF, or by alkylation with alkyl iodide after treatment with a base such as LiHMDS; optionally, subsequent saponification under conditions known in the art, afford (XI).

Compounds of Formula (IX) are also known in the art, and can be alkylated, by means of Suzuki-type procedures, using conditions known to the skilled person, such as the use of a boronic acid/ester, in the presence of a catalyst, such as $Pd(PPh_3)_4$, in a reaction-inert solvent, such as 1,4-dioxane, under thermal conditions, such as heating. Subsequent saponification and hydrogenation under conditions analogous to those described herein, yield intermediate of Formula (XI).

Subsequent Weinreb amide formation and amide to ketone conversion with Grignard, as described herein, afford the desired intermediates (IV-a) or (IV-b).

Experimental Procedure 5

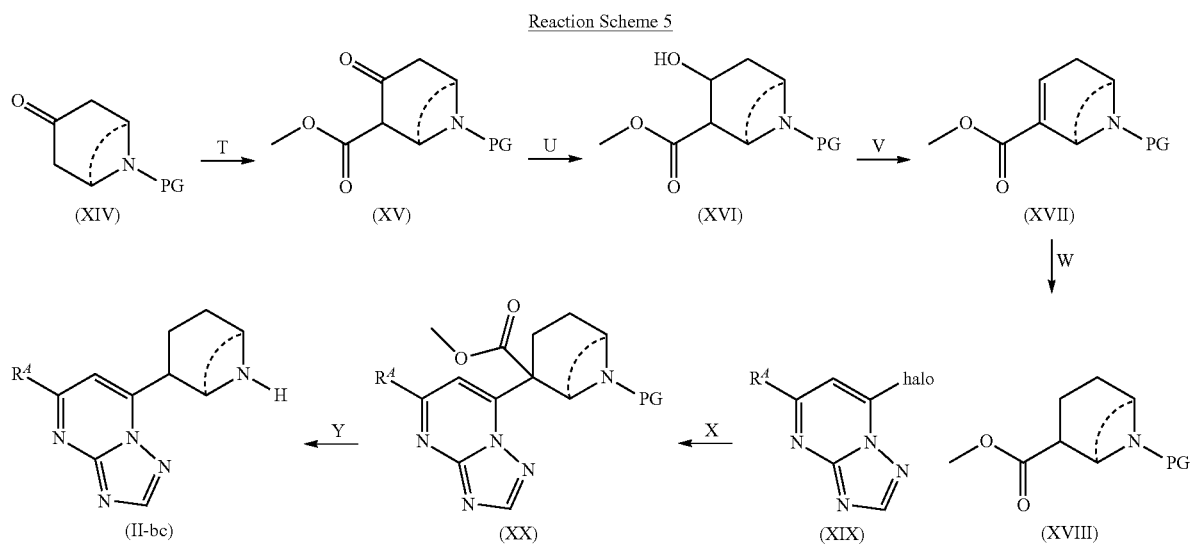

Reaction Scheme 5

T: reaction with methyl cyanoformate
U: reduction
V: dehydration
W: hydrogenation
X: coupling
Y: decarboxylation and protecting group cleavage Formation of intermediates of Formula (II-bc), wherein ---- represents CH$_2$ or CH$_2$CH$_2$ can be prepared by a series of synthetic steps starting from commercially available starting materials of Formula (XIV), such as N-Boc-nortropinone [185099-67-6] or 6-Boc-3-oxo-6-azabicyclo[3.1.1] heptane [1246281-86-6]. Reaction with methyl cyanoformate in the presence of a base such as nBuLi and NH$^i$Pr$_2$ in a reaction-inert solvent, such as THF at an appropriate temperature, such as at −78° C., affords keto-ester (XV), which then can be reduced under art-known conditions with NaBH$_4$, for example in MeOH at about 0° C. and subsequently dehydrated with for example, trifluoroacetic anhydride in the presence of a base such as triethylamine and DMAP in a reaction inert solvent such as DCM, keeping the temperature below 60° C. Hydrogenation under art-known conditions, such as for example in the presence of palladium on carbon catalyst in MeOH affords intermediate (XVIII), which can then be reacted with intermediates of Formula (XIX) which are either commercially available or made according to art-known procedures, in the presence of a base such as for example LDA, in a reaction-inert solvent, such as THF at a temperature between −78 to −60° C. Reaction with concentrated HCl under thermal conditions, such as for example, heating at 150° C. renders intermediate (II-bc) with concomitant cleavage of the protecting group, when acid labile, such as for example, Boc. An alternative manner of making an intermediate of Formula (II-bc) wherein R$^4$ is CHF$_2$ and --- is CH$_2$CH$_2$ from a commercially available starting material, is described herein in the examples.

Pharmacology

The compounds according to the invention inhibit PDE2 enzyme activity, in particular PDE2A, and hence raise the levels of cAMP or cGMP within cells that express PDE2. Accordingly, inhibition of PDE2 enzyme activity may be useful in the treatment of diseases caused by deficient amounts of cAMP or cGMP in cells. PDE2 inhibitors may also be of benefit in cases in which raising the amount of cAMP or cGMP above normal levels results in a therapeutic effect. Inhibitors of PDE2 may be used to treat neurological and psychiatric disorders.

Hence, the present invention relates to a compound of Formula (I) or a pharmaceutically acceptable salt or a solvate thereof according to the present invention, for use as a medicine, as well as to the use of a compound of Formula (I) or a pharmaceutically acceptable salt or a solvate thereof according to the invention or a pharmaceutical composition according to the invention for the manufacture of a medicament. The present invention also relates to a compound of Formula (I) or a pharmaceutically acceptable salt or a solvate thereof according to the present invention or a pharmaceutical composition according to the invention for use in the treatment or prevention of, in particular treatment of, a condition in a mammal, including a human, the treatment or prevention of which is affected or facilitated by the inhibition of phosphodiesterase 2 enzyme. The present invention also relates to the use of a compound of Formula (I) or a pharmaceutically acceptable salt or a solvate thereof according to the present invention or a pharmaceutical composition according to the invention for the manufacture of a medicament for the treatment or prevention of, in particular treatment of, a condition in a mammal, including a human, the treatment or prevention of which is affected or facilitated by the inhibition of phosphodiesterase 2 enzyme.

The present invention also relates to a compound of Formula (I) or a pharmaceutically acceptable salt or a solvate thereof according to the invention, or a pharmaceutical composition according to the invention for use in the treatment, prevention, amelioration, control or reduction of the risk of various neurological and psychiatric disorders associated with phosphodiesterase 2 dysfunction in a mammal, including a human, the treatment or prevention of which is affected or facilitated by the inhibition of phosphodiesterase 2.

Also, the present invention relates to the use of a compound of Formula (I) or a pharmaceutically acceptable salt or a solvate thereof according to the invention or a pharmaceutical composition according to the manufacture of a medicament for treating, preventing, ameliorating, controlling or reducing the risk of various neurological and psychiatric disorders associated with phosphodiesterase 2 dysfunction in a mammal, including a human, the treatment or prevention of which is affected or facilitated by the inhibition of phosphodiesterase 2.

Where the invention is said to relate to the use of a compound of Formula (I) or a pharmaceutically acceptable salt or a solvate thereof or composition according to the invention for the manufacture of a medicament for e.g. the treatment of a subject, e.g. a mammal, it is understood that such use is to be interpreted in certain jurisdictions as a method of e.g. treatment of a subject, comprising administering to a subject in need of such e.g. treatment, an effective amount of a compound of Formula (I) or a pharmaceutically acceptable salt or a solvate thereof or composition according to the invention.

In particular, the indications that may be treated with PDE2 inhibitors, either alone or in combination with other drugs, include, but are not limited to, those diseases thought to be mediated in part by the basal ganglia, prefrontal cortex and hippocampus.

These indications include neurological and psychiatric disorders selected from psychotic disorders and conditions; anxiety disorders; movement disorders; drug abuse; mood disorders; neurodegenerative disorders; disorders or conditions comprising as a symptom a deficiency in attention and/or cognition; disorders related to memory acquisition and consolidation; stroke; and autistic disorder or autism.

In particular, the psychotic disorders and conditions associated with PDE2 dysfunction include one or more of the following conditions or diseases: schizophrenia, for example of the paranoid, disorganized, catatonic, undifferentiated or residual type; schizophreniform disorder; schizoaffective disorder, such as delusional or depressive type; delusional disorder; substance-induced psychotic disorder such as psychosis induced by alcohol, amphetamine, *cannabis*, cocaine, hallucinogens, inhalants, opioids, or phencyclidine; personality disorders of the paranoid type; and personality disorder of the schizoid type.

In particular, the anxiety disorders include panic disorder; agoraphobia; specific phobia; social phobia; obsessive-compulsive disorder; post-traumatic stress disorder; acute stress disorder; and generalized anxiety disorder.

In particular, movement disorders include Huntington's disease and dyskinesia; Parkinson's disease; restless leg syndrome and essential tremor. Additionally, Tourette's syndrome and other tic disorders can be included.

In particular, the central nervous system disorder is a substance-related disorder selected from the group of alcohol abuse; alcohol dependence; alcohol withdrawal; alcohol withdrawal delirium; alcohol-induced psychotic disorder; amphetamine dependence; amphetamine withdrawal; cocaine dependence; cocaine withdrawal; nicotine dependence; nicotine withdrawal; opioid dependence and opioid withdrawal.

In particular, mood disorders and mood episodes include depression, mania and bipolar disorders. Preferably, the mood disorder is selected from the group of bipolar disorders (I and II); cyclothymic disorder; depression; dysthymic disorder; major depressive disorder; treatment-resistant depression; and substance-induced mood disorder.

In particular, neurodegenerative disorders include Parkinson's disease; Huntington's disease; dementia such as for example Alzheimer's disease; multi-infarct dementia; AIDS-related dementia or frontotemporal dementia. The neurodegenerative disorder or condition comprises dysfunction of striatal medium spiny neurons responses.

In particular, disorders or conditions comprising as a symptom a deficiency in attention and/or cognition include dementia, such as Alzheimer's disease; multi-infarct dementia; dementia due to Lewy body disease; alcoholic dementia or substance-induced persisting dementia; dementia associated with intracranial tumours or cerebral trauma; dementia associated with Huntington's disease; dementia associated with Parkinson's disease; AIDS-related dementia; dementia due to Pick's disease; dementia due to Creutzfeldt-Jakob disease; other diseases include delirium; amnestic disorder; post-traumatic stress disorder; stroke; progressive supranuclear palsy; mental retardation; a learning disorder; attention-deficit/hyperactivity disorder (ADHD); mild cognitive disorder; Asperger's syndrome; age-related cognitive impairment; and cognitive impairment related to perception, concentration, learning or memory.

In particular, disorders related to memory acquisition and consolidation include, memory disorders, such as age-associated memory losses, memory deficiency.

Preferably, the psychotic disorder is selected from the group of schizophrenia, delusional disorder, schizoaffective disorder, schizophreniform disorder and substance-induced psychotic disorder.

Preferably, the central nervous system disorder is a personality disorder selected from the group of obsessive-compulsive personality disorder and schizoid, schizotypal disorder.

Preferably, the central nervous system disorder is a mood disorder selected from the group of bipolar disorders (I & II), cyclothymic disorder, depression, dysthymic disorder, major depressive disorder; treatment-resistant depression; and substance-induced mood disorder.

Preferably, the central nervous system disorder is attention-deficit/hyperactivity disorder.

Preferably, the central nervous system disorder is a cognitive disorder selected from the group of delirium, substance-induced persisting delirium, dementia, dementia due to HIV disease, dementia due to Huntington's disease, dementia due to Parkinson's disease, dementia of the Alzheimer's type, substance-induced persisting dementia and mild cognitive impairment.

Preferably the disorders treated by the compounds of formula (I) or a pharmaceutically acceptable salt or a solvate thereof of the present invention are selected from schizophrenia; obsessive-compulsive disorder; generalized anxiety disorder; Huntington's disease; dyskinesia; Parkinson's disease; depression; bipolar disorders; dementia such as Alzheimer's disease; attention-deficit/hyperactivity disorder; drug abuse; stroke; and autism.

Preferably, the disorders treated by the compounds of formula (I) or a pharmaceutically acceptable salt or a solvate thereof of the present invention are schizophrenia, including positive and negative symptoms thereof, and cognitive deficits, such as impaired attention or memory.

Of the disorders mentioned above, the treatment of anxiety, obsessive-compulsive disorder, post-traumatic stress disorder; generalized anxiety disorder, schizophrenia, depression, attention-deficit/hyperactivity disorder, Alzheimer's disease, dementia due to Huntington's disease, dementia due to Parkinson's disease, dementia of the Alzheimer's type, substance-induced persisting dementia and mild cognitive impairment are of particular importance.

Of the disorders mentioned above, the treatment of anxiety, obsessive-compulsive disorder, schizophrenia, depression, attention-deficit/hyperactivity disorder, and Alzheimer's disease are of particular importance.

Other central nervous system disorders include schizoanxiety disorder, and comorbid depression and anxiety, in particular major depressive disorder with comorbid generalized anxiety disorder, social anxiety disorder, or panic disorder; it is understood that comorbid depression and anxiety may also be referred to by the terms anxious depression, mixed anxiety depression, mixed anxiety-depressive disorder, or major depressive disorder with anxiety symptoms, which are used indistinctively herein.

At present, the fourth edition of the Diagnostic & Statistical Manual of Mental Disorders (DSM-IV) of the American Psychiatric Association provides a diagnostic tool for the identification of the disorders described herein. The person skilled in the art will recognize that alternative nomenclatures, nosologies, and classification systems for neurological and psychiatric disorders described herein exist, and that these evolve with medical and scientific progresses. For example, the "American Psychiatric Association: Diagnostic and Statistical Manual of Mental Disorders, Fifth Edition. Arlington, Va., American Psychiatric Association, 2013" (DSM-5™) utilizes terms such as depressive disorders, in particular, major depressive disorder, persistent depressive disorder (dysthymia), substance-medication-induced depressive disorder; neurocognitive disorders (NCDs) (both major and mild), in particular, neurocognitive disorders due to Alzheimer's disease, vascular NCD (such as vascular NCD present with multiple infarctions), NCD due to HIV infection, NCD due to traumatic brain injury (TBI), NCD due to Parkinson's disease, NCD due to Huntington's disease, frontotemporal NCD, NCD due to prion disease, and substance/medication-induced NCD; neurodevelopmental disorders, in particular, intellectual disability, specific learning disorder, neurodevelopmental motor disorder, communication disorder, and attention-deficit/hyperactivity disorder (ADHD); substance-related disorders and addictive disorders, in particular, alcohol use disorder, amphetamine use disorder, *cannabis* use disorder, cocaine use disorder, other hallucinogen use disorder, tobacco use disorder, opiod use disorder, and phencyclidine use disorder; schizophrenia spectrum and other psychotic disorders, in particular, schizophrenia, schizophreniform disorder, schizoaffective disorder, delusional disorder, brief psychotic disorder, substance/medication-induced psychotic disorder; and cyclothymic disorder (which under DSM-5™ falls under the bipolar and related disorders category). Such terms may be used by the skilled person as an alternative nomenclature for some of the diseases or conditions referred to herein. An additional neurodevelopmental disorder includes autism spectrum disorder (ASD), which encompasses according to the DSM-5™, disorders previously known by the terms early infantile autism, childhood autism, Kanner's autism, high-functioning autism, atypical autism, pervasive developmental disorder not otherwise specified, childhood disintegrative disorder, and Asperger's disorder.

Therefore, the invention also relates to a compound of Formula (I) or a pharmaceutically acceptable salt or a solvate thereof according to the invention, for use in the treatment of any one of the diseases mentioned hereinbefore.

The invention also relates to a compound of Formula (I) or a pharmaceutically acceptable salt or a solvate thereof according to the invention for use in treating any one of the diseases mentioned hereinbefore.

The invention also relates to a compound of Formula (I) or a pharmaceutically acceptable salt or a solvate thereof according to the invention, for the treatment or prevention, in particular treatment, of any one of the diseases mentioned hereinbefore.

The invention also relates to the use of a compound of Formula (I) or a pharmaceutically acceptable salt or a solvate thereof according to the invention, for the manufacture of a medicament for the treatment or prevention of any one of the disease conditions mentioned hereinbefore.

The invention also relates to the use of a compound of Formula (I) or a pharmaceutically acceptable salt or a solvate thereof according to the invention for the manufacture of a medicament for the treatment of any one of the disease conditions mentioned hereinbefore.

The compound of Formula (I) or a pharmaceutically acceptable salt or a solvate thereof of the present invention can be administered to mammals, preferably humans, for the treatment or prevention of any one of the diseases mentioned hereinbefore.

In view of the utility of the compounds of Formula (I), and the pharmaceutically acceptable salts and the solvates thereof, according to the invention, there is provided a method of treating a disorder or disease mentioned hereinbefore, comprising administering to a subject in need thereof, a therapeutically effective amount of a compound of Formula (I) or a pharmaceutically acceptable salt or a solvate thereof or pharmaceutical compositions described herein.

Said methods comprise the administration, i.e. the systemic or topical administration, preferably oral administration, of a therapeutically effective amount of a compound of Formula (I) or a pharmaceutically acceptable salt or a solvate thereof according to the invention to warm-blooded animals, including humans.

Therefore, the invention also relates to a method for the prevention and/or treatment of any one of the diseases mentioned hereinbefore comprising administering a therapeutically effective amount of a compound of Formula (I) or a pharmaceutically acceptable salt or a solvate thereof according to the invention to a patient in need thereof.

The PDE2 inhibitor described herein can be used alone, in combination or in combination with other pharmaceutical agents such as other agents used in the treatment of psychoses, such as schizophrenia and bipolar disorder, obsessive-compulsive disorder, Parkinson's disease, cognitive impairment and/or memory loss, e.g. nicotinic α-7 agonists, PDE4 inhibitors (Rolipram, GEBR-7b, GSK356278, GSK256066, Apremilast, MK-0952, Roflumilast, AN2898, AN2728, Ariflo Cilomilast, Dotraverine, Ronomilast Elbimilast, Revamilast, Tetomilast, E6005, GDP-1116, HT0712, MK-0873), PDE5 inhibitors (Sildenafil, Vardenafil, Tadalafil, Udenafil, Avanafil, Mirodenafil, Lodenafil, Dasantafil, PF-00489791), PDE9 (PF-04447943), other PDE2 inhibitors (Bay 60-7550, PF-999, ND-7001), PDE10 inhibitors (PF-02545920, AMG579), PDE2 and 10 inhibitors, calcium channel blockers, muscarinic m1 and m2 modulators, adenosine receptor modulators, ampakines, NMDA-R modulators, mGluR modulators, dopamine modulators, serotonin modulators, cannabinoid modulators, HDAC inhibitors (Vorinostat SAHA, Panobinostat, Quisinostat, Valproic acid) and cholinesterase inhibitors (e.g. donepezil, rivastigmine, and galantamine). In such combinations, the compound of Formula (I) or a pharmaceutically acceptable salt or a solvate thereof of the present invention may be utilized in combination with one or more other drugs in the treatment, prevention, control, amelioration, or reduction of risk of diseases or conditions for which the compound of Formula (I) or the other drugs may have utility, where the combination of the drugs together are safer or more effective than either drug alone.

One skilled in the art will recognize that a therapeutically effective amount of the PDE2 inhibitor of the present invention is the amount sufficient to inhibit the PDE2 enzyme and that this amount varies inter alia, depending on the type of disease, the concentration of the compound in the therapeutic formulation, and the condition of the patient. Generally, an amount of PDE2 inhibitor to be administered as a therapeutic agent for treating diseases in which inhibition of the PDE2 enzyme is beneficial, such as the disorders described herein, will be determined on a case by case by an attending physician.

Generally, a suitable dose is one that results in a concentration of the PDE2 inhibitor at the treatment site in the range of 0.5 nM to 200 µM, and more usually 5 nM to 50 µM. To obtain these treatment concentrations, a patient in need of treatment likely will be administered between 0.001 mg/kg to 15 mg/kg body weight, in particular from 0.01 mg/kg to 2.50 mg/kg body weight, in particular, from 0.01 to 1.5 mg/kg body weight, in particular from 0.1 mg/kg to 0.50 mg/kg body weight. The amount of a compound according to the present invention, also referred to here as the active ingredient, which is required to achieve a therapeutical effect will, of course vary on case-by-case basis, vary with the particular compound, the route of administration, the age and condition of the recipient, and the particular disorder or disease being treated. A method of treatment may also include administering the active ingredient on a regimen of between one and four intakes per day. In these methods of treatment the compound according to the invention is preferably formulated prior to admission. As described herein below, suitable pharmaceutical formulations are prepared by known procedures using well known and readily available ingredients.

Pharmaceutical Compositions

The present invention also provides compositions for preventing or treating diseases in which inhibition of PDE2 is beneficial, such as neurological and psychiatric disorders. Said compositions comprising a therapeutically effective amount of a compound of Formula (I) and a pharmaceutically acceptable carrier or diluent.

While it is possible for the active ingredient to be administered alone, it is preferable to present it as a pharmaceutical composition. Accordingly, the present invention further provides a pharmaceutical composition comprising a compound according to the present invention, together with a pharmaceutically acceptable carrier or diluent. The carrier or diluent must be "acceptable" in the sense of being compatible with the other ingredients of the composition and not deleterious to the recipients thereof.

The pharmaceutical compositions of this invention may be prepared by any methods well known in the art of pharmacy. A therapeutically effective amount of the particular compound, in base form or addition salt form, as the active ingredient is combined in intimate admixture with a pharmaceutically acceptable carrier, which may take a wide variety of forms depending on the form of preparation desired for administration. These pharmaceutical compositions are desirably in unitary dosage form suitable, preferably, for systemic administration such as oral, percutaneous or parenteral administration; or topical administration such as via inhalation, a nose spray, eye drops or via a cream, gel, shampoo or the like. For example, in preparing the compositions in oral dosage form, any of the usual pharmaceutical media may be employed, such as, for example, water, glycols, oils, alcohols and the like in the case of oral liquid preparations such as suspensions, syrups, elixirs and solutions: or solid carriers such as starches, sugars, kaolin, lubricants, binders, disintegrating agents and the like in the case of powders, pills, capsules and tablets. Because of their ease in administration, tablets and capsules represent the most advantageous oral dosage unit form, in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. In the compositions suitable for percutaneous administration, the carrier optionally comprises a penetration enhancing agent and/or a suitable wettable agent, optionally combined with suitable additives of any nature in minor proportions, which additives do not cause any significant deleterious effects on the skin. Said additives may facilitate the administration to the skin and/or may be helpful for preparing the desired compositions. These compositions may be administered in various ways, e.g., as a transdermal patch, as a spot-on or as an ointment.

It is especially advantageous to formulate the aforementioned pharmaceutical compositions in dosage unit form for ease of administration and uniformity of dosage. Dosage unit form as used in the specification and claims herein refers to physically discrete units suitable as unitary dosages, each unit containing a predetermined quantity of active ingredient calculated to produce the desired therapeutic effect in association with the required pharmaceutical carrier. Examples of such dosage unit forms are tablets (including scored or coated tablets), capsules, pills, powder packets, wafers, injectable solutions or suspensions, teaspoonfuls, tablespoonfuls and the like, and segregated multiples thereof.

Depending on the mode of administration, the pharmaceutical composition will comprise from 0.05 to 99% by weight, preferably from 0.1 to 70% by weight, more preferably from 0.1 to 50% by weight of the active ingredient, and, from 1 to 99.95% by weight, preferably from 30 to 99.9% by weight, more preferably from 50 to 99.9% by weight of a pharmaceutically acceptable carrier, all percentages being based on the total weight of the composition.

The present compound can be used for systemic administration such as oral, percutaneous or parenteral administration; or topical administration such as via inhalation, a nose spray, eye drops or via a cream, gel, shampoo or the like. The compound is preferably orally administered.

The exact dosage and frequency of administration depends on the compound, the particular condition being treated, the severity of the condition being treated, the age, weight, sex, extent of disorder and general physical condition of the particular patient as well as other medication the individual may be taking, as is well known to those skilled in the art. Furthermore, it is evident that said effective daily amount may be lowered or increased depending on the response of the treated subject and/or depending on the evaluation of the physician prescribing the compound of the instant invention.

The amount of the compound of Formula (I) that can be combined with a carrier material to produce a single dosage form will vary depending upon the disease treated, the mammalian species, and the particular mode of administration. However, as a general guide, suitable unit doses for the compound of the present invention can, for example, preferably contain between 0.1 mg to about 1000 mg of the active compound. A preferred unit dose is between 1 mg to about 500 mg. A more preferred unit dose is between 1 mg to about 300 mg. An even more preferred unit dose is between 1 mg to about 100 mg. Such unit doses can be administered more than once a day, for example, 2, 3, 4, 5 or 6 times a day, but preferably 1 or 2 times per day, so that the total dosage for a 70 kg adult is in the range of 0.001 to about 15 mg per kg weight of subject per administration. A preferred dosage is 0.01 to about 1.5 mg per kg weight of subject per administration, and such therapy can extend for a number of weeks or months, and in some cases, years. It will be understood, however, that the specific dose level for any particular patient will depend on a variety of factors including the activity of the specific compound employed; the age, body weight, general health, sex and diet of the individual being treated; the time and route of administration; the rate of excretion; other drugs that have previously been administered; and the severity of the particular disease undergoing therapy, as is well understood by those of skill in the area.

A typical dosage can be one 1 mg to about 100 mg tablet or 1 mg to about 300 mg taken once a day, or, multiple times per day, or one time-release capsule or tablet taken once a day and containing a proportionally higher content of active ingredient. The time-release effect can be obtained by capsule materials that dissolve at different pH values, by capsules that release slowly by osmotic pressure, or by any other known means of controlled release.

It can be necessary to use dosages outside these ranges in some cases as will be apparent to those skilled in the art. Further, it is noted that the clinician or treating physician will know how and when to start, interrupt, adjust, or terminate therapy in conjunction with individual patient response.

For the compositions, methods and kits provided above, one of skill in the art will understand that the preferred compound for use in each is the compound noted herein.

Experimental Part

As used herein, the term "ACN" means acetonitrile, "AcOH" or "TFA" means acetic acid, "Boc" means tert-butyloxycarbonyl, "Boc$_2$O" means di-tert-butyl decarbonate, "d" means day(s), "DMAP" 4-dimethylaminopyridine, "DSC" means differential scanning calorimetry, "LCMS" means liquid chromatography/mass spectrometry, "HPLC" means high-performance liquid chromatography, "RP HPLC" means reverse phase high-performance liquid chromatography, "aq." means aqueous, "DCM" means dichloromethane, "DIPE" means diisopropyl ether, "DIPEA" means diisopropylethyl amine, "DMF" means N,N-dimethylformamide, "DMSO" means dimethyl sulfoxide, "EDCI" means 1-ethyl-3-(3-dimethylaminopropyl)carbodiimide, "EtOH" means ethanol, "Et$_2$O" means diethylether, "EtOAc" means ethyl acetate, "Et$_3$N" or "TEA" means triethylamine, "HATU" means 1-[Bis(dimethylamino)methylene]-1H-1,2,3-triazolo[4,5-b]pyridinium 3-oxide hexafluorophosphate, "HBTU" means O-(benzotriazol-1-yl)-N,N,N'N,'-tetramethyluroniumhexafluoro-phosphate, "LiHMDS" means Lithium bis(trimethylsilyl)amide, "THF" means tetrahydrofuran, "min" means minutes, "h" means hours, "mCPBA" means 3-chloroperbenzoic acid, "MeOH" means methanol, "MTBE" means methyl tert-butyl ether, "Pd/C" means Palladium on carbon, "Pd(PPh$_3$)$_4$" means tetrakis(triphenylphosphine)palladium(0), "iPrOH" means 2-propanol, "RM" or "rm" means reaction mixture, "RT" or "rt" means room temperature, "OL" means organic layer, "R$_t$" means retention time (in minutes), "quant." means quantitative, "sat." means saturated, "SFC" means supercritical fluid chromatography, "sol." means solution, "m.p." means melting point, "q.s." means quantum sufficit.

Thin layer chromatography (TLC) was carried out on silica gel 60 F254 plates (Merck) using reagent grade solvents. Open column chromatography was performed on silica gel, mesh 230-400 particle size and 60 Å pore size (Merck) under standard techniques. Automated flash column chromatography was performed using ready-to-connect cartridges from Merck, on irregular silica gel, particle size 15-40 μm (normal phase disposable flash columns) on an SPOT or LAFLASH system from Armen Instrument.

When a stereocenter is indicated with 'RS' this means that a racemic mixture was obtained at the indicated centre, unless otherwise indicated. The stereochemical configuration for centres in some compounds may be designated "R" or "S" when the mixture(s) was separated; for some compounds, the stereochemical configuration at indicated centres has been designated as "*R" or "*S" when the absolute stereochemistry is undetermined although the compound itself has been isolated as a single stereoisomer and is enantiomerically/diastereomerically pure.

The absolute stereochemical configuration for some of the compounds was determined using vibrational circular dichroism (VCD). They were measured on a Bruker Equinox 55 equipped with a PMA 37, in a KBr liquid cell using CD$_2$Cl$_2$ as solvent (PEM: 1350 cm-1, LIA: 1 mV, resolution: 4 cm$^{-1}$). A description on the use of VCD for the determination of absolute configuration can be found in Dyatkin A. B. et. al, Chirality, 14:215-219 (2002). Ab initio calculations: A thorough conformational search was performed at molecular mechanics level using Macromodel to do a mixed torsional/low-mode sampling with the OPLS-2005 force field. The located minima were optimized using Jaguar on the B3LYP/6-31G level with a Poisson-Boltzmann continuum solvation model to mimic a dichloromethane solvent. All conformations within 10 kJ/mol interval were used to simulate VCD and IR spectrum. Dipole and rotational strengths were calculated at the same B3LYP/6-31G level, using Jaguar. The calculated VCD spectra, generated after scaling the frequencies with a factor of 0.97, converting to a Lorentzian bandshape, and summing up the contribution of each conformer assuming a Boltzmann ensemble, were visually compared with the experimental spectra for assigning the correct stereo chemistry.

As understood by a person skilled in the art, compounds synthesised using the protocols as indicated may exist as a solvate e.g. hydrate, and/or contain residual solvent or minor impurities. Compounds isolated as a salt form, may be integer stoichiometric i.e. mono- or di-salts, or of intermediate stoichiometry.

The following examples are intended to illustrate but not to limit the scope of the present invention. Unless otherwise noted, all starting materials were obtained from commercial suppliers and used without further purification.

A. SYNTHESIS OF INTERMEDIATES

Intermediate 1

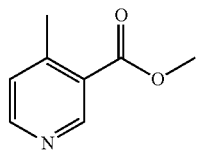

Procedure a: 4-Methyl-3-pyridinecarboxylic acid hydrochloride (1:1) (40 g, 230.4 mmol) was added to a refluxing mixture of sulphuric acid (20 mL) and MeOH (400 mL). The mixture was refluxed overnight, then it was evaporated and the resulting slurry was added to a cold solution of NaHCO$_3$ (64 g) in water (360 mL). The product was extracted with DCM and the OL was dried over MgSO$_4$, filtered and evaporated, yielding intermediate 1 (28.70 g, 83%).

Procedure b: A metal reactor was charged with 3-bromo-4-methyl-pyridine (200 g, 0.116 mol) and a mixture of DMF/MeOH (1 L/1 L). To this was added Et$_3$N (400 g, 0.395 mol), palladium (II) acetate (8 g, 0.036 mol) and 1,1'-bis(diphenylphosphino)ferrocene (16 g, 0.029 mol). The reactor was closed and pressurized with CO gas (3 MPa) and the reaction mixture was stirred and heated overnight at 140° C. The RM was cooled, filtered and concentrated in vacuo. The residue was purified by flash column chromatography over silica gel (gradient eluent: EtOAc/Petroleum ether from 1/1 to 1/0). The product fractions were collected and the solvent was evaporated to afford the desired intermediate 1 (90 g, 51%).

Intermediate 2

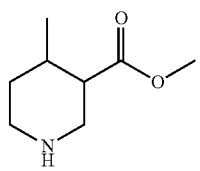

Procedure a: A hydrogenation flask was charged with AcOH (500 mL) and then PtO$_2$ (15.02 g, 66.2 mmol) was added. Intermediate 1 (50 g, 330.8 mmol) was added and the mixture was hydrogenated at 50° C. for 7 days. The RM was filtered over Dicalite® and the filtrate was evaporated to yield intermediate 2 (52 g), which was used in the next step without further purification.

Procedure b: Platinum oxide (5 g, 0.022 mol) was added to a solution of intermediate 1 (90 g, 0.595 mol) and AcOH (1 L). The r.m. was stirred and hydrogenated for 5 days at 50° C. under a pressure of 3.5 kPa. The cooled RM was concentrated in vacuo to give intermediate 2 as the acetic acid salt (140 g, 97%, 90% purity determined by $^1$H-NMR).

Intermediate 3

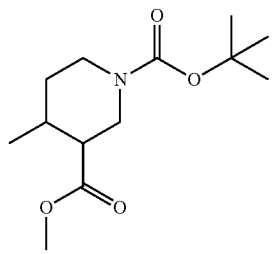 [SMILES: COC(=O)C1CN(C(=O)OC(C)(C)C)CCC1C]

Procedure a: To a solution of intermediate 2 (52 g, 330.8 mmol) in DCM (869 mL), DIPEA (85.5 g, 661.5 mmol) and DMAP (4.04 g, 33.08 mmol) were added. Then di-tert-butyl dicarbonate (72.19 g, 330.8 mmol) was added to this solution in small portions and the reaction was stirred at RT for 1 h. The RM was washed with water and brine and the organic layer was dried over MgSO$_4$, filtered and evaporated. The product was purified by column chromatograph (silica gel, eluent: DCM, 1% MeOH in DCM, 2%, 4%). The desired fractions were evaporated, yielding intermediate 3 (64.1 g, 75%).

Procedure b: To a stirred and cooled (0° C.) solution of intermediate 2 (140 g, 0.595 mol) in DCM (1.5 L) was added sequentially di-tert-butyl dicarbonate (130 g, 0.596 mol), Et$_3$N (225 g, 1.74 mol) and DMAP (10 g, 0.082 mol) and stirring was continued at RT for 2 h. The reaction mixture was poured onto H$_2$O (500 mL) and extracted with DCM (2×100 mL). The organic layers were separated, dried (Na$_2$SO$_4$), and the solvent was evaporated to give crude intermediate 3 (150 g, 90%, 90% purity determined by $^1$H-NMR) which was used as such in the next.

Intermediate 4

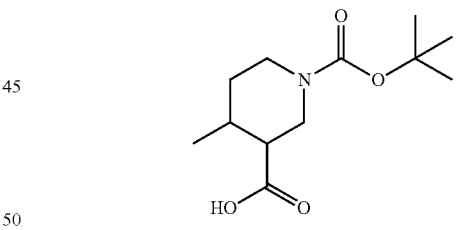

Procedure a: Intermediate 3 (64.1 g, 249.1 mmol) was stirred in MeOH (500 mL) at RT. NaOH (2 M, 747.3 mL) was added and the mixture was stirred for 2 h at RT. The RM was acidified with HCl 1N and the product was extracted with Et$_2$O. The OL was washed with brine and dried over MgSO$_4$, filtered and evaporated, yielding intermediate 4 (59.70 g) as a white solid.

Procedure b: To a stirred solution of intermediate 3 (150 g, 90% pure, 0.524 mol) in MeOH (0.9 L) was added a solution of a 2M NaOH solution (1.8 mol). After 14 h at RT, the RM was extracted with MTBE (2×0.8 L). The aqueous layer was acidified with 10% citric acid and then extracted with EtOAc (4×1 L). The combined organic layers were dried over Na$_2$SO$_4$, filtered and concentrated in vacuo to give crude intermediate 4 (142 g, 90% purity determined by $^1$H-NMR, 100%) which was used as such in the next step.

Intermediate 5

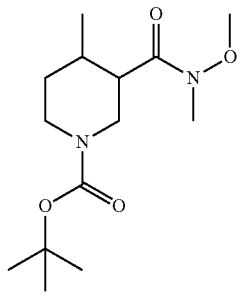 [SMILES: CON(C)C(=O)C1CN(C(=O)OC(C)(C)C)CCC1C]

Procedure a: To a solution of intermediate 4 (59.7 g, 0.25 mol) in THF (800 mL), was added di-1H-imidazol-1-yl-methanone (54 g, 0.33 mol) and the mixture was stirred at RT for 1 h. In another flask, to a suspension of N-methoxy-methanamine hydrochloride (1:1) (32.93 g, 0.34 mol) in ACN (500 mL), was added trimethylamine (35.75 g, 0.35 mol). Both mixtures were combined and stirred at 50° C. while monitoring. The intermediate product crystallized out of the RM and did not react with N-methoxy-methanamine to form the desired product. DCM was added until the intermediate dissolved. The reaction was left stirring for 1 week at 80° C. The solvents were evaporated. The residue was dissolved in DCM and washed with water, 20% AcOH solution and finally with a saturated NaHCO$_3$ solution. The OL was dried over MgSO$_4$, filtered and evaporated. The product was purified by column chromatography (silica gel, eluent: 2% MeOH in DCM, 4%). The pure fractions were evaporated, yielding intermediate 5 (70 g, quantitative).

Procedure b: To a stirred and ice-cooled solution of intermediate 4 (140 g, 0.518 mol) in DCM (2 L) was added N,O-dimethylhydroxylamine (113 g, 1.16 mol) and Et$_3$N (113 g, 1.79 mol). Then HATU (235 g, 0.618 mol) was added and stirring was continued for 14 h. The solvent was evaporated and a NaHCO$_3$ solution (0.5 L) was added and then extracted with DCM (3×1 L). The combined organic layers were separated, dried over Na$_2$SO$_4$, filtered and concentrated in vacuo. The residue was purified by silica gel flash chromatography eluting with 1-10% EtOAc in petroleum ether to afford intermediate 5 (152 g, 100%).

Intermediate 6

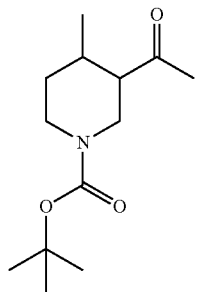 [SMILES: CC(=O)C1CN(C(=O)OC(C)(C)C)CCC1C]

Procedure a: Intermediate 5 (70 g, 244.4 mmol) in THF (250 mL) was charged in a flask under N$_2$ and cooled to −15° C. Methylmagnesium bromide (1.4 M in toluene/THF 75/25, 206 mL) was added dropwise, with the temperature not exceeding 0° C. After addition, the RM was stirred at RT for 1 h. Then the RM was poured on ice with 20 mL AcOH. The product was extracted with Et$_2$O and the OL was washed with a 5% NaHCO$_3$ solution. The OL was dried over MgSO$_4$, filtered and evaporated to give intermediate 6 (53.35 g, 90%).

Procedure b: To a stirred and cooled solution (0° C.) of intermediate 5 (150 g, 0.524 mol) in THF (2 L) was added dropwise a 3M methylmagnesium bromide solution in THF (0.75 L, 2.25 mol) and stirring was continued at RT for 2 h. The reaction mixture was poured onto aqueous NH$_4$Cl solution and extracted with DCM. The combined organic layers were dried over Na$_2$SO$_4$, filtered and concentrated in vacuo. The residue was purified by silica gel chromatography eluting with 1-5% EtOAc in petroleum ether to afford intermediate 6 (120 g, 95%).

Intermediate 7

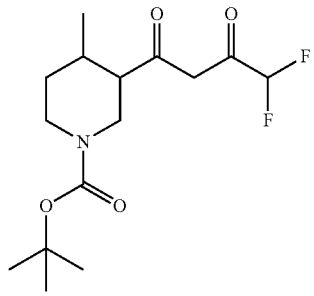 [SMILES: CC1CCN(C(=O)OC(C)(C)C)CC1C(=O)CC(=O)C(F)F]

Intermediate 6 (53.35 g, 0.22 mol) was stirred in toluene (1500 mL) at 0° C. under N$_2$. Potassium tert-butoxide (34.14 g) was added at 0-5° C. and 2,2-difluoro-acetic acid ethyl ester (33.01 g, 0.27 mol) was added dropwise at 0-5° C. The RM was stirred at RT for 2 h, then washed with 10% H$_2$SO$_4$ in water and the OL was dried on MgSO$_4$, filtered and evaporated, yielding intermediate 7 (70.50 g, quantitative).

Intermediate 8

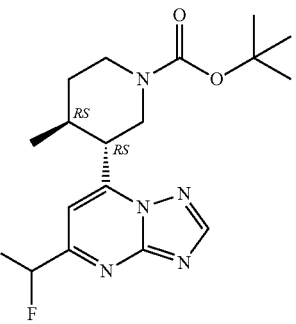

Intermediate 7 (70.5 g, 220.8 mmol), 1H-1,2,4-triazol-5-amine hydrochloride (1:1) (53.22 g, 441.52 mmol) and DMF (1500 mL) were stirred at 80° C. for 24 h. Et$_3$N (20 g) and di-tert-butyl dicarbonate (20 g) were added. The mixture was stirred for 30 min, evaporated and then dissolved in EtOAc, washed with water and brine. The OL was dried over MgSO$_4$, filtered and evaporated. Four isomers were observed. The first fraction crystallized from Et$_2$O. The crystals were filtered off and dried, yielding intermediate 8 (24.60 g, 30%). The mother liquor yielded a second fraction of the compound. The crystals were filtered off and dried, yielding intermediate 8 (2.53 g, 3%).

N.B. "RS" means the intermediate is a racemic mixture of two enantiomers of trans relative configuration.

Intermediates 9, 9A and 9B

Intermediate 9

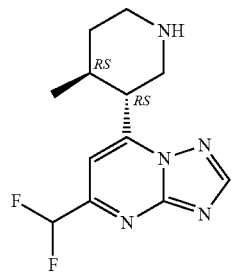

Intermediate 9a

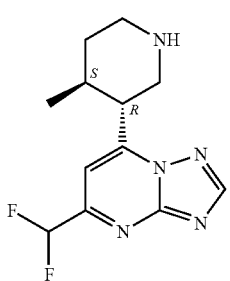

Intermediate 9b

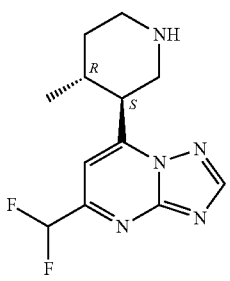

To a solution of intermediate 8 (24.6 g, 67 mmol) in MeOH (350 mL), was added HCl-iPrOH (350 mL) and the RM was stirred for 2 h at RT. The RM was evaporated and the product was crystallized from EtOH. The crystals were filtered off and dried, yielding 20.33 g of a crude, to which water, Na$_2$CO$_3$ and DCM were added. The OL was dried over MgSO$_4$, filtered and evaporated, yielding 12.80 g of intermediate 9. This free base was separated into enantiomers 9a and 9b by purification by Prep SFC (Stationary phase: Chiralpak Diacel AD 30×250 mm, mobile phase: CO$_2$, ((MeOH-iPrOH 50/50) with 0.4% iPrNH$_2$), yielding intermediate 9a (5 g, 19%, R$_t$=7.57 min) and intermediate 9b (5.13 g, 19%, R$_t$=9.36 min).

Intermediates 9a and 9b were isolated as free bases or alternatively, they were dissolved in MeOH, followed by addition of HCl/i-PrOH and the mixture evaporated. The hydrochloride salts (in each instance, .HCl) were crystallized from ACN, filtered off and dried.

Intermediate 10

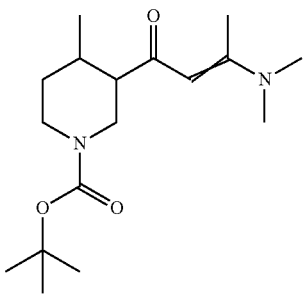 [SMILES: CC(=CC(=O)C1CN(C(=O)OC(C)(C)C)CCC1C)N(C)C]

A stirred mixture of I-6 (7.3 g, 0.03 mol) in N,N-dimethylacetamide dimethyl acetal (20 mL, 0.91 g/mL, 0.14 mol) was heated at 100° C. for 4 h. The RM was concentrated in vacuo, co-evaporated with toluene (2×20 mL) to yield I-7 as a brown residue (9.4 g, yield 100.1%) which was used as such in the next step.

Intermediate 11 (I-11)

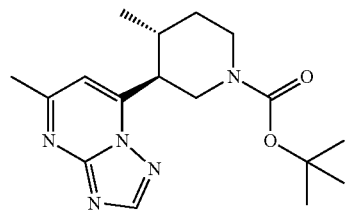 [SMILES: Cc1cc([C@@H]2CN(C(=O)OC(C)(C)C)CC[C@H]2C)n2ncnc2n1]

To a mixture of I-10 (9.4 g, 0.03 mol) in AcOH (50 mL, 1.05 g/mL, 1.75 mol) was added a mixture of 3-amino-1,2,4-triazole (2.68 g, 0.03 mol) in HOAc (50 mL, 1.05 g/mL, 1.75 mol) and the ensuing RM was heated on a Drysyn® metal heating block of 130° C. for 15 min. The RM was cooled, concentrated in vacuo, diluted with DCM (0.2 L) and treated with 1 NaOH until pH-8. The layers were separated and the aqueous layer was extracted with DCM (2×50 mL). The combined organic layers were dried (MgSO$_4$), filtered and concentrated in vacuo to give a dark brown oil which was purified by silica gel chromatography using a Redisep® 120 g Flash column eluting with a gradient of 0-3% 7N NH$_3$/MeOH in DCM to afford intermediate 11 as a tan oil, in a ~1:4=cis:trans mixture (2.15 g, yield 21.42%).

Intermediate 12

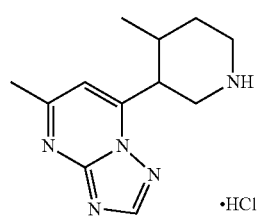 [SMILES: Cc1cc(C2CNCCC2C)n2ncnc2n1 ; Cl]

A stirred mixture of I-11 (2.15 g, 0.0065 mol) in MeOH (50 mL, 0.79 g/mL, 1.23 mol) was treated with HCl (6M in iPrOH) (50 mL, 6 M, 0.3 mol) and after 16 h at RT the RM was concentrated in vacuo to give an off white solid. This was triturated with a mixture of Et$_2$O (200 mL) and ACN (30 mL) for 16 h. The solid was collected by filtration and dried to afford intermediate 12 as an off white solid as a cis/trans mixture (18%/82%) (1.7 g, yield 97.87%).

Intermediate 12A and Intermediate 12B

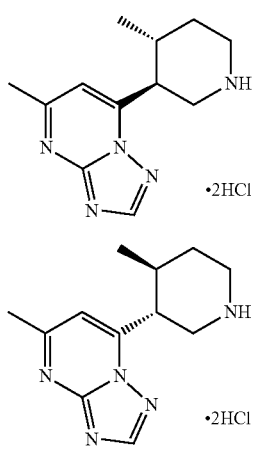

A stirred mixture of I-11 (23 g, 0.0694 mol) in MeOH (165 mL) was treated with HCl (6M in iPrOH) (165 mL, 6 M, 0.986 mol) and after 16 h at RT the RM was concentrated in vacuo to give an off white solid. This was diluted with water and DCM and treated with Na$_2$CO$_3$. The OL was dried over MgSO$_4$, filtered and concentrated in vacuo to afford a residue which was purified using SCF (Stationary phase: Chiralpak® Diacel AD 20×250 mm, mobile phase: CO$_2$, MeOH-iPrOH (50-50)+0.4% iPrNH$_2$) to afford intermediates 12a and 12b and. These were dissolved in MeOH (100 mL) and treated with HCl (6M in iPrOH) (100 mL) at 0° C. for 2 h. The volatiles were evaporated under reduced pressure and the resulting residues were stirred at 0° C. in Et$_2$O to give intermediate 12a (9.25 g, 43%, R$_t$=3.54 min, $[\alpha]^{20}_D$=−17.47° (c 0.54, DMF)) and intermediate 12b (8.8 g, 42%, R$_t$=3.24 min, $[\alpha]^{20}_D$=+16.5° (c 0.52, DMF)).

Intermediate 13

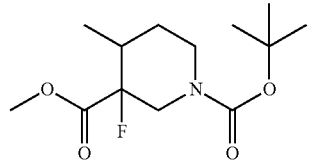 [SMILES: COC(=O)C1(F)CN(C(=O)OC(C)(C)C)CCC1C]

To a solution of LDA (2 M in THF/heptane/ethylbenzene, 42.7 mL, 2 M, 85.493 mmol) in 100 ml THF (245 mL) was added dropwise a solution of intermediate 3 (20 g, 77.721 mmol) in THF (50 mL) at 0° C. The solution was stirred for 30 min and then transferred to a solution of N-fluorobenzenesulfonimide (30.6 g, 97.1 mmol) in 100 ml THF at 0° C. The RM was stirred for 15 min at 0° C. and then at rt overnight. The RM was evaporated, EtOAc was added and the RM was washed subsequently with water, 0.1N HCl-solution, saturated NaHCO$_3$ solution and brine. The OL was dried on MgSO$_4$, filtered and evaporated. The product was purified on silica gel, eluent: DCM→1% MeOH in DCM. The pure fractions were evaporated to yield intermediate 13 (21.4 g, quantitative).

Intermediate 14

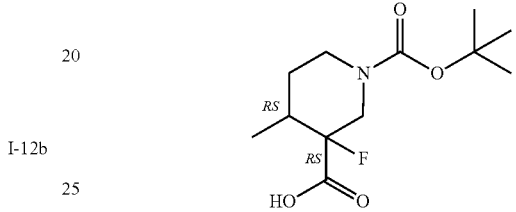

A solution of intermediate 13 (21.4 g, 77.728 mmol) was stirred in MeOH (500 mL) at RT. NaOH (486 mL, 2 M, 973 mmol) was added and the mixture was stirred for 2 h at rt. The RM was acidified with HCl 1N and the product was extracted with Et$_2$O. The OL was washed with brine and dried on MgSO$_4$, filtered and evaporated. The product was purified on silicagel, eluent: DCM→5% MeOH in DCM. The pure fractions were evaporated to yield 14 (15 g, 74%).

Intermediate 15

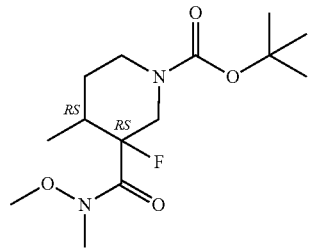 [SMILES: CON(C)C(=O)C1(F)CN(C(=O)OC(C)(C)C)CCC1C]

Intermediate 14 (15 g, 57.407 mmol) was dissolved in DCM (1000 mL). Then N,O-dimethylhydroxylamine hydrochloride (11.2 g, 114.8 mmol) and Et$_3$N (17.4 g, 172 mmol) were added. The reaction mixture was cooled to 0° C. Then HATU (24.0 g, 63.1 mmol) was added. The reaction mixture was stirred at rt for 2 h. The RM was poured into aq. NaHCO$_3$ (100 mL). The OL was separated, dried with MgSO$_4$, and the solvent was evaporated. The residue was purified by flash column chromatography over silica gel eluent: DCM→1% MeOH in DCM. The product fractions were collected and the solvent was evaporated to give the desired product 15 (8.49, 49% g).

Intermediate 16

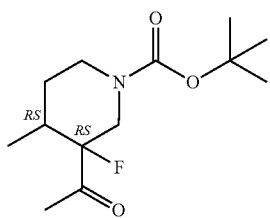 [SMILES: CC(=O)C1(F)CN(C(=O)OC(C)(C)C)CCC1C]

Intermediate 15 (8.49, 27.9 mmol) in THF (60 mL) was brought in a flask under $N_2$ and cooled to −15° C. Methyl magnesium bromide (16.3 mL, 3M, 48.8 mmol) was added dropwise, temperature not exceeding 0° C. After addition, the RM was stirred for 1 h at RT. Then the RM was poured on ice with 20 mL AcOH. The product was extracted with $Et_2O$ and the OL was washed with a 5% $NaHCO_3$ solution. The OL was dried on $MgSO_4$, filtered and evaporated and purified on silicagel, eluent: DCM. The pure fractions were evaporated to give intermediate 16 (3.20 g, 44%).

Intermediate 17

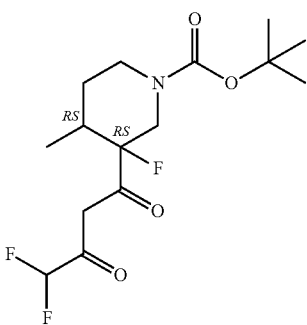 [SMILES: CC1CCN(C(=O)OC(C)(C)C)CC1(F)C(=O)CC(=O)C(F)F]

Intermediate 16 (3.2 g, 0.0123 mol) was stirred in toluene (150 mL) at 0° C. under $N_2$. Potassium tert-butoxide (1.94 g, 17.3 mmol) was added at 0-5° C., ethyldifluoroacetate (1.84 g, 0.0149 mol) was added dropwise at 0-5° C. RM was stirred at RT for 2 hr. The RM was washed with 10% $H_2SO_4$ in water and the OL was dried on $MgSO_4$, filtered and evaporated to yield intermediate 17 (4.16 g, 99%).

Intermediate 18

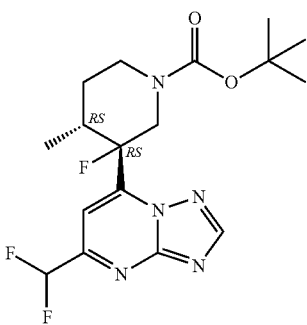 [SMILES: C[C@@H]1CCN(C(=O)OC(C)(C)C)C[C@@]1(F)c1cc(C(F)F)nc2ncnn12]

Intermediate 17 (4.16 g, 12.3 mmol) and 1H-1,2,4-triazol-5-amine hydrochloride (2.97 g, 24.7 mmol) in DMF (40 mL) were stirred at 80° C. for 16 h. The RM was evaporated, DCM was added and 2 g $(Boc)_2O$ and 2 mL of $Et_3N$ was added. The mixture was stirred for 30 min, washed with water, the OL was dried on $MgSO_4$, filtered and evaporated. The product (4 isomers) was purified on silicagel, eluent: DCM→2% MeOH in DCM. The fractions were evaporated, yielding 3.55 g of a crude that was purified via Prep HPLC (stationary phase: Uptisphere® C18 ODB—10 μm, 200 g, 5 cm, mobile phase: 0.25% $NH_4HCO_3$ solution in water, $CH_3CN$) to afford intermediate 18 (730 mg, 15%).

Intermediate 19

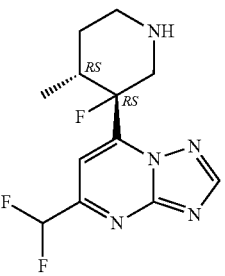 [SMILES: C[C@@H]1CCNC[C@@]1(F)c1cc(C(F)F)nc2ncnn12]

To intermediate 18 (0.73 g, 1.894 mmol) in MeOH (20 mL) was added HCl (6M in iPrOH) (20 mL, 6 M, 120 mmol) and this was stirred at RT overnight. The solvents were evaporated to yield intermediate 19 (600 mg, 99%).

Alternative Procedure to Intermediate 19 and Separation into Intermediates 19A and 19B

INTERMEDIATE 19

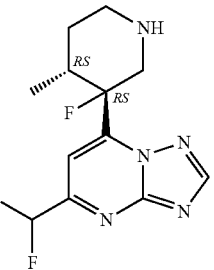

INTERMEDIATE 19A

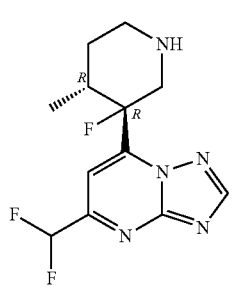

INTERMEDIATE 19B

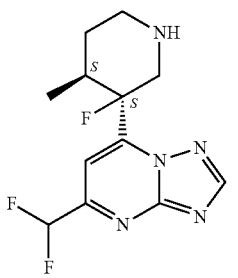

To intermediate 18 (4.5 g, 11.7 mmol) in DCM (52 mL) was added trifluoroacetic acid (TFA) (6M in iPrOH) (5.4 mL, 6 M, 70 mmol) and this was stirred at RT for 1 h. The solvents were evaporated and the resulting residue was dissolved in DCM and washed with a saturated aqueous solution of NaHCO$_3$. The OL was separated and the aqueous layer back-extracted 2×DCM. The combined OL were dried over MgSO$_4$, filtered and evaporated under reduced pressure. The resulting residue was purified via flash column chromatography on silica gel using as eluent a gradient DCM/NH$_3$(MeOH), 99/1 to 93/7, to give intermediate 19 (2.2 g, 66% yield) as a racemic mixture. This was separated in enantiomers by prep SFC (Stationary phase: Chiralpak Diacel AD 20×250 mm, mobile phase: CO$_2$, EtOH+0.4% iPrNH$_2$) to afford intermediates 19a (955 mg, 29%, Rt=2.36 min) and 19b (970 mg, 29%, Rt=2.99 min).

Intermediate 20

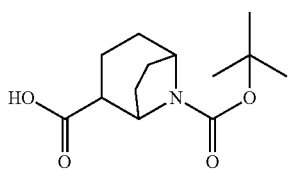 [SMILES: CC(C)(C)OC(=O)N1C2CCC(C(=O)O)C1CC2]

8-Azabicyclo[3.2.1]octane-2,8-dicarboxylic acid, 8-(1,1-dimethylethyl) 2-methyl ester [1033820-28-8] (4.77 g, 17.71 mmol) was stirred in MeOH (41.608 mL) at RT. NaOH (106 mL, 1 M, 106 mmol) was added and the mixture was stirred overnight at rt. The MeOH was evaporated. The RM was acidified with HCl 1N and the product was extracted with chloroform. The OL was dried on MgSO$_4$, filtered and evaporated to give intermediate 20 (4.52 g, 100%).

Intermediate 21

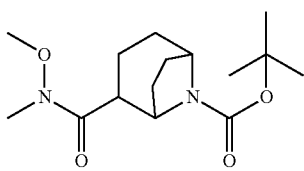 [SMILES: CON(C)C(=O)C1CCC2CCC1N2C(=O)OC(C)(C)C]

Intermediate 20 (4.52 g, 17.704 mmol) was dissolved in DCM (200 mL). Then N,O-dimethylhydroxylamine hydrochloride (3.454 g, 35.407 mmol) and Et$_3$N (5.37 g, 53.1 mmol) were added. The reaction mixture was cooled to 0° C. Then HATU (7.41 g, 19.5 mmol) was added. The reaction mixture was stirred at RT for 2 h. The reaction mixture was poured into aq. NaHCO$_3$ (100 mL). The OL was separated, dried with MgSO$_4$, and the solvent was evaporated. The residue was purified by flash column chromatography over silica gel eluent: DCM→1% MeOH in DCM. The product fractions were collected and the solvent was evaporated to give intermediate 21 (3.03 g, 57%).

Intermediate 22

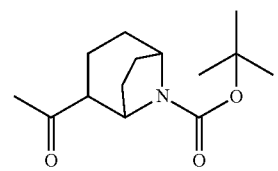 [SMILES: CC(=O)C1CCC2CCC1N2C(=O)OC(C)(C)C]

Intermediate 21 (3.03 g, 10.2 mmol) in THF (50 mL) was brought in a flask under N$_2$ and cooled to −15° C. Methylmagnesium bromide (12.7 mL, 1.4 M, 17.8 mmol) was added dropwise, temperature not exceeded 0° C. After addition, the RM was stirred for 1 h at RT. Then the RM was poured on ice with AcOH (20 mL). The product was extracted with Et$_2$O and the OL was washed with a 5% NaHCO$_3$ solution. The OL was dried on MgSO$_4$, filtered and evaporated and purified on silicagel, eluent: DCM. The pure fractions were evaporated to give intermediate 22 (2.57 g, 100%).

Intermediate 23

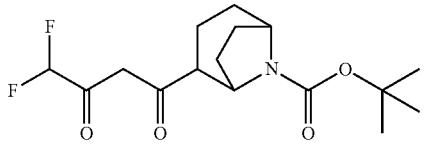 [SMILES: CC(C)(C)OC(=O)N1C2CCC(C(=O)CC(=O)C(F)F)C1CC2]

Intermediate 22 (2.57 g, 0.0101 mol) was stirred in toluene (150 mL) at 0° C. under N$_2$. Potassium tert.-butoxide (1.59 g, 14.2 mmol) was added at 0-5° C., ethyldifluoroacetate (1.52 g, 0.0122 mol) was added dropwise at 0-5° C. RM was stirred at RT for 2 h. The RM was washed with 10% H$_2$SO$_4$ in water and the OL was dried on MgSO$_4$, filtered and evaporated to yield intermediate 23 (3.34 g, 99%).

Intermediate 24

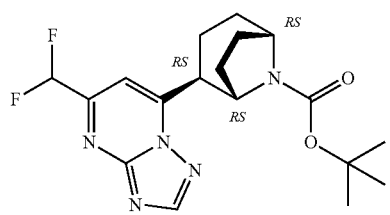

Intermediate 23 (3.34 g, 10.1 mmol) and 1H-1,2,4-triazol-5-amine hydrochloride (2.43 g, 20.2 mmol) in DMF (30 mL)

were stirred at 80° C. for 16 h. The RM was evaporated, DCM was added and 2 g (Boc)$_2$O and Et$_3$N (2 mL) was added. The mixture was stirred for 30 min, washed with water, the OL was dried on MgSO$_4$, filtered and evaporated. The product (4 isomers) was purified on silica gel, eluent: DCM→2% MeOH in DCM. The fractions were evaporated, yielding 3.07 g of a crude that was purified via Prep HPLC (stationary phase: Uptisphere® C18 ODB—10 µm, 200 g, 5 cm I.D., mobile phase: 0.25% NH$_4$HCO$_3$ solution in water, MeOH) to give intermediate 24 (1.07 g, 28%).

Intermediate 25

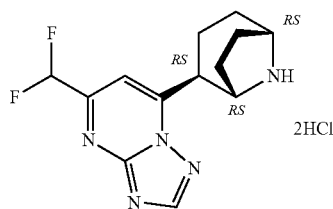

To intermediate 24 (1.07 g, 2.82 mmol) in MeOH (30 mL) was added HCl (6M in iPrOH 30 mL, 6 M, 179 mmol) and the reaction mixture was stirred at RT overnight. The solvents were evaporated and the product was crystallized from ether. Crystals were filtered off and dried to yield intermediate 25 as the hydrochloric acid salt (1.12 g, 112%).

Alternative Procedure to Intermediate 25

Step 1. Intermediate 43

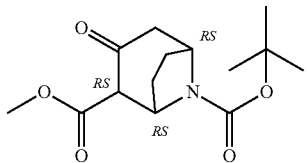 [SMILES: COC(=O)C1C(=O)CC2CCC1N2C(=O)OC(C)(C)C]

n-Butyllithium (nBuLi, 106.5 mL, 266.3 mmol, 2.5 M in hexanes) was added at 0° C. to a solution of diisopropylamine (26.95 g, 266.3 mmol) in THF (500 mL). The reaction mixture was stirred at 0° C. for 30 min, then it was cooled to −78° C. and treated with a solution of N-Boc-nortropinone (50 g, 221.9 mmol) in THF (75 mL). The resulting mixture was stirred at −78° C. for 90 min, then methyl cyanoformate (22.9 mL, 288.5 mmol) was added. The RM was allowed to warm to RT and stirred overnight. The reaction mixture was quenched with a saturated aqueous NH$_4$Cl solution, then it was diluted with EtOAc. The organic layer was separated, then washed with water and brine, dried over MgSO$_4$, filtered and concentrated under reduced pressure. The resulting residue was purified by flash column chromatography on silica gel using as eluent a gradient: 100% DCM to 1% MeOH in DCM, to provide intermediate 43 (60.25 g, 95.8%).

Step 2. Intermediate 44

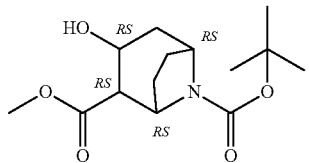 [SMILES: COC(=O)C1C(O)CC2CCC1N2C(=O)OC(C)(C)C]

Sodium borohydride (16.02 g, 423.5 mmol) was added to a cold (ice-bath) solution of intermediate 43 (60 g, 211.8 mmol) in methanol (700 mL) and the reaction mixture allowed to stir for 5 h. The completed reaction was quenched with a saturated aqueous NH$_4$Cl solution, then the solvent was evaporated to dryness under reduced pressure. The resulting residue was dissolved in water and extracted 3×DCM. The combined organic layers were dried over MgSO$_4$, filtered and concentrated in vacuo, to afford intermediate 44 (59 g, 97.6%) which was used as such without further purification.

Step 3. Intermediate 45

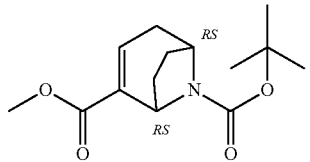 [SMILES: COC(=O)C1=CCC2CCC1N2C(=O)OC(C)(C)C]

Trifluoroacetic anhydride (57.5 mL, 413.5 mmol) was added dropwise very slowly (CAUTION! Exothermic) to a solution of intermediate 44 (59 g, 206.8 mmol), triethylamine (115 mL, 827.1 mmol) and 4-(dimethylamino) pyridine (2.52 g, 20.7 mmol) in DCM (800 mL), while keeping the temperature below 60° C. The reaction mixture was stirred at RT overnight, then it was cooled in an ice bath and quenched with water. The pH of the resulting solution was adjusted to 8-8.5 using a saturated aqueous NaHCO$_3$ solution and allowed to stir at RT for 1 hour. The aqueous was then extracted 3×DCM, then the combined organic layers were dried over MgSO$_4$, filtered and concentrated in vacuo. The resulting residue was purified by flash column chromatography on silica gel, using as eluent a gradient 100% DCM to 2% MeOH in DCM, to afford Intermediate 45 (33.7 g, 61%).

Step 4. Intermediate 46

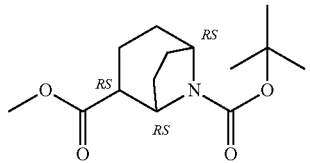 [SMILES: COC(=O)C1CCC2CCC1N2C(=O)OC(C)(C)C]

MeOH (59 mL) was added to a flask containing intermediate 45 (2.44 g, 9.13 mmol) and Pd/C (10%) (0.971 g, 0.913 mmol) under a nitrogen atmosphere. This was evacuated and backfilled with hydrogen gas and stirred at RT overnight. The reaction mixture was filtered over a pad of Celite®, then the solvent was removed in vacuo. The resulting residue was purified by flash column chromatography on silica gel, using as eluent a gradient 100% DCM to 2% MeOH in DCM, to afford intermediate 46 (2 g, 81%).

Step 5. Intermediate 47

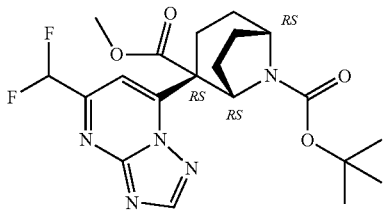

LDA (54.3 mL, 108.7 mmol, 2 M in cyclohexane/ethylbenzene/THF) was added dropwise at −78° C. to −60° C. to a solution of intermediate 46 (24.4 g, 90.6 mmol) in anhydrous THF (363 mL), under an atmosphere of nitrogen. After the addition, the reaction mixture was warmed to −30° C. and stirred for 10 min, before being cooled back to −78° C. 7-Chloro-5-(difluoromethyl)-[1,2,4]triazolo[1,5-a]pyrimidine ([1340394-63-9], 18.5 g, 90.6 mmol) was dissolved in a minimum amount of THF and added dropwise with a syringe. The reaction mixture was stirred at −60° C. for 1 h, then the temperature was raised to RT and the reaction was quenched with a saturated aqueous NH$_4$Cl solution. The volatiles were evaporated in vacuo and the resulting residue partitioned between EtOAc and water. The layers were separated, then the aqueous layer was extracted 2×EtOAc. The combined OL were washed with brine, dried over MgSO$_4$, filtered and concentrated under reduced pressure. The resulting residue was crystallized from diethylether, to afford intermediate 47 (23.8 g, 60%). The filtrate was evaporated and the resulting residue was purified by flash column chromatography on silica gel, using as eluent a gradient 100% DCM to 2% MeOH in DCM, to afford intermediate 47 (2 g, 5%), after recrystallization from diethylether.

Step 6. Intermediate 25, Intermediate 25A and Intermediate 25B

INTERMEDIATE 25

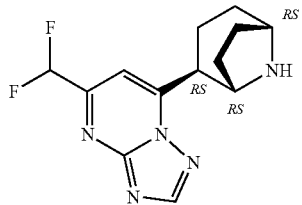

INTERMEDIATE 25A

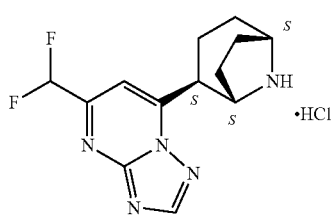

INTERMEDIATE 25B

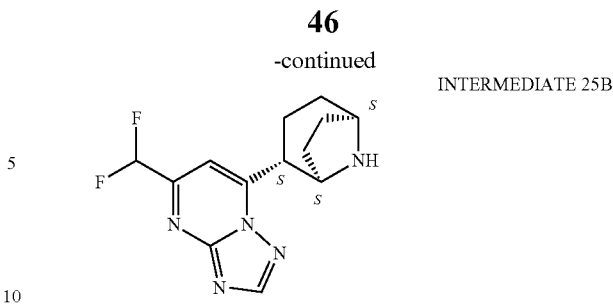

Intermediate 47 (25.8 g, 58.9 mmol) was stirred in a concentrated HCl solution (266 mL, 3.19 mol, 37% in H$_2$O) at 150° C. overnight. The volatiles were evaporated in vacuo and the resulting residue was co-evaporated twice with toluene. The product was treated with a saturated aqueous NaHCO$_3$ solution until basic pH. The aqueous layer was extracted with DCM, then the organic layer was dried on MgSO$_4$, filtered and evaporated under reduced pressure. The resulting residue was purified by flash column chromatography on silica gel, using as eluent a gradient 100% DCM to 8% MeOH/NH$_3$ in DCM, to afford the intermediate 25 as a racemic mixture (13 g, 79%). This material was purified via Prep SFC (Stationary phase: Chiralpak Diacel AD 20×250 mm, Mobile phase: CO$_2$, EtOH+0.4 iPrNH$_2$). The 1S,4S,5S-enantiomer was converted to its HCl salt and recrystallized from CH$_3$CN to provide intermediate 25a (5.58 g, 30%, Rt=2.91 min, $[\alpha]^{20}_D$=−66.6 (c=0.48, DMF)).

Intermediate 26

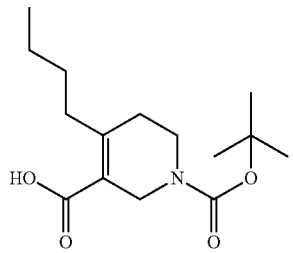

A mixture of 1-tert-butyl 3-methyl 4-(((trifluoromethyl)sulfonyl)oxy)-5,6-dihydropyridine-1,3(2H)-dicarboxylate [161491-25-4] (15 g, 38.53 mmol, prepared according to *Angew. Chem. Int. Ed.* 2015, 54, 12942-12946), N-butylboronic acid [4426-47-5] (5.89 g, 57.8 mmol), Pd(PPh$_3$)$_4$ [14221-01-3] (1.78 g, 1.54 mmol) and Na$_2$CO$_3$ [497-19-8] (8.167 g, 77.052 mmol) in 1,4-dioxane [123-91-1] (300 mL) was stirred and heated at 90° C. overnight. The volatiles were evaporated in vacuo and the resulting residue treated with an aqueous 1N HCl solution. The aqueous layer was extracted with DCM, then the combined OL was dried over MgSO$_4$, filtered and evaporated in vacuo. The resulting residue was purified via flash column chromatography on silica gel, using as eluent a gradient DCM-MeOH (9:1, v/v)/DCM, 0/100 to 30/70). This afforded 3.65 g of 1-tert-butyl-5-methyl-4-butyl-3,6-dihydro-2H-pyridine-1,5-dicarboxylate, which was dissolved in a mixture of methanol and aqueous 1 N NaOH solution (1:1, v/v, 200 mL) and stirred overnight at RT. The volatiles were evaporated under reduced pressure, and the resulting residue placed in ice and acidified with an aqueous 1 N HCl solution. The aqueous layer was extracted with chloroform, then the combined OL was dried over MgSO$_4$, filtered and evaporated under reduced pressure. The resulting residue was purified via flash column chromatography on silica gel, using as eluent a gradient 1% MeOH in DCM to 2% MeOH in DCM, to afford intermediate 26 (1.69 g, 15.5% yield).

Intermediate 27

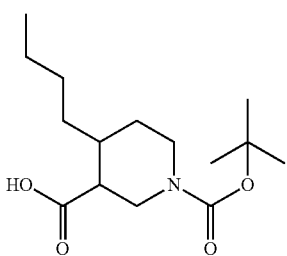 [SMILES: CCCCC1CCN(C(=O)OC(C)(C)C)CC1C(=O)O]

Intermediate 26 (1.47 g, 5.188 mmol) was added to a suspension of Pd/C (10%) (668 mg, 0.63 mmol) in MeOH [67-56-1] (134 mL). The mixture was then placed under an atmosphere of $H_2$ and stirred for 36 h. After this time, the catalyst was filtered over a pad of Celite and the solvent evaporated under reduced pressure to provide intermediate 27 (1.45 g, 98%).

Intermediate 28

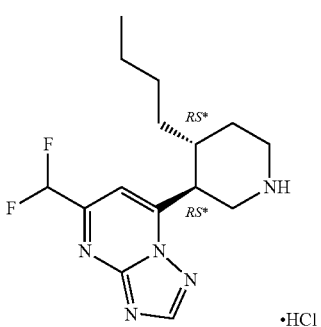 [SMILES: CCCC[C@@H]1CCNC[C@H]1c1cc(C(F)F)nc2ncnn12 ; Cl]

By following a procedure similar to the one reported for the synthesis of intermediate 8, intermediate 28 was synthesised starting from intermediate 27 was obtained intermediate 28 (200 mg).

Intermediates 29, 29A and 29B

INTERMEDIATE 29

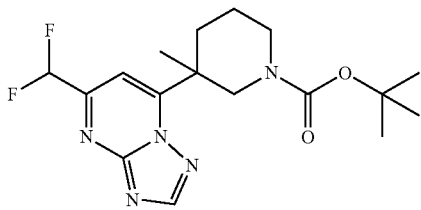

INTERMEDIATE 29 a

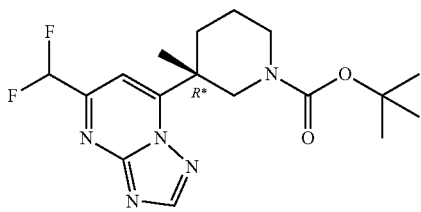

INTERMEDIATE 29b

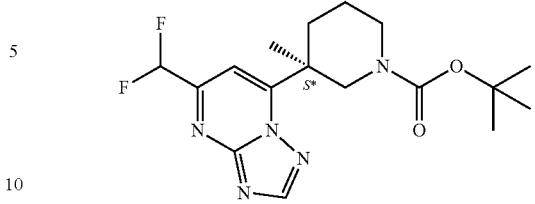

NaH (60% dispersion in mineral oil, 1.5 g, 39.05 mmol) was added to a solution of tert-butyl 3-[5-(difluoromethyl)-[1,2,4]triazolo[1,5-a]pyrimidin-7-yl]piperidine-1-carboxylate which was prepared analogously to intermediate 8 and 11, starting from 3-pyridine carboxylic acid (11.5 g, 32.54 mmol) in DMF (500 mL) at RT and under a flow of $N_2$. The reaction mixture was stirred for 30 min at RT, then methyl iodide (5.54 g, 39.05 mmol) was added dropwise and the mixture was stirred overnight at RT. Water was added and the product was extracted with EtOAc. The OL was washed with brine, dried over $MgSO_4$, filtered and evaporated. The resulting residue was purified via prep HPLC (stationary phase: Uptisphere® C18 ODB—10 µm, 200 g, 5 cm I.D., mobile phase: 0.25% $NH_4HCO_3$ solution in water, MeOH) to give intermediate 29 (4.32 g, 36%) as a racemic mixture. This was separated in enantiomers by prep SFC (Stationary phase: Chiralcel Diacel OJ 20×250 mm, mobile phase: $CO_2$, iPrOH+0.2% $iPrNH_2$) to afford intermediates 29a (2 g, 17%) and 29b (2 g, 17%).

Intermediate 30A

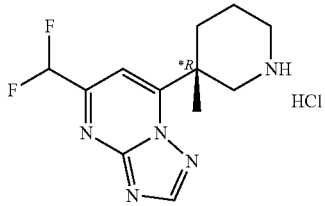 [SMILES: C[C@@]1(c2cc(C(F)F)nc3ncnn23)CCCNC1 ; Cl]

To intermediate 29a (500 mg, 1.36 mmol) in MeOH (20 mL) was added HCl (6M in iPrOH 20 mL, 6 M, 120 mmol) and the reaction mixture was stirred at RT overnight. The solvents were evaporated to give intermediate 30a as the hydrochloric acid salt (400 mg, 97%).

Intermediate 30B

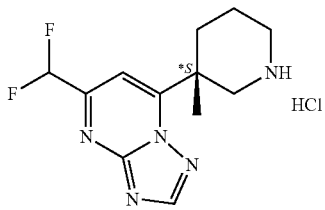 [SMILES: C[C@@]1(c2cc(C(F)F)nc3ncnn23)CCCNC1 ; Cl]

Intermediate 30b was obtained in the same manner as described for intermediate 30a, starting from 29b (400 mg, 97%).

Alternative Procedure to Intermediate 29

Step 1. Intermediate 31

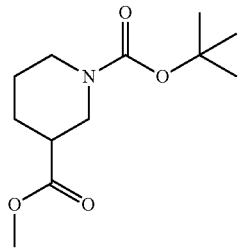 [SMILES: COC(=O)C1CCCN(C(=O)OC(C)(C)C)C1]

K₂CO₃ (33.15 g, 0.24 mol) was added to a stirred solution of 1-(tert-butoxycarbonyl)piperidine-3-carboxylic acid [84358-12-3] (50.0 g, 0.22 mol) in DMF (600 mL) at RT. Methyl iodide (34.05 g, 0.24 mol) was added after 30 minutes and the reaction mixture was stirred for another 2.5 h at rt. The volatiles were evaporated in vacuo and the resulting residue placed in water and extracted with DIPE. The combined OL was dried over MgSO₄, filtered and evaporated to provide 54.75 g of intermediate 31, which was used as such in the next step.

Step 2. Intermediate 32

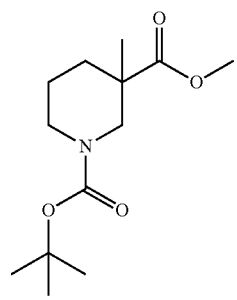 [SMILES: COC(=O)C1(C)CCCN(C(=O)OC(C)(C)C)C1]

LiHMDS (450 mL, 0.45 mol, 1 M) was added dropwise to a solution of intermediate 31 (54.75 g, 0.22 mmol) in THF (1 L) at −78° C. and under an atmosphere of N₂. The solution was stirred at −78° C. for 1 hour and then methyl iodide (63.9 g, 0.45 mmol) was added dropwise at this temperature. After the addition was completed, the reaction mixture was allowed to warm to RT. The RM was then treated with a saturated aqueous NH₄Cl solution. The aqueous layer was extracted with Et₂O. The combined OL were dried over MgSO₄, filtered and evaporated. The resulting residue was purified via flash column chromatography, using as eluent a 20% solution of EtOAc in heptane, to provide intermediate 32 (55.5 g, 96% yield).

Intermediate 29

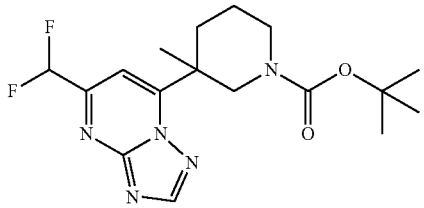 [SMILES: CC(C)(C)OC(=O)N1CCCC(C)(c2cc(C(F)F)nc3ncnn23)C1]

By following a procedure similar to the one reported for the synthesis of intermediate 8, starting from intermediate 32 intermediate 29 (36.7 g, 43.5% yield) was obtained.

Intermediate 33

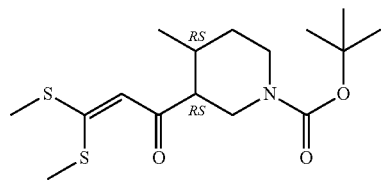 [SMILES: CSC(=CC(=O)C1CN(C(=O)OC(C)(C)C)CCC1C)SC]

NaH (60% dispersion in mineral oil, 0.97 g, 24.2 mmol) was added to intermediate 6 (5 g, 20.7 mmol) in anhydrous THF (35 mL), in a 250 mL four-necked RBF, at 0° C. under N₂ flow. After 10 minutes, carbon disulfide (1.46 mL, 24.1 mmol) was added dropwise and then methyl iodide (2.71 mL, 43.5 mmol) was added dropwise. The mixture was stirred overnight at RT. Water was added and the product was extracted with EtOAc. The OL was washed with brine, dried on MgSO₄, filtered and evaporated yielding intermediate 33 (8.2 g, 92%) which was used as such in the next step.

Intermediate 34

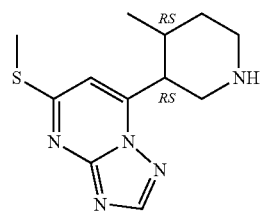 [SMILES: CSc1cc(C2CNCCC2C)n2ncnc2n1]

Intermediate 33 (1 g, 2.89 mmol) and 1H-1,2,4-triazol-5-amine hydrochloride (0.35 g, 2.89 mmol) were stirred at 150° C. for 3 hours in a melt reaction. The RM was cooled to RT and dissolved in DCM. The OL was washed with satd aq soln NaHCO₃, water, brine, dried on MgSO4, filtered and evaporated. The product was purified on silicagel, eluent DCM/MeOH, 100/0 to 98/2 yielding intermediate 34 (200 mg, 26%).

Intermediate 35

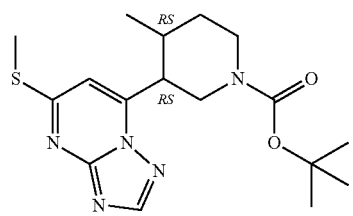 [SMILES: CSc1cc(C2CN(C(=O)OC(C)(C)C)CCC2C)n2ncnc2n1]

To intermediate 34 (200 mg, 0.76 mmol) in DCM (3.3 mL) was added (Boc)₂O (199 mg, 0.91 mmol), Et₃N (127 uL, 0.91 mmol) and the RM stirred at RT overnight. The solvent was evaporated, then the residue placed in DCM and washed with water (3×), then brine. The OL was separated, dried (MgSO4), filtered and evaporated, to give intermediate 35 (199 mg, 72%) which was used without further purification in the next step.

Intermediate 36

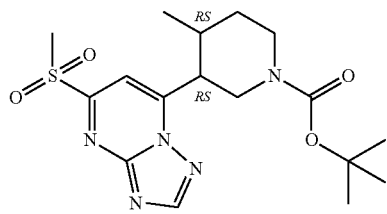 [SMILES: CC1CCN(C(=O)OC(C)(C)C)CC1c1cc(S(C)(=O)=O)nc2ncnn12]

To intermediate 35 (347 mg, 0.95 mmol) in CCl₃ (12 mL) was added mCPBA (659 mg, 3.82 mmol) and the RM was refluxed for 2 hours. The RM was diluted with CHCl₃, washed with NaOH 1N, dried on MgSO₄, filtered and evaporated, yielding intermediate 36 (301 mg, 79%) which was used as such in the next step.

Intermediate 37

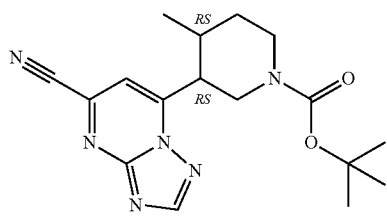 [SMILES: CC1CCN(C(=O)OC(C)(C)C)CC1c1cc(C#N)nc2ncnn12]

Intermediate 36 (799 mg, 2.02 mmol) and sodium cyanide (202 mg, 4.04 mmol) were stirred in DMSO (5 mL) at RT for 30 minutes. The RM was poured in water and extracted with EtOAc. The OL was washed with brine, dried on MgSO₄, filtered and evaporated to give intermediate 37 (550 mg, 80%) which used as such in the next step.

Intermediate 38

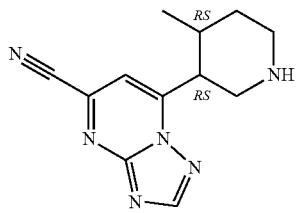 [SMILES: CC1CCNCC1c1cc(C#N)nc2ncnn12]

To intermediate 37 (520 mg, 1.52 mmol) in DCM (3.0 mL) was added TFA (6 mL) and the RM was stirred for 1 hours at 0° C. The RM was poured onto saturated Na₂CO₃ solution, then the OL was washed again with saturated Na₂CO₃, brine, dried on MgSO4 and evaporated, to give intermediate 38 (273 mg, 73%).

Intermediate 39

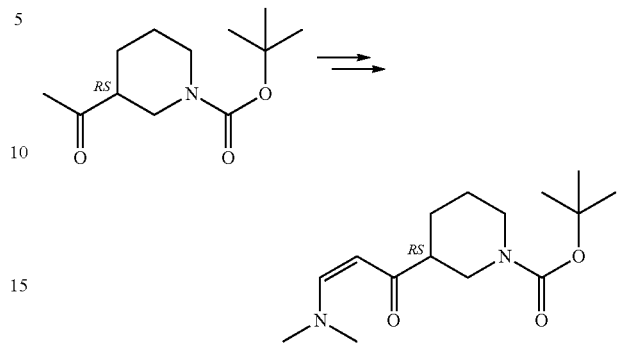

Intermediate 6' (obtained from intermediate 31 following the same transformations as for intermediates 3-6) (50 g, 0.22) was added to N,N-dimethylformamide dimethyl acetal (110 mL) and the mixture was refluxed for 4 days. The reaction mixture was evaporated and additional N,N-dimethylformamide dimethyl acetal was added and the mixture was refluxed for an additional 4 hours. The solvent was evaporated and the product was purified on silicagel, eluent: 1% MeOH in DCM, 2%. The pure fractions were evaporated, yielding intermediate 39 (60 g, 97%).

Intermediate 40

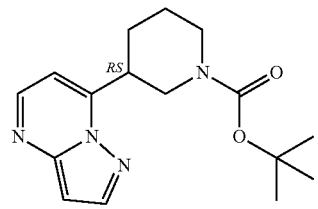 [SMILES: CC(C)(C)OC(=O)N1CCCC(c2ccnc3ccnn23)C1]

A solution of intermediate 39 (60 g, 0.21 mol) and 1H-1,2,4-triazol-5-amine hydrochloride (22.3 g, 0.27 mol) in acetic acid (53 mL) was stirred at reflux during 1 hour. Water was added and the product was extracted with ether. The OL was washed with brine and dried on MgSO₄, filtered and evaporated, yielding intermediate 40 (62 g, 96%).

Intermediate 41

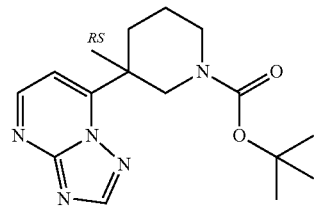 [SMILES: CC(C)(C)OC(=O)N1CCCC(C)(c2ccnc3ncnn23)C1]

Intermediate 40 (500 mg, 1.65 mmol) was stirred in DMF (50 mL) at RT under N₂ flow. NaH (60% dispersion in mineral oil, 72 mg, 1.8 mmol) was added and the mixture stirred for 30 min. Methyl iodide (2.57 mg, 1.8 mmol) was added and the mixture was stirred for 2 hours at RT. The reaction was quenched with water and evaporated. Water was added and the product was extracted with EtOAc. The OL was washed with brine, dried on MgSO₄, filtered and evaporated. This was purified by Prep HPLC on (RP Vydac Denali C18—10 μm, 200 g, 5 cm; mobile phase (0.25% NH₄HCO₃ solution in water, MeOH), yielding intermediate 41 (250 mg, 48%).

Intermediate 42

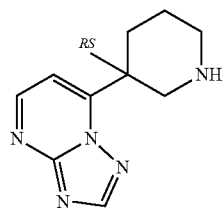 [SMILES: CC1(c2ccnc3ncnn23)CCCNC1]

Intermediate 41 (200 mg, 0.85 mmol) was stirred in MeOH (20 mL) and 6N HCl in i-PrOH (23 mL) was added. The mixture was stirred for 1 hour. The RM was evaporated, yielding intermediate 42 (250 mg, 100%).

Intermediate 48

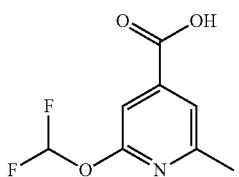

Step 1. Intermediate 49

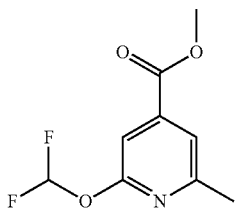

NaH (1.37 g, 34.4 mmol, 60% dispersion in mineral oil) was added to a slurry of methyl 2-hydroxy-6-methylisonicotinate (2.3 g, 13.76 mmol) in ACN (150 mL) at 0° C. and under an atmosphere of N₂. The rm was allowed to reach rt and stirred for 45 min. 2,2-Difluoro-2-(fluorosulfonyl)acetic acid (3.16 g, 17.76 mmol) was then added dropwise to the reaction mixture, which was further stirred at rt for 15 hours. After this time it was quenched with a saturated aqueous solution of NH₄Cl, and the resulting mixture extracted with DCM (100 mL×3). The combined organic extracts were dried over MgSO₄, filtered and concentrated under reduced pressure. The resulting residue was purified by flash column chromatography using as eluent a gradient heptane/EtOAc, 100/0 to 50/50, to afford intermediate 49 (2.21 g, 73.9%).

Step 2. Intermediate 48

An aqueous solution of NaOH (15 mL, 15 mmol, 1 M) was added to a solution of intermediate 49 (2.11 g, 9.72 mmol) in ethanol (15 mL). The resulting mixture was stirred for 1 h, then it was treated with an aqueous solution of HCl (15 mL, 15 mmol, 1 N). A white precipitate was formed and it was filtered, washed with cold water, then dried in the vacuum oven overnight to give intermediate 48 (1.75 g, 88.6%).

Intermediate 50

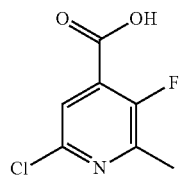

Step 1. Intermediate 51

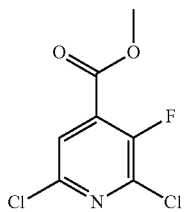

Concentrated H₂SO₄ (0.791 mL, 4.85 mmol, 1.84 g/mL) was added to a solution of 2,6-dichloro-3-fluoro-isonicotinic acid ([149468-00-8], 5.5 g, 26.19 mmol) in MeOH (99 mL), and the resulting mixture was heated to 85° C. for 12 h. After this time, more H₂SO₄ (0.791 mL, 14.846 mmol, 1.84 g/mL) was added and the rm stirred at 90° C. for 24 h. The reaction was cooled to rt, the solvent evaporated and ice was added to the resulting residue. A precipitate formed and it was filtered, washed with ice cold water and dried in the vacuum oven for 2 d, to provide intermediate 51 (4.35 g, 19.4 mmol,) as a beige solid.

Step 2. Intermediates 52A and 52B

INTERMEDIATE 52A

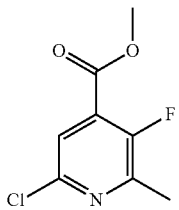

INTERMEDIATE 52B

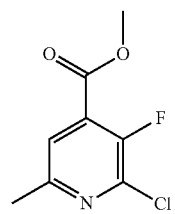

A solution of intermediate 51 (3.95 g, 17.6 mmol) and trimethylboroxine (1.66 mL, 5.82 mmol, 3.5 M in THF) in anhydrous 1,4-dioxane (128 mL) was degassed for 15 minutes. Palladium (II) acetate (198 mg, 0.88 mmol), tricyclophenylphosphine (494 mg, 1.76 mmol) and potassium phosphate tribasic (11.23 g, 53.0 mmol) were added sequentially and the resulting mixture was degassed, then stirred and heated at 110° C. for 18 h in a pressure tube. The rm was cooled to rt and the solvent evaporated in vacuo. The resulting residue was partitioned between water and EtOAc. The resulting biphasic mixture was separated and the aqueous layer extracted with EtOAc (3×). The combined organic layers were washed with brine (1×), dried over MgSO$_4$, filtered and the solvent evaporated in vacuo. The resulting residue was purified via flash column chromatography on silicagel, using as eluent a gradient heptane/EtOAc, 100/0 to 90/10, to provide intermediate 52a (980 mg, 27%) and its regioisomer 52b (460 mg, 12.8%).

Step 3. Intermediate 50

A solution of LiOH (277 mg, 11.5 mmol) in water (10 mL) was added to a stirred solution of intermediate 52a (785 mg, 3.85 mmol) in THF (10 mL). The rm was stirred at rt for 1.5 h, then the volatiles were evaporated in vacuo. The pH of the resulting aqueous residue was brought to ~2 by treatment with an aqueous HCl (1 M) solution. A white precipitate was formed and it was filtered, washed with ice cold water and dried in the vacuum oven for 2 d, to give intermediate 50 (491 mg, 67%) as a white solid.

Intermediate 53

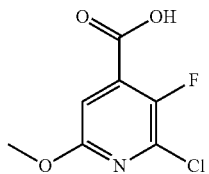

Step 1. Intermediate 54

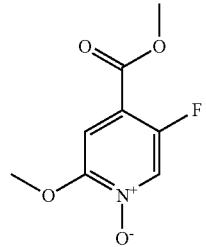

Methyltrioxorhenium (VII) (0.443 g, 1.78 mmol) was added in one portion to a cold (0° C.) solution of methyl 5-fluoro-2-methoxyisonicotinate (4 g, 21.6 mmol) in DCM (71 mL), followed by dropwise addition of hydrogen peroxide (64.3 mL, 0.735 mol, 35% in water). The rm was left to warm to rt, and then heated to 35° C. After 24 h, more methyltrioxorhenium (VII) (0.2 g, 0.80 mmol) was added and the rm was left stirring at 35° C. for 2 d. Portions of methyltrioxorhenium (VII) (0.2 g, 0.802 mmol) and hydrogen peroxide (30 mL, 0.343 mol, 35% in water) were added 3× over 8 h, and the rm stirred at 27° C. for 16 h. The rm was cooled in an ice bath, then it was quenched by portionwise addition of manganese dioxide (CAUTION! Strong gas and heat evolution) until gas evolution ceased, giving a black mixture. This was combined with another reaction mixture batch resulting from a reaction starting with 1 g of methyl 5-fluoro-2-methoxyisonicotinate. The combined reaction mixtures were filtered through a Celite® plug, which was washed with DCM. The biphasic filtrate was separated and the aqueous phase was extracted with DCM (3×20 mL). The combined organic layers were dried over MgSO$_4$, filtered and evaporated in vacuo. The resulting residue (4.9 g) was purified via flash column chromatography on silica gel, using as eluent a gradient heptane/EtOAc, 100/0 to 0/100, to intermediate 54 (585 mg).

Step 2. Intermediate 55

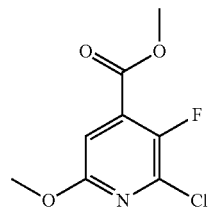

A suspension of intermediate 54 (585 mg, 2.91 mmol) in phosphorus oxychloride (4.1 mL, 43.6 mmol) was stirred and warmed to 105° C. in an oil bath. After 1.5 h, the solvent was removed in vacuo. Ice (10 mL) was added to the resulting residue and the aqueous mixture was extracted with DCM (3×20 mL). The combined organic layers were washed with brine, dried over MgSO$_4$ and evaporated in vacuo. The resulting residue (580 mg) was purified by column chromatography on silica gel, using as eluent a gradient heptane/DCM, 100/0 to 50/50, to provide intermediate 55 (522 mg, 72.7%,)

Step 3. Intermediate 53

A solution of LiOH (152 mg mg, 6.35 mmol) in water (5.7 mL) was added to a stirred solution of intermediate 55 (522 mg, 2.12 mmol) in THF (5.7 mL). The rm was stirred at rt for 1.5 h, then the volatiles were evaporated in vacuo. The pH of the resulting aqueous residue was brought to ~3 by treatment with an aqueous HCl (1 M) solution. A white precipitate was formed and it was filtered, washed with ice cold water and dried in the vacuum oven to give intermediate 53 (172 mg, 39%) as a white solid. The filtrate was evaporated to dryness under reduced pressure, to give the lithium salt of compound 53 (366 mg).

B—SYNTHESIS OF FINAL COMPOUNDS

Compound 1A and Compound 1B

Co. No. 1a

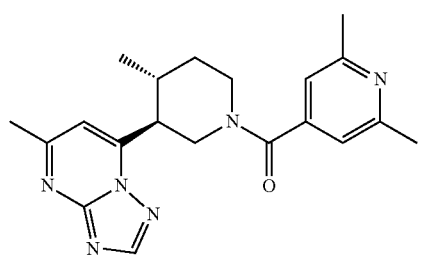

-continued

Co. No. 1b

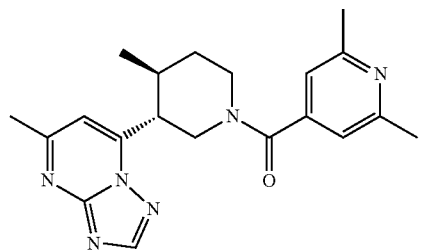

A mixture of I-12 (0.27 g, 0.001 mol) and 2,6-dimethylisonicotinic acid (0.16 g, 0.001 mol) in DCM (10 mL) was treated with DIPEA (0.69 mL, 0.75 g/mL, 0.004 mol) and HBTU (0.38 g, 0.001 mol). Stirring was continued for 16 h. The RM was diluted with water (5 mL), acidified with 1 M HCl until pH-3 and the layers were separated and the OL was washed with 1 M NaOH until pH-9, water, then dried over $MgSO_4$, filtered and concentrated in vacuo to give an oil (0.8 g). A purification was performed via Prep HPLC (stationary phase: RP XBridge® Prep C18 OBD—10 μm, 50×150 mm, mobile phase: 0.25% $NH_4HCO_3$ solution in water, MeOH) yielding two fractions. A purification was performed using Prep SFC (stationary phase: Chiralpak® Diacel AD 20×250 mm, mobile phase: $CO_2$, EtOH with 0.4% $iPrNH_2$) yielding 4 fractions of which two afforded compounds 1b (64 mg, 18%) and 1a (70 mg, 19%).

Compounds 2a to 3b were prepared in an analogous manner to compounds 1a and 1b from the indicated starting material:

| Co. No. | Structure | Prepared from | Yield % |
|---|---|---|---|
| 2a | 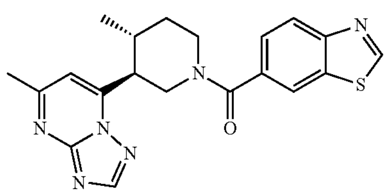 [SMILES: Cc1cc([C@@H]2CN(C(=O)c3ccc4ncsc4c3)CC[C@H]2C)n2ncnc2n1] | I-12a | 82 |
| 2b | 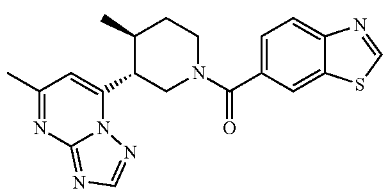 [SMILES: Cc1cc([C@H]2CN(C(=O)c3ccc4ncsc4c3)CC[C@@H]2C)n2ncnc2n1] | | 82 |
| 3a | 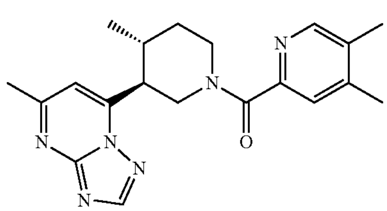 | I-12a [802256-42-4] | 12 |

-continued

| Co. No. | Structure | Prepared from | Yield % |
|---|---|---|---|
| 3b | 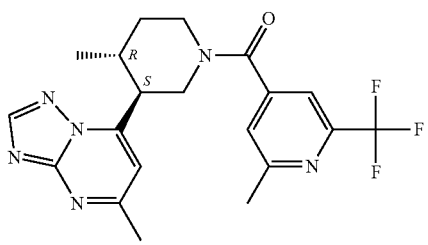 | I-12b | |

Compound 4

2-Methyl-6-(trifluoromethyl)isonicotinic acid (101 mg, 0.493 mmol) was stirred in DCM (20 mL). DIPEA (0.34 mL, 0.75 g/mL, 1.97 mmol) and HBTU (206 mg, 0.542 mmol) were added, stirring was continued for 20 min at RT. I-13a (150 mg, 0.493 mmol) was added and stirring was continued overnight at RT. The RM was quenched with water, stirred 20 min then the OL was separated. The aqueous layer was back extracted 2×DCM. The combined organic layers were washed with brine, then separated and dried over $MgSO_4$, filtered and concentrated in vacuo. This material was purified by silicagel flash chromatography eluting with 0-5% MeOH in DCM to afford crude compound 4 (120 mg, yield 52.931%). A purification was performed via Prep HPLC (stationary phase: RP Vydac Denali C18—10 μm, 200 g, 5 cm I.D., mobile phase: 0.25% $NH_4HCO_3$ solution in water, MeOH) yielding, after co-evaporation with MeOH and drying in the vacuum oven overnight, compound 4 (74 mg, 36%).

Compounds 5 to 23 were prepared in a similar way as compound 6 using enantiopure intermediate I-13a.

| Co. No. | Structure | Yield (%) |
|---|---|---|
| 5 | 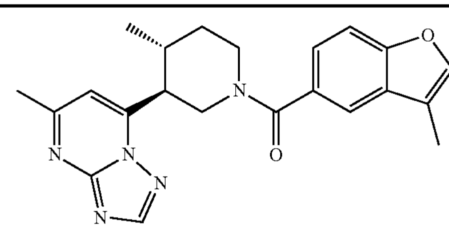 | 54 |

| Co. No. | Structure | Yield (%) |
|---|---|---|
| 6 | 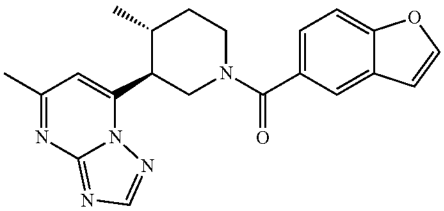 [SMILES: Cc1cc([C@@H]2CN(C(=O)c3ccc4occc4c3)CC[C@H]2C)n2ncnc2n1] | 61 |
| 7 | 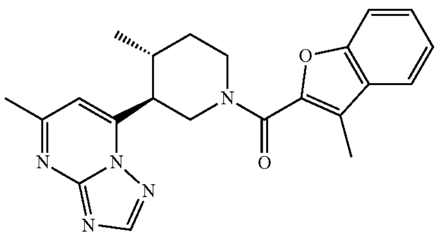 [SMILES: Cc1cc([C@@H]2CN(C(=O)c3oc4ccccc4c3C)CC[C@H]2C)n2ncnc2n1] | 56 |
| 8 | 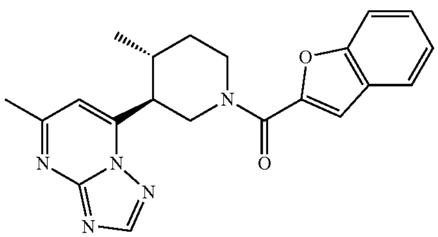 [SMILES: Cc1cc([C@@H]2CN(C(=O)c3cc4ccccc4o3)CC[C@H]2C)n2ncnc2n1] | 48 |
| 9 | 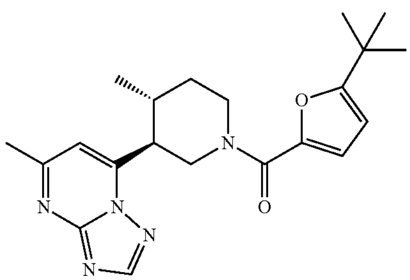 [SMILES: Cc1cc([C@@H]2CN(C(=O)c3ccc(C(C)(C)C)o3)CC[C@H]2C)n2ncnc2n1] | 58 |
| 10 | 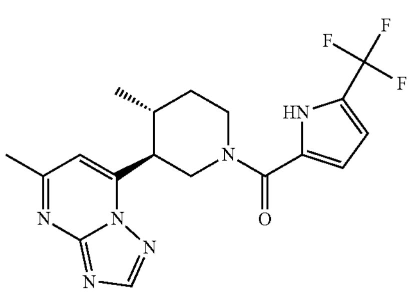 [SMILES: Cc1cc([C@@H]2CN(C(=O)c3ccc(C(F)(F)F)[nH]3)CC[C@H]2C)n2ncnc2n1] | 8 |
| 11 | 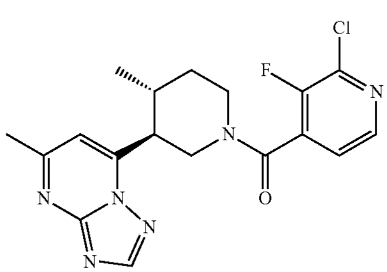 [SMILES: Cc1cc([C@@H]2CN(C(=O)c3ccnc(Cl)c3F)CC[C@H]2C)n2ncnc2n1] | 10 |
| 12 | | 57 |
| 13 | | 55 |
| 14 | | 45 |
| 15 | | 11 |
| 16 | | 48 |
| 17 | | 7.8 |

-continued

| Co. No. | Structure | Yield (%) |
|---|---|---|
| 18 | 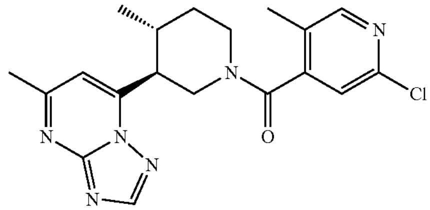 [SMILES: Cc1cc([C@@H]2CN(C(=O)c3cc(Cl)ncc3C)CC[C@H]2C)n2ncnc2n1] | 19 |
| 19 | 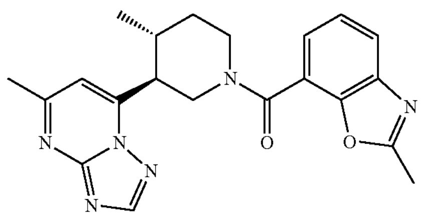 | 55 |
| 20 | 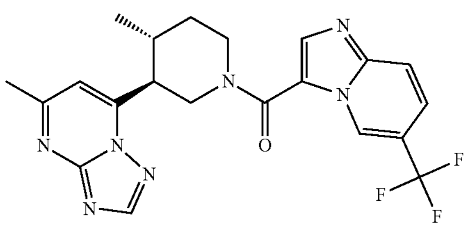 [SMILES: Cc1cc([C@@H]2CN(C(=O)c3cnc4ccc(C(F)(F)F)cn34)CC[C@H]2C)n2ncnc2n1] | 50 |
| 21 | 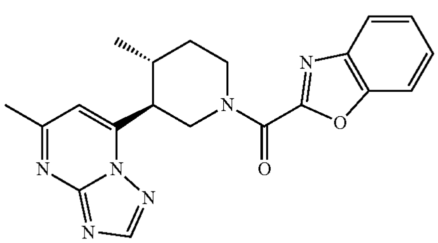 [SMILES: Cc1cc([C@@H]2CN(C(=O)c3nc4ccccc4o3)CC[C@H]2C)n2ncnc2n1] | 42 |
| 22 | 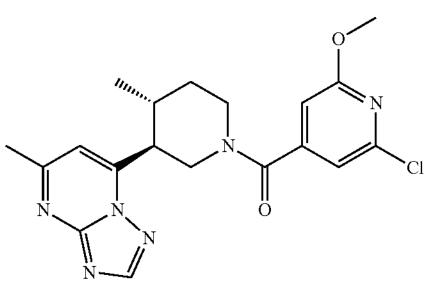 [SMILES: COc1cc(C(=O)N2CC[C@@H](C)[C@H](c3cc(C)nc4ncnn34)C2)cc(Cl)n1] | 58 |
| 23 | 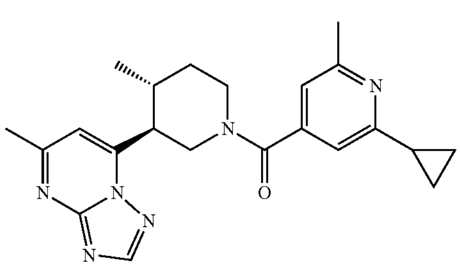 [SMILES: Cc1cc(C(=O)N2CC[C@@H](C)[C@H](c3cc(C)nc4ncnn34)C2)cc(C2CC2)n1] | 52 |

Compound 24A and Compound 24B

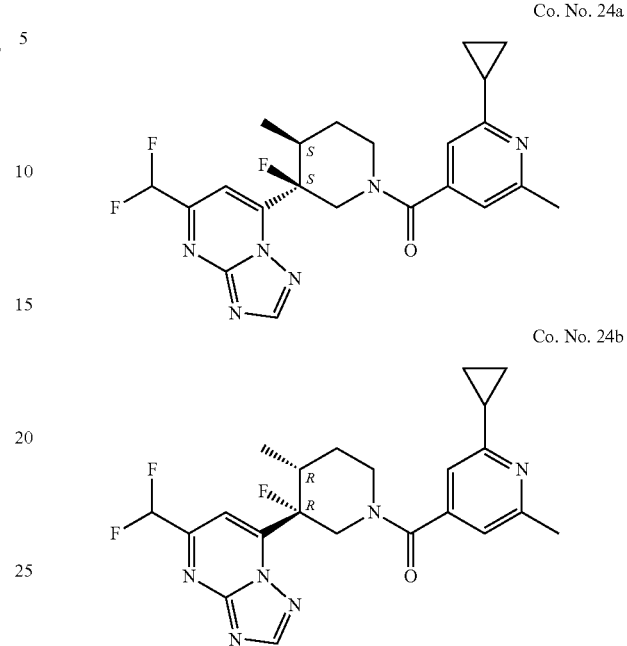

Co. No. 24a

Co. No. 24b

To a stirred mixture of 2-cyclopropyl-6-methyl-pyridine-4-carboxylic acid (0.16 g, 0.00075 mol) in DCM (20 mL, 1.33 g/mL, 0.31 mol) was added HBTU (0.28 g, 0.00075 mol) and DIPEA (0.54 mL, 0.75 g/mL, 0.0031 mol). After the mixture was stirred 30 min, I-19 (0.2 g, 0.00062 mol) was added in one portion. The RM was left stirring for 1 h and then 1 M NaOH (5 mL) was added, the layers were separated and the OL was washed with water (10 mL), dried over $MgSO_4$, filtered and concentrated in vacuo to afford an oil. This was purified by flash chromatography using a 24 g Redisep® Flash column eluting with a gradient of 0-5% MeOH in DCM to afford an oil was which crystallized from DIPE (10 mL) to afford a white solid (0.23 g, yield 83.2%). A purification was performed via Prep SFC (stationary phase: Chiralpak® Diacel AD 30×250 mm, mobile phase: $CO_2$, iPrOH with 0.2% $iPrNH_2$) to afford the two fractions. Both fractions were transferred to tubes and dried in a vacuum oven (45° C., 16 h) and this afforded amorphous solids Co. No. 24a (0.11 g, yield 39.7%) and Co. No. 24b (0.11 g, yield 38.3%).

Compounds 25A and 25B

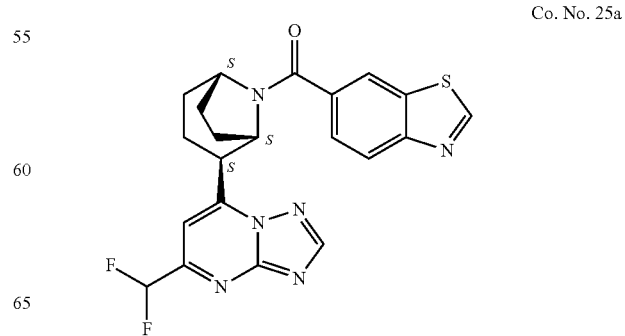

Co. No. 25a

Co. No. 25b

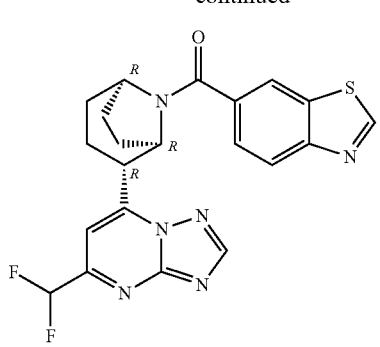

Benzothiazole-6-carboxylic acid (142 mg, 0.792 mmol) was stirred in DCM (15 mL), DIPEA (0.82 mL, 4.8 mmol) and HBTU (300 mg, 0.792 mmol) were added. Stirring was continued for 0.5 h at RT. Intermediate 25 (250 mg, 0.792 mmol) was added to the solution and stirring was continued for 2 h at RT. NaOH solution (1N, 1 mL) was added and stirred for 5 min. The product filtered on an extrelute filter and the filtrate was evaporated. The product was purified on silica gel, eluent: DCM→4% MeOH in DCM. The pure fractions were evaporated to give a mixture of compounds 25a and 25b (340 mg). This was purified via Prep SFC (Stationary phase: Chiralcel® Diacel OD 20×250 mm, Mobile phase: $CO_2$, EtOH+0.4 iPrNH$_2$) to give both products which were crystallized from Et$_2$O and afforded Co. No. 25a (121 mg, 35%) and Co. No. 25b (128 mg, 37%).

Compounds 26A and 26B

Co. No. 26a

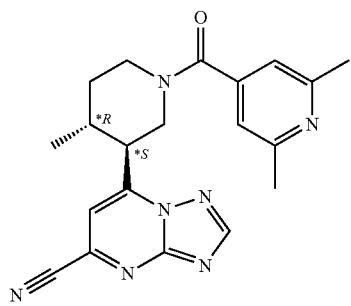

Co. No. 26b

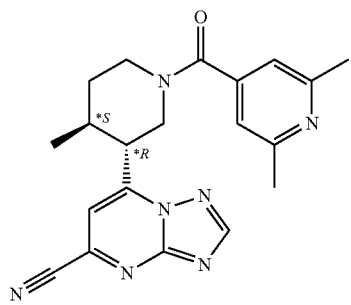

2,6-Dimethylisonicotinic acid (154.845 mg, 1.0 mmol) was stirred DCM (10 mL). DIPEA (0.53 mL, 3.1 mmol) and HBTU (427 mg, 1.1 mmol) were added, stirring was continued for 0.5 hours at RT. Intermediate 38 (273 mg, 1.1 mmol) was dissolved in DCM (5 mL) and this mixture was added to the solution, which was stirred was continued for 3.5 hours at room temperature. The RM was quenched with water, then the two layers were separated and the WL back-extracted with DCM. The OL was dried on MgSO$_4$, filtered and evaporated. The product was purified on silica gel, eluent: DCM/MeOH, 100/0 to 97/3 to 94/6 which afforded the two pairs of diastereomers as a mixture. A purification was performed via Prep SFC (Stationary phase: Chiralcel® Diacel OD 20×250 mm, Mobile phase: $CO_2$, EtOH+0.4 iPrNH$_2$) which afforded the two trans enantiomers. A purification was performed via Prep HPLC (Stationary phase: RP XBridge Prep C18 ODB—5 μm, 30×250 mm, Mobile phase: 0.25% NH$_4$HCO$_3$ solution in water, CH$_3$CN to give compound 26a (26 mg, yield 6.761%) and 26b (20 mg, yield 5.201%).

Compound 321

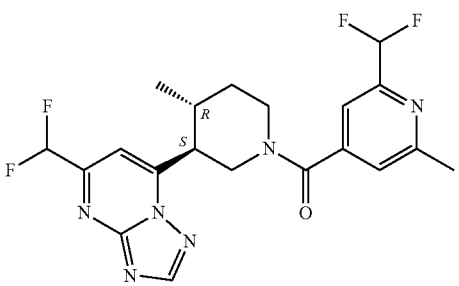

Intermediate 9b (. 2HCl, 1.2 g, 3.527 mmol), 2-(difluoromethyl)-6-methyl-4-pyridinecarboxylic acid (660 mg, 3.527 mmol), EDCI (1.352 g, 7.053 mmol), and DIPEA (1.823 g, 14.107 mmol) in DCM (71.4 mL) were stirred at RT for 4 h. The RM was washed with NaOH 1N, the OL was dried over MgSO$_4$, filtered and evaporated. The product was purified on silicagel, eluent MeOH/DCM 0/100 to 3/97. The pure fractions were evaporated and crystallized from DIPE. The crystals were filtered off and dried to give compound 321 (920 mg, 60%).

Compound 333

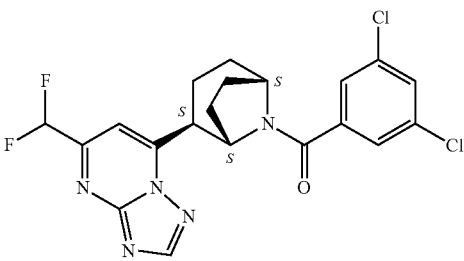

To a stirred solution of intermediate 25a (100 mg, 0.317 mmol) in dry ACN (5 mL), was added 3,5-dichlorobenzoic acid (72.593 mg, 0.38 mmol). TEA (0.22 mL, 1.58 mmol) was added, followed by 1-propanephosphonic anhydride ([68957-94-8], 0.28 mL, 0.48 mmol) and the mixture was stirred at RT for 3 h, giving a white precipitate in a brown solution. The solvent was removed in vacuo, and the crude was partitioned between DCM (10 mL) and a saturated aqueous NaHCO$_3$ solution (10 mL). The OL was washed with a saturated aqueous Na$_2$CO$_3$ solution (1×15 mL), dried (MgSO$_4$), filtered, the solvent was removed in vacuo, and coevaporated with toluene (1×20 mL), giving a white precipitate in a brown solution, which was dried overnight to give brown and white crystals. Recrystallisation from Et$_2$O yielded off white crystals, which were oven dried overnight in a 40° C. vacuum oven, giving compound 333 (88 mg, 61%), as off white crystals.

Table 1 below lists additional compounds that were prepared by analogy to the above Examples. In case no salt form is indicated, the compound was obtained as a free base. 'Co. No.' means compound number. Reagents used in the synthesis of the compounds are either commercially available or can be made by procedures known to the skilled person. Compounds made by analogy to compound 321 are indicated (N.B. EDCI coupling); compounds made by analogy to compound 333 are indicated (N.B. phosphonic acid anhydride) in the reagent column.

TABLE 1

| Co. No. | Structure | Prepared from | Yield (%) |
|---|---|---|---|
| 27 | 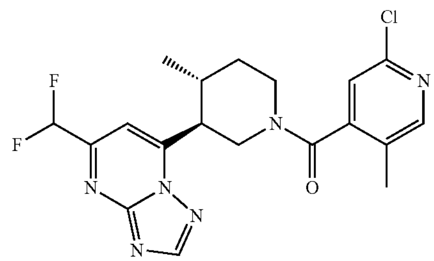 [SMILES: Cc1cnc(Cl)cc1C(=O)N1CC[C@@H](C)[C@H](c2cc(C(F)F)nc3ncnn23)C1] | I-9b | 78 |
| 28 | 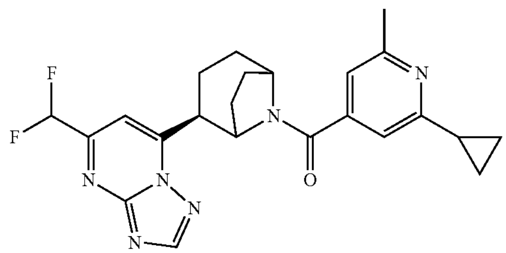 [SMILES: Cc1cc(C(=O)N2C3CCC2[C@@H](c2cc(C(F)F)nc4ncnn24)CC3)cc(C2CC2)n1] | I-25 | 35 |
| 29 | 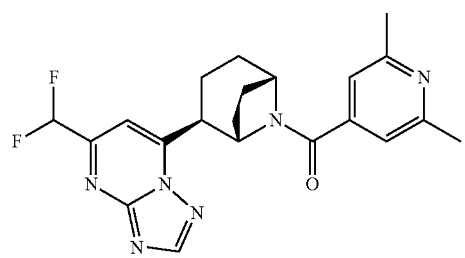 [SMILES: Cc1cc(C(=O)N2[C@H]3CC[C@H](c4cc(C(F)F)nc5ncnn45)[C@@H]2CC3)cc(C)n1] | I-25 | 39 |
| 30 | 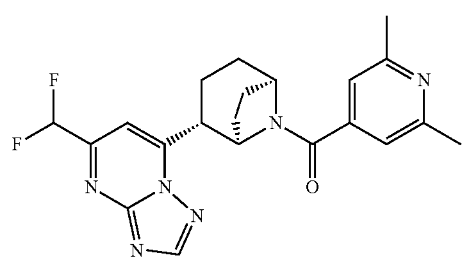 [SMILES: Cc1cc(C(=O)N2[C@H]3CC[C@@H]2[C@H](c2cc(C(F)F)nc4ncnn24)CC3)cc(C)n1] | I-25 | 38 |
| 31 | 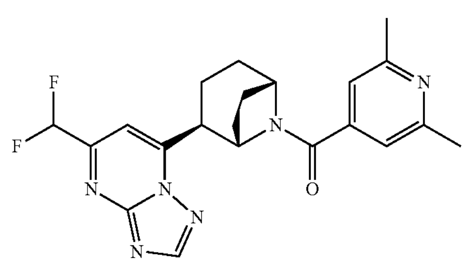 | I-25 | 26 |

Racemic endo

TABLE 1-continued
| Co. No. | Structure | Prepared from | Yield (%) |
|---|---|---|---|
| 32 | 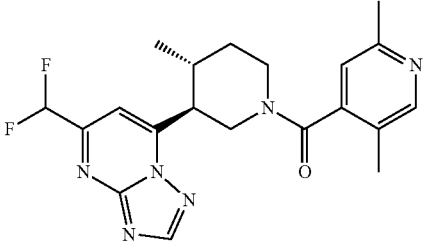 | I-9b | 55 |
| 33 | 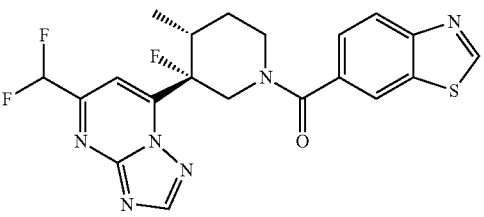 [SMILES: C[C@@H]1CCN(C(=O)c2ccc3ncsc3c2)C[C@@]1(F)c1cc(C(F)F)nc2ncnn12] | I-19 | 44 |
| 34 | 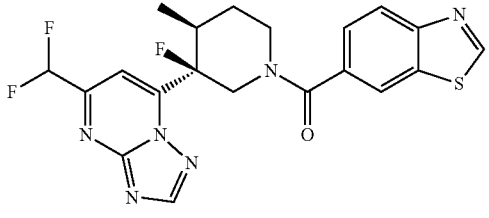 [SMILES: C[C@H]1CCN(C(=O)c2ccc3ncsc3c2)C[C@]1(F)c1cc(C(F)F)nc2ncnn12] | I-19 | 41 |
| 35 | 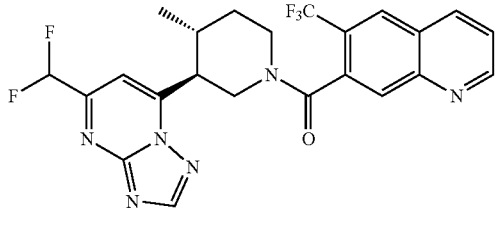 [SMILES: C[C@@H]1CCN(C(=O)c2cc3ncccc3cc2C(F)(F)F)C[C@H]1c1cc(C(F)F)nc2ncnn12] | I-9b | 68 |
| 36 | 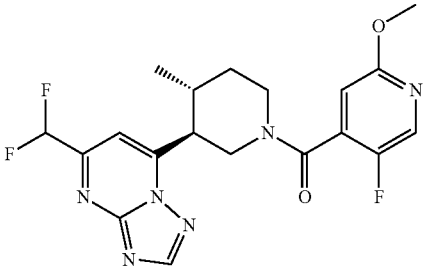 [SMILES: COc1cc(C(=O)N2CC[C@@H](C)[C@H](c3cc(C(F)F)nc4ncnn34)C2)c(F)cn1] | I-9b | 73 |
| 37 | 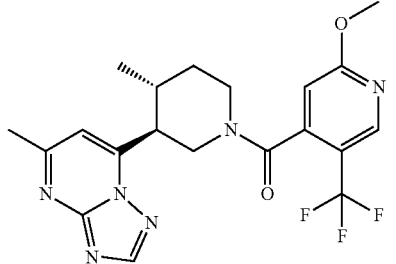 [SMILES: COc1cc(C(=O)N2CC[C@@H](C)[C@H](c3cc(C)nc4ncnn34)C2)c(C(F)(F)F)cn1] | I-12a | 52 |

TABLE 1-continued

| Co. No. | Structure | Prepared from | Yield (%) |
|---|---|---|---|
| 38 | 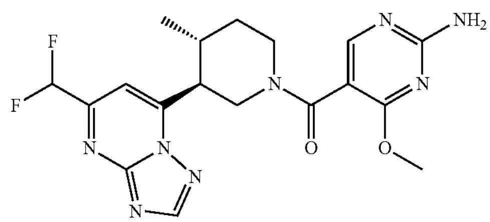 [SMILES: COc1nc(N)ncc1C(=O)N1CC[C@@H](C)[C@H](c2cc(C(F)F)nc3ncnn23)C1] | I-9b | 41 |
| 39 | 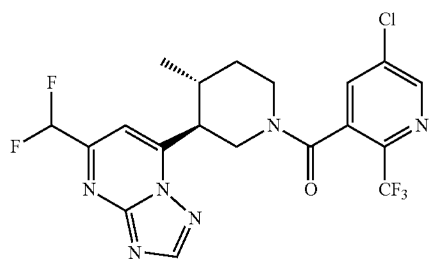 [SMILES: C[C@@H]1CCN(C(=O)c2cc(Cl)cnc2C(F)(F)F)C[C@H]1c1cc(C(F)F)nc2ncnn12] | I-9b | 21 |
| 40 | 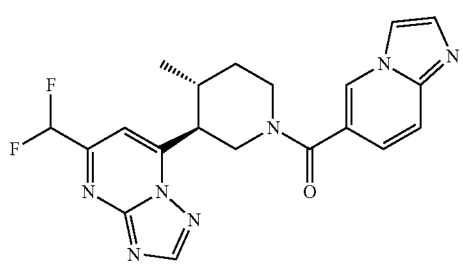 [SMILES: C[C@@H]1CCN(C(=O)c2ccc3nccn3c2)C[C@H]1c1cc(C(F)F)nc2ncnn12] | I-9b | 78 |
| 41 | 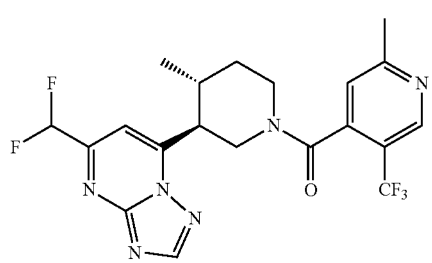 [SMILES: Cc1cc(C(=O)N2CC[C@@H](C)[C@H](c3cc(C(F)F)nc4ncnn34)C2)c(C(F)(F)F)cn1] | I-9b | 38 |
| 42 | 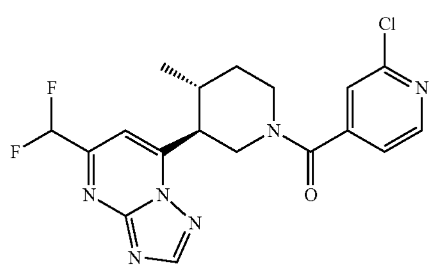 [SMILES: C[C@@H]1CCN(C(=O)c2ccnc(Cl)c2)C[C@H]1c1cc(C(F)F)nc2ncnn12] | I-9b | 60 |

TABLE 1-continued

| Co. No. | Structure | Prepared from | Yield (%) |
|---|---|---|---|
| 43 | 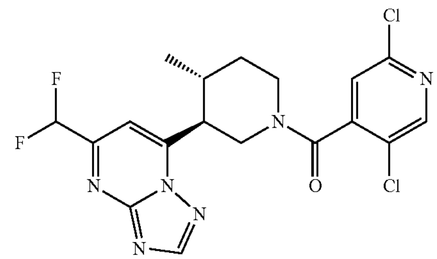 | I-9b | 55 |
| 44 | trans mixture | I-28 | 29 |
| 45 | pure enantiomer, trans | I-28 | 12 |
| 46 | pure enantiomer, trans | I-28 | 12 |
| 47 | 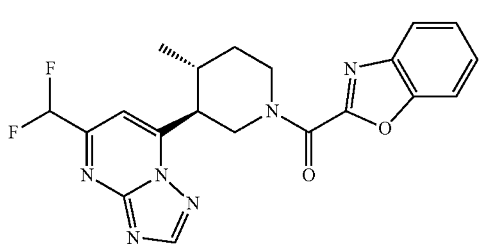 [SMILES: C[C@@H]1CCN(C(=O)c2nc3ccccc3o2)C[C@H]1c1cc(C(F)F)nc2ncnn12] | I-9b | 44 |

TABLE 1-continued

| Co. No. | Structure | Prepared from | Yield (%) |
|---|---|---|---|
| 48 | 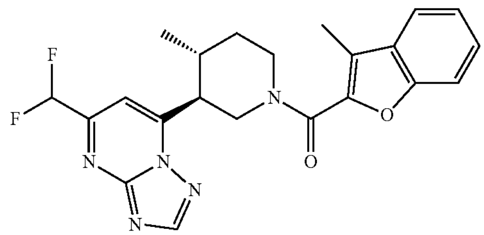 [SMILES: Cc1c(C(=O)N2CC[C@@H](C)[C@H](c3cc(C(F)F)nc4ncnn34)C2)oc2ccccc12] | I-9b | 77 |
| 49 | 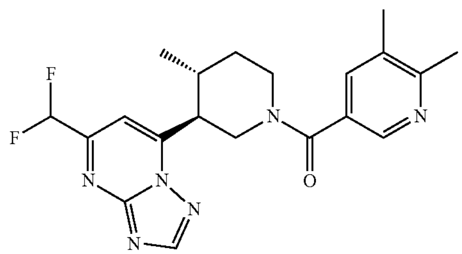 [SMILES: Cc1cc(C(=O)N2CC[C@@H](C)[C@H](c3cc(C(F)F)nc4ncnn34)C2)cnc1C] | I-9b | 62 |
| 50 | 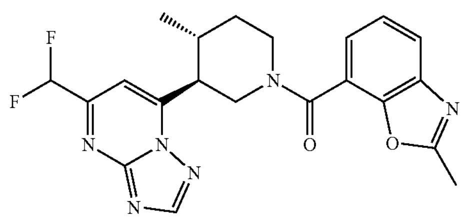 [SMILES: Cc1nc2cccc(C(=O)N3CC[C@@H](C)[C@H](c4cc(C(F)F)nc5ncnn45)C3)c2o1] | I-9b | 68 |
| 51 | 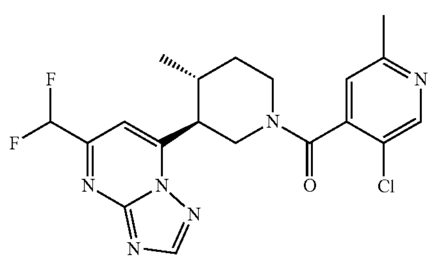 | I-9b | 31 |
| 52 | 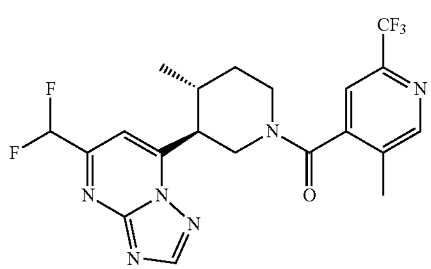 [SMILES: Cc1cnc(C(F)(F)F)cc1C(=O)N1CC[C@@H](C)[C@H](c2cc(C(F)F)nc3ncnn23)C1] | I-9b | 6 |
| 53 | 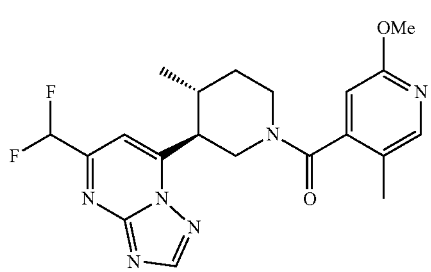 [SMILES: COc1cc(C(=O)N2CC[C@@H](C)[C@H](c3cc(C(F)F)nc4ncnn34)C2)c(C)cn1] | I-9b | 17 |

TABLE 1-continued

| Co. No. | Structure | Prepared from | Yield (%) |
|---|---|---|---|
| 54 | 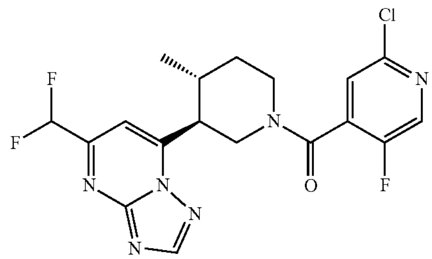 [SMILES: C[C@@H]1CCN(C(=O)c2cc(Cl)ncc2F)C[C@H]1c1cc(C(F)F)nc2ncnn12] | I-9b | 53 |
| 55 | 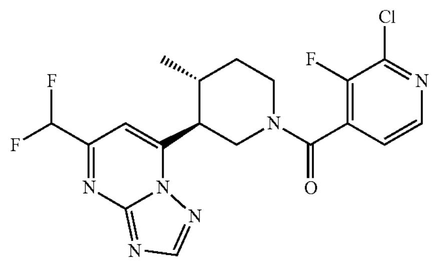 [SMILES: C[C@@H]1CCN(C(=O)c2ccnc(Cl)c2F)C[C@H]1c1cc(C(F)F)nc2ncnn12] | I-9b | 63 |
| 56 | 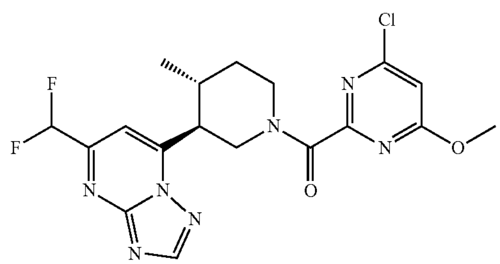 [SMILES: COc1cc(Cl)nc(C(=O)N2CC[C@@H](C)[C@H](c3cc(C(F)F)nc4ncnn34)C2)n1] | I-9b | 51 |
| 57 | 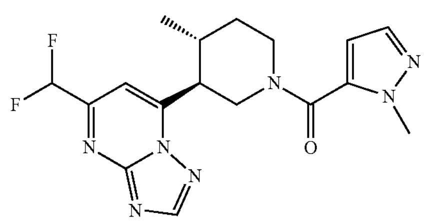 [SMILES: C[C@@H]1CCN(C(=O)c2ccnn2C)C[C@H]1c1cc(C(F)F)nc2ncnn12] | I-9b | 61 |
| 58 | 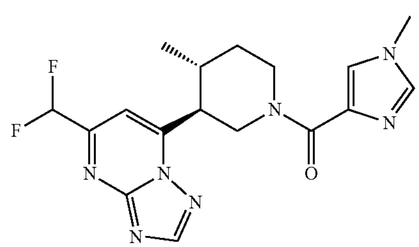 [SMILES: C[C@@H]1CCN(C(=O)c2cn(C)cn2)C[C@H]1c1cc(C(F)F)nc2ncnn12] | I-9b | 75 |
| 59 | 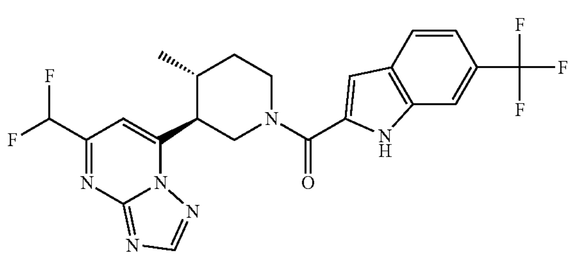 [SMILES: C[C@@H]1CCN(C(=O)c2cc3ccc(C(F)(F)F)cc3[nH]2)C[C@H]1c1cc(C(F)F)nc2ncnn12] | I-9b | 72 |

TABLE 1-continued

| Co. No. | Structure | Prepared from | Yield (%) |
|---|---|---|---|
| 60 | 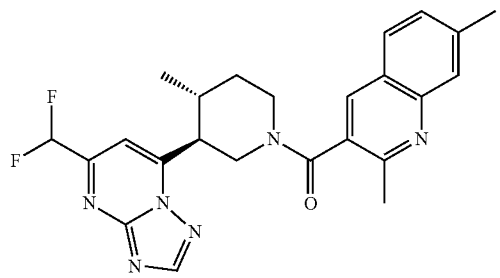 [SMILES: Cc1ccc2cc(C(=O)N3CC[C@@H](C)[C@H](c4cc(C(F)F)nc5ncnn45)C3)c(C)nc2c1] | I-9b | 64 |
| 61 | 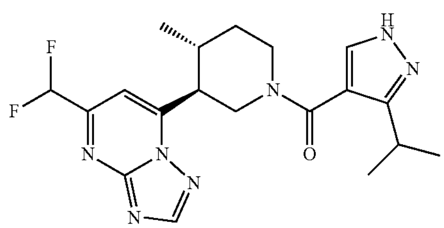 [SMILES: CC(C)c1n[nH]cc1C(=O)N1CC[C@@H](C)[C@H](c2cc(C(F)F)nc3ncnn23)C1] | I-9b | 73 |
| 62 | 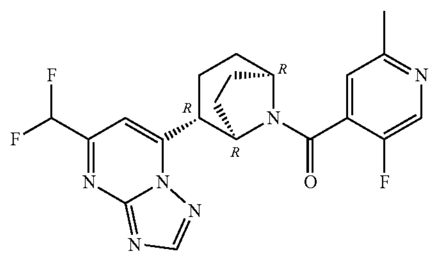 | I-25 | 42 |
| 63 | 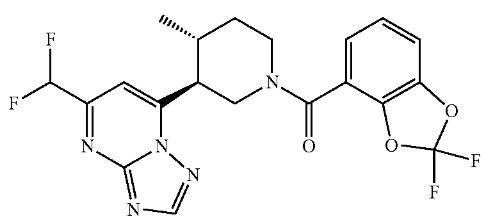 [SMILES: C[C@@H]1CCN(C(=O)c2cccc3c2OC(F)(F)O3)C[C@H]1c1cc(C(F)F)nc2ncnn12] | I-9b | 40 |
| 64 | 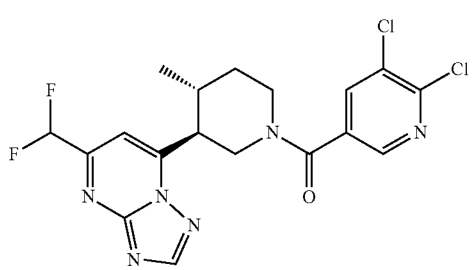 [SMILES: C[C@@H]1CCN(C(=O)c2cnc(Cl)c(Cl)c2)C[C@H]1c1cc(C(F)F)nc2ncnn12] | I-9b | 60 |
| 65 | 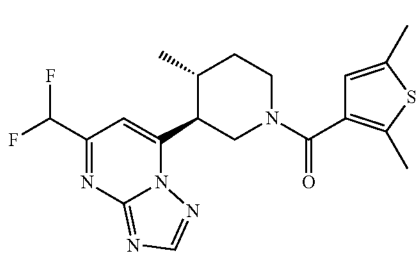 [SMILES: Cc1cc(C(=O)N2CC[C@@H](C)[C@H](c3cc(C(F)F)nc4ncnn34)C2)c(C)s1] | I-9b | 49 |

TABLE 1-continued

| Co. No. | Structure | Prepared from | Yield (%) |
|---|---|---|---|
| 66 | 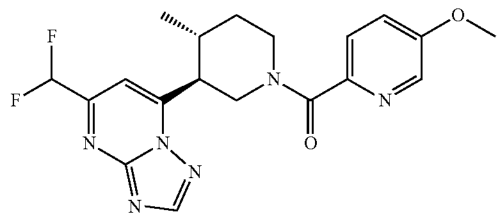 [SMILES: COc1ccc(C(=O)N2CC[C@@H](C)[C@H](c3cc(C(F)F)nc4ncnn34)C2)nc1] | I-9b | 57 |
| 67 | 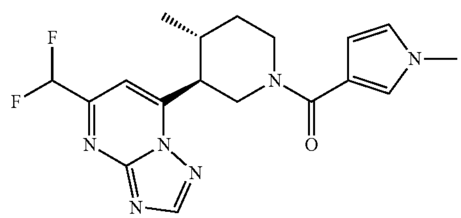 [SMILES: C[C@@H]1CCN(C(=O)c2ccn(C)c2)C[C@H]1c1cc(C(F)F)nc2ncnn12] | I-9b | 63 |
| 68 | 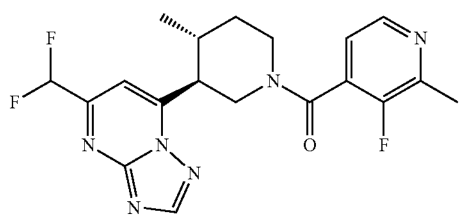 [SMILES: Cc1nccc(C(=O)N2CC[C@@H](C)[C@H](c3cc(C(F)F)nc4ncnn34)C2)c1F] | I-9b | 48 |
| 69 | 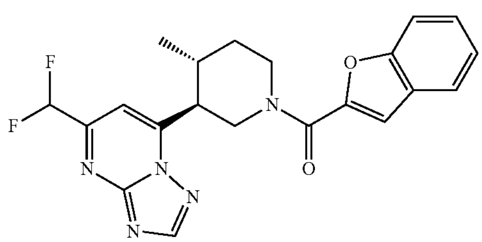 [SMILES: C[C@@H]1CCN(C(=O)c2cc3ccccc3o2)C[C@H]1c1cc(C(F)F)nc2ncnn12] | I-9b | 78 |
| 70 | 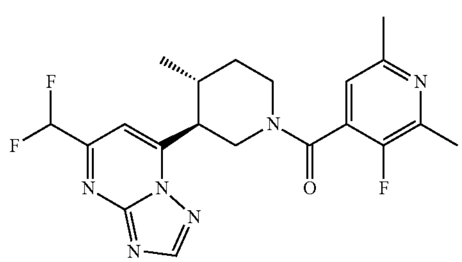 [SMILES: Cc1cc(C(=O)N2CC[C@@H](C)[C@H](c3cc(C(F)F)nc4ncnn34)C2)c(F)c(C)n1] | I-9b | 58 |
| 71 | 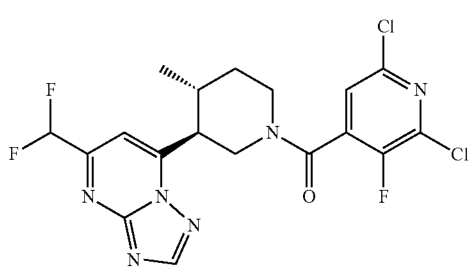 [SMILES: C[C@@H]1CCN(C(=O)c2cc(Cl)nc(Cl)c2F)C[C@H]1c1cc(C(F)F)nc2ncnn12] | I-9b | 73 |

TABLE 1-continued
| Co. No. | Structure | Prepared from | Yield (%) |
|---|---|---|---|
| 72 | 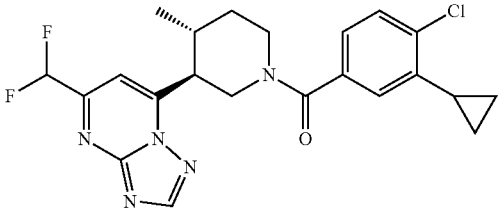 [SMILES: C[C@@H]1CCN(C(=O)c2ccc(Cl)c(C3CC3)c2)C[C@H]1c1cc(C(F)F)nc2ncnn12] | I-9b | 38 |
| 73 | 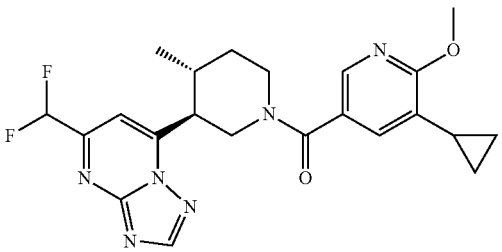 [SMILES: COc1ncc(C(=O)N2CC[C@@H](C)[C@H](c3cc(C(F)F)nc4ncnn34)C2)cc1C1CC1] | I-9b | 39 |
| 74 | 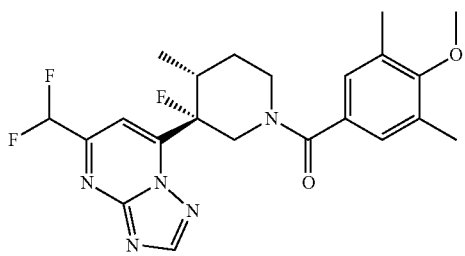 [SMILES: COc1c(C)cc(C(=O)N2CC[C@@H](C)[C@](F)(c3cc(C(F)F)nc4ncnn34)C2)cc1C] | I-19 | 30 |
| 75 | 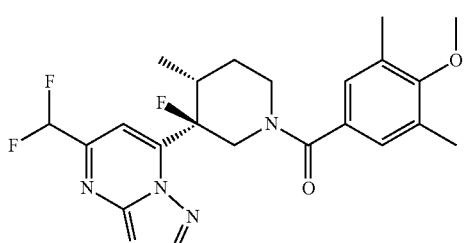 | I-19 | 32 |
| 76 | 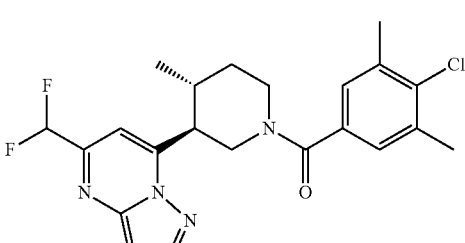 | I-9b | 36 |
| 77 | 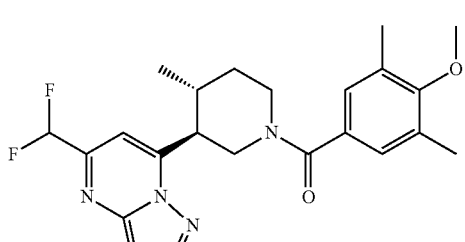 | I-9b | 42 |

TABLE 1-continued

| Co. No. | Structure | Prepared from | Yield (%) |
|---|---|---|---|
| 78 | 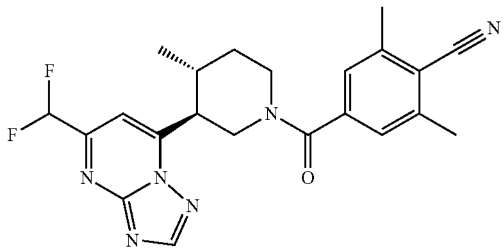 [SMILES: Cc1cc(C(=O)N2CC[C@@H](C)[C@H](c3cc(C(F)F)nc4ncnn34)C2)cc(C)c1C#N] | I-9b | 58 |
| 79 | 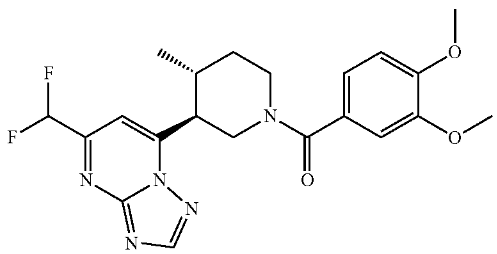 [SMILES: COc1ccc(C(=O)N2CC[C@@H](C)[C@H](c3cc(C(F)F)nc4ncnn34)C2)cc1OC] | I-9b | 74 |
| 80 | 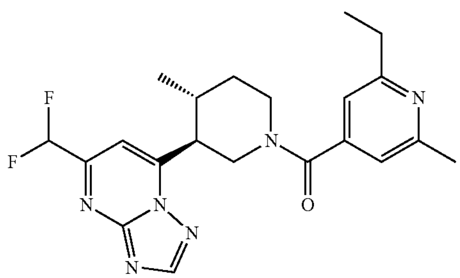 [SMILES: CCc1cc(C(=O)N2CC[C@@H](C)[C@H](c3cc(C(F)F)nc4ncnn34)C2)cc(C)n1] | I-9b | 54 |
| 81 | 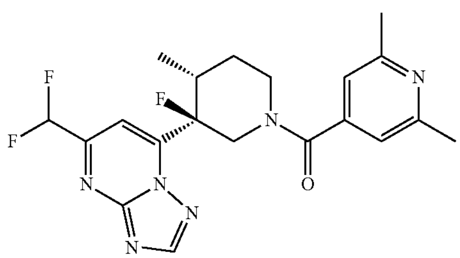 [SMILES: Cc1cc(C(=O)N2CC[C@@H](C)[C@@](F)(c3cc(C(F)F)nc4ncnn34)C2)cc(C)n1] | I-19 | 30 |
| 82 | 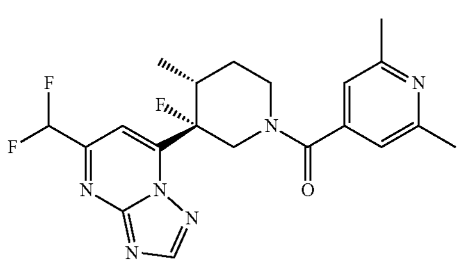 [SMILES: Cc1cc(C(=O)N2CC[C@@H](C)[C@](F)(c3cc(C(F)F)nc4ncnn34)C2)cc(C)n1] | I-19 | 31 |

TABLE 1-continued

| Co. No. | Structure | Prepared from | Yield (%) |
|---|---|---|---|
| 83 | 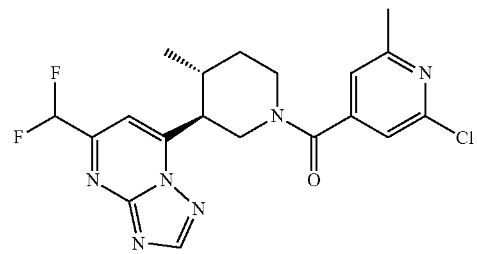 [SMILES: Cc1cc(C(=O)N2CC[C@@H](C)[C@H](c3cc(C(F)F)nc4ncnn34)C2)cc(Cl)n1] | I-9b | 81 |
| 84 | 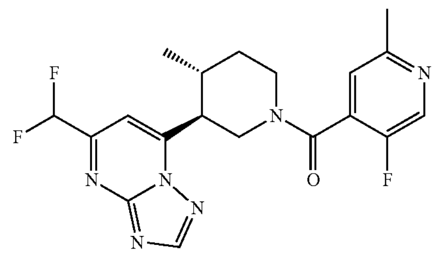 [SMILES: Cc1cc(C(=O)N2CC[C@@H](C)[C@H](c3cc(C(F)F)nc4ncnn34)C2)c(F)cn1] | I-9b | 30 |
| 85 | 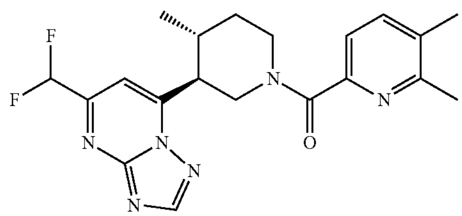 [SMILES: Cc1ccc(C(=O)N2CC[C@@H](C)[C@H](c3cc(C(F)F)nc4ncnn34)C2)nc1C] | I-9b | 22 |
| 86 | 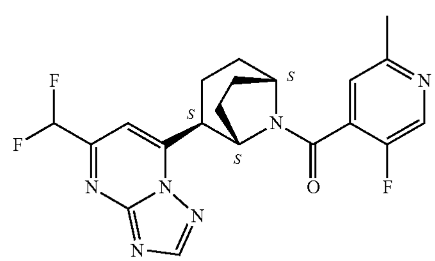 | I-25 | 41 |
| 87 | 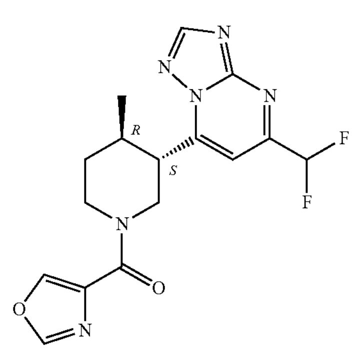 | I-9b | 65 |

TABLE 1-continued

| Co. No. | Structure | Prepared from | Yield (%) |
| --- | --- | --- | --- |
| 88 | 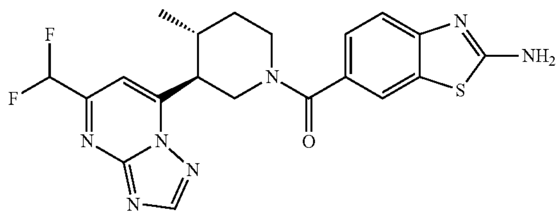 [SMILES: C[C@@H]1CCN(C(=O)c2ccc3nc(N)sc3c2)C[C@H]1c1cc(C(F)F)nc2ncnn12] | I-9b [332898-48-3] | 27 |
| 89 | 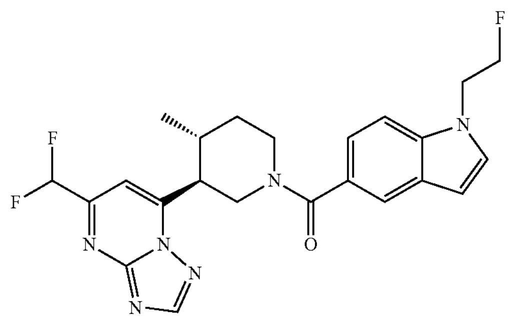 [SMILES: C[C@@H]1CCN(C(=O)c2ccc3c(ccn3CCF)c2)C[C@H]1c1cc(C(F)F)nc2ncnn12] | I-9b | 46 |
| 90 | 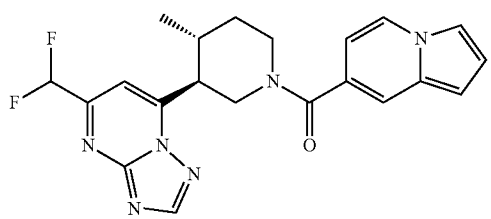 [SMILES: C[C@@H]1CCN(C(=O)c2ccn3cccc3c2)C[C@H]1c1cc(C(F)F)nc2ncnn12] | I-9b [1533853-53-0] | 73 |
| 91 | 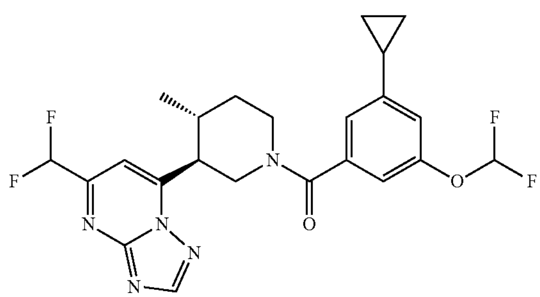 [SMILES: C[C@@H]1CCN(C(=O)c2cc(OC(F)F)cc(C3CC3)c2)C[C@H]1c1cc(C(F)F)nc2ncnn12] | I-9b | 33 |
| 92 | 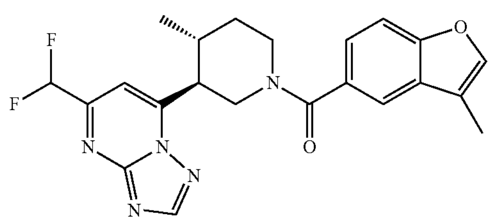 [SMILES: Cc1coc2ccc(C(=O)N3CC[C@@H](C)[C@H](c4cc(C(F)F)nc5ncnn45)C3)cc12] | I-9b [501892-99-5] | 61 |

TABLE 1-continued

| Co. No. | Structure | Prepared from | Yield (%) |
|---|---|---|---|
| 93 | 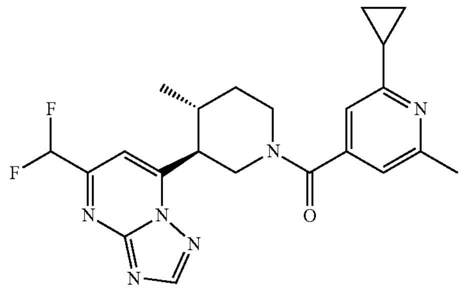 [SMILES: Cc1cc(C(=O)N2CC[C@@H](C)[C@H](c3cc(C(F)F)nc4ncnn34)C2)cc(C2CC2)n1] | I-9b | 15 |
| 94 | 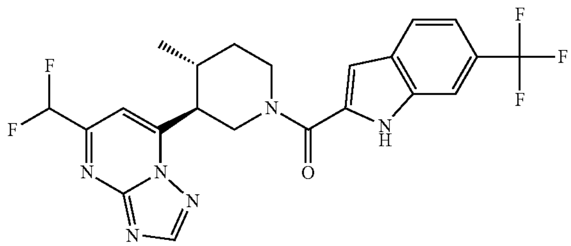 [SMILES: C[C@@H]1CCN(C(=O)c2cc3ccc(C(F)(F)F)cc3[nH]2)C[C@H]1c1cc(C(F)F)nc2ncnn12] | I-9b [327-20-8] | 25 |
| 95 | 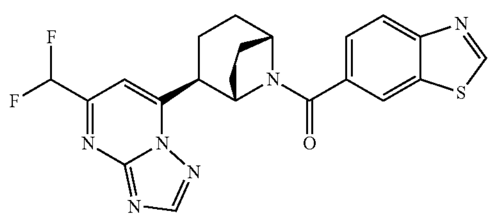 [SMILES: O=C(c1ccc2ncsc2c1)N1[C@H]2CC[C@H](c3cc(C(F)F)nc4ncnn34)[C@@H]1CC2] | I-25 | 36 |
| 96 | 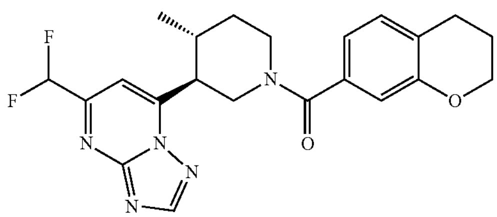 [SMILES: C[C@@H]1CCN(C(=O)c2ccc3c(c2)OCCC3)C[C@H]1c1cc(C(F)F)nc2ncnn12] | I-9b [103203-84-5] | 83 |
| 97 | 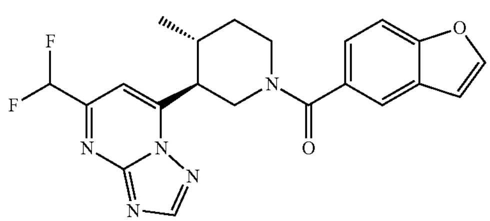 [SMILES: C[C@@H]1CCN(C(=O)c2ccc3occc3c2)C[C@H]1c1cc(C(F)F)nc2ncnn12] | I-9b [90721-27-0] | |
| 98 | 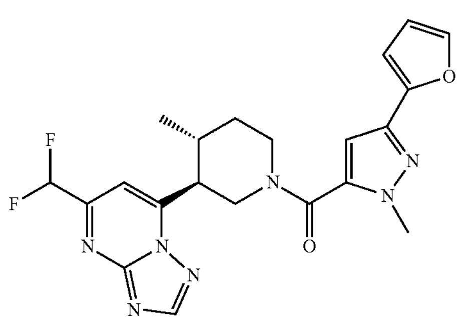 [SMILES: C[C@@H]1CCN(C(=O)c2cc(-c3ccco3)nn2C)C[C@H]1c1cc(C(F)F)nc2ncnn12] | I-9b [859851-00-6] | 60 |

TABLE 1-continued

| Co. No. | Structure | Prepared from | Yield (%) |
|---|---|---|---|
| 99 | 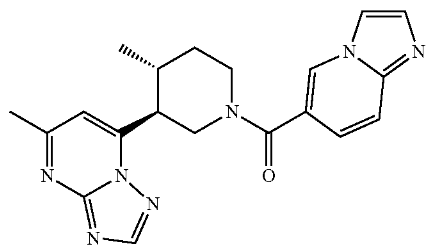 [SMILES: Cc1cc([C@@H]2CN(C(=O)c3ccc4nccn4c3)CC[C@H]2C)n2ncnc2n1] | I-9b [139022-25-6] | 24 |
| 100 | 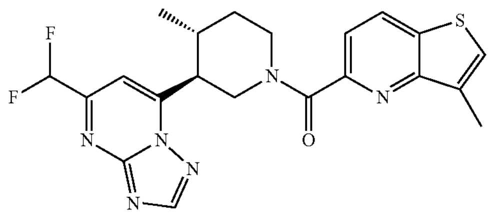 [SMILES: Cc1csc2ccc(C(=O)N3CC[C@@H](C)[C@H](c4cc(C(F)F)nc5ncnn45)C3)nc12] | I-9b [1372924-05-4] | 53 |
| 101 | 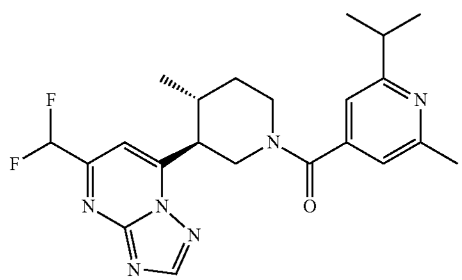 [SMILES: Cc1cc(C(=O)N2CC[C@@H](C)[C@H](c3cc(C(F)F)nc4ncnn34)C2)cc(C(C)C)n1] | I-9b [1011264-07-5] | 28 |
| 102 | 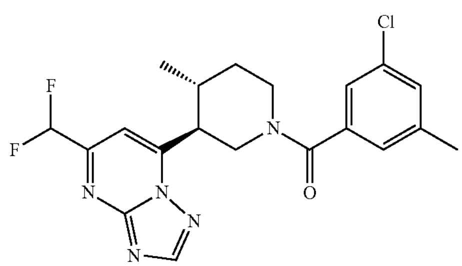 [SMILES: Cc1cc(Cl)cc(C(=O)N2CC[C@@H](C)[C@H](c3cc(C(F)F)nc4ncnn34)C2)c1] | I-9b [1427392-05-9] | 61 |
| 103 | 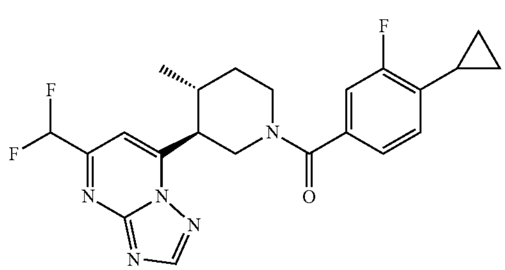 [SMILES: C[C@@H]1CCN(C(=O)c2ccc(C3CC3)c(F)c2)C[C@H]1c1cc(C(F)F)nc2ncnn12] | I-9b [1247451-23-5] | 48 |
| 104 | 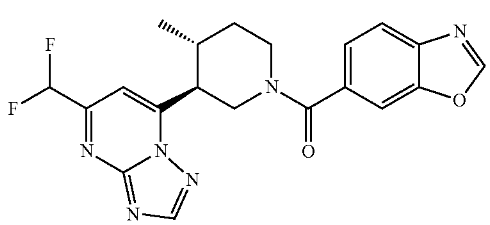 [SMILES: C[C@@H]1CCN(C(=O)c2ccc3ncoc3c2)C[C@H]1c1cc(C(F)F)nc2ncnn12] | I-9b [154235-77-5] | 21 |

TABLE 1-continued

| Co. No. | Structure | Prepared from | Yield (%) |
|---|---|---|---|
| 105 | 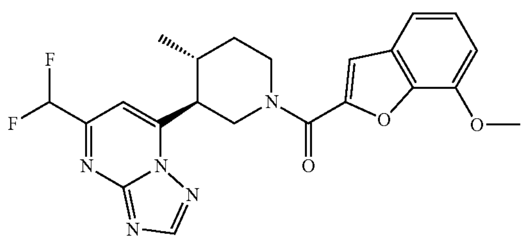 [SMILES: COc1cccc2cc(C(=O)N3CC[C@@H](C)[C@H](c4cc(C(F)F)nc5ncnn45)C3)oc12] | I-9b [4790-79-8] | 60 |
| 106 | 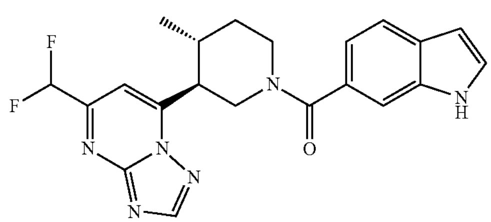 [SMILES: C[C@@H]1CCN(C(=O)c2ccc3cc[nH]c3c2)C[C@H]1c1cc(C(F)F)nc2ncnn12] | I-9b [1670-82-2] | 76 |
| 107 | 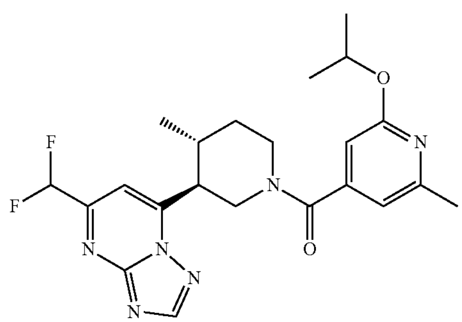 [SMILES: Cc1cc(C(=O)N2CC[C@@H](C)[C@H](c3cc(C(F)F)nc4ncnn34)C2)cc(OC(C)C)n1] | I-9b [1011264-06-4] | 47 |
| 108 | 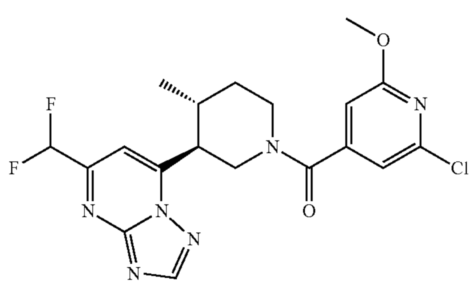 [SMILES: COc1cc(C(=O)N2CC[C@@H](C)[C@H](c3cc(C(F)F)nc4ncnn34)C2)cc(Cl)n1] | I-9b [15855-06-8] | 49 |
| 109 | 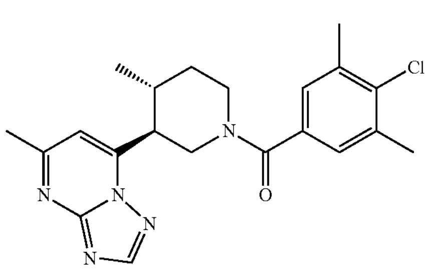 [SMILES: Cc1cc([C@@H]2CN(C(=O)c3cc(C)c(Cl)c(C)c3)CC[C@H]2C)n2ncnc2n1] | I-9b [90649-78-8] | 21 |

TABLE 1-continued

| Co. No. | Structure | Prepared from | Yield (%) |
|---|---|---|---|
| 110 | 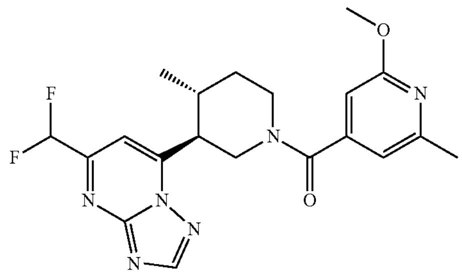 | I-9b [1803602-19-8] | 51 |
| 111 | 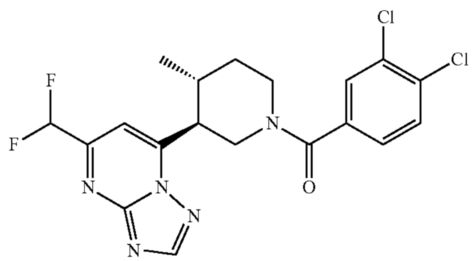 | I-9b [51-44-5] | 9 |
| 112 | 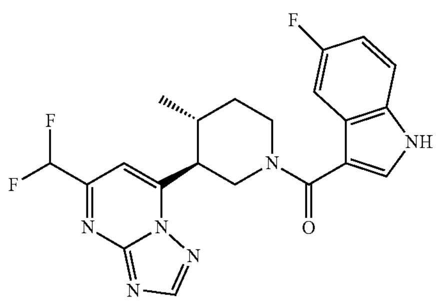 [SMILES: C[C@@H]1CCN(C(=O)c2c[nH]c3ccc(F)cc23)C[C@H]1c1cc(C(F)F)nc2ncnn12] | I-9b [23077-43-2] | 41 |
| 113 | 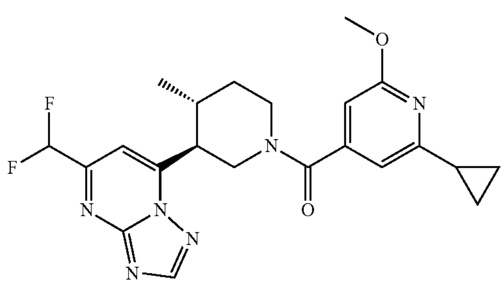 [SMILES: COc1cc(C(=O)N2CC[C@@H](C)[C@H](c3cc(C(F)F)nc4ncnn34)C2)cc(C2CC2)n1] | I-9b [1256820-02-6] | 42 |
| 114 | 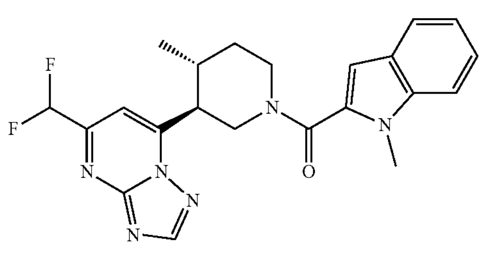 [SMILES: C[C@@H]1CCN(C(=O)c2cc3ccccc3n2C)C[C@H]1c1cc(C(F)F)nc2ncnn12] | I-9b [16136-58-6] | 64 |

TABLE 1-continued

| Co. No. | Structure | Prepared from | Yield (%) |
|---|---|---|---|
| 115 | 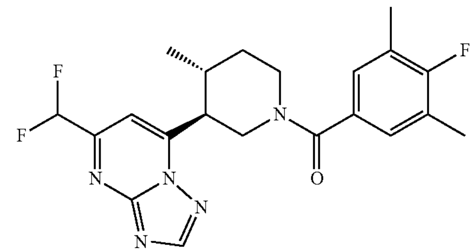 [SMILES: Cc1cc(C(=O)N2CC[C@@H](C)[C@H](c3cc(C(F)F)nc4ncnn34)C2)cc(C)c1F] | I-9b [120512-59-6] | 64 |
| 116 | 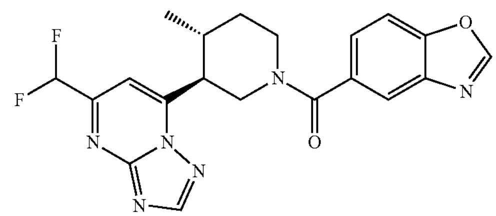 [SMILES: C[C@@H]1CCN(C(=O)c2ccc3ocnc3c2)C[C@H]1c1cc(C(F)F)nc2ncnn12] | I-9b [15112-41-1] | 73 |
| 117 | 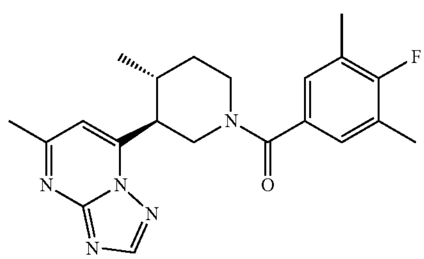 [SMILES: Cc1cc([C@@H]2CN(C(=O)c3cc(C)c(F)c(C)c3)CC[C@H]2C)n2ncnc2n1] | I-12a [120512-59-6] | 27 |
| 118 | 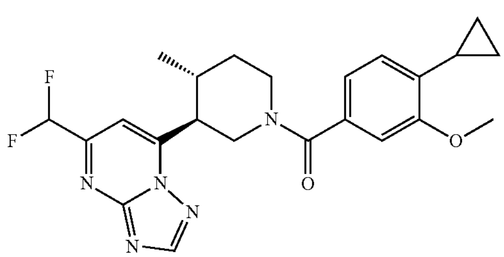 [SMILES: COc1cc(C(=O)N2CC[C@@H](C)[C@H](c3cc(C(F)F)nc4ncnn34)C2)ccc1C1CC1] | I-9b [1248462-73-8] | 46 |
| 119 | 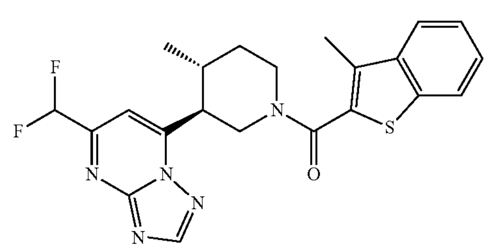 [SMILES: Cc1c(C(=O)N2CC[C@@H](C)[C@H](c3cc(C(F)F)nc4ncnn34)C2)sc2ccccc12] | I-9b [3133-78-6] | 67 |
| 120 | 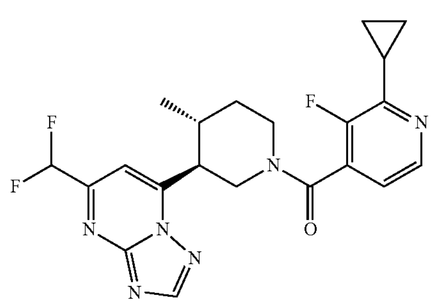 [SMILES: C[C@@H]1CCN(C(=O)c2ccnc(C3CC3)c2F)C[C@H]1c1cc(C(F)F)nc2ncnn12] | I-9b | 45 |

TABLE 1-continued

| Co. No. | Structure | Prepared from | Yield (%) |
|---|---|---|---|
| 121 | 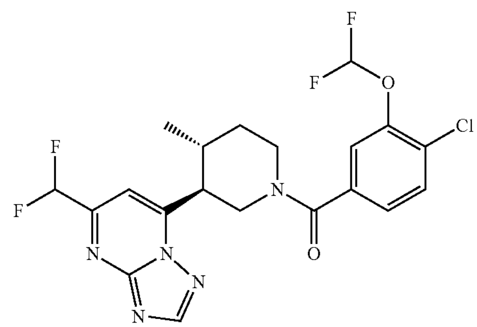 [SMILES: C[C@@H]1CCN(C(=O)c2ccc(Cl)c(OC(F)F)c2)C[C@H]1c1cc(C(F)F)nc2ncnn12] | I-9b [1427355-37-0] | 65 |
| 122 | 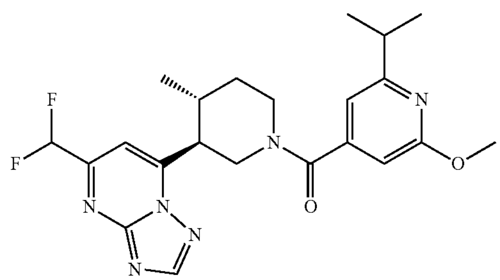 [SMILES: COc1cc(C(=O)N2CC[C@@H](C)[C@H](c3cc(C(F)F)nc4ncnn34)C2)cc(C(C)C)n1] | I-9b [1256790-25-6] | 36 |
| 123 | 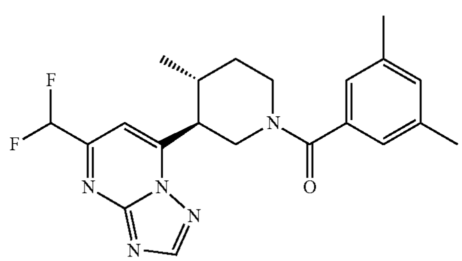 [SMILES: Cc1cc(C)cc(C(=O)N2CC[C@@H](C)[C@H](c3cc(C(F)F)nc4ncnn34)C2)c1] | I-9b [6613-44-1] | 38 |
| 124 | 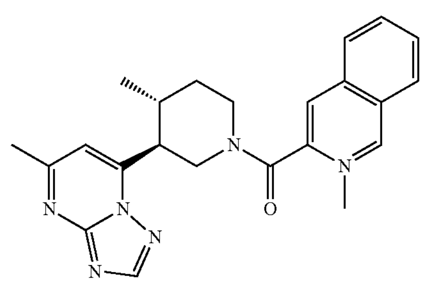 | I-9b [470702-35-3] | 60 |
| 125 | 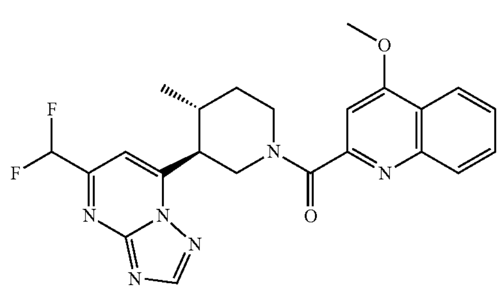 [SMILES: COc1cc(C(=O)N2CC[C@@H](C)[C@H](c3cc(C(F)F)nc4ncnn34)C2)nc2ccccc12] | I-9b [15733-83-2] | 74 |

TABLE 1-continued

| Co. No. | Structure | Prepared from | Yield (%) |
|---|---|---|---|
| 126 | 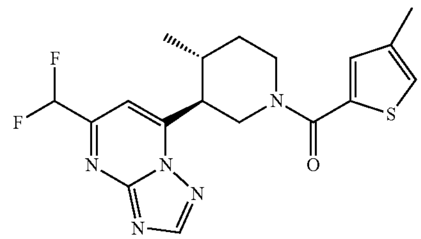 [SMILES: Cc1csc(C(=O)N2CC[C@@H](C)[C@H](c3cc(C(F)F)nc4ncnn34)C2)c1] | I-9b [14282-78-1] | 35 |
| 127 | 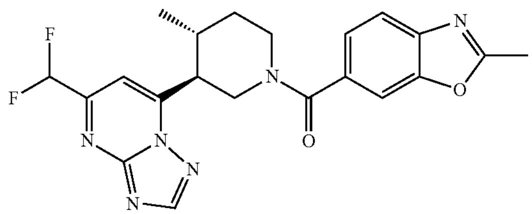 [SMILES: Cc1nc2ccc(C(=O)N3CC[C@@H](C)[C@H](c4cc(C(F)F)nc5ncnn45)C3)cc2o1] | I-9b [13452-14-7] | 29 |
| 128 | 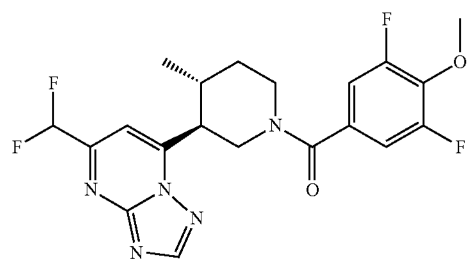 [SMILES: COc1c(F)cc(C(=O)N2CC[C@@H](C)[C@H](c3cc(C(F)F)nc4ncnn34)C2)cc1F] | I-9b [319-60-8] | 63 |
| 129 | 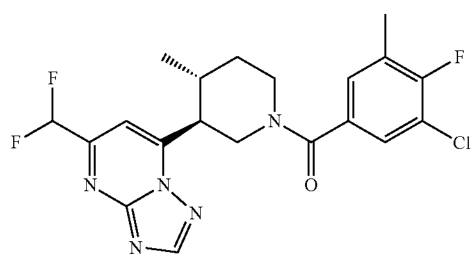 [SMILES: Cc1cc(C(=O)N2CC[C@@H](C)[C@H](c3cc(C(F)F)nc4ncnn34)C2)cc(Cl)c1F] | I-9b [1427392-05-9] | 44 |
| 130 | 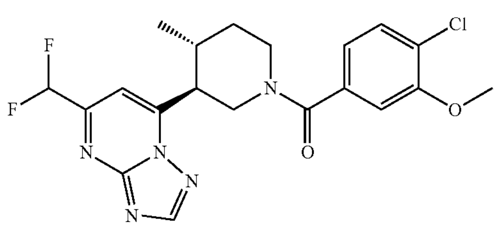 [SMILES: COc1cc(C(=O)N2CC[C@@H](C)[C@H](c3cc(C(F)F)nc4ncnn34)C2)ccc1Cl] | I-9b [85740-98-3] | 63 |
| 131 | 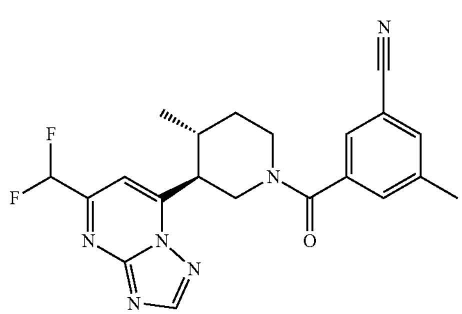 [SMILES: Cc1cc(C#N)cc(C(=O)N2CC[C@@H](C)[C@H](c3cc(C(F)F)nc4ncnn34)C2)c1] | I-9b [78621-81-5] | 46 |

TABLE 1-continued

| Co. No. | Structure | Prepared from | Yield (%) |
|---|---|---|---|
| 132 | 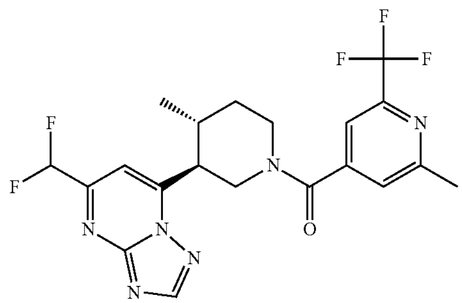 [SMILES: Cc1cc(C(=O)N2CC[C@@H](C)[C@H](c3cc(C(F)F)nc4ncnn34)C2)cc(C(F)(F)F)n1] | I-9b [1211590-99-6] | 45 |
| 133 | 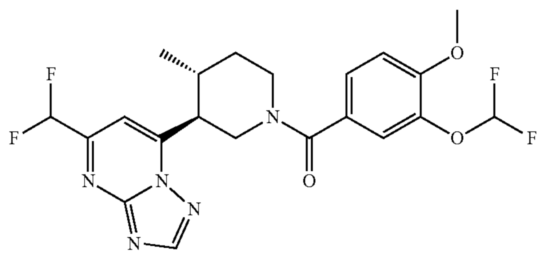 [SMILES: COc1ccc(C(=O)N2CC[C@@H](C)[C@H](c3cc(C(F)F)nc4ncnn34)C2)cc1OC(F)F] | I-9b [162401-65-2] | 61 |
| 134 | 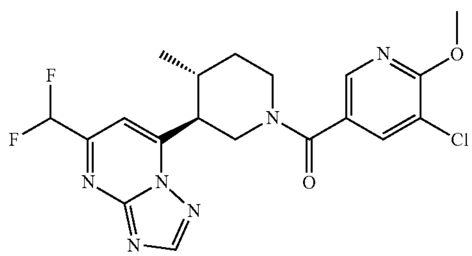 [SMILES: COc1ncc(C(=O)N2CC[C@@H](C)[C@H](c3cc(C(F)F)nc4ncnn34)C2)cc1Cl] | I-9b [884494-85-3] | 59 |
| 135 | 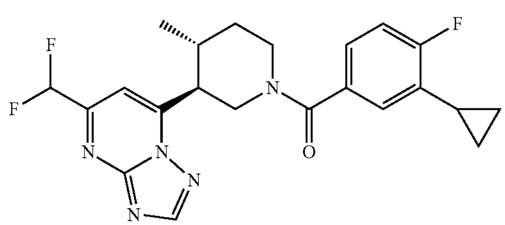 [SMILES: C[C@@H]1CCN(C(=O)c2ccc(F)c(C3CC3)c2)C[C@H]1c1cc(C(F)F)nc2ncnn12] | I-9b | 53 |
| 136 | 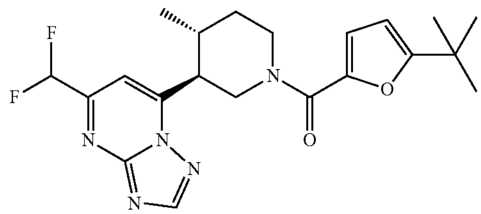 [SMILES: C[C@@H]1CCN(C(=O)c2ccc(C(C)(C)C)o2)C[C@H]1c1cc(C(F)F)nc2ncnn12] | I-9b [56311-39-8] | 53 |
| 137 | 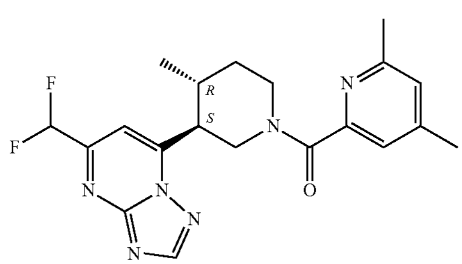 | I-9b 4,6-dimethylpyridine-2-carboxylic acid [18088-10-3] | 34 |

TABLE 1-continued

| Co. No. | Structure | Prepared from | Yield (%) |
|---|---|---|---|
| 138 | 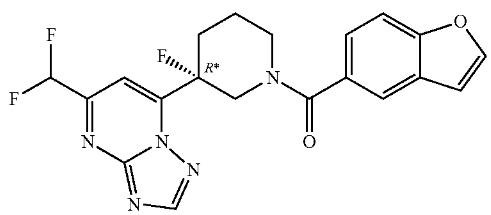 [SMILES: O=C(c1ccc2occc2c1)N1CCC[C@](F)(c2cc(C(F)F)nc3ncnn23)C1] | I-19 Benzofuran-5-carboxylic acid [90721-27-0] | 25 (63% coupling, 40% SFC) |
| 139 | 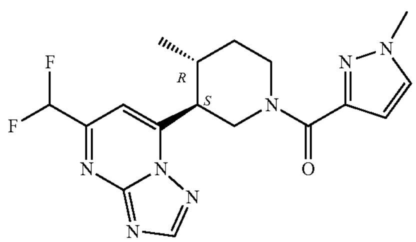 | I-9b 1-methyl-1H-pyrazole-3-carboxylic acid [25016-20-0] | 67 |
| 140 | 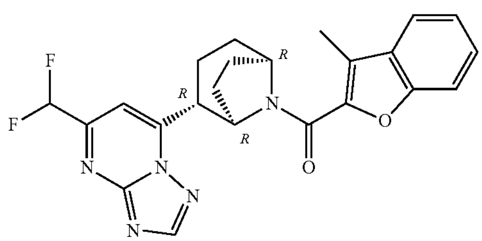 | I-25 3-methylbenzofuran-2-carbonyl chloride [2256-86-2] | 36 |
| 141 | 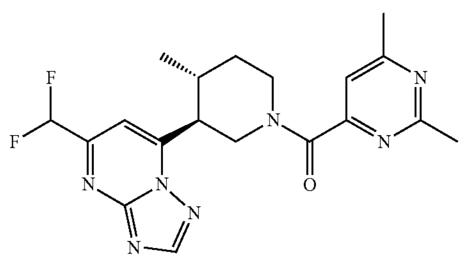 [SMILES: Cc1cc(C(=O)N2CC[C@@H](C)[C@H](c3cc(C(F)F)nc4ncnn34)C2)nc(C)n1] | I-9b 2,6-dimethylpyrimidine-4-carboxylic acid [54198-74-2] | 14 |
| 142 | 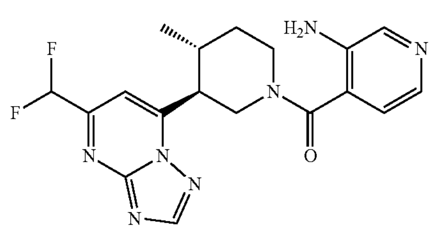 [SMILES: C[C@@H]1CCN(C(=O)c2ccncc2N)C[C@H]1c1cc(C(F)F)nc2ncnn12] | I-9b 3-aminopyridine-4-carboxylic acid [7529-20-6] | 59 |
| 143 | 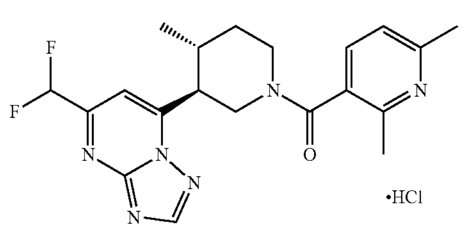 [SMILES: Cc1ccc(C(=O)N2CC[C@@H](C)[C@H](c3cc(C(F)F)nc4ncnn34)C2)c(C)n1 ; Cl] | I-9b 2,6-dimethyl-nicotinic acid [5860-71-9] | 44 |

TABLE 1-continued

| Co. No. | Structure | Prepared from | Yield (%) |
|---|---|---|---|
| 144 | 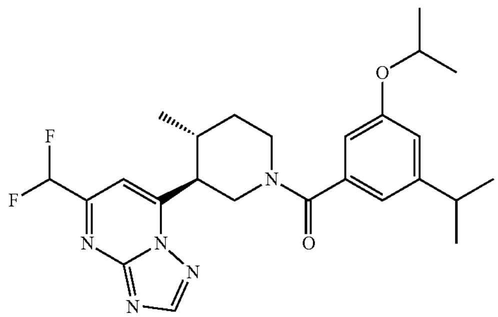 [SMILES: CC(C)Oc1cc(C(=O)N2CC[C@@H](C)[C@H](c3cc(C(F)F)nc4ncnn34)C2)cc(C(C)C)c1] | I-9b 5-(tert-butyl)isoxazole-3-carboxylic acid [90607-21-9] | 52 |
| 145 | 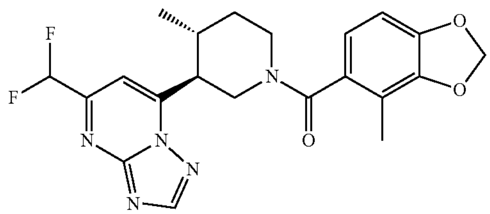 [SMILES: Cc1c(C(=O)N2CC[C@@H](C)[C@H](c3cc(C(F)F)nc4ncnn34)C2)ccc2c1OCO2] | I-9b 4-methyl-2H-1,3-benzodioxole-5-carboxylic acid [162506-58-3] | 60 |
| 146 | 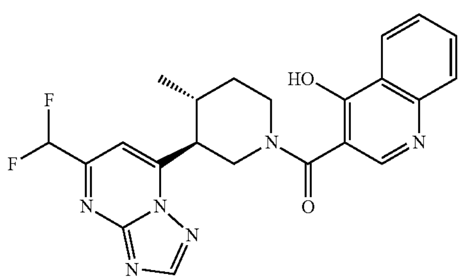 [SMILES: C[C@@H]1CCN(C(=O)c2cnc3ccccc3c2O)C[C@H]1c1cc(C(F)F)nc2ncnn12] | I-9b 4-hydroxyquinoline-3-carboxylic acid [34785-11-0] | 19 |
| 147 | 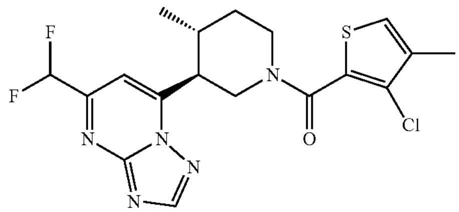 [SMILES: Cc1csc(C(=O)N2CC[C@@H](C)[C@H](c3cc(C(F)F)nc4ncnn34)C2)c1Cl] | I-9b 3-chloro-4-methylthiophene-2-carboxylic acid [229342-86-3] | 52 |
| 148 | 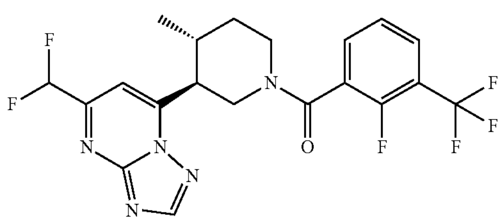 [SMILES: C[C@@H]1CCN(C(=O)c2cccc(C(F)(F)F)c2F)C[C@H]1c1cc(C(F)F)nc2ncnn12] | I-9b 2-fluoro-3-(trifluoromethyl)benzoic acid [115029-22-6] | 63 |
| 149 | 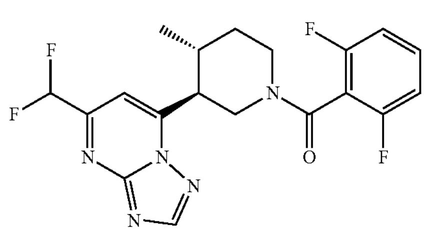 [SMILES: C[C@@H]1CCN(C(=O)c2c(F)cccc2F)C[C@H]1c1cc(C(F)F)nc2ncnn12] | I-9b 2,6-difluorobenzoic acid [385-00-2] | 54 |

TABLE 1-continued

| Co. No. | Structure | Prepared from | Yield (%) |
|---|---|---|---|
| 150 | 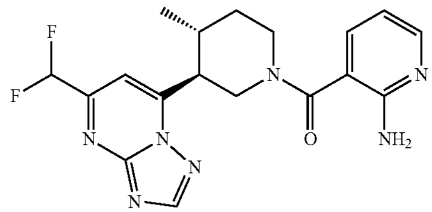 [SMILES: C[C@@H]1CCN(C(=O)c2cccnc2N)C[C@H]1c1cc(C(F)F)nc2ncnn12] | I-9b<br>2-aminonicotinic acid<br>[5345-47-1] | 67 |
| 151 | 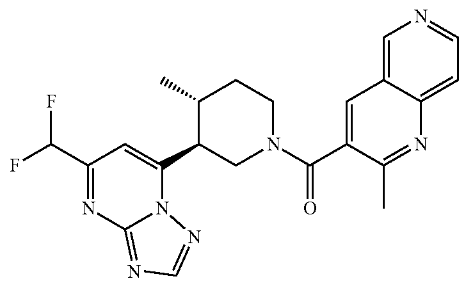 [SMILES: Cc1nc2ccncc2cc1C(=O)N1CC[C@@H](C)[C@H](c2cc(C(F)F)nc3ncnn23)C1] | I-9b<br>2-methyl-1,6-naphthydrine-3-carboxylic acid<br>[387350-63-2] | 75 |
| 152 | 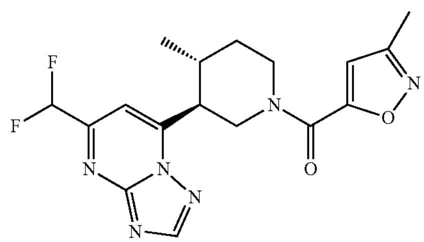 [SMILES: Cc1cc(C(=O)N2CC[C@@H](C)[C@H](c3cc(C(F)F)nc4ncnn34)C2)on1] | I-9b<br>3-methylisoxazole-5-carboxylic acid<br>[4857-42-5] | 63 |
| 153 | 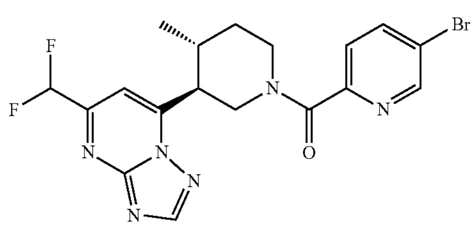 [SMILES: C[C@@H]1CCN(C(=O)c2ccc(Br)cn2)C[C@H]1c1cc(C(F)F)nc2ncnn12] | I-9b<br>5-bromopyridine-2-carboxylic acid<br>[30766-11-1] | 45 |
| 154 | 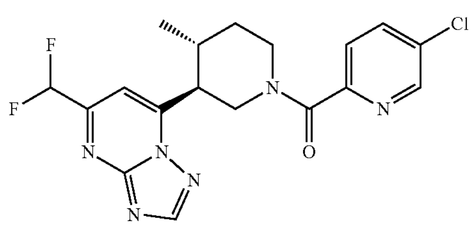 [SMILES: C[C@@H]1CCN(C(=O)c2ccc(Cl)cn2)C[C@H]1c1cc(C(F)F)nc2ncnn12] | I-9b<br>5-chloropyridine-2-carboxylic acid<br>[36070-80-1] | 65 |
| 155 | 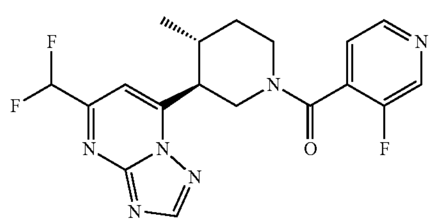 [SMILES: C[C@@H]1CCN(C(=O)c2ccncc2F)C[C@H]1c1cc(C(F)F)nc2ncnn12] | I-9b<br>3-fluoro-4-pyridinecarboxylic acid<br>[131307-35-2] | 60 |

TABLE 1-continued

| Co. No. | Structure | Prepared from | Yield (%) |
|---|---|---|---|
| 156 | 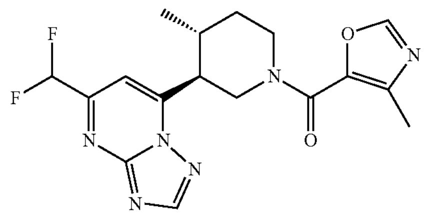 [SMILES: Cc1ncoc1C(=O)N1CC[C@@H](C)[C@H](c2cc(C(F)F)nc3ncnn23)C1] | I-9b<br>4-methyloxazole-5-carboxylic acid<br>[2510-32-9] | 65 |
| 157 | 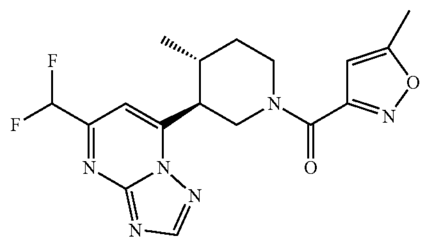 [SMILES: Cc1cc(C(=O)N2CC[C@@H](C)[C@H](c3cc(C(F)F)nc4ncnn34)C2)no1] | I-9b<br>5-methylisoxazole-3-carboxylic acid<br>[3405-77-4] | 65 |
| 158 | 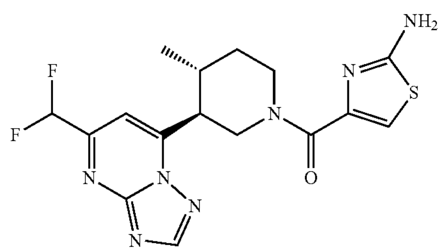 [SMILES: C[C@@H]1CCN(C(=O)c2csc(N)n2)C[C@H]1c1cc(C(F)F)nc2ncnn12] | I-9b<br>2-aminothiazole-4-carboxylic acid<br>[112539-08-9] | 68 |
| 159 | 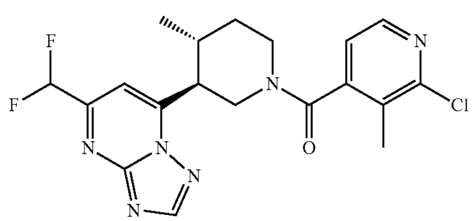 [SMILES: Cc1c(C(=O)N2CC[C@@H](C)[C@H](c3cc(C(F)F)nc4ncnn34)C2)ccnc1Cl] | I-9b<br>2-chloro-3-methylisonicotinic acid<br>[133928-73-1] | 54 |
| 160 | 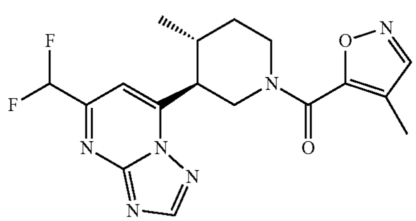 [SMILES: Cc1cnoc1C(=O)N1CC[C@@H](C)[C@H](c2cc(C(F)F)nc3ncnn23)C1] | I-9b<br>4-methylisoxazole-5-carboxylic acid<br>[261350-46-3] | 52 |
| 161 | 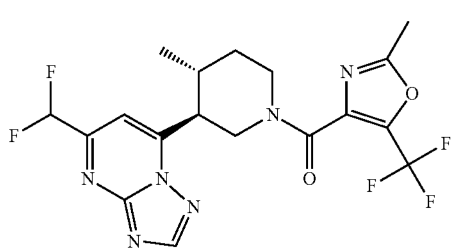 [SMILES: Cc1nc(C(=O)N2CC[C@@H](C)[C@H](c3cc(C(F)F)nc4ncnn34)C2)c(C(F)(F)F)o1] | I-9b<br>2-methyl-5-(trifluoromethyl)-oxazole-4-carboxylic acid<br>[18955-88-9] | 68 |

TABLE 1-continued

| Co. No. | Structure | Prepared from | Yield (%) |
|---|---|---|---|
| 162 | 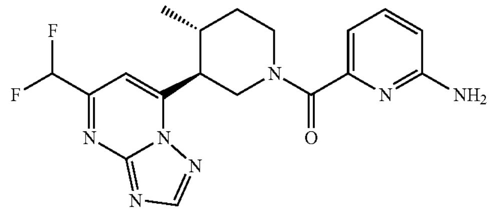 [SMILES: C[C@@H]1CCN(C(=O)c2cccc(N)n2)C[C@H]1c1cc(C(F)F)nc2ncnn12] | I-9b 6-amino-pyridine-2-carboxylic acid [23628-31-1] | 53 |
| 163 | 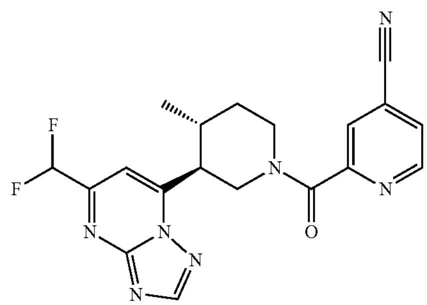 [SMILES: C[C@@H]1CCN(C(=O)c2cc(C#N)ccn2)C[C@H]1c1cc(C(F)F)nc2ncnn12] | I-9b 4-cyanopyridine-2-carboxylic acid [640296-19-1] | 67 |
| 164 | 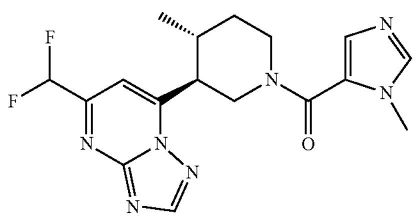 [SMILES: C[C@@H]1CCN(C(=O)c2cncn2C)C[C@H]1c1cc(C(F)F)nc2ncnn12] | I-9b 1-methyl-1H-imidazole-5-carboxylic acid [41806-40-0] | 69 |
| 165 | 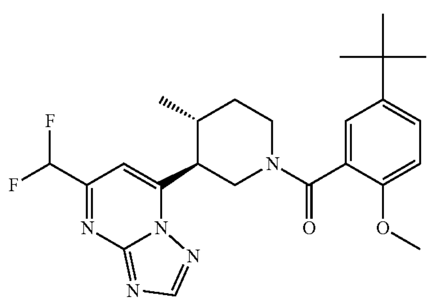 [SMILES: COc1ccc(C(C)(C)C)cc1C(=O)N1CC[C@@H](C)[C@H](c2cc(C(F)F)nc3ncnn23)C1] | I-9b 5-tert-butyl-2-methoxybenzoic acid [73469-54-2] | 61 |
| 166 | 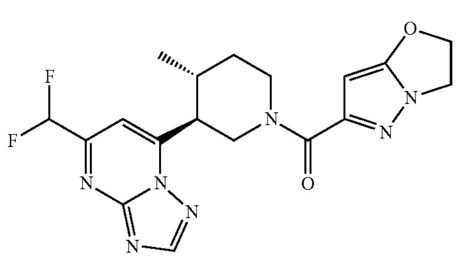 [SMILES: C[C@@H]1CCN(C(=O)c2cc3n(n2)CCO3)C[C@H]1c1cc(C(F)F)nc2ncnn12] | I-9b 2H,3H-pyrazolo[3,2-B][1,3]oxazole-6-carboxylic acid [1239722-75-8] | 62 |

TABLE 1-continued

| Co. No. | Structure | Prepared from | Yield (%) |
|---|---|---|---|
| 167 | 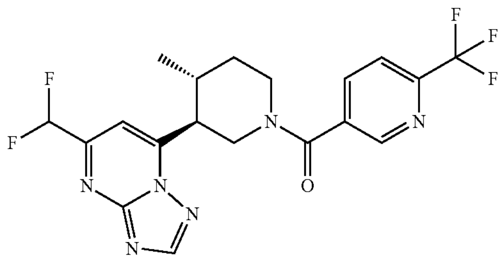 [SMILES: C[C@@H]1CCN(C(=O)c2ccc(C(F)(F)F)nc2)C[C@H]1c1cc(C(F)F)nc2ncnn12] | I-9b 6-(trifluoromethyl) nicotinic acid [231291-22-8] | 48 |
| 168 | 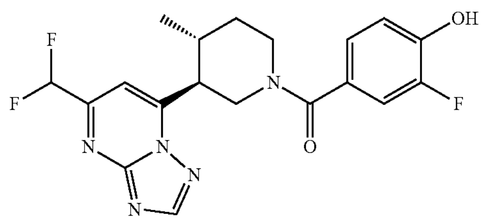 [SMILES: C[C@@H]1CCN(C(=O)c2ccc(O)c(F)c2)C[C@H]1c1cc(C(F)F)nc2ncnn12] | I-9b [350-29-8] | 25 |
| 169 | 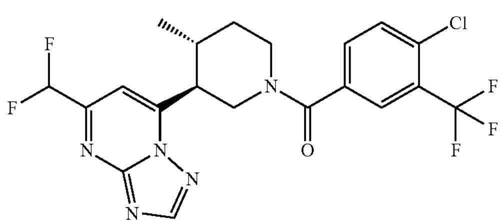 | I-9b [1737-36-6] | 67 |
| 170 | 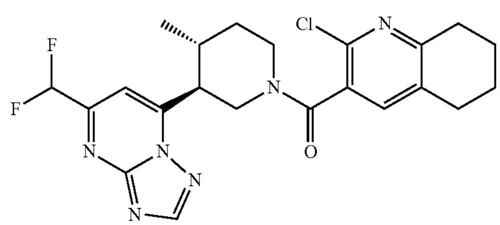 [SMILES: C[C@@H]1CCN(C(=O)c2cc3c(nc2Cl)CCCC3)C[C@H]1c1cc(C(F)F)nc2ncnn12] | I-9b [99058-34-1] | 69 |
| 171 | 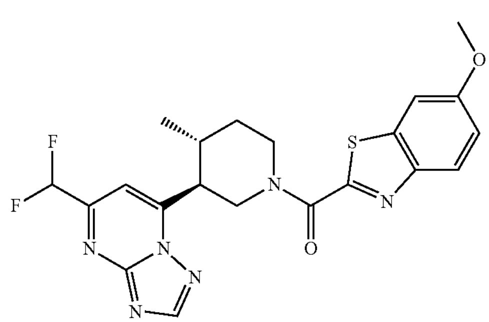 [SMILES: COc1ccc2nc(C(=O)N3CC[C@@H](C)[C@H](c4cc(C(F)F)nc5ncnn45)C3)sc2c1] | I-9b [946-13-4] | 40 |

TABLE 1-continued

| Co. No. | Structure | Prepared from | Yield (%) |
|---|---|---|---|
| 172 | 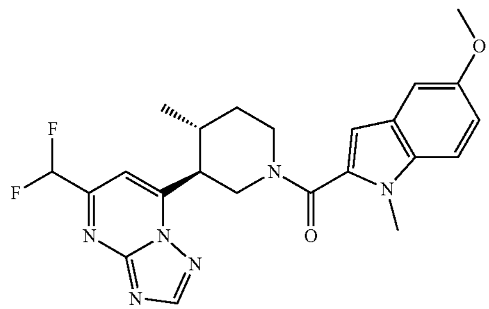 [SMILES: COc1ccc2c(c1)cc(C(=O)N1CC[C@@H](C)[C@H](c3cc(C(F)F)nc4ncnn34)C1)n2C] | I-9b [59908-54-2] | 58 |
| 173 | 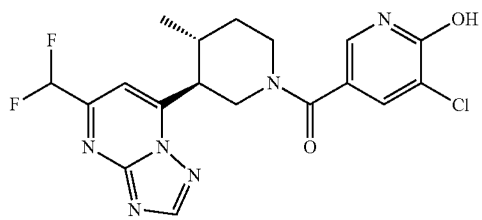 [SMILES: C[C@@H]1CCN(C(=O)c2cnc(O)c(Cl)c2)C[C@H]1c1cc(C(F)F)nc2ncnn12] | I-9b [54127-63-8] | 31 |
| 174 | 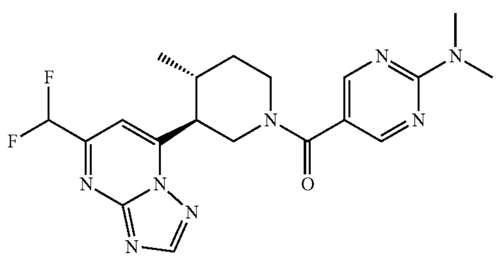 [SMILES: C[C@@H]1CCN(C(=O)c2cnc(N(C)C)nc2)C[C@H]1c1cc(C(F)F)nc2ncnn12] | I-9b [180283-66-3] | 64 |
| 175 | 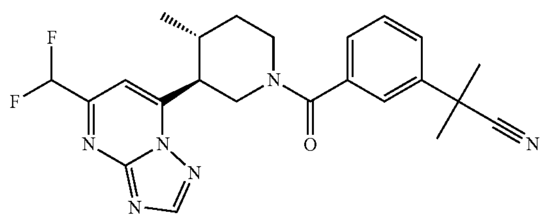 [SMILES: C[C@@H]1CCN(C(=O)c2cccc(C(C)(C)C#N)c2)C[C@H]1c1cc(C(F)F)nc2ncnn12] | I-9b [872091-00-4] | 59 |
| 176 | 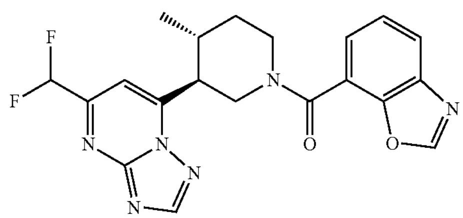 [SMILES: C[C@@H]1CCN(C(=O)c2cccc3ncoc23)C[C@H]1c1cc(C(F)F)nc2ncnn12] | I-9b [208772-24-1] | 59 |
| 177 | 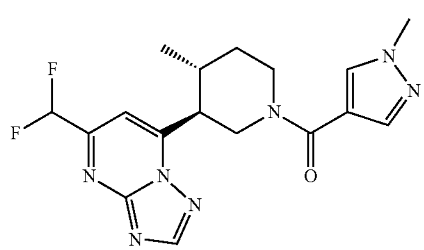 [SMILES: C[C@@H]1CCN(C(=O)c2cnn(C)c2)C[C@H]1c1cc(C(F)F)nc2ncnn12] | I-9b [5952-92-1] | 75 |

TABLE 1-continued

| Co. No. | Structure | Prepared from | Yield (%) |
|---|---|---|---|
| 178 | 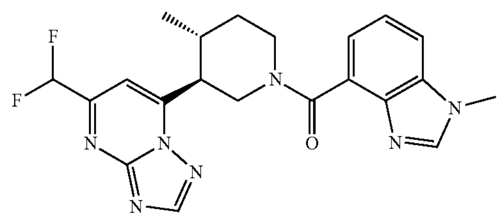 [SMILES: C[C@@H]1CCN(C(=O)c2cccc3c2ncn3C)C[C@H]1c1cc(C(F)F)nc2ncnn12] | I-9b [1187332-69-9] | 66 |
| 179 | 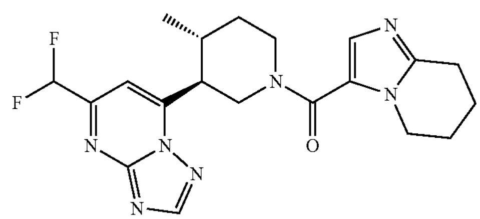 [SMILES: C[C@@H]1CCN(C(=O)c2cnc3n2CCCC3)C[C@H]1c1cc(C(F)F)nc2ncnn12] | I-9b [55365-04-3] | 68 |
| 180 | 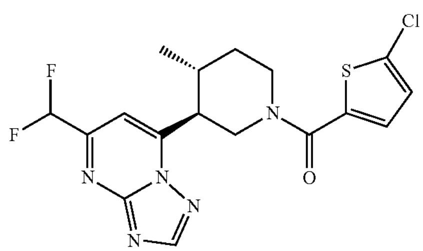 [SMILES: C[C@@H]1CCN(C(=O)c2ccc(Cl)s2)C[C@H]1c1cc(C(F)F)nc2ncnn12] | I-9b [24065-33-6] | 66 |
| 181 | 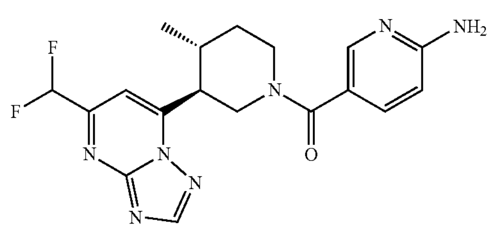 [SMILES: C[C@@H]1CCN(C(=O)c2ccc(N)nc2)C[C@H]1c1cc(C(F)F)nc2ncnn12] | I-9b [3167-49-5] | 63 |
| 182 | 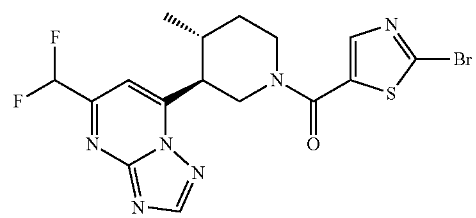 [SMILES: C[C@@H]1CCN(C(=O)c2cnc(Br)s2)C[C@H]1c1cc(C(F)F)nc2ncnn12] | I-9b [54045-76-0] | 65 |
| 183 | 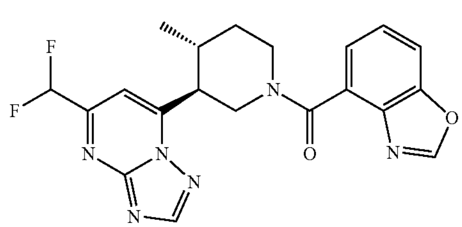 [SMILES: C[C@@H]1CCN(C(=O)c2cccc3ocnc23)C[C@H]1c1cc(C(F)F)nc2ncnn12] | I-9b [208772-23-0] | 48 |

TABLE 1-continued

| Co. No. | Structure | Prepared from | Yield (%) |
|---|---|---|---|
| 184 | 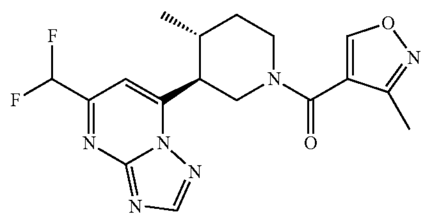 [SMILES: Cc1nocc1C(=O)N1CC[C@@H](C)[C@H](c2cc(C(F)F)nc3ncnn23)C1] | I-9b [17153-20-7] | 67 |
| 185 | 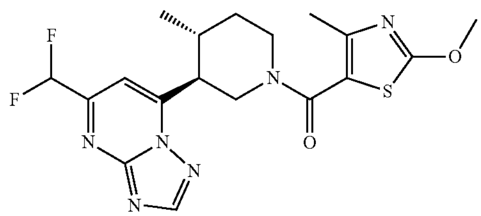 [SMILES: COc1nc(C)c(C(=O)N2CC[C@@H](C)[C@H](c3cc(C(F)F)nc4ncnn34)C2)s1] | I-9b [126909-38-4] | 56 |
| 186 | 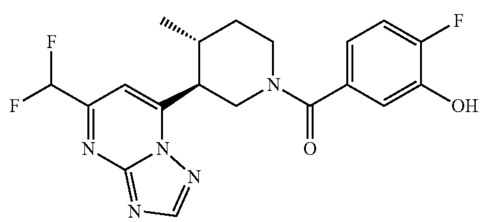 [SMILES: C[C@@H]1CCN(C(=O)c2ccc(F)c(O)c2)C[C@H]1c1cc(C(F)F)nc2ncnn12] | I-9b [51446-31-2] | 24 |
| 187 | 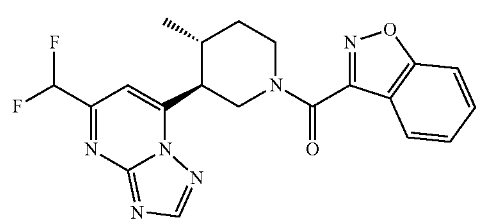 [SMILES: C[C@@H]1CCN(C(=O)c2noc3ccccc23)C[C@H]1c1cc(C(F)F)nc2ncnn12] | I-9b [28691-47-6] | 58 |
| 188 | 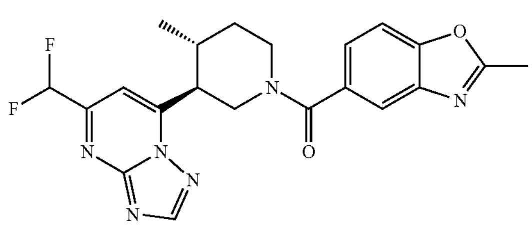 [SMILES: Cc1nc2cc(C(=O)N3CC[C@@H](C)[C@H](c4cc(C(F)F)nc5ncnn45)C3)ccc2o1] | I-9b [90322-32-0] | 58 |
| 189 | 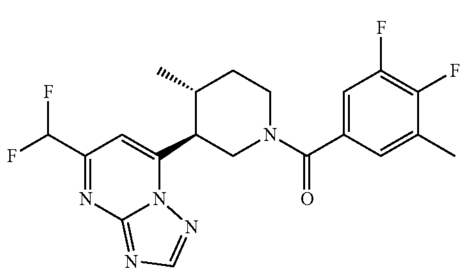 [SMILES: Cc1cc(C(=O)N2CC[C@@H](C)[C@H](c3cc(C(F)F)nc4ncnn34)C2)cc(F)c1F] | I-9b [1017778-60-7] | 26 |

TABLE 1-continued

| Co. No. | Structure | Prepared from | Yield (%) |
|---|---|---|---|
| 190 | 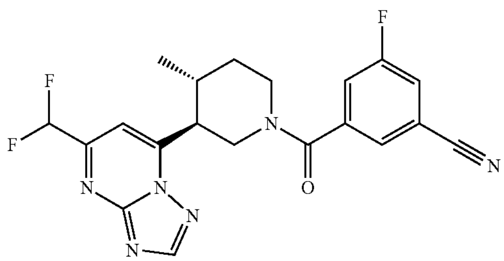 [SMILES: C[C@@H]1CCN(C(=O)c2cc(F)cc(C#N)c2)C[C@H]1c1cc(C(F)F)nc2ncnn12] | I-9b [327056-74-6] | 62 |
| 191 | 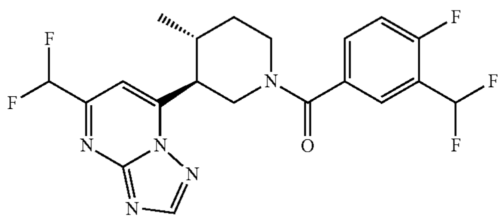 [SMILES: C[C@@H]1CCN(C(=O)c2ccc(F)c(C(F)F)c2)C[C@H]1c1cc(C(F)F)nc2ncnn12] | I-9b | 60 |
| 192 | 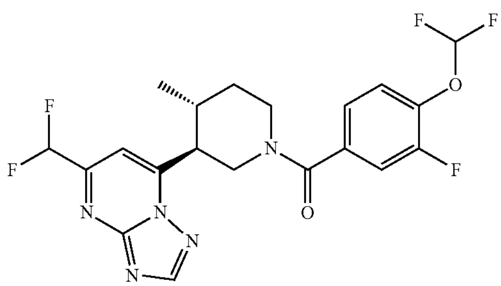 [SMILES: C[C@@H]1CCN(C(=O)c2ccc(OC(F)F)c(F)c2)C[C@H]1c1cc(C(F)F)nc2ncnn12] | I-9b [88696-49-7] | 21 |
| 193 | 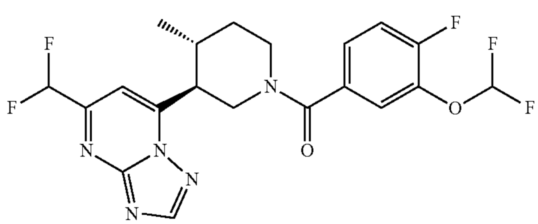 [SMILES: C[C@@H]1CCN(C(=O)c2ccc(F)c(OC(F)F)c2)C[C@H]1c1cc(C(F)F)nc2ncnn12] | I-9b [1214383-15-9] | 57 |
| 194 | 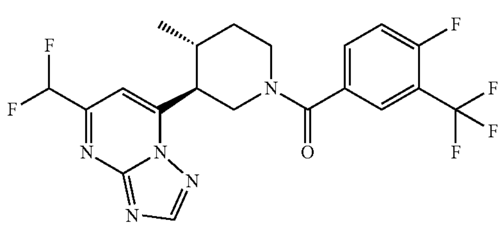 [SMILES: C[C@@H]1CCN(C(=O)c2ccc(F)c(C(F)(F)F)c2)C[C@H]1c1cc(C(F)F)nc2ncnn12] | I-9b [67515-55-3] | 25 |
| 195 | 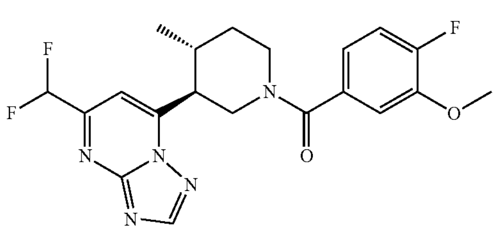 [SMILES: COc1cc(C(=O)N2CC[C@@H](C)[C@H](c3cc(C(F)F)nc4ncnn34)C2)ccc1F] | I-9b [82846-18-2] | 76 |

TABLE 1-continued

| Co. No. | Structure | Prepared from | Yield (%) |
|---|---|---|---|
| 196 | 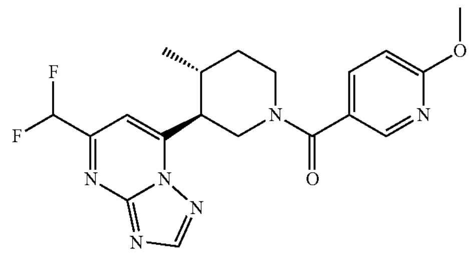 [SMILES: COc1ccc(C(=O)N2CC[C@@H](C)[C@H](c3cc(C(F)F)nc4ncnn34)C2)cn1] | I-9b [26218-80-4] | 45 |
| 197 | 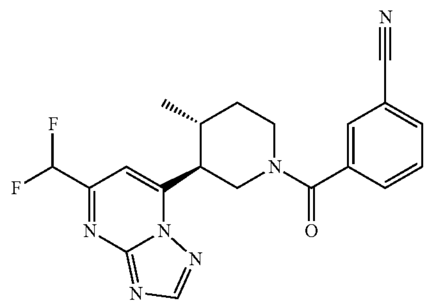 [SMILES: C[C@@H]1CCN(C(=O)c2cccc(C#N)c2)C[C@H]1c1cc(C(F)F)nc2ncnn12] | I-9b [1877-72-1] | 22 |
| 198 | ·HCl | I-9b [113100-61-1] | 49 |
| 199 | 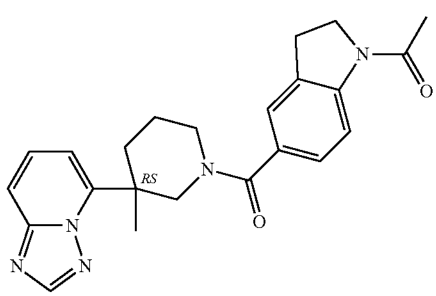 [SMILES: CC(=O)N1CCc2cc(C(=O)N3CCCC(C)(c4cccc5ncnn45)C3)ccc21] | I-42 | 8.7 |
| 200 | 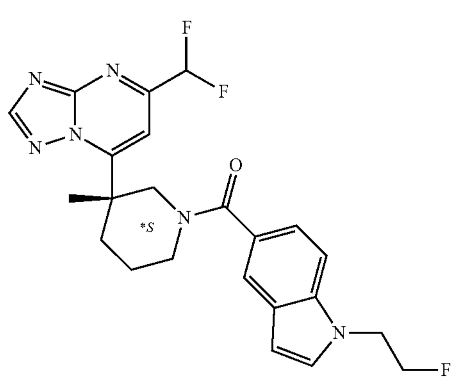 [SMILES: C[C@]1(c2cc(C(F)F)nc3ncnn23)CCCN(C(=O)c2ccc3c(ccn3CCF)c2)C1] | I-30 | 54 |

TABLE 1-continued

| Co. No. | Structure | Prepared from | Yield (%) |
|---|---|---|---|
| 201 | 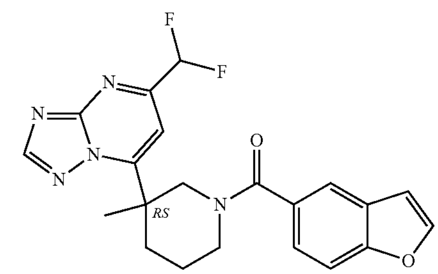 [SMILES: CC1(c2cc(C(F)F)nc3ncnn23)CCCN(C(=O)c2ccc3occc3c2)C1] | I-30 | 30 |
| 202 | 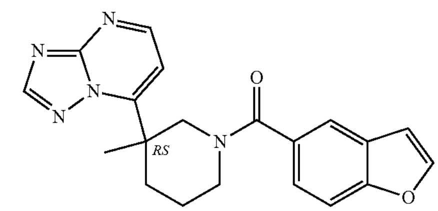 [SMILES: CC1(c2ccnc3ncnn23)CCCN(C(=O)c2ccc3occc3c2)C1] | I-42 | 31 |
| 203 | 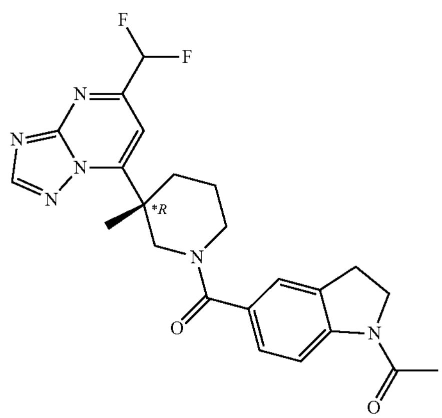 [SMILES: CC(=O)N1CCc2cc(C(=O)N3CCC[C@@](C)(c4cc(C(F)F)nc5ncnn45)C3)ccc21] | I-30a | 87 |
| 204 | 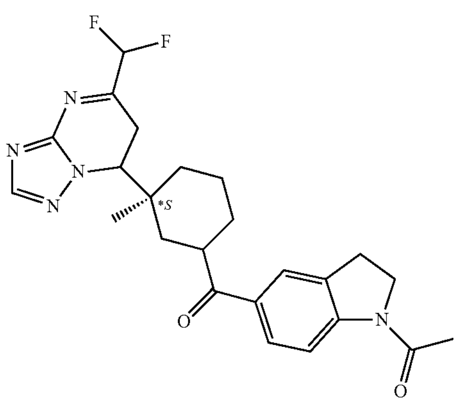 [SMILES: CC(=O)N1CCc2cc(C(=O)C3CCC[C@](C)(C4CC(C(F)F)=Nc5ncnn54)C3)ccc21] | I-30b | 89 |
| 205 | 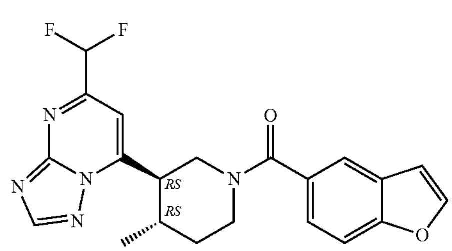 [SMILES: C[C@H]1CCN(C(=O)c2ccc3occc3c2)C[C@@H]1c1cc(C(F)F)nc2ncnn12] | I-12 | 22 |

TABLE 1-continued

| Co. No. | Structure | Prepared from | Yield (%) |
|---|---|---|---|
| 206 | 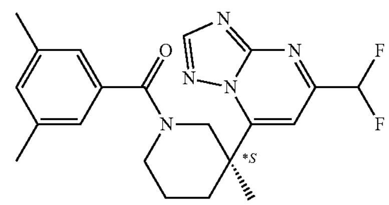 [SMILES: Cc1cc(C)cc(C(=O)N2CCC[C@](C)(c3cc(C(F)F)nc4ncnn34)C2)c1] | I-30b | 60 |
| 207 | 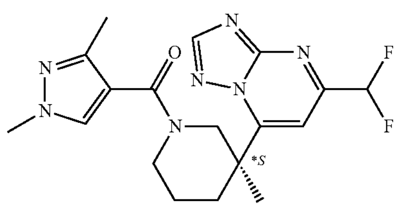 [SMILES: Cc1nn(C)cc1C(=O)N1CCC[C@](C)(c2cc(C(F)F)nc3ncnn23)C1] | I-30b | 40 |
| 208 | 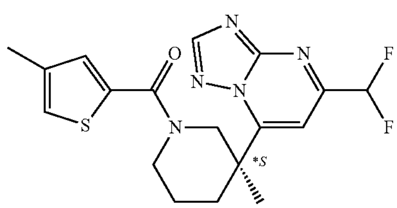 [SMILES: Cc1csc(C(=O)N2CCC[C@](C)(c3cc(C(F)F)nc4ncnn34)C2)c1] | I-30b | 75 |
| 209 | 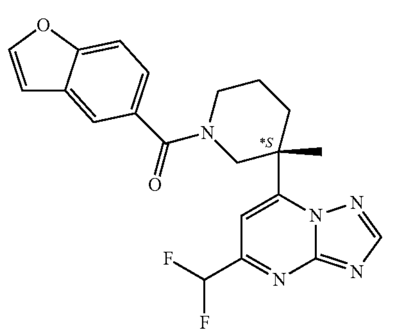 [SMILES: C[C@]1(c2cc(C(F)F)nc3ncnn23)CCCN(C(=O)c2ccc3occc3c2)C1] | I-30b | 57 |
| 210 | 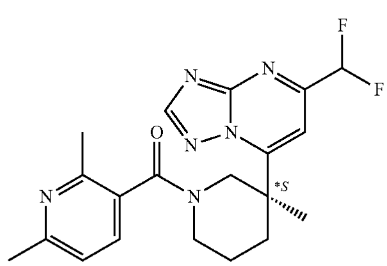 [SMILES: Cc1ccc(C(=O)N2CCC[C@](C)(c3cc(C(F)F)nc4ncnn34)C2)c(C)n1] | I-30b | 65 |
| 211 | 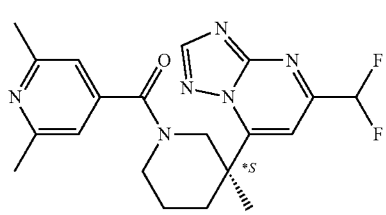 [SMILES: Cc1cc(C(=O)N2CCC[C@](C)(c3cc(C(F)F)nc4ncnn34)C2)cc(C)n1] | I-30b | 25 |

TABLE 1-continued

| Co. No. | Structure | Prepared from | Yield (%) |
|---|---|---|---|
| 212 | 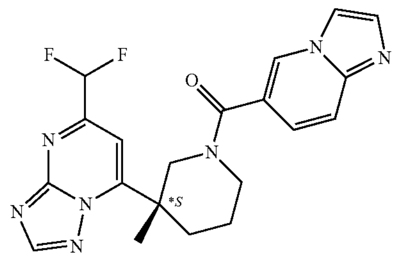 [SMILES: C[C@]1(c2cc(C(F)F)nc3ncnn23)CCCN(C(=O)c2ccc3nccn3c2)C1] | I-12 | 14 |
| 213 | 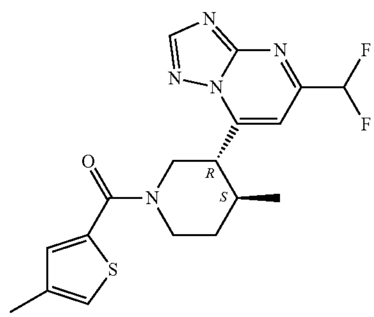 | I-9a | 61 |
| 214 | 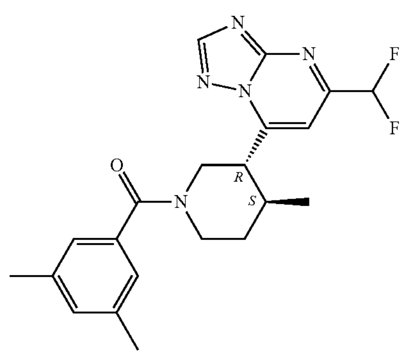 | I-9a | 55 |
| 215 | 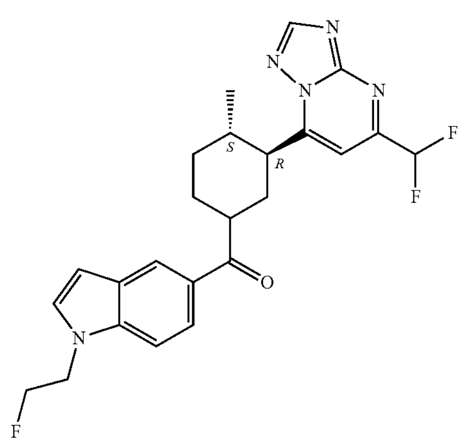 | I-9a | 54 |

TABLE 1-continued

| Co. No. | Structure | Prepared from | Yield (%) |
|---|---|---|---|
| 216 | 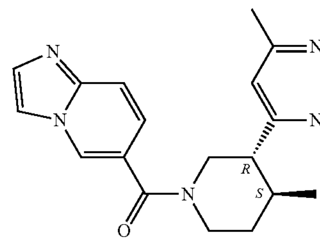 | I-9a | 29 |
| 217 | 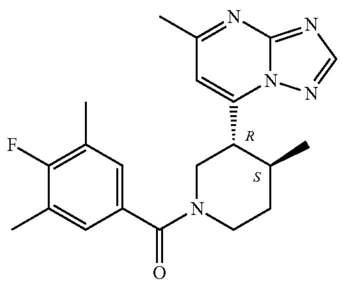 | I-9a | 25 |
| 218 | 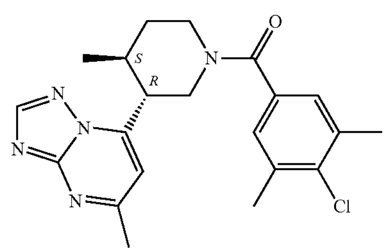 | I-9a | 26 |
| 219 | 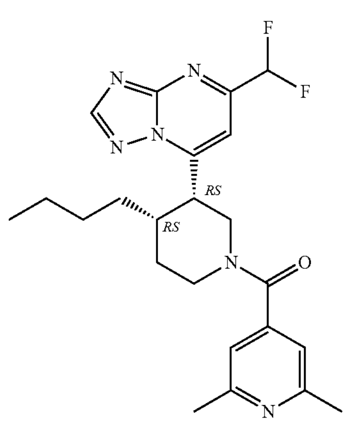 [SMILES: CCCC[C@H]1CCN(C(=O)c2cc(C)nc(C)c2)C[C@H]1c1cc(C(F)F)nc2ncnn12] | I-28 | 6 |

TABLE 1-continued

| Co. No. | Structure | Prepared from | Yield (%) |
|---|---|---|---|
| 220 | (structure) Free base or •HCl | I-9a | 42 |
| 221 | (structure) | I-9a | 58 |
| 222 | (structure) | I-9b | 24 |

TABLE 1-continued
| Co. No. | Structure | Prepared from | Yield (%) |
|---|---|---|---|
| 223 | 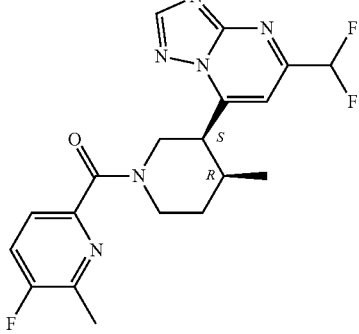<br>•1.30 HCl•H$_2$O | I-9b | 37 |
| 224 | 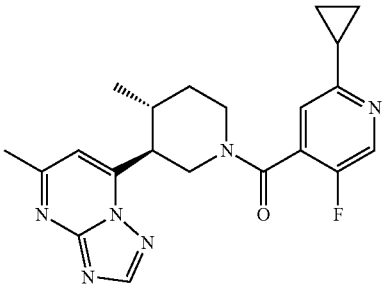 [SMILES: Cc1cc([C@@H]2CN(C(=O)c3cc(C4CC4)ncc3F)CC[C@H]2C)n2ncnc2n1] | I-12a | 55 |
| 225 | 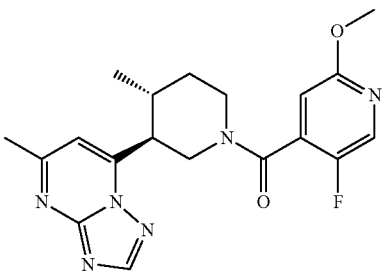 | I-12a | 58 |
| 226 | 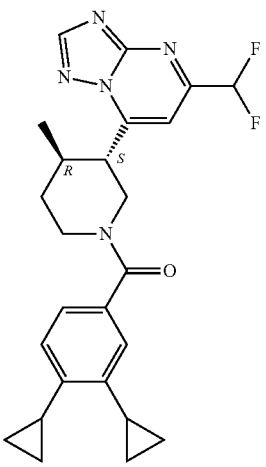 | I-9b | 14 |

TABLE 1-continued

| Co. No. | Structure | Prepared from | Yield (%) |
|---|---|---|---|
| 227 | 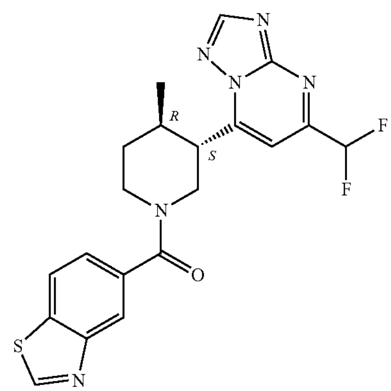 | I-9b | 49 |
| 228 | 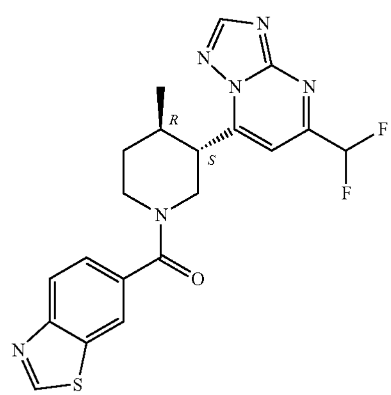 | I-9b | 50 |
| 229 | 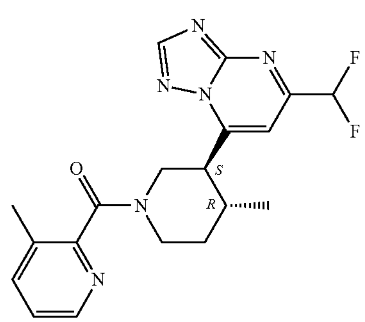 | I-9b | 83 |
| 230 | 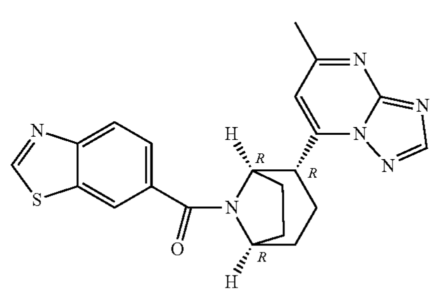 | I-25 | 32 |

TABLE 1-continued
| Co. No. | Structure | Prepared from | Yield (%) |
|---|---|---|---|
| 231 | 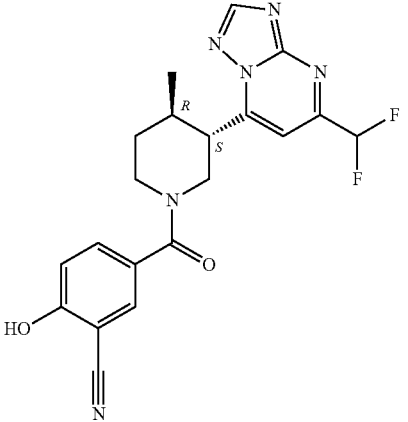 | I-9b | 29 |
| 232 | 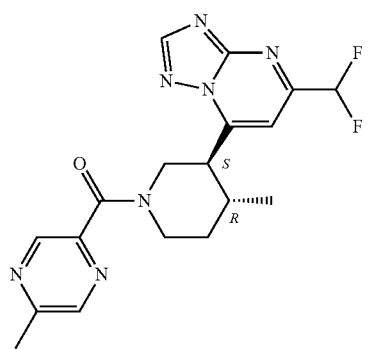 | I-9b | 65 |
| 233 | 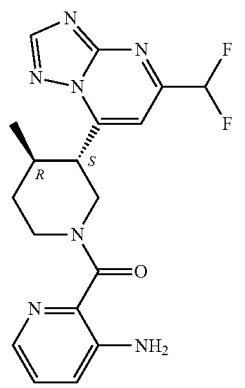 | I-9b | 57 |

TABLE 1-continued

| Co. No. | Structure | Prepared from | Yield (%) |
|---------|-----------|---------------|-----------|
| 234 | 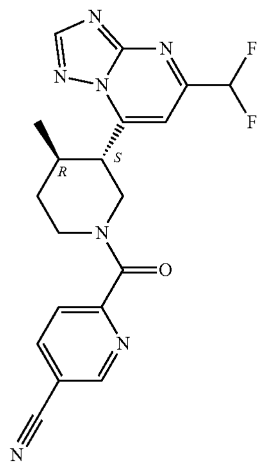 | I-9b | 63 |
| 235 | 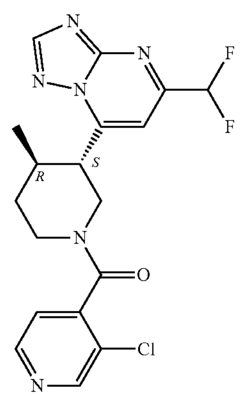 | I-9b | 62 |
| 236 | 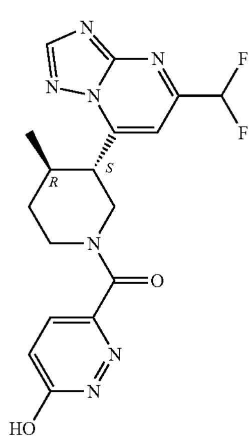 | I-9b | 2 |

TABLE 1-continued

| Co. No. | Structure | Prepared from | Yield (%) |
|---|---|---|---|
| 237 | 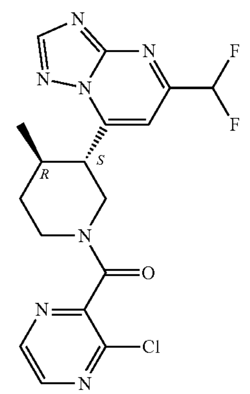 | I-9b | 54 |
| 238 | 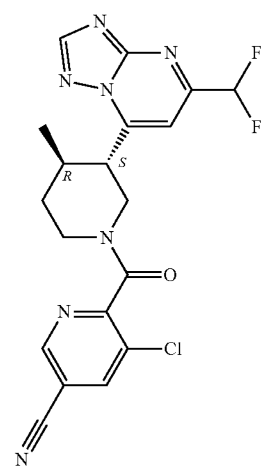 | I-9b | 49 |
| 239 | 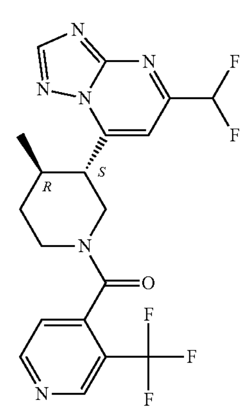 | I-9b | 45 |

TABLE 1-continued

| Co. No. | Structure | Prepared from | Yield (%) |
|---|---|---|---|
| 240 | 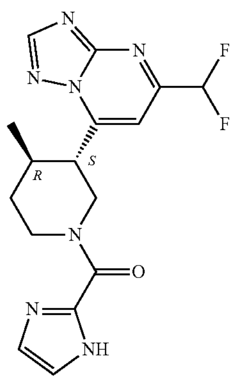 | I-9b | 59 |
| 241 | 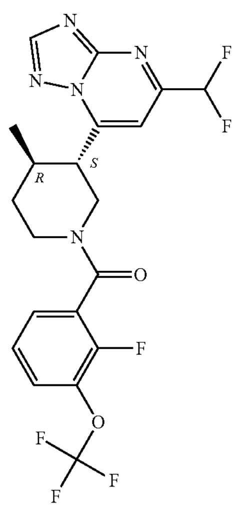 | I-9b | 66 |
| 242 | 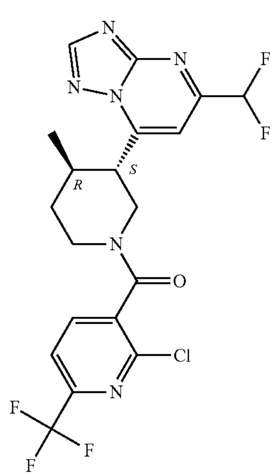 | I-9b | 67 |

TABLE 1-continued

| Co. No. | Structure | Prepared from | Yield (%) |
|---|---|---|---|
| 243 | 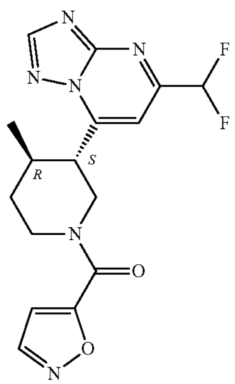 | I-9b | 44 |
| 244 | 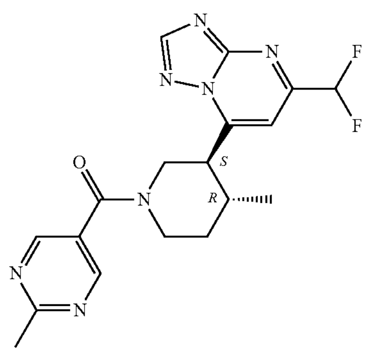 | I-9b | 53 |
| 245 | 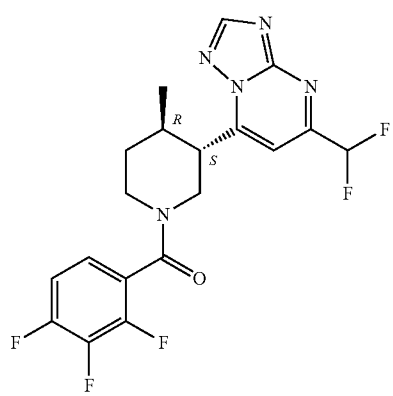 | I-9b | 62 |
| 246 | 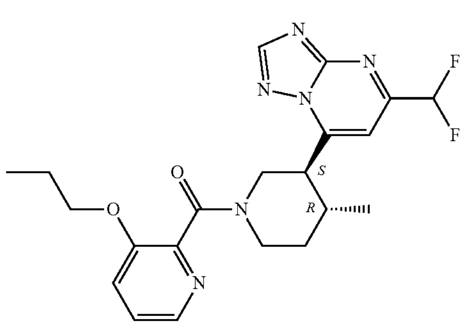 | I-9b | 58 |

TABLE 1-continued

| Co. No. | Structure | Prepared from | Yield (%) |
|---|---|---|---|
| 247 | 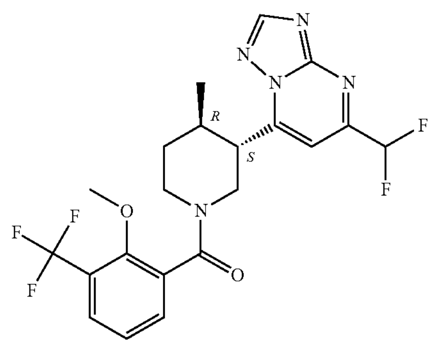 | I-9b | 53 |
| 248 | 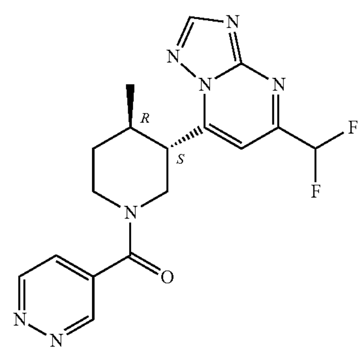 | I-9b | 63 |
| 249 | 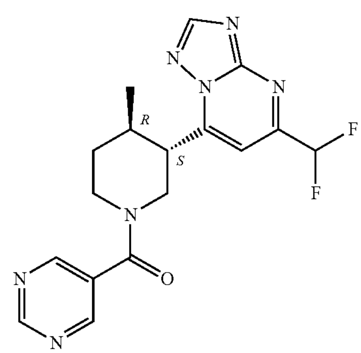 | I-9b | 53 |
| 250 | 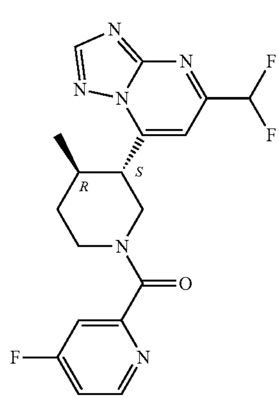 | I-9b | 66 |

TABLE 1-continued

| Co. No. | Structure | Prepared from | Yield (%) |
|---|---|---|---|
| 251 | 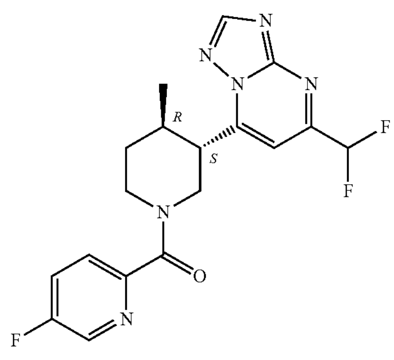 | I-9b | 70 |
| 252 | 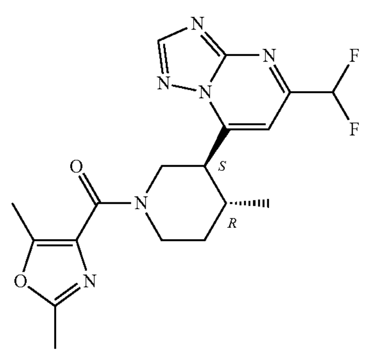 | I-9b | 62 |
| 253 | 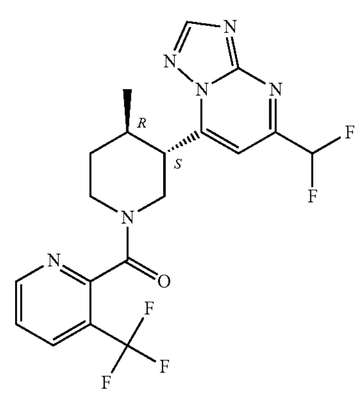 | I-9b | 62 |
| 254 | 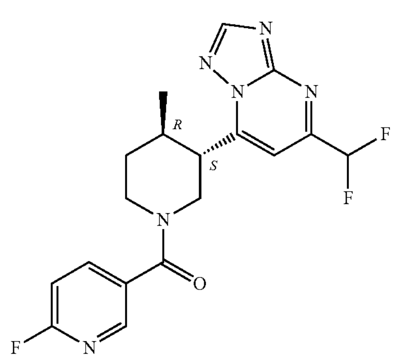 | I-9b | 50 |

TABLE 1-continued

| Co. No. | Structure | Prepared from | Yield (%) |
|---|---|---|---|
| 255 | 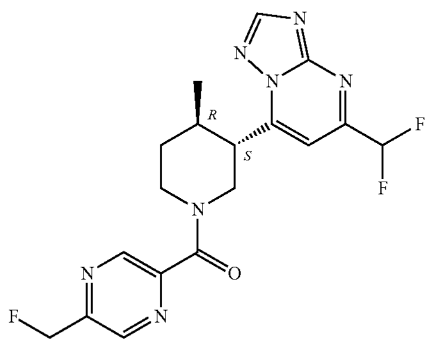 | I-9b | 64 |
| 256 | 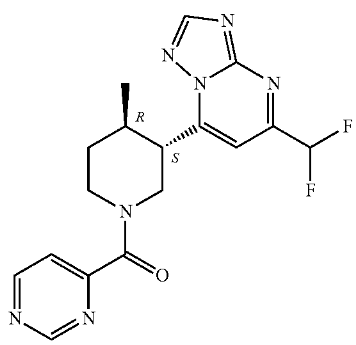 | I-9b | 63 |
| 257 | 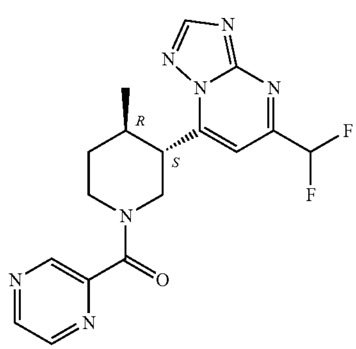 | I-9b | 59 |
| 258 | 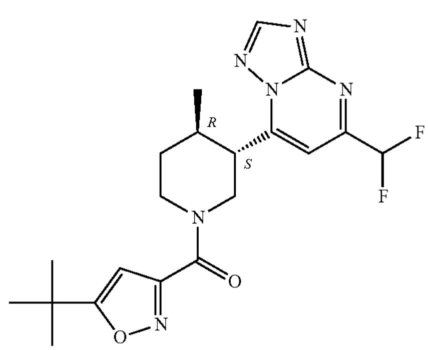 | I-9b | 53 |

TABLE 1-continued

| Co. No. | Structure | Prepared from | Yield (%) |
|---|---|---|---|
| 259 | 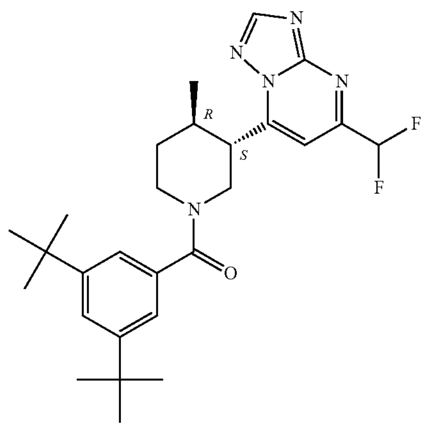 | I-9b | 63 |
| 260 | 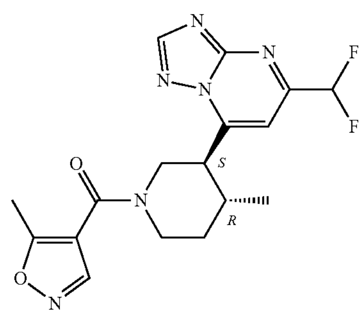 | I-9b | 40 |
| 261 | 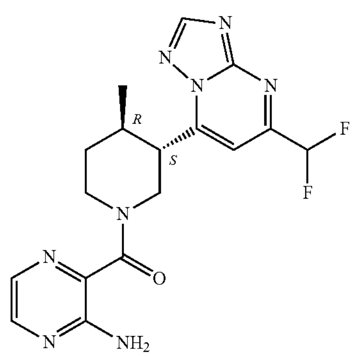 | I-9b | 64 |
| 262 | 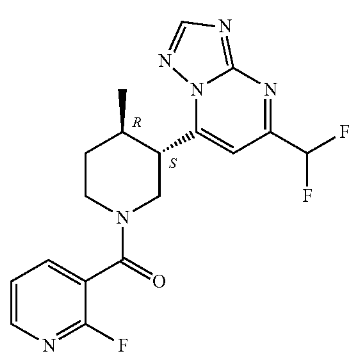 | I-9b | 68 |

TABLE 1-continued

| Co. No. | Structure | Prepared from | Yield (%) |
|---|---|---|---|
| 263 | 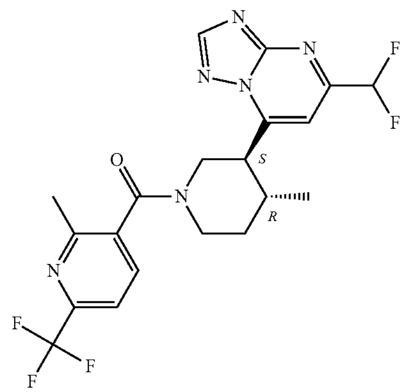 | I-9b | 27 |
| 264 | 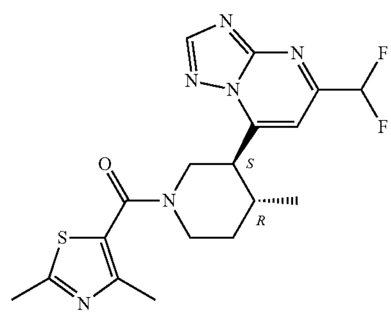 | I-9b | 58 |
| 265 | 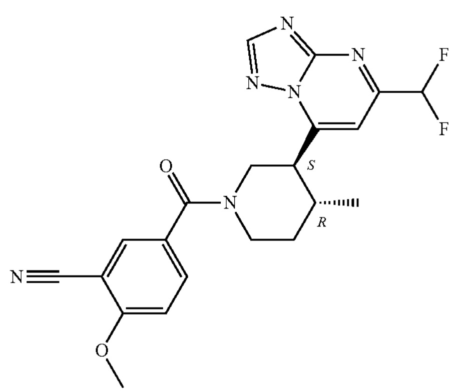 | I-9b | 62 |
| 266 | 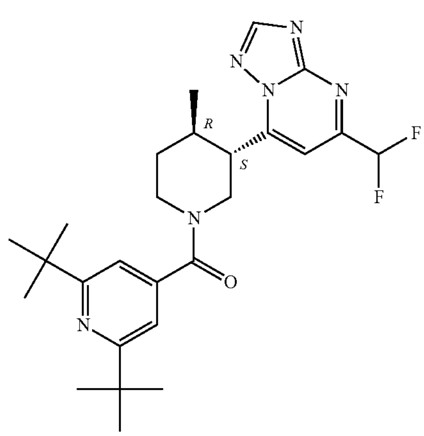 | I-9b | 72 |

TABLE 1-continued

| Co. No. | Structure | Prepared from | Yield (%) |
|---|---|---|---|
| 267 | 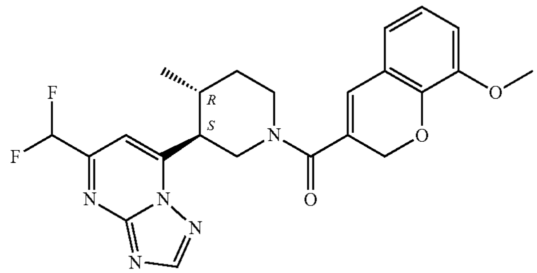 | I-9b | 57 |
| 268 | 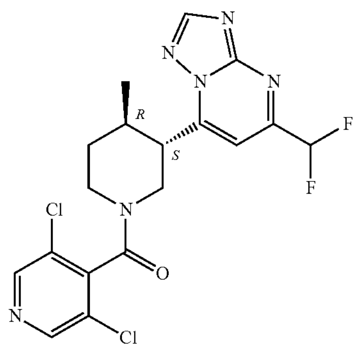 | I-9b | 61 |
| 269 | 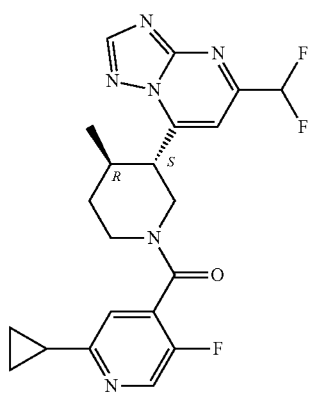 | I-9b | 61 |
| 270 | 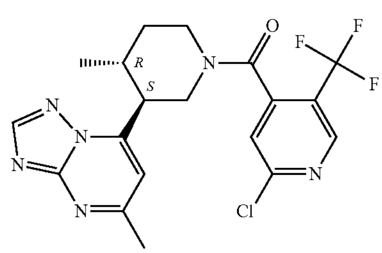 | I-9b | 45 |
| 271 | 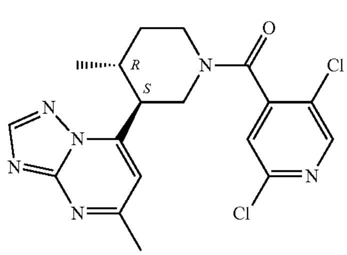 | I-9b | 32 |

TABLE 1-continued

| Co. No. | Structure | Prepared from | Yield (%) |
|---|---|---|---|
| 272 | 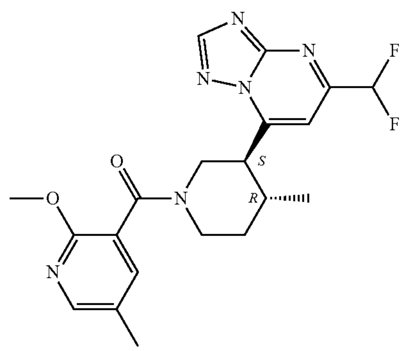 | I-9b | 30 |
| 273 | 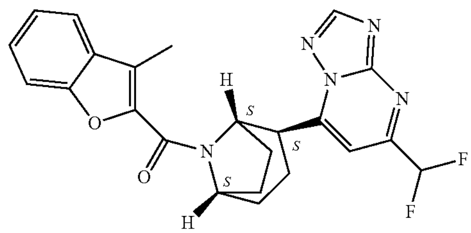 | I-25 | 37 |
| 274 | 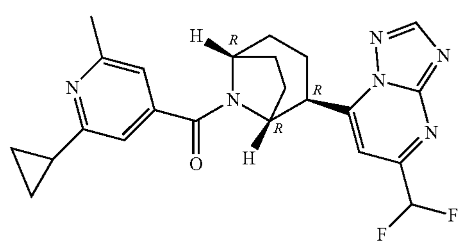 | I-25 | 35 |
| 275 | 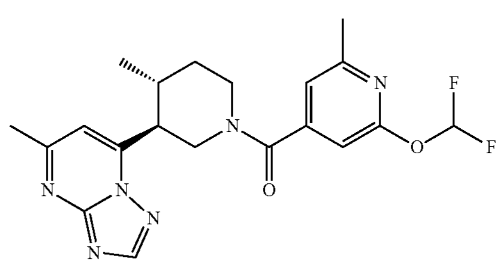 [SMILES: Cc1cc(C(=O)N2CC[C@@H](C)[C@H](c3cc(C)nc4ncnn34)C2)cc(OC(F)F)n1] | I-12a | 31 |
| 276 | 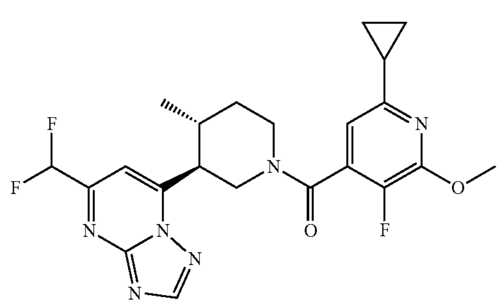 [SMILES: COc1nc(C2CC2)cc(C(=O)N2CC[C@@H](C)[C@H](c3cc(C(F)F)nc4ncnn34)C2)c1F] | I-9b | 3 |

TABLE 1-continued

| Co. No. | Structure | Prepared from | Yield (%) |
|---|---|---|---|
| 277 | 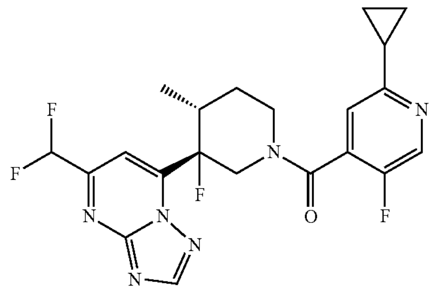 [SMILES: C[C@@H]1CCN(C(=O)c2cc(C3CC3)ncc2F)C[C@@]1(F)c1cc(C(F)F)nc2ncnn12] | I-19a | 71 |
| 278 | 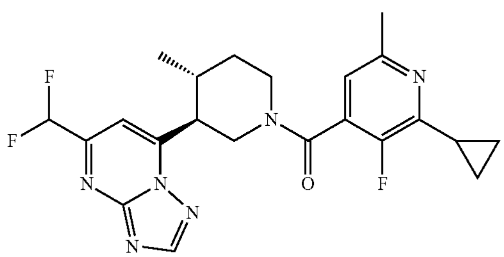 [SMILES: Cc1cc(C(=O)N2CC[C@@H](C)[C@H](c3cc(C(F)F)nc4ncnn34)C2)c(F)c(C2CC2)n1] | I-9b | 14 |
| 279 | 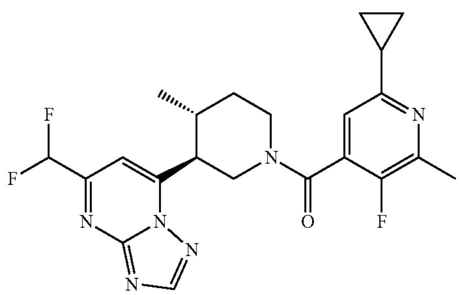 [SMILES: Cc1nc(C2CC2)cc(C(=O)N2CC[C@@H](C)[C@H](c3cc(C(F)F)nc4ncnn34)C2)c1F] | I-9b | 11 |
| 280 | 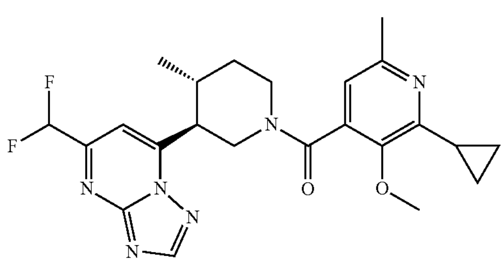 [SMILES: COc1c(C(=O)N2CC[C@@H](C)[C@H](c3cc(C(F)F)nc4ncnn34)C2)cc(C)nc1C1CC1] | I-9b | 3 |
| 281 | 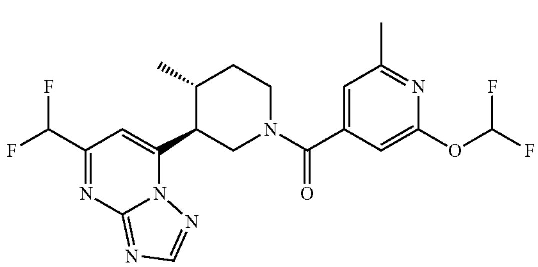 [SMILES: Cc1cc(C(=O)N2CC[C@@H](C)[C@H](c3cc(C(F)F)nc4ncnn34)C2)cc(OC(F)F)n1] | I-9b | 30 |

TABLE 1-continued

| Co. No. | Structure | Prepared from | Yield (%) |
|---|---|---|---|
| 282 | 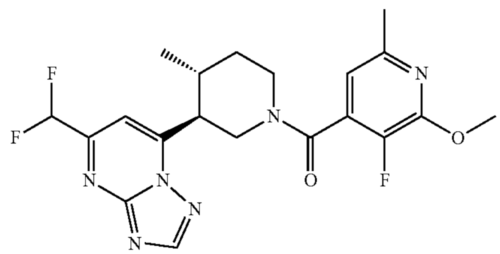 [SMILES: COc1nc(C)cc(C(=O)N2CC[C@@H](C)[C@H](c3cc(C(F)F)nc4ncnn34)C2)c1F] | I-9b | 24 |
| 283 | 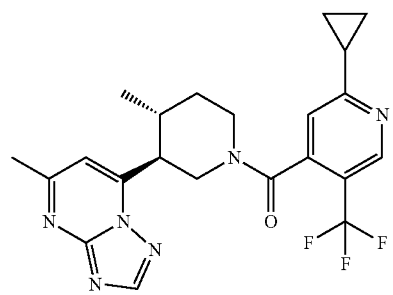 [SMILES: Cc1cc([C@@H]2CN(C(=O)c3cc(C4CC4)ncc3C(F)(F)F)CC[C@H]2C)n2ncnc2n1] | I-12a | 48 |
| 284 | 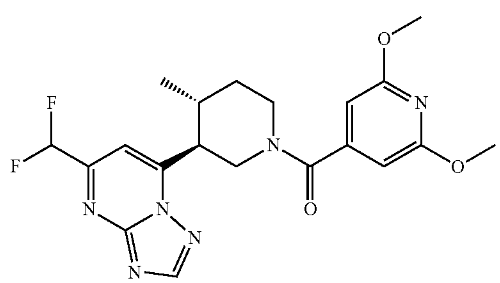 [SMILES: COc1cc(C(=O)N2CC[C@@H](C)[C@H](c3cc(C(F)F)nc4ncnn34)C2)cc(OC)n1] | I-9b | 62 |
| 285 | 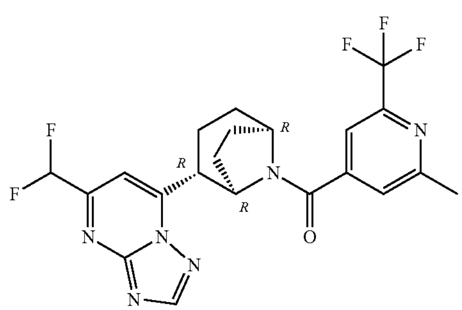 | I-25 | 7.7 |
| 286 | 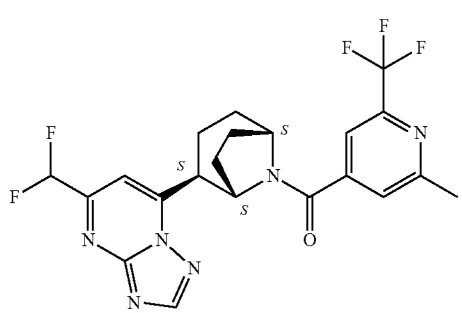 | I-25 | 9.7 |

TABLE 1-continued

| Co. No. | Structure | Prepared from | Yield (%) |
|---|---|---|---|
| 287 | 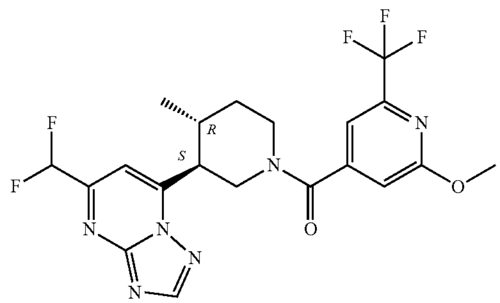 | I-9b | 62 |
| 288 | 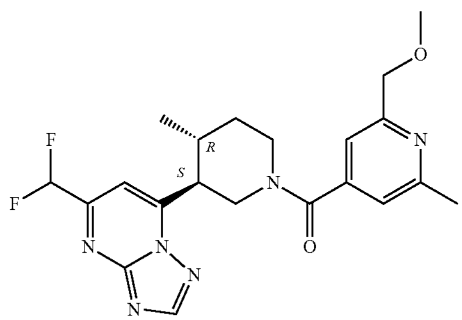 | I-9b | 26 |
| 289 | 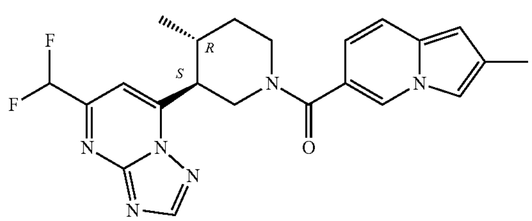 | I-9b | 53 |
| 290 | 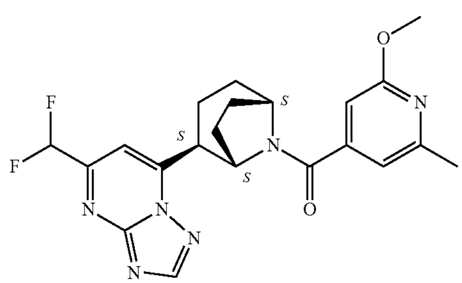 | I-25a | 40 |
| 291 | 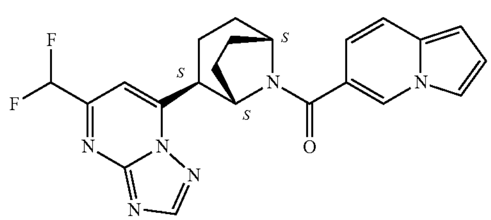 | I-25a | 65 |

TABLE 1-continued

| Co. No. | Structure | Prepared from | Yield (%) |
|---------|-----------|---------------|-----------|
| 292 | 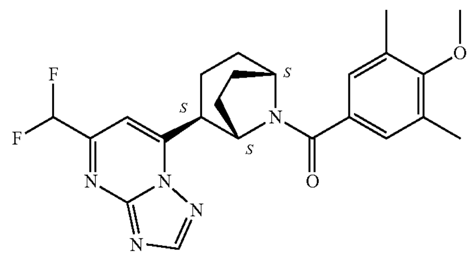 | I-25a | 59 |
| 293 | 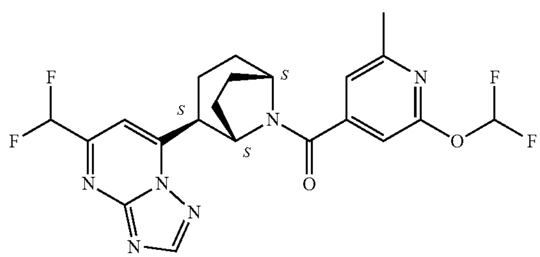 | I-25a | 65 |
| 294 | 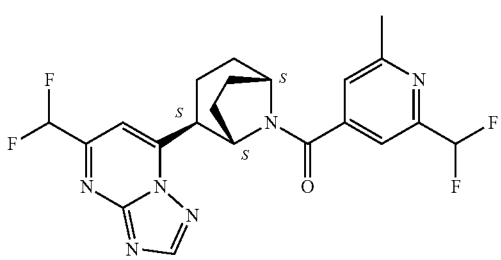 | I-25a | 60 |
| 295 | 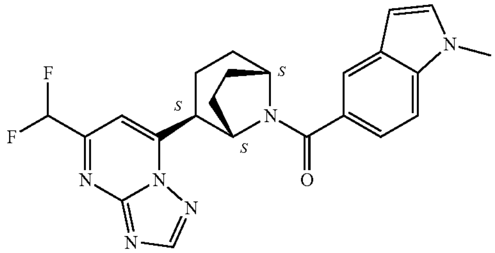 | I-25a | 94 |
| 296 | 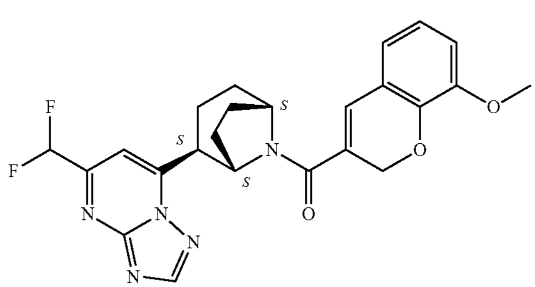 | I-25a | 39 |

TABLE 1-continued
| Co. No. | Structure | Prepared from | Yield (%) |
|---|---|---|---|
| 297 | 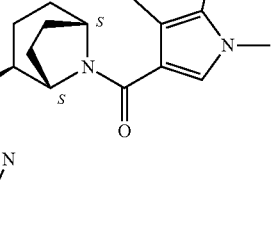 | I-25a | 61 |
| 298 | 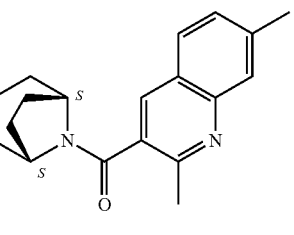 | I-25a | 56 |
| 299 | 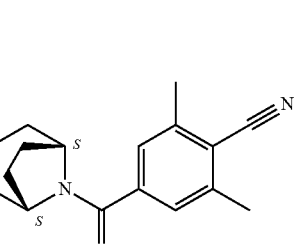 | I-25a | 54 |
| 300 | 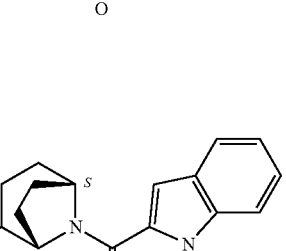 | I-25a | 22 |
| 301 | 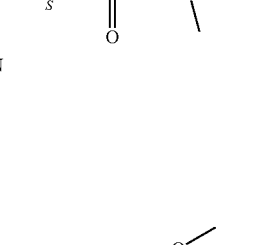 | I-25a | 60 |

TABLE 1-continued

| Co. No. | Structure | Prepared from | Yield (%) |
|---|---|---|---|
| 302 | 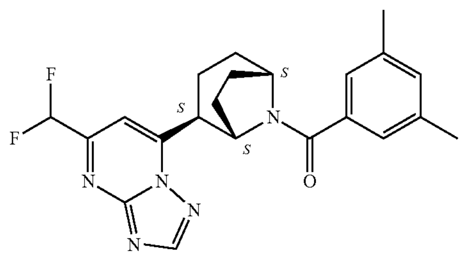 | I-25a | 61 |
| 303 | 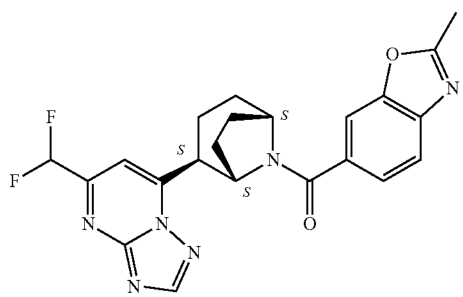 | I-25a | 41 |
| 304 | 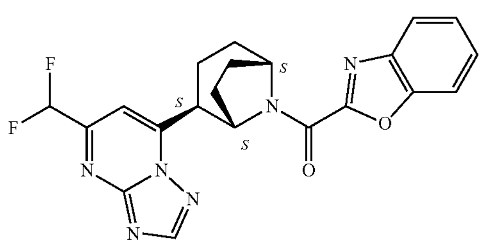 | I-25a | 56 |
| 305 | 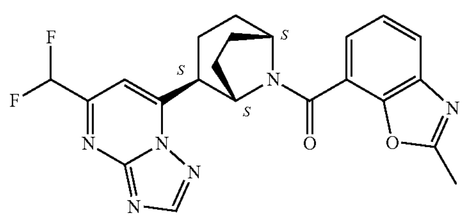 | I-25a | 64 |
| 306 | 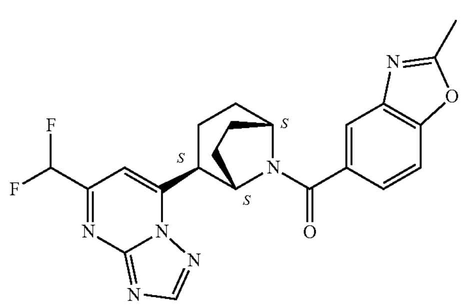 | I-25a | 68 |

TABLE 1-continued

| Co. No. | Structure | Prepared from | Yield (%) |
|---|---|---|---|
| 307 | 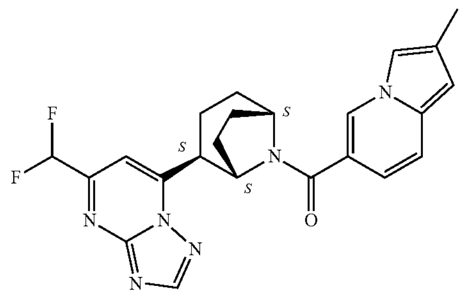 | I-25a | 55 |
| 308 | 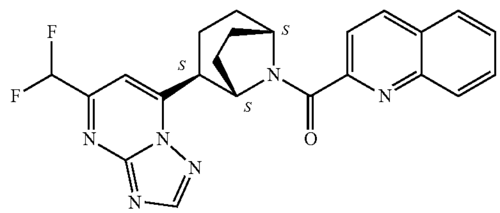 | I-25a | 48 |
| 309 | 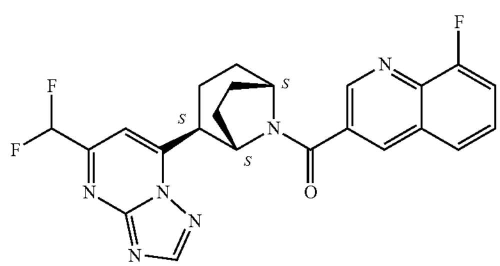 | I-25a | 65 |
| 310 | 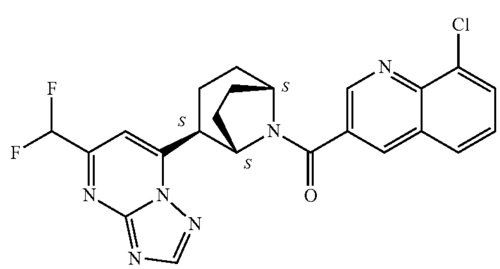 | I-25a | 52 |
| 311 | 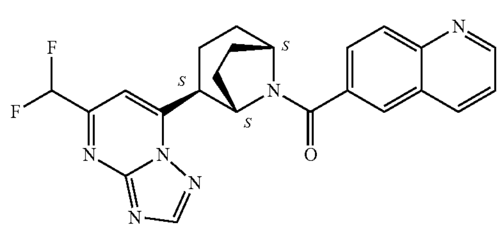 | I-25a | 62 |
| 312 | 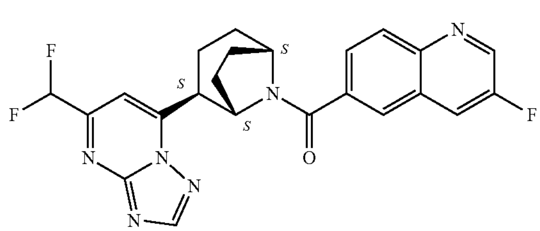 | I-25a | 63 |

TABLE 1-continued

| Co. No. | Structure | Prepared from | Yield (%) |
|---|---|---|---|
| 313 | 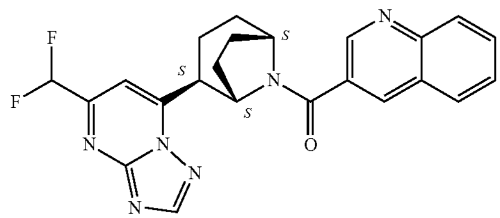 | I-25a | 63 |
| 314 | 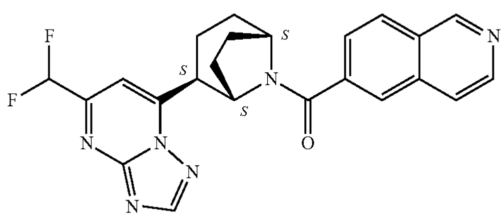 | I-25a | 64 |
| 315 | 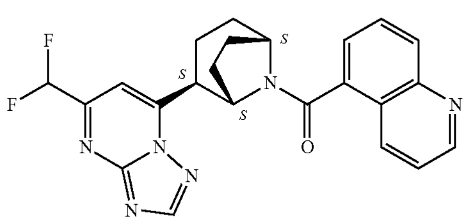 | I-25a | 63 |
| 316 | 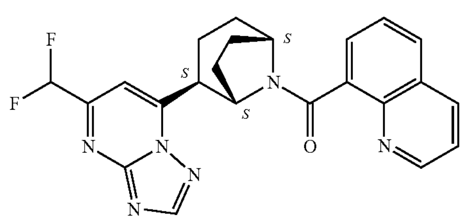 | I-25a | 100 |
| 317 | 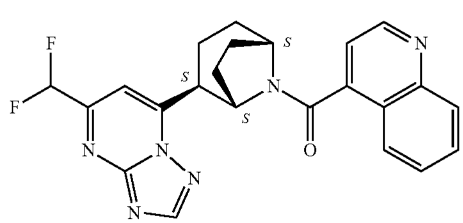 | I-25a | 61 |
| 318 | 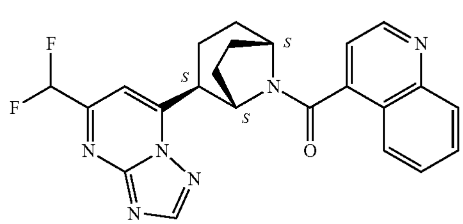 | I-25a | 86 |

US 10,947,242 B2
TABLE 1-continued
| Co. No. | Structure | Prepared from | Yield (%) |
|---|---|---|---|
| 319 | 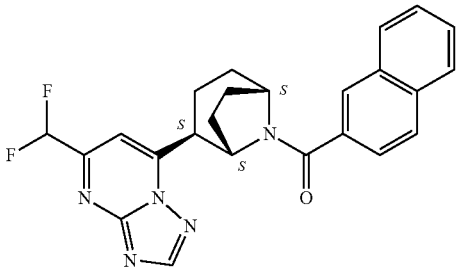 | I-25a | 57 |
| 320 | 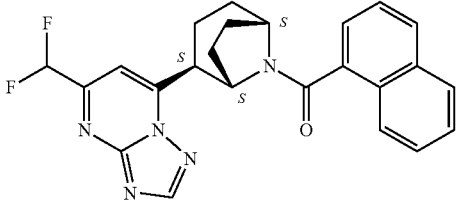 | I-25a | 50 |
| 321 | 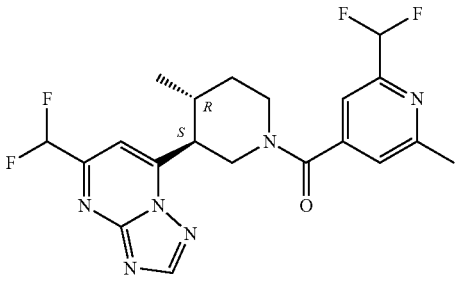 | I-9b (N.B. EDCI coupling) | 60 |
| 322 | 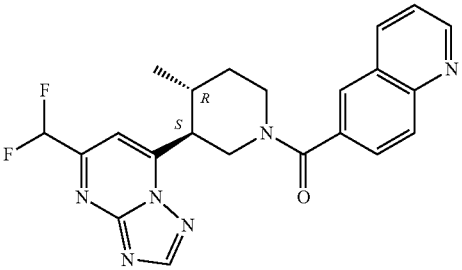 | I-9b (N.B. EDCI coupling) | 69 |
| 323 | 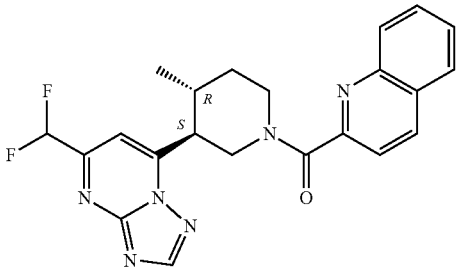 | I-9b (N.B. EDCI coupling) | 59 |

TABLE 1-continued

| Co. No. | Structure | Prepared from | Yield (%) |
|---|---|---|---|
| 324 | 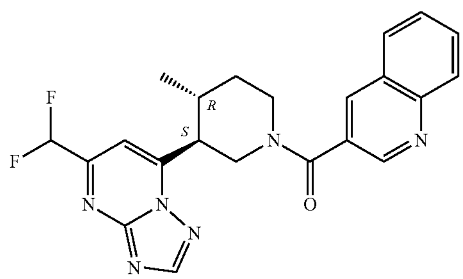 | I-9b (N.B. EDCI coupling) | 79 |
| 325 | 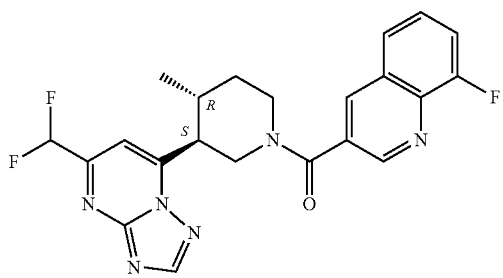 | I-9b (N.B. EDCI coupling) | 62 |
| 326 | 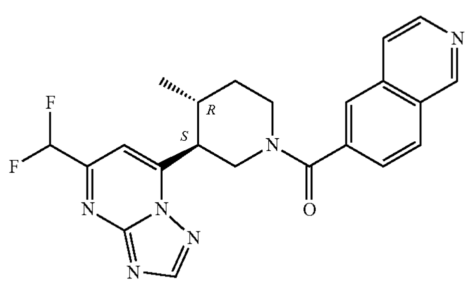 | I-9b (N.B. EDCI coupling) | 66 |
| 327 | 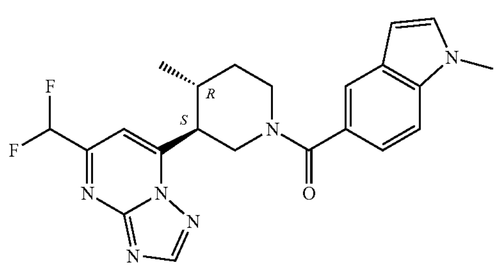 | I-9b (N.B. EDCI coupling) | 73 |
| 328 | 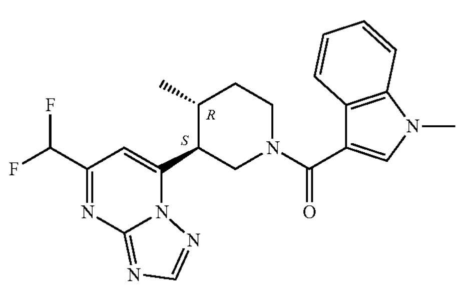 | I-9b (N.B. EDCI coupling) | 56 |

TABLE 1-continued

| Co. No. | Structure | Prepared from | Yield (%) |
|---|---|---|---|
| 329 | 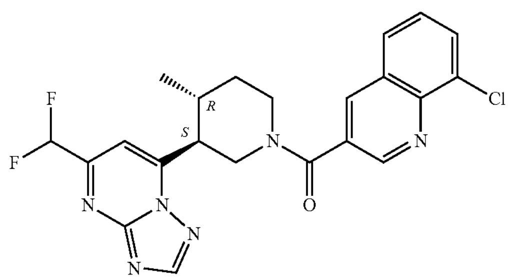 | I-9b (N.B. EDCI coupling) | 71 |
| 331 | 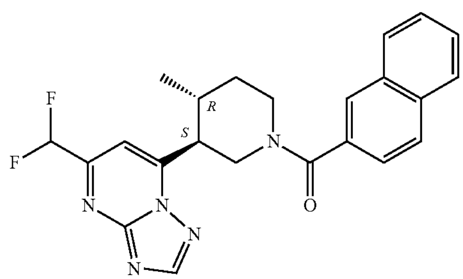 | I-9b (N.B. EDCI coupling) | 66 |
| 332 | 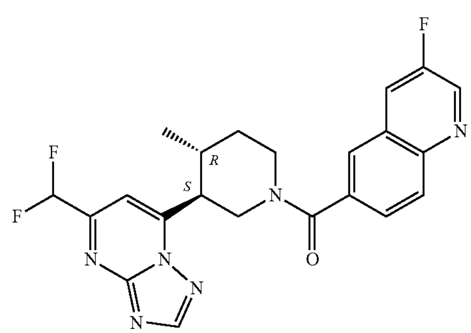 | I-9b | 32 |
| 333 | 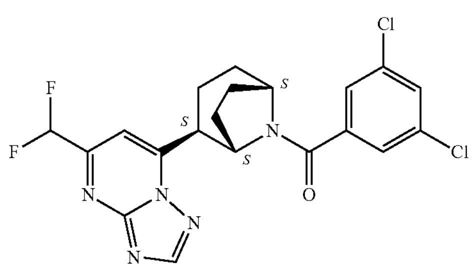 | I-25a (N.B. phosphonic acid anhydride) | 61 |
| 334 | 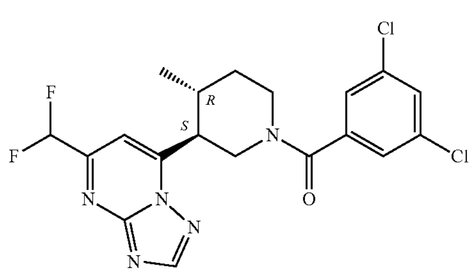 | I-9b (N.B. phosphonic acid anhydride) | 66 |

TABLE 1-continued
| Co. No. | Structure | Prepared from | Yield (%) |
|---|---|---|---|
| 335 | 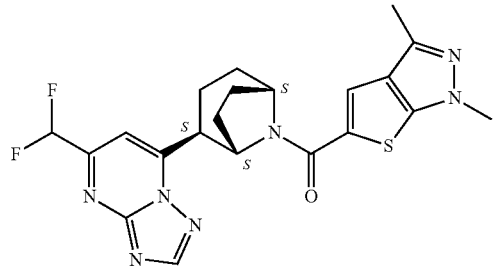 | I-25a | 71 |
| 336 | 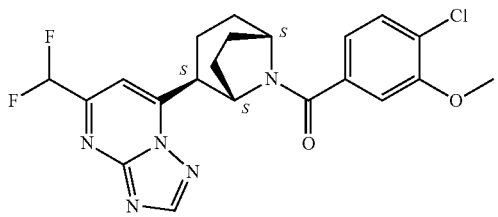 | I-25a (N.B. phosphonic acid anhydride) | 52 |
| 337 | 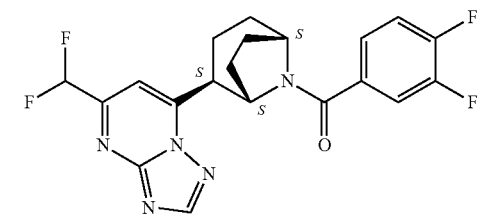 | I-25a | 62 |
| 338 | 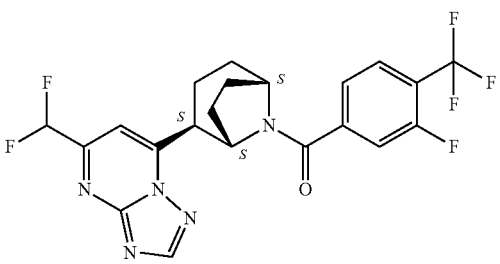 | I-25a | 33 |
| 339 | 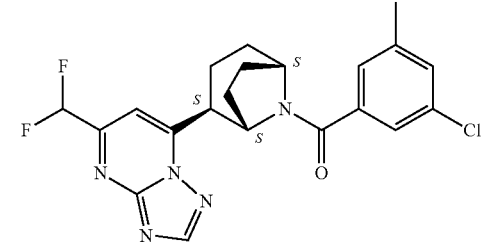 | I-25a | 69 |
| 340 | 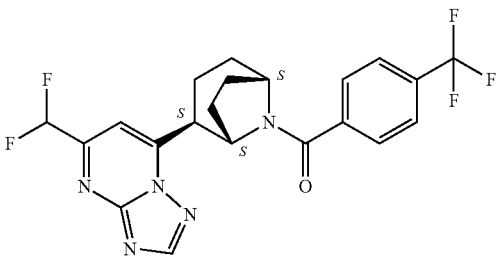 | I-25a | 38 |

TABLE 1-continued

| Co. No. | Structure | Prepared from | Yield (%) |
|---|---|---|---|
| 341 | 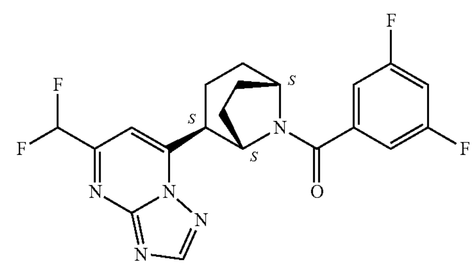 | I-25a | 72 |
| 342 | 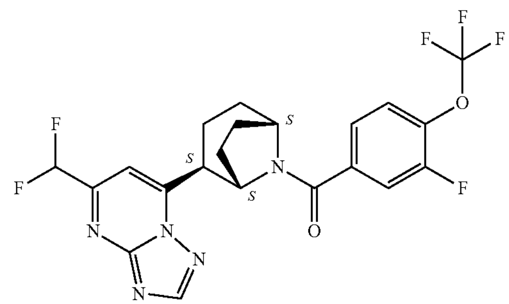 | I-25a | 42 |
| 343 | 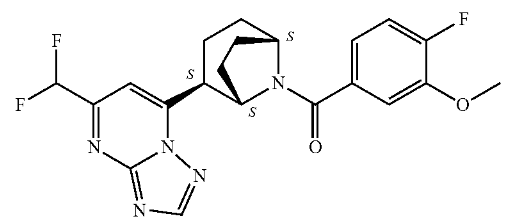 | I-25a (N.B. phosphonic acid anhydride) | 58 |
| 344 | 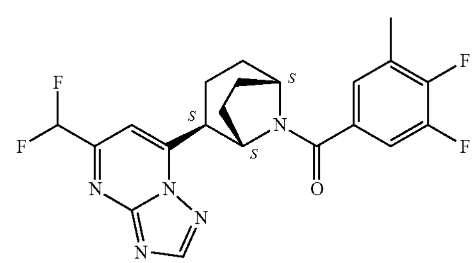 | I-25a | 64 |
| 345 | 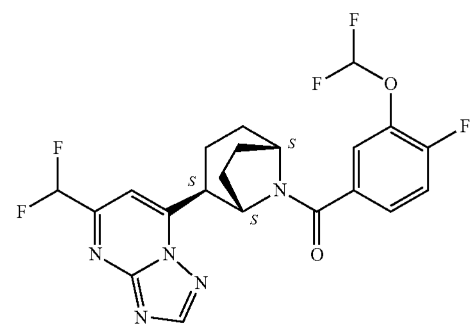 | I-25a (N.B. phosphonic acid anhydride) | 42 |

TABLE 1-continued

| Co. No. | Structure | Prepared from | Yield (%) |
|---|---|---|---|
| 346 | 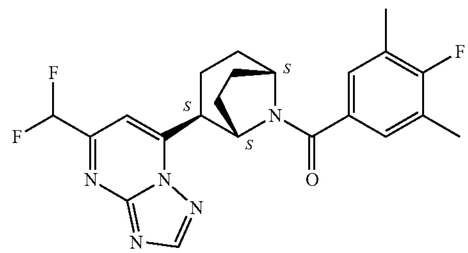 | I-25a | 41 |
| 347 | 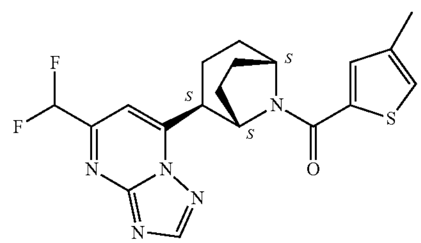 | I-25a | 52 |
| 348 | 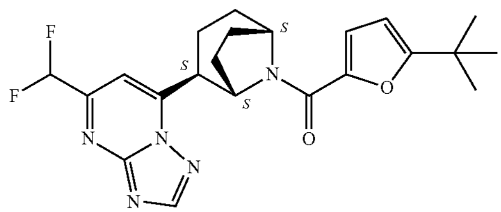 | I-25a | 51 |
| 349 | 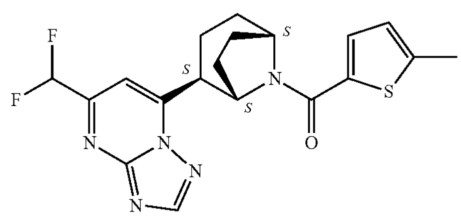 | I-25 | 46 |
| 350 | 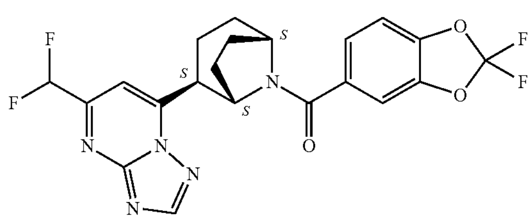 | I-25a | 55 |
| 351 | 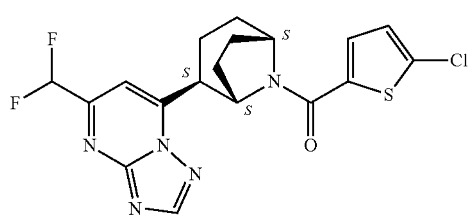 | I-25a | |

TABLE 1-continued

| Co. No. | Structure | Prepared from | Yield (%) |
|---|---|---|---|
| 352 | 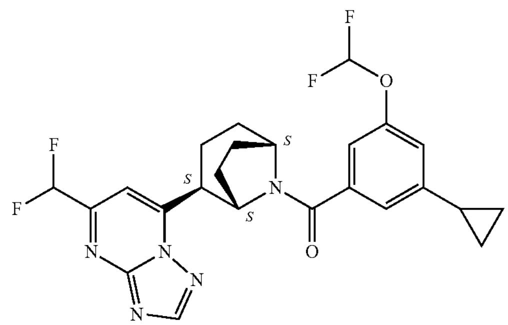 | I-25a | 67 |
| 353 | 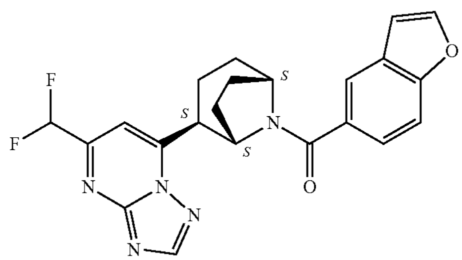 | I-25a | 66 |
| 354 | 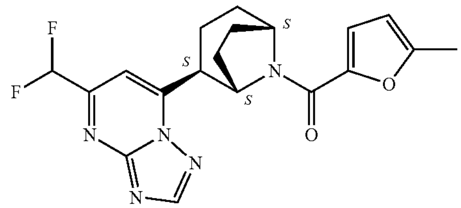 | I-25a | 59 |
| 355 | 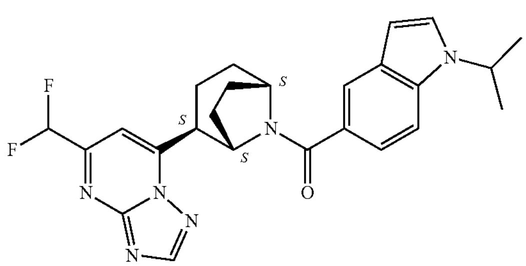 | I-25a (N.B. phosphonic acid anhydride) | 34 |
| 356 | 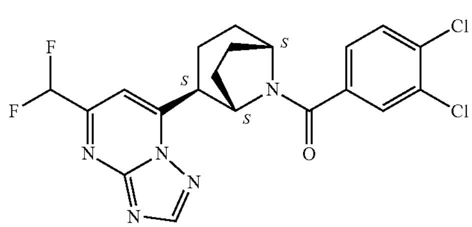 | I-25a | 78 |
| 357 | 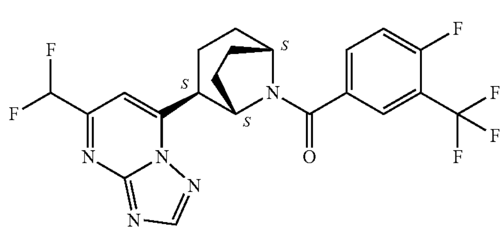 | I-25a | 65 |

TABLE 1-continued

| Co. No. | Structure | Prepared from | Yield (%) |
|---|---|---|---|
| 358 | 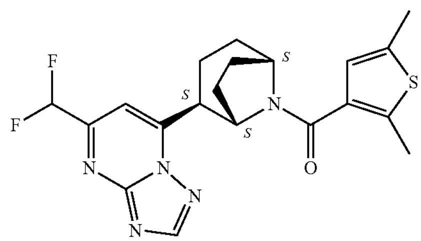 | I-25a | 17 |
| 359 | 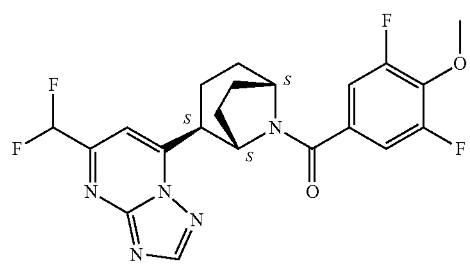 | I-25a | 58 |
| 360 | 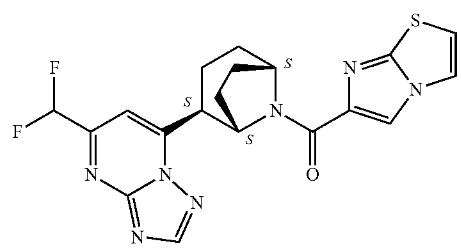 | I-25a | 43 |
| 361 | 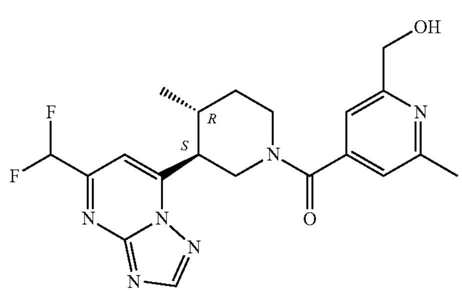 | I-9b | 15 |
| 362 | 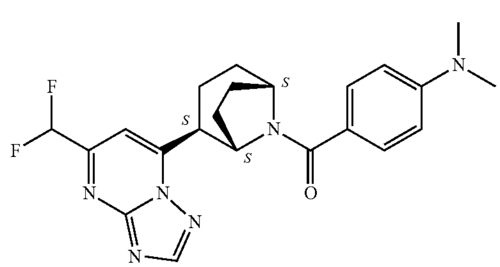 | I-25a | 47 |

TABLE 1-continued

| Co. No. | Structure | Prepared from | Yield (%) |
|---|---|---|---|
| 363 | 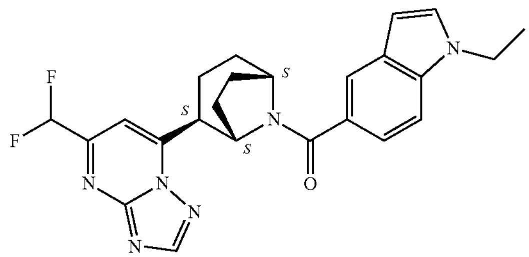 | I-25a | 49 |
| 364 | 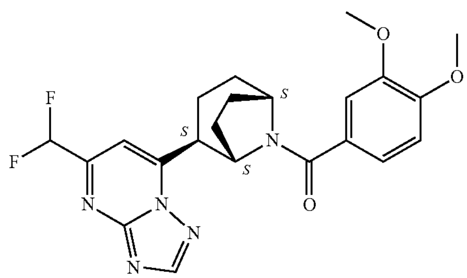 | I-25a | 68 |
| 365 | 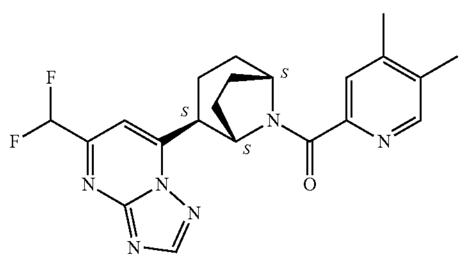 | I-25a | 13 |
| 366 | 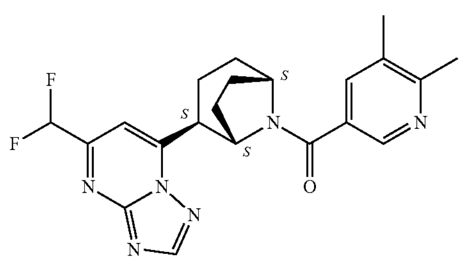 | I-25a | 59 |
| 367 | 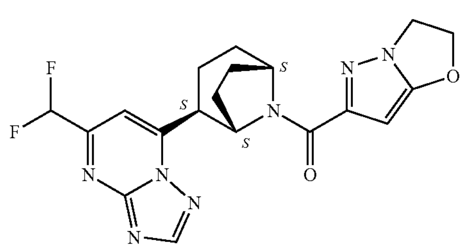 | I-25a | 68 |

TABLE 1-continued

| Co. No. | Structure | Prepared from | Yield (%) |
|---|---|---|---|
| 368 | 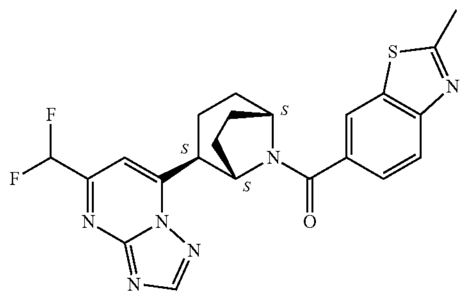 | I-25a | 50 |
| 369 | 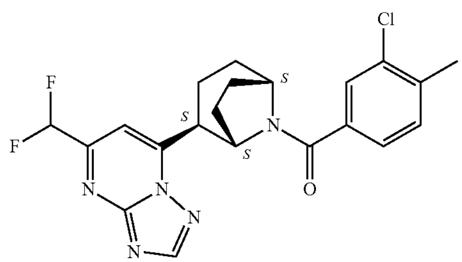 | I-25a | 26 |
| 370 | 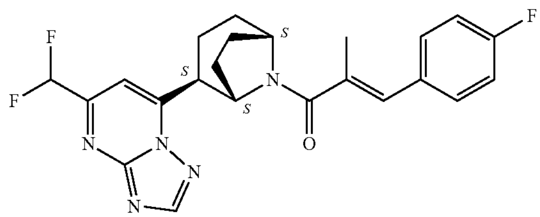 | I-25a | 60 |
| 371 | 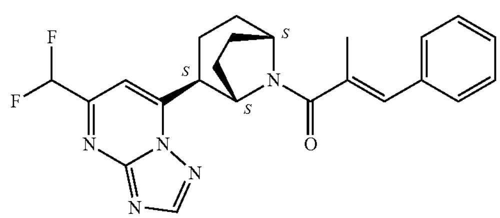 | I-25a | 34 |
| 372 | 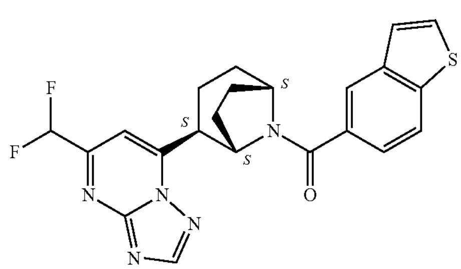 | I-25a | 37 |

TABLE 1-continued

| Co. No. | Structure | Prepared from | Yield (%) |
|---|---|---|---|
| 373 | 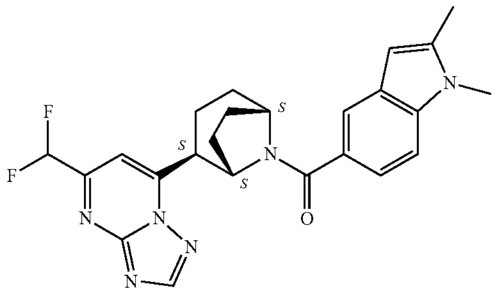 | I-25a | 63 |
| 374 | 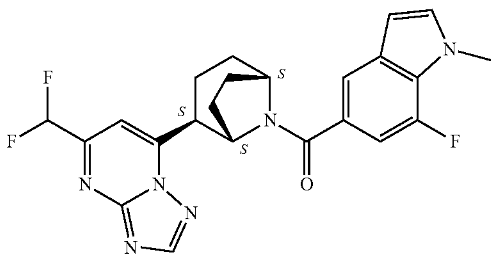 | I-25a | 53 |
| 375 | 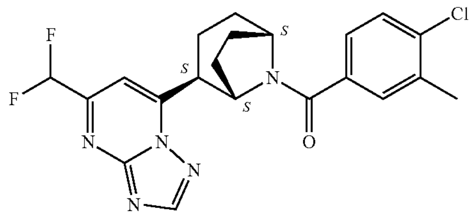 | I-25a | 71 |
| 376 | 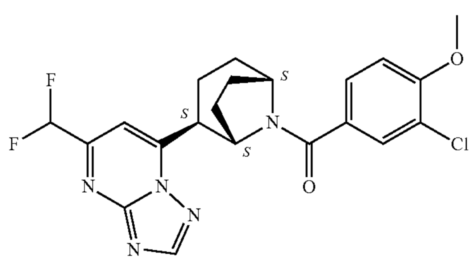 | I-25a | 57 |
| 377 | 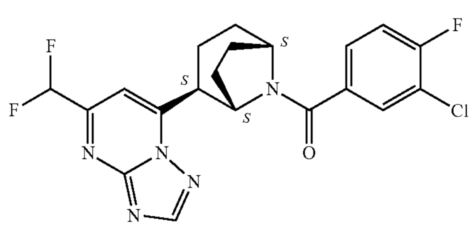 | I-25 | 41 |
| 378 | 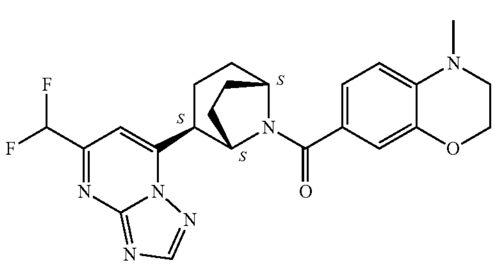 | I-25 | 58 |

TABLE 1-continued

| Co. No. | Structure | Prepared from | Yield (%) |
|---|---|---|---|
| 379 | 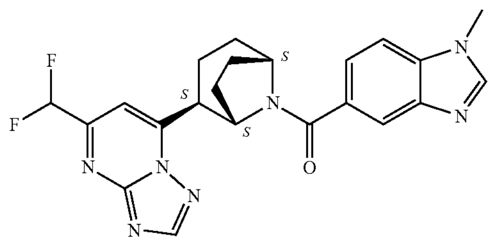 | I-25a | 63 |
| 380 | 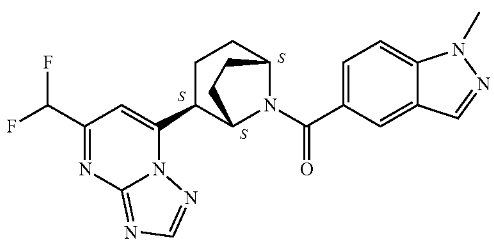 | I-25a | 68 |
| 381 | 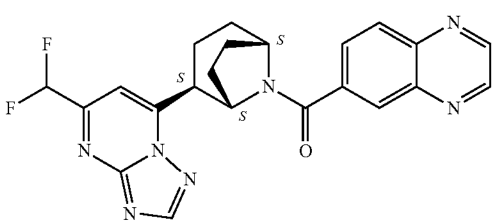 | I-25a | 59 |
| 382 | 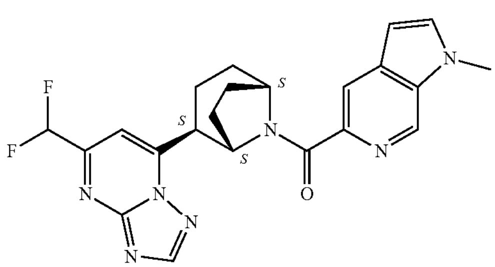 | I-25a | 54 |
| 383 | 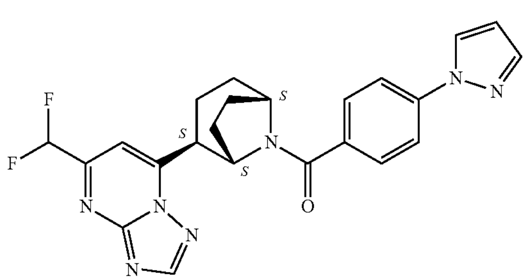 | I-25a | 55 |
| 384 | 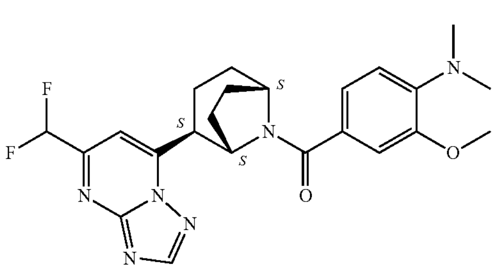 | I-25a | 22 |

TABLE 1-continued

| Co. No. | Structure | Prepared from | Yield (%) |
|---|---|---|---|
| 385 | 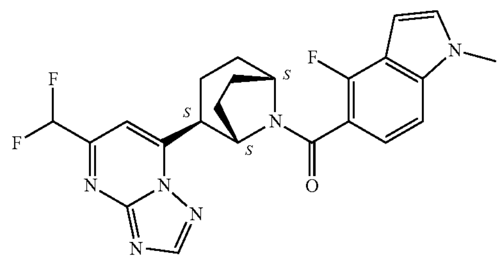 | I-25a | 72 |
| 403 | 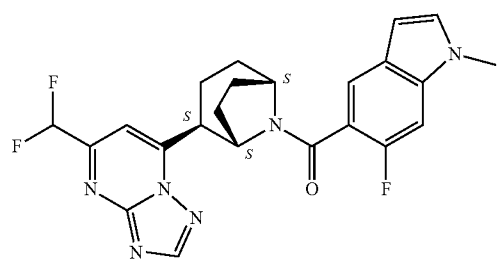 | I-25a | 57.7 |
| 404 | 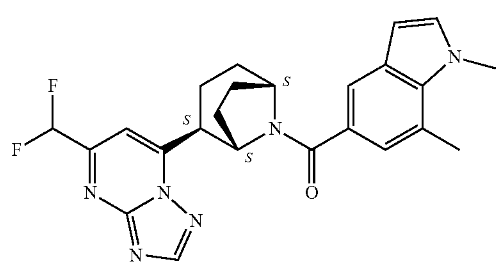 | I-25a | 67 |
| 405 | 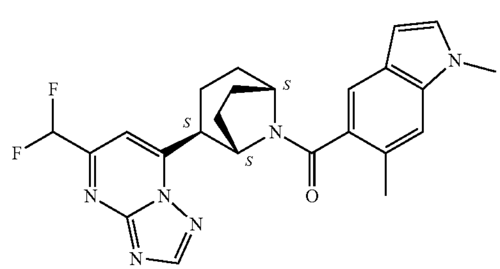 | I-25 | 68.7 |
| 406 | 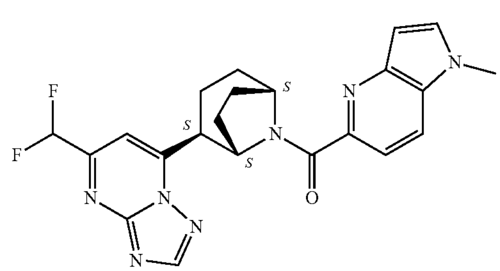 | I-25 | 71.5 |

Conversions and Synthesis of Final Compounds by Other Routes

Compound 386 and Compound 282/387

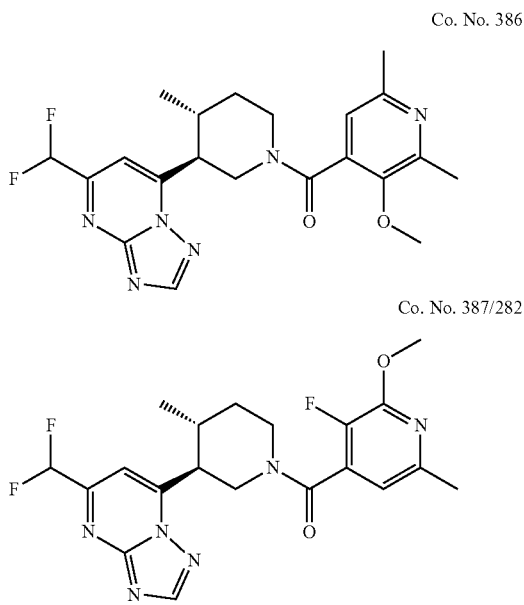

Co. No. 386

Co. No. 387/282

Step 1. Compound 388 and Compound 389

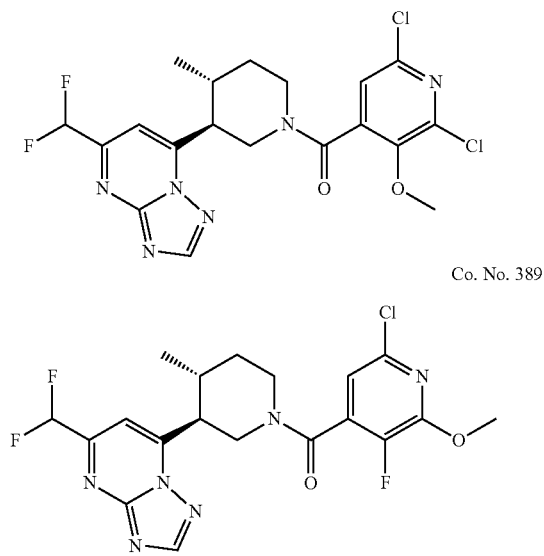

Co. No. 388

Co. No. 389

NaOMe (10.5 mL, 56.7 mmol, 30% in MeOH) was added to a solution of compound 71 (654 mg, 1.42 mmol) in MeOH (13 mL) and the resulting mixture was stirred at 0° C. for 1 h. The RM was quenched with a saturated aqueous NH$_4$Cl solution. The volatiles were removed under vacuo and the remaining aqueous residue partitioned with DCM. The aqueous layer was extracted with DCM (2×10 mL). The combined organic layers were dried over MgSO$_4$, filtered and evaporated in vacuo to afford a mixture of compounds 388 and 389 as a white foam (656 mg), which was used as such in the next step Step 2. Compound 386 and Compound 282/387

The mixture from the previous step was dissolved in 1,4-dioxane (10 mL) and the resulting solution was placed in a microwave tube and degassed for 5 minutes. K$_2$CO$_3$ (668 mg, 4.83 mmol) was then added, followed by trimethylboroxine (0.789 mL, 2.76 mmol, 3.5 M in THF) and Pd(PPh$_3$)$_4$ (159.5 mg, 0.14 mmol). The reaction mixture was then heated at 100° C. for 2.5 h under microwave irradiation. More trimethylboroxine (0.394 mL, 1.38 mmol, 3.5 M in THF) was added and the reaction mixture was heated at 100° C. under microwave irradiation for another hour. The solvent was evaporated in vacuo and the resulting residue was dissolved in a 1:1 mixture of DCM/water (40 mL). The biphasic mixture was separated and the aqueous phase was extracted with DCM (2×10 mL). The combined organic layers were dried over MgSO$_4$, filtered and concentrated under reduced pressure. The resulting residue (843 mg) was purified via flash column chromatography on silica gel, using as eluent a gradient DCM/MeOH, 100/0 to 97/3. The fractions corresponding to the title compounds were collected. One fraction was recrystallized from DIPE, to provide compound 282/387 (146 mg, 24%,). The second fraction was purified by prep HPLC using as stationary phase: RP XBridge Prep C18 OBD—10 μm, 30×150 mm and as mobile phase: 0.25% NH$_4$HCO$_3$ solution in water, CH$_3$CN to provide compound 386 as a white solid (82 mg, 13.8%).

Compound 390 (and Compound 391

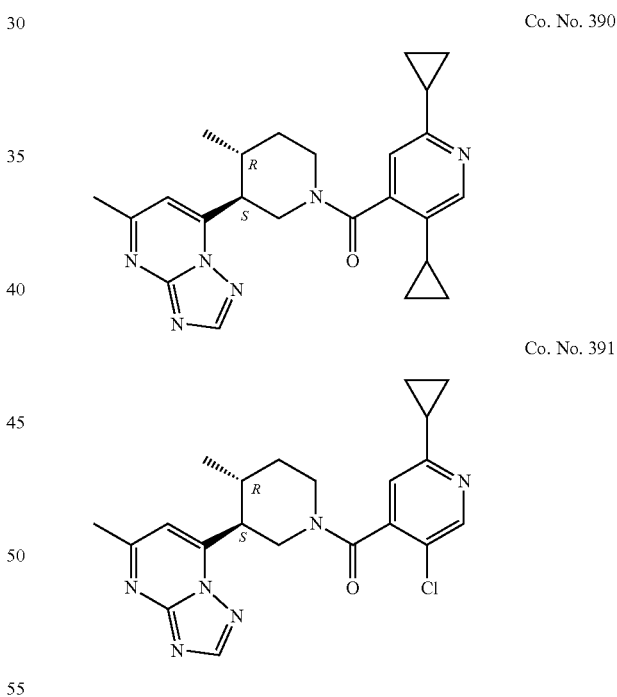

Co. No. 390

Co. No. 391

A pressure tube was charged with compound 271 (150 mg, 0.37 mmol), cyclopropylboronic acid (127.2 mg, 1.48 mmol) and toluene (3.0 mL) and this was degassed for 15 min before adding consecutively palladium(II) acetate (4.1 mg, 0.0185 mmol), tricyclohexylphosphine (10.4 mg, 0.037 mmol), distilled water (0.734 mL, 40.65 mmol) and potassium phosphate tribasic (235.7 mg, 1.11 mmol). The tube was capped and the ensuing RM was placed in an oil bath of 100° C. and stirred for 16 h. The resulting solution was cooled to RT and filtered through a Celite® pad, which was washed with toluene and EtOAc. The filtrate was evaporated to dryness under reduced pressure. The resulting residue was dissolved in EtOAc and washed with water and brine, then dried over MgSO$_4$, filtered and evaporated in vacuo. The resulting residue (155 mg) was purified via Prep HPLC, using as stationary phase: RP XBridge Prep C18 OBD—10 µm, 30×150 mm and mobile phase: 0.5% NH$_4$Ac solution in water+10% CH$_3$CN, MeOH, to provide compound 390 (18 mg, 11.7%) and compound 391 (66 mg, 43.4%), after trituration with heptane.

Compound 392

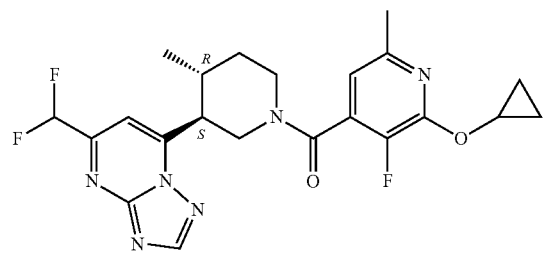

Step 1. Compound 393

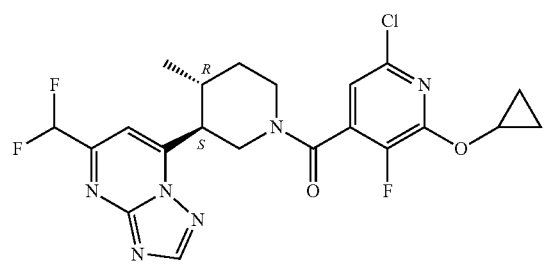

Cesium fluoride (577 mg, 3.8 mmol) was added to a solution of compound 71 (436 mg, 0.95 mmol) in DMF (7.35 mL) and the resulting mixture was stirred and degassed for 15 minutes. Cyclopropanol (0.072 mL, 1.14 mmol) was added and the RM was heated at 110° C. for 2 h under microwave irradiation. The solvent was removed in vacuo, then the resulting residue was dissolved in a 1:1 mixture of DCM/water (20 mL). The resulting biphasic mixture was separated, then the aqueous layer was extracted with DCM (2×10 mL). The combined organic layers were dried over MgSO$_4$, filtered and the solvent removed under reduced pressure. The resulting residue was purified by flash column chromatography on silica gel, using as eluent a gradient DCM/MeOH, 100/0 to 99/1, to provide compound 393 (308 mg) as an impure material, which was used as such in the next step.

STEP 2. COMPOUND 392 A solution of compound 393 (308 mg, 0.64 mmol) in 1,4-dioxane (4.6 mL) was degassed for 15 minutes, then K$_2$CO$_3$ (310 mg, 2.24 mmol), trimethylboroxine (0.550 mL, 1.92 mmol, 3.5 M in THF) and Pd(PPh$_3$)$_4$ (74.015 mg, 0.064 mmol) were sequentially added and the resulting mixture was heated at 100° C. for 2.5 h in a pressure tube. The solvent was removed in vacuo, and the resulting residue was partitioned between DCM (10 mL) and water (10 mL). The resulting biphasic mixture was separated and the aqueous layer extracted with DCM (3×10 mL). The combined organic layers were dried over MgSO$_4$, filtered and the solvent removed under reduced pressure. The resulting residue (340 mg) was purified via Prep HPLC, using as stationary phase: RP Vydac® Denali® C18—10 µm, 200 g, 5 cm I.D and mobile phase: MeOH, to give compound 392 (55 mg, 18.6%) as white crystals after recrystallization from DIPE.

Compound 394

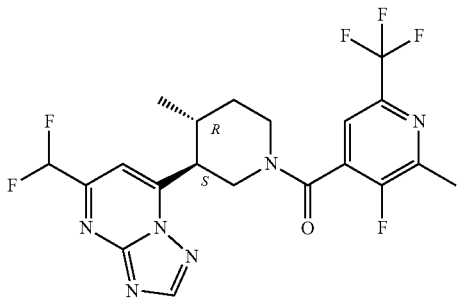

Step 1. Compound 395

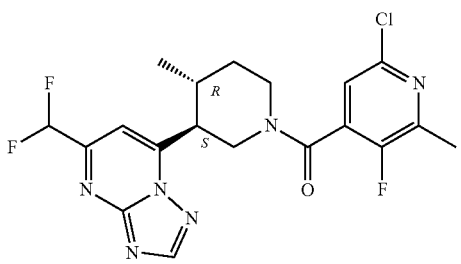

EDCI (993 mg, 5.2 mmol) and 6-chloro-3-fluoro-2-methyl-isonicotinic acid (intermediate 50, 492 mg, 2.6 mmol) were consecutively added to a stirred suspension of intermediate 9-b (750 mg, 2.47 mmol) in DCM (20 mL). DIPEA (1.78 mL, 10.4 mmol) was then added to the mixture, and the resulting yellow solution was stirred at RT for 5 h. The RM was quenched with an aqueous solution of NaOH (20 mL, 1 M). The aqueous layer was extracted with DCM (3×10 mL) and the combined organic layers were dried over MgSO$_4$, filtered and concentrated in vacuo. The resulting residue (1.5 g) was purified via flash column chromatography on silica gel, using as eluent a gradient DCM/MeOH, 100/0 to 99/1, to provide compound 395 (720 mg, 62%), as a white foam.

Step 2. Intermediate 56

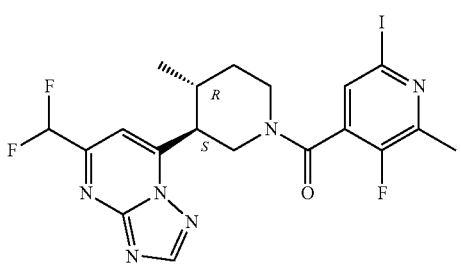

Iodotrimethylsilane (0.065 mL, 0.46 mmol) was added to a solution of compound 395 (200 mg, 0.46 mmol) in propionitrile (0.8 mL), under a nitrogen atmosphere. Sodium iodide (205 mg, 1.37 mmol) was then added and the resulting solution was heated to 80° C. After 5 h LCMS analysis showed only 15% conversion, therefore another portion of iodotrimethylsilane (0.065 mL, 0.456 mmol) was added and the RM was stirred at 80° C. for 22 h. After this time, another portion of iodotrimethylsilane (0.065 mL, 0.456 mmol) and sodium iodide (205 mg, 1.37 mmol) were added, and the RM stirred for 12 h. The solvent was removed in vacuo, then the resulting residue was partitioned between water and DCM. The resulting biphasic mixture was separated and the aqueous layer extracted with DCM (3×20 mL). The combined organic layers were dried over MgSO$_4$, filtered and the solvent removed in vacuo. The resulting residue (1.5 g) was purified by flash column chromatography on silica gel, using as eluent a gradient DCM/MeOH, 100/0 to 97.5/2.5, to give intermediate 56 (162 mg) as an impure material, used as such in the next step.

STEP 3. COMPOUND 394 Methyl 2,2-difluoro-2-(fluorosulfonyl)acetate (0.192 mL, 1.51 mmol) was added to a mixture of intermediate 56 (160 mg, 0.3 mmol) and copper iodide (75 mg, 0.39 mmol) in anhydrous DMF (0.958 mL) in a pressure tube. The resulting mixture was heated to 80° C. for 2 h in an oil bath. The RM was cooled to RT, then quenched with a saturated aqueous NH$_4$Cl solution. The resulting mixture was extracted with EtOAc (3×15 mL). The combined organic layers were dried over MgSO$_4$, filtered and the solvent removed in vacuo. The resulting residue was purified via flash column chromatography, using as eluent a gradient heptane/EtOAc, 100/0 to 60/40, to provide compound 394 (17.5 mg, 12%).

Compound 396

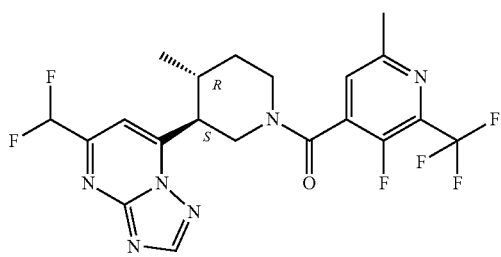

Step 1. Compound 397

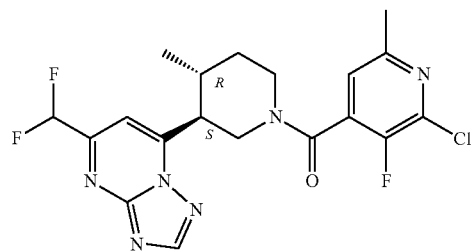

EDCI (934 mg, 4.87 mmol) and 2-chloro-3-fluoro-6-methyl isonicotinic acid (485 mg, 2.56 mmol) were added to a stirred suspension of intermediate 9-b (740.1 mg, 2.44 mmol) in DCM (18.5 mL). DIPEA (1.68 mL, 9.74 mmol) was added and the RM was stirred for 2 h at RT. The RM was quenched with an aqueous solution of NaOH (30 mL, 1 M). The aqueous layer was extracted with DCM (3×15 mL) and the combined organic layers were dried over MgSO$_4$, filtered and concentrated in vacuo. The resulting residue (1.5 g) was purified via flash column chromatography on silica gel, using as eluent a gradient DCM/MeOH, 100/0 to 99/1, to provide compound 397 (854 mg, 80%) as a white powder.

Step 2. Intermediate 57

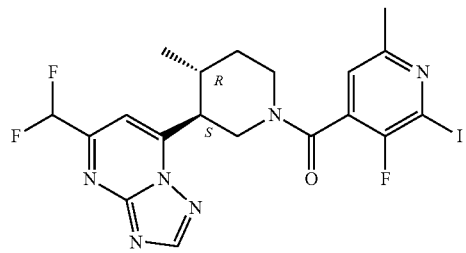

Iodotrimethylsilane (0.26 mL, 1.82 mmol) was added to a solution of compound 397 (400 mg, 0.91 mmol) in propionitrile (1.6 mL), under a nitrogen atmosphere. Sodium iodide (410 mg, 2.73 mmol) was then added and the resulting solution was heated to 80° C. for 1.5 h. The solvent was removed in vacuo, then the resulting residue was partitioned between water and EtOAc. The resulting biphasic mixture was separated and the aqueous layer extracted with EtOAc (3×20 mL). The combined organic layers were dried over MgSO$_4$, filtered and the solvent removed under reduced pressure. The resulting residue was purified by flash column chromatography on silica gel, using as eluent a gradient DCM/MeOH, 100/0 to 97.5/2.5, to give intermediate 57 (197 mg) as an impure material which was used as such in the next step.

STEP 3. COMPOUND 396 (Copper iodide (92 mg, 0.48 mmol) was added to a solution of intermediate 57 (197 mg, 0.37 mmol) in anhydrous DMF (1.18 mL) and the resulting mixture was degassed with nitrogen for 10 minutes. Methyl 2,2-difluoro-2-(fluorosulfonyl)acetate (0.236 mL, 1.86 mmol) was then added and the RM was stirred and heated at 80° C. for 2 h, after which time it was left to cool to RT overnight. The RM was quenched with a saturated aqueous NH$_4$Cl solution. The resulting mixture was extracted with EtOAc (6×20 mL). The combined organic layers were dried over MgSO$_4$, filtered and the solvent removed in vacuo. The resulting residue (550 mg) was purified via Prep HPLC using as stationary phase: RP XBridge Prep C18 OBD—10 µm, 50×150 mm and as mobile phase: CH$_3$CN, to provide compound 396 (7.4 mg, 4%).

Compound 398

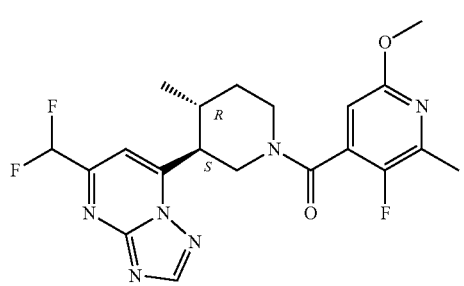

Step 1. Compound 399

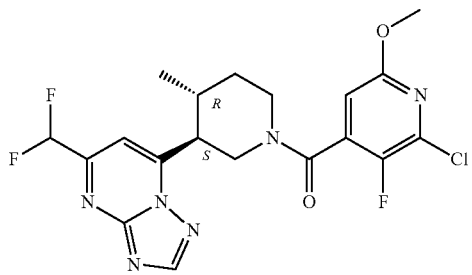

EDCI (320.5 mg, 1.67 mmol), followed by DIPEA (0.57 mL, 3.34 mmol) were added to a stirred solution of intermediate 9-b (242. mg, 0.8 mmol) and 2-chloro-3-fluoro-6-methoxy-isonicotinic acid (intermediate 53, 172 mg, 0.84 mmol) in DCM (6.35 mL). The RM was stirred at RT overnight. Another portion of EDCI (80 mg, 0.417 mmol) and DIPEA (0.1 mL, 0.75 g/mL, 0.58 mmol) were added and the RM stirred for 12 h, then it was quenched with an aqueous solution of NaOH (20 mL, 1 M). The aqueous layer was extracted with DCM (3×20 mL) and the combined organic layers were dried over MgSO$_4$, filtered and concentrated in vacuo. The resulting residue (600 mg) was purified via flash column chromatography on silica gel, using as eluent a gradient DCM/MeOH, 100/0 to 98.5/1.5, to provide compound 399 (136 mg, 80%) as a white foam.

Step 2. Compound 398

A solution of compound 399 (136 mg, 0.299 mmol) in 1,4-dioxane (2.17 mL) was degassed for 15 minutes in a pressure tube. K$_2$CO$_3$ (144.6 mg, 1.05 mmol), trimethylboroxine (0.256 mL, 0.897 mmol, 3.5 M in THF) and Pd(PPh$_3$)$_4$ (34.5 mg, 0.03 mmol) were sequentially added and the resulting mixture was heated at 100° C. for 2 h. The solvent was removed in vacuo, and the resulting residue was partitioned between DCM and water. The resulting biphasic mixture was separated and the aqueous layer extracted with DCM (3×15 mL). The combined organic layers were dried over MgSO$_4$, filtered and the solvent removed under reduced pressure. The resulting residue (220 mg) was purified via flash column chromatography on silica gel, using as eluent a gradient DCM/MeOH, 100/0 to 96/4 to provide compound 398 (88 mg, 68%).

Compound 400

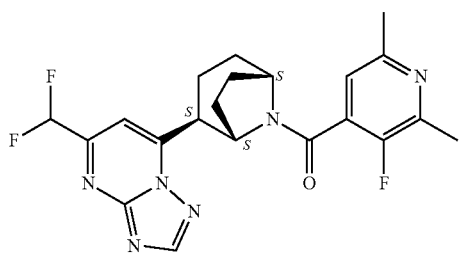

Step 1. Compound 401

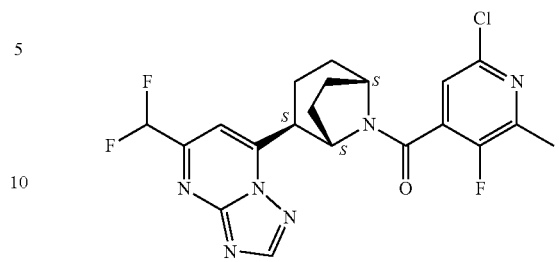

DIPEA (0.65 mL, 3.77 mmol) and HBTU (300 mg, 0.79 mmol) were added to a solution of 6-chloro-3-fluoro-2-methyl isonicotinic acid (intermediate 50, 150 mg, 0.79 mmol) in DCM (30 mL). Intermediate 25-a (238 mg, 0.75 mmol) was then added, and the RM stirred for ~1.5 h at RT. The RM was quenched with an aqueous solution of NaOH (1 mL, 1 M), and then filtered through an Extrelute® filter. The solvent was removed under reduced pressure. The resulting residue was purified via flash column chromatography on silica gel, using as eluent a gradient DCM/MeOH 100/0 to 98/2 to provide compound 401 (320.5 mg, 83%) as a colourless oil Step 2. Compound 400

A solution of compound 401 (320 mg, 0.71 mmol) in 1,4-dioxane (5.1 mL) was degassed for 15 minutes. K$_2$CO$_3$ (343.3 mg, 2.45 mmol), trimethylboroxine (0.608 mL, 2.129 mmol, 3.5 M in THF) and Pd(PPh$_3$)$_4$ (82.0 mg, 0.071 mmol) were sequentially added and the resulting mixture was heated at 100° C. for 2 h in a pressure tube. The solvent was removed in vacuo, and the resulting residue was partitioned between DCM (20 mL) and water (20 mL). The biphasic mixture was separated and the aqueous layer extracted with DCM (3×15 mL). The combined organic layers were dried over MgSO$_4$, filtered and solvent removed under reduced pressure. The resulting residue was purified via flash column chromatography on silica gel, using as eluent a gradient DCM/MeOH 100/0 to 95/5. This provided a mixture of endo/exo isomers (230 mg) which were separated via prep HPLC, using as stationary phase: RP XBridge® Prep C18 OBD—10 μm, 50×150 mm and mobile phase:MeOH. The fractions containing the product were evaporated and the resulting residue was recrystallised from Et$_2$O, to provide compound 400 (57 mg, 18.6%)

Compound 402

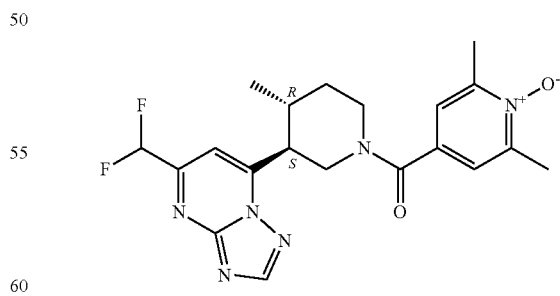

mCPBA (307.825 mg, 1.25 mmol) was added to a solution of compound 1 from WO2017/076900 (250 mg, 0.624 mmol) in DCM (1.6 mL), at 10° C., and the resulting mixture was stirred in an Easymax® for 3 d. After this time, the RM was quenched with a saturated aqueous NaHCO$_3$ solution (1.5 mL). The biphasic mixture was separated and the aqueous layer was extracted with DCM (3×5 mL). The combined organic layers were dried over MgSO$_4$, filtered and concentrated in vacuo. The resulting residue was purified via flash column chromatography on silica gel, using as eluent a gradient DCM/MeOH, 100/0 to 96/4 to give compound 402 (250 mg, 96% as a white powder.

Analytical Part

Melting Points

Values are either peak values or melt ranges, and are obtained with experimental uncertainties that are commonly associated with this analytical method.

The melting point was determined with a DSC823e (Mettler-Toledo). The melting point was measured with a temperature gradient of 10° C./min. Maximum temperature was 300° C.

TABLE 2

| Co. No. | MP (° C.) |
| --- | --- |
| 22 | 217.82 |
| 23 | 169.13 |
| 25a | 240.33 |
| 25b | 239.55 |
| 29 | 176.52 |
| 31 | 190.16 |
| 40 | 181.11 |
| 49 | 263.81 |
| 52 | 228.39 |
| 69 | 209.73 |
| 72 | 177.60 |
| 77 | 177.37 |
| 79 | 227.10 |
| 93 | 201.12 |
| 102 | 215.44 |
| 106 | 273.02 |
| 108 | 151.39 |
| 111 | 188.75 |
| 116 | 192.09 |
| 118 | 179.82 |
| 120 | 173.99 |
| 122 | 160.20 |
| 123 | 203.87 |
| 126 | 114.32 |
| 127 | 139.13 |
| 129 | 140.78 |
| 130 | 193.85 |
| 131 | 224.39 |
| 132 | 116.57 |
| 133 | 152.33 |
| 137 | 229.91 |
| 189 | 152.03 |
| 191 | 162.07 |
| 192 | 110.16 |
| 194 | 167.52 |
| 201 | 140.14 |
| 202 | 78.65 |
| 203 | 204.03 |
| 204 | 205.47 |
| 206 | 145.73 |
| 207 | 173.79 |
| 209 | 145.19 |
| 210 | 195.81 |
| 211 | 117.50 |
| 213 | 169.70 |
| 214 | 203.97 |
| 220 | 155.37 |
| 221 | 122.37 |
| 224 | 153.14 |
| 225 | 178.64 |
| 228 | 178.21 |
| 270 | 213.25 |
| 271 | 247.40 |
| 281 | 114.59 |
| 282/387 | 193.33 |
| 295 | 178.8 |
| 336 | 255.11 |
| 310 | 240.9 |

TABLE 2-continued

| Co. No. | MP (° C.) |
| --- | --- |
| 321 | 137.5 |
| 322 | 180.27 |
| 324 | 204.06 |
| 325 | 226.36 |
| 327 | 194.86 |
| 328 | 247.48 |
| 329 | 227.79 |
| 331 | 193.87 |
| 332 | 183.18 |
| 333 | 291.55 |
| 334 | 239.87 |
| 336 | 255.11 |
| 355 | 146.08 |
| 356 | 187.93 |
| 360 | 264.8 |
| 363 | 221.75 |
| 353 | 230.66 |
| 375 | 171.51 |
| 376 | 175.71 |
| 377 | 183.67 |
| 385 | 220.89 |

LC/MS Methods

The High Performance Liquid Chromatography (HPLC) measurement was performed using a LC pump, a diode-array (DAD) or a UV detector and a column as specified in the respective methods. If necessary, additional detectors were included (see table of methods below).

Flow from the column was brought to the Mass Spectrometer (MS) which was configured with an atmospheric pressure ion source. It is within the knowledge of the skilled person to set the tune parameters (e.g. scanning range, dwell time . . . ) in order to obtain ions allowing the identification of the compound's nominal monoisotopic molecular weight (MW). Data acquisition was performed with appropriate software.

Compounds are described by their experimental retention times ($R_t$) and ions. If not specified differently in the table of data, the reported molecular ion corresponds to the $[M+H]^+$ (protonated molecule) and/or $[M-H]^-$ (deprotonated molecule). In case the compound was not directly ionizable the type of adduct is specified (i.e. $[M+NH_4]^+$, $[M+HCOO]^-$, etc. . . . ). For molecules with multiple isotopic patterns (Br, Cl), the reported value is the one obtained for the lowest isotope mass. All results were obtained with experimental uncertainties that are commonly associated with the method used. Hereinafter, "SQD" means Single Quadrupole Detector, "MSD" Mass Selective Detector, "RT" room temperature, "BEH" bridged ethylsiloxane/silica hybrid, "DAD" Diode Array Detector, "HSS" High Strength silica.

TABLE 3A

LCMS Method codes (Flow expressed in mL/min; column temperature (T) in ° C.; Run time in minutes)

| METHOD CODE | INSTRUMENT | COLUMN | MOBILE PHASE | GRADIENT | FLOW COL T | RUN TIME (MIN) |
|---|---|---|---|---|---|---|
| A | Waters: Acquity ® UPLC ®-DAD-SQD | Waters: BEH C18 (1.7 μm, 2.1 * 50 mm) | A: 10 mM CH3COONH4 in 95% H2O + 5% CH3CN B: CH3CN | From 95% A to 5% A in 1.3 min, held for 0.7 min. | 0.8 55 | 2 |
| B | Waters: Acquity ® UPLC ®-DAD and SQD | Waters: BEH C18 (1.7 μm, 2.1 * 50 mm) | A: 25 mM CH3COONH4 in 95% H2O + 5% CH3CN B: CH3CN | From 95% A to 5% A in 1.3 min, held for 0.7 min. | 0.8 55 | 2 |
| C | Waters: Acquity ® UPLC ®-DAD and SQD | Waters: HSS T3 (1.8 μm, 2.1 * 100 mm) | A: 10 mM CH3COONH4 in 95% H2O + 5% CH3CN B: CH3CN | From 100% A to 5% A in 2.10 min, to 0% A in 0.90 min, to 5% A in 0.5 min | 0.7 55 | 3.5 |
| D | Waters: Alliance ®-DAD-ZQ and ELSD 2000 Alltech | Xterra MS C18 column (3.5 μm, 4.6 × 100 mm) | A: 10 mM CH3COONH4 in 95% H2O + 5% CH3CN B: CH3CN C: CH3OH D: (40% CH3CN and 40% CH3OH and 20% H2O with 0.25% CH3COOH | From 100% A to 1% A, 49% B and 50% C in 6.5 min, to 1% A and 99% B in 0.5 min, to 100% D in 1 min held for 1.0 min to 100% A in 0.5 min and held for 1.5 min. | 1.6 40 | 11 |
| E | Waters: Acquity ® UPLC ®-DAD-ELSD and SQD | Waters: BEH C18 (1.7 μm, 2.1 * 50 mm) | A: 0.1% HCOOH + 5% CH3OH in H2O B: CH3CN | From 95% A to 0% A in 2.50 min, to 5% A in 0.5 min | 0.7 55 | 3 |

TABLE 3B

Analytical LCMS DATA - $R_t$ means retention time (in minutes), $[M + H]^+$ means the protonated mass of the compound, method refers to the method used for (LC)MS analysis.

| Co. No. | Rt (min) | $[M + H]^+$ | $[M + H]^-$ | Method |
|---|---|---|---|---|
| 1a | 1.33 | 365 | 363 | C |
| 1b | 1.33 | 365 | 363 | C |
| 2a | 1.38 | 393 | 391 | C |
| 2b | 1.38 | 393 | 391 | C |
| 3a | 1.43 | 365 | 363 | C |
| 3b | 1.43 | 365 | 363 | C |
| 4 | 0.82 | 419 | 417 | A |
| 5 | 0.87 | 390 | 388 | A |
| 6 | 0.8 | 376 | 374 | A |
| 7 | 0.94 | 390 | 388 | A |
| 8 | 0.87 | 376 | 374 | A |
| 9 | 0.96 | 382 | 380 | A |
| 10 | 0.99 | 443 | 441 | A |
| 11 | 0.76 | 389 | 387 | A |
| 12 | 0.84 | 425 | 423 | A |
| 13 | 0.7 | 456 | 514 $[M + CH_3COO]^-$ | A |
| 14 | 0.66 | 339 | 337 | A |
| 15 | 0.69 | 371 | 369 | A |
| 16 | 0.85 | 370 | 428 | A |
| 17 | 0.82 | 405 | 403 | A |
| 18 | 0.72 | 385 | 383 | A |
| 19 | 0.68 | 391 | 389 | A |
| 20 | 0.84 | 444 | 442 | A |
| 21 | 0.82 | 377 | 375 | A |
| 22 | 0.84 | 401 | 459 $[M + CH_3COO]^-$ | A |
| 23 | 1.57 | 391 | 389 | C |
| 24a | 1.85 | 445 | 503 $[M + CH_3COO]^-$ | C |
| 24b | 1.86 | 445 | 443 | C |
| 25a | 1.54 | 441 | 439 | C |
| 25b | 1.55 | 441 | 439 | C |
| 26a | 1.46 | 376 | 374 | C |
| 26b | 1.46 | 376 | 374 | C |
| 27 | 1.65 | 421 | 419 | C |
| 28 | 1.73 | 439 | 437 | C |
| 29 | 0.72 | 413 | 411 | A |
| 30 | 0.72 | 413 | 411 | A |
| 31 | 0.72 | 413 | 411 | A |
| 32 | 0.74 | 401 | 399 | A |
| 33 | 1.66 | 447 | 445 | C |
| 34 | 1.66 | 447 | 445 | C |
| 35 | 1.59 | 492 | 490 | C |
| 36 | 0.85 | 421 | 419 | A |
| 37 | 1.68 | 435 | 433 | C |

TABLE 3B-continued

Analytical LCMS DATA - $R_t$ means retention time (in minutes), [M + H]$^+$ means the protonated mass of the compound, method refers to the method used for (LC)MS analysis.

| Co. No. | Rt (min) | [M + H]$^+$ | [M + H]$^-$ | Method |
|---|---|---|---|---|
| 38 | 1.36 | 419 | 417 | C |
| 39 | 1.84 | 475 | 473 | C |
| 40 | 0.69 | 412 | 410 | A |
| 41 | 0.85 | 455 | 453 | A |
| 42 | 1.6 | 407 | 405 | C |
| 43 | 0.9 | 441 | 439 | A |
| 44 | 0.96 | 443 | 441 | A |
| 45 | 0.98 | 443 | 441 | A |
| 46 | 0.98 | 443 | 441 | A |
| 47 | 1.79 | 413 | 411 | C |
| 48 | 1.03 | 426 | 424 | A |
| 49 | 0.88 | 401 | 399 | A |
| 50 | 1.58 | 427 | 425 | C |
| 51 | 0.81 | 421 | 419 | A |
| 52 | 0.9 | 455 | 453 | A |
| 53 | 0.82 | 417 | 415 | A |
| 54 | 0.87 | 425 | 423 | A |
| 55 | 1.7 | 425 | 423 | C |
| 56 | 1.64 | 434 | 432 | C |
| 57 | 1.45 | 376 | 374 | C |
| 58 | 1.31 | 376 | 374 | C |
| 59 | 1.8 | 480 | 478 | C |
| 60 | 1.74 | 451 | 449 | C |
| 61 | 0.74 | 404 | 402 | A |
| 62 | 1.50 | 417 | 415 | C |
| 63 | 1.88 | 452 | 450 | C |
| 64 | 1.8 | 441 | 439 | C |
| 65 | 1.84 | 406 | 404 | C |
| 66 | 1.53 | 403 | 401 | C |
| 67 | 1.53 | 375 | 373 | C |
| 68 | 0.78 | 405 | 403 | A |
| 69 | 0.96 | 412 | 410 | A |
| 70 | 0.81 | 419 | 417 | A |
| 71 | 0.99 | 459 | 457 | A |
| 72 | 2.02 | 446 | 444 | C |
| 73 | 0.95 | 443 | 441 | A |
| 74 | 1.97 | 448 | 446 | C |
| 75 | 1.97 | 448 | 506 [M + CH$_3$COO]$^-$ | C |
| 76 | 1.1 | 434 | 432 | A |
| 77 | 0.97 | 430 | 428 | A |
| 78 | 0.94 | 425 | 423 | A |
| 79 | 0.82 | 432 | 430 | A |
| 80 | 1.6 | 415 | 413 | C |
| 81 | 1.57 | 419 | 417 | C |
| 82 | 1.58 | 419 | 417 | C |
| 83 | 0.9 | 421 | 419 | A |
| 84 | 0.78 | 405 | 403 | A |
| 85 | 1.63 | 401 | 399 | C |
| 86 | 1.5 | 417 | 415 | C |
| 87 | 0.68 | 363 | 361 | A |
| 88 | 0.71 | 444 | 442 | A |
| 89 | 0.91 | 457 | 455 | A |
| 90 | 0.9 | 411 | 409 | A |
| 91 | 1.05 | 478 | 476 | A |
| 92 | 1.85 | 426 | 424 | C |
| 93 | 1.77 | 427 | 425 | C |
| 94 | 1.99 | 479 | 477 | C |
| 95 | 1.37 | 405 | 403 | C |
| 96 | 1.77 | 428 | 426 | C |
| 97 | 0.88 | 412 | 470 [M + CH$_3$COO]$^-$ | A |
| 98 | 1.7 | 442 | 440 | C |
| 99 | 1.2 | 376 | 374 | C |
| 100 | 1.72 | 443 | 441 | C |
| 101 | 0.99 | 429 | 427 | A |
| 102 | 1.01 | 420 | 418 | A |
| 103 | 1.03 | 430 | 428 | A |
| 104 | 1.52 | 413 | 411 | C |
| 105 | 1.86 | 442 | 440 | C |
| 106 | 1.67 | 411 | 409 | C |
| 107 | 1.04 | 445 | 443 | A |
| 108 | 0.95 | 437 | 435 | A |
| 109 | 1.9 | 398 | 396 | C |
| 110 | 0.86 | 417 | 415 | A |
| 111 | 1.04 | 440 | 438 | A |
| 112 | 1.67 | 429 | 427 | C |
| 113 | 1.03 | 443 | 441 | A |
| 114 | 1 | 425 | 423 | A |
| 115 | 1.02 | 418 | 416 | A |
| 116 | 0.76 | 413 | 411 | A |
| 117 | 1.79 | 382 | 380 | C |
| 118 | 1.01 | 442 | 440 | A |
| 119 | 1.96 | 442 | 440 | C |
| 120 | 1.78 | 431 | 429 | C |
| 121 | 1 | 472 | 470 | A |
| 122 | 2 | 445 | 443 | C |
| 123 | 1 | 400 | 398 | A |
| 124 | 0.78 | 415 | 413 | A |
| 125 | 1.78 | 453 | 451 | C |
| 126 | 0.95 | 392 | 390 | A |
| 127 | 1.61 | 427 | 425 | C |
| 128 | 1.8 | 438 | 436 | C |
| 129 | 1.95 | 438 | 436 | C |
| 130 | 0.94 | 436 | 434 | A |
| 131 | 0.88 | 411 | 409 | A |
| 132 | 0.93 | 455 | 453 | A |
| 133 | 0.93 | 468 | 466 | A |
| 134 | 1.78 | 437 | 435 | C |
| 135 | 1.03 | 430 | 428 | A |
| 136 | 1.99 | 418 | 416 | C |
| 137 | 0.93 | 401 | 399 | A |
| 138 | 0.88 | 416 | 474 [M + CH$_3$COO]$^-$ | A |
| 139 | 1.43 | 376 | 374 | C |
| 140 | 1.98 | 438 | 436 | C |
| 141 | 0.81 | 402 | 400 | A |
| 142 | 1.32 | 388 | 386 | C |
| 143 | 0.77 | 401 |  | A |
| 144 | 1.94 | 472 | 470 | C |
| 145 | 0.89 | 430 | 428 | A |
| 146 | 1.32 | 439 | 437 | C |
| 147 | 1.88 | 426 | 424 | C |
| 148 | 1.89 | 458 | 456 | C |
| 149 | 1.72 | 408 | 406 | C |
| 150 | 1.38 | 388 | 386 | C |
| 151 | 1.41 | 438 | 436 | C |
| 152 | 1.56 | 377 | 375 | C |
| 153 | 1.70 | 451 | 449 | C |
| 154 | 1.67 | 407 | 405 | C |
| 155 | 1.47 | 391 | 389 | C |
| 156 | 1.46 | 377 | 375 | C |
| 157 | 1.60 | 377 | 375 | C |
| 158 | 1.33 | 394 | 392 | C |
| 159 | 1.65 | 421 | 419 | C |
| 160 | 1.57 | 377 | 375 | C |
| 161 | 1.76 | 445 | 443 | C |
| 162 | 1.36 | 388 | 386 | C |
| 163 | 1.52 | 398 | 396 | C |
| 164 | 1.32 | 376 | 374 | C |
| 165 | 2.04 | 459 | 456 | C |
| 166 | 1.43 | 404 | 402 | C |
| 167 | 1.73 | 441 | 439 | C |
| 168 | 0.75 | 406 | 404 | A |
| 169 | 1.98 | 474 | 472 | C |
| 170 | 1.83 | 461 | 459 | C |
| 171 | 1.96 | 459 | 457 | C |
| 172 | 1.86 | 455 | 453 | C |
| 173 | 1.35 | 423 | 421 | C |
| 174 | 1.58 | 417 | 415 | C |
| 175 | 1.77 | 439 | 437 | C |
| 176 | 1.52 | 413 | 411 | C |
| 177 | 1.36 | 376 | 374 | C |
| 178 | 1.45 | 426 | 424 | C |
| 179 | 1.46 | 416 | 414 | C |
| 180 | 1.88 | 412 | 410 | C |
| 181 | 1.32 | 388 | 386 | C |
| 182 | 1.73 | 459 | 457 | C |

TABLE 3B-continued

Analytical LCMS DATA - $R_t$ means retention time (in minutes), [M + H]$^+$ means the protonated mass of the compound, method refers to the method used for (LC)MS analysis.

| Co. No. | Rt (min) | [M + H]$^+$ | [M + H]$^-$ | Method |
|---|---|---|---|---|
| 183 | 1.54 | 413 | 411 | C |
| 184 | 1.50 | 377 | 375 | C |
| 185 | 0.83 | 423 | 421 | A |
| 186 | 0.76 | 406 | 404 | A |
| 187 | 1.79 | 413 | 411 | C |
| 188 | 1.62 | 427 | 425 | C |
| 189 | 1.00 | 422 | 420 | A |
| 190 | 0.87 | 415 | 413 | A |
| 191 | 0.93 | 440 | 438 | A |
| 192 | 0.96 | 456 | 454 | A |
| 193 | 0.96 | 456 | 454 | A |
| 194 | 1.93 | 458 | 456 | C |
| 195 | 0.88 | 420 | 418 | A |
| 196 | 0.81 | 403 | 401 | A |
| 197 | 0.86 | 397 | 395 | A |
| 198 | 0.69 | 390 | 388 | A |
| 199 | 0.66 | 405 | 405 | B |
| 200 | 0.88 | 457 | | A |
| 201 | 0.92 | 412 | 470 [M + CH$_3$COO]$^-$ | A |
| 202 | 0.76 | 362 | | A |
| 203 | 0.76 | 455 | 455 | A |
| 204 | 0.76 | 455 | | A |
| 205 | 0.89 | 412 | | A |
| 206 | 1.00 | 400 | | A |
| 207 | 0.65 | 390 | 448 [M + CH$_3$COO]$^-$ | A |
| 208 | 0.93 | 392 | | A |
| 209 | 0.91 | 412 | | A |
| 210 | 0.75 | 401 | | A |
| 211 | 0.75 | 401 | | A |
| 212 | 0.69 | 412 | | A |
| 213 | 0.91 | 392 | 390 | A |
| 214 | 0.99 | 400 | 398 | A |
| 215 | 0.92 | 457 | | A |
| 216 | 1.20 | 376 | 374 | C |
| 217 | 1.79 | 382 | 380 | C |
| 218 | 1.90 | 398 | 396 | C |
| 219 | 0.94 | 443 | 441 | A |
| 220 (.HCl) | 0.78 | 401 | | A |
| 221 | 0.89 | 412 | 410 | A |
| 222 | 0.90 | 405 | 403 | A |
| 223 | 0.94 | 405 | 403 | A |
| 224 | 0.79 | 395 | 393 | A |
| 225 | 1.52 | 385 | 383 | C |
| 226 | 1.11 | 452 | 450 | A |
| 227 | 1.60 | 429 | 427 | C |
| 228 | 0.92 | 429 | 427 | A |
| 229 | 0.87 | 387 | 385 | A |
| 230 | 1.37 | 405 | 403 | C |
| 231 | 0.64 | 413 | 411 | A |
| 232 | 1.46 | 388 | 386 | C |
| 233 | 1.37 | 388 | 386 | C |
| 234 | 1.51 | 398 | 396 | C |
| 235 | 1.53 | 407 | 405 | C |
| 236 | 1.25 | 390 | 388 | C |
| 237 | 1.54 | 408 | 406 | C |
| 238 | 1.62 | 432 | 430 | C |
| 239 | 1.63 | 441 | 439 | C |
| 240 | 1.38 | 362 | 360 | C |
| 241 | 1.93 | 474 | 472 | C |
| 242 | 1.85 | 475 | 473 | C |
| 243 | 1.49 | 363 | 361 | C |
| 244 | 1.36 | 388 | 386 | C |
| 245 | 1.81 | 426 | 424 | C |
| 246 | 1.65 | 431 | 429 | C |
| 247 | 1.90 | 470 | 468 | C |
| 248 | 1.28 | 374 | 372 | C |
| 249 | 1.32 | 374 | 372 | C |
| 250 | 1.53 | 391 | 389 | C |
| 251 | 1.55 | 391 | 389 | C |
| 252 | 1.57 | 391 | 389 | C |
| 253 | 1.65 | 441 | 439 | C |
| 254 | 1.53 | 391 | 389 | C |
| 255 | 1.51 | 406 | 404 | C |
| 256 | 1.34 | 374 | 372 | C |
| 257 | 1.38 | 374 | 372 | C |
| 258 | 1.93 | 419 | 417 | C |
| 259 | 2.35 | 484 | 482 | C |
| 260 | 1.51 | 377 | 375 | C |
| 261 | 1.36 | 389 | 387 | C |
| 262 | 1.51 | 391 | 389 | C |
| 263 | 1.78 | 455 | 453 | C |
| 264 | 1.54 | 407 | 405 | C |
| 265 | 1.65 | 427 | 425 | C |
| 266 | 2.41 | 485 | 483 | C |
| 267 | 0.91 | 456 | 454 | A |
| 268 | 1.67 | 441 | 439 | C |
| 269 | 0.90 | 431 | 429 | A |
| 270 | 0.85 | 439 | 437 | A |
| 271 | 0.78 | 405 | 403 | A |
| 272 | 0.73 | 417 | 415 | A |
| 273 | 1.98 | 438 | 436 | C |
| 274 | 1.73 | 439 | 437 | C |
| 275 | 1.73 | 417 | 415 | C |
| 276 | 1.06 | 461 | 459 | A |
| 277 | 0.97 | 449 | 507 [M + CH$_3$COO]$^-$ | A |
| 278 | 1.01 | 445 | 443 | A |
| 279 | 0.97 | 445 | 443 | A |
| 280 | 1.16 | 483 | 481 | A |
| 281 | 1.89 | 453 | 451 | C |
| 282/387 | 0.93 | 435 | 433 | A |
| 283 | 1.75 | 445 | 443 | C |
| 284 | 5.27 | 433 | 431 | A |
| 285 | 1.76 | 467 | 465 | C |
| 286 | 1.76 | 467 | 465 | C |
| 287 | 1.79 | 453 | 451 | C |
| 288 | 0.78 | 431 | 429 | A |
| 289 | 1.01 | 425 | 423 | A |
| 290 | 0.87 | 429 | 427 | A |
| 291 | 0.92 | 423 | 421 | A |
| 292 | 1.83 | 442 | 442 440 | C |
| 293 | 0.95 | 465 | 463 | A |
| 294 | 0.82 | 449 | 447 | A |
| 295 | 0.9 | 437 | 435 | A |
| 296 | 0.94 | 468 | 466 | A |
| 297 | 0.91 | 437 | 435 | A |
| 298 | 0.86 | 463 | 461 | A |
| 299 | 0.92 | 437 | 435 | A |
| 300 | 0.98 | 437 | 435 | A |
| 301 | 0.89 | 445 | 443 | A |
| 302 | 0.98 | 412 | 410 | A |
| 303 | 0.79 | 439 | 437 | A |
| 304 | 0.92 | 425 | 423 | A |
| 305 | 0.76 | 439 | 437 | A |
| 306 | 0.79 | 439 | 437 | A |
| 307 | 0.99 | 437 | 435 | A |
| 308 | 0.87 | 435 | 433 | A |
| 309 | 0.81 | 453 | 451 | A |
| 310 | 0.87 | 469 | 467 | A |
| 311 | 0.75 | 435 | 433 | A |
| 312 | 0.82 | 453 | 431 | A |
| 313 | 0.8 | 435 | 433 | A |
| 314 | 0.75 | 435 | 433 | A |
| 315 | 0.76 | 435 | 433 | A |
| 316 | 1.08 | 435 | — | E |
| 317 | 0.76 | 435 | 433 | A |
| 318 | 1.15 | 435 | — | E |
| 319 | 0.97 | 434 | 432 | A |
| 320 | 0.94 | 434 | 432 | A |
| 321 | 0.88 | 437 | 435 | A |
| 322 | 0.75 | 423 | 421 | A |
| 323 | 0.87 | 423 | 421 | A |
| 324 | 0.81 | 423 | 481 [M + CH$_3$COO]$^-$ | A |
| 325 | 0.82 | 441 | 439 | A |

TABLE 3B-continued

Analytical LCMS DATA - $R_t$ means retention time (in minutes), [M + H]$^+$ means the protonated mass of the compound, method refers to the method used for (LC)MS analysis.

| Co. No. | Rt (min) | [M + H]$^+$ | [M + H]$^-$ | Method |
|---|---|---|---|---|
| 326 | 0.75 | 423 | 421 | A |
| 327 | 0.9 | 425 | 423 | A |
| 328 | 0.91 | 425 | 483 [M + CH$_3$COO$^-$] | A |
| 329 | 0.88 | 457 | 515 [M + CH$_3$COO$^-$] | A |
| 331 | 0.98 | 422 | 480 [M + CH$_3$COO$^-$] | A |
| 332 | 0.83 | 441 | 499 [M + CH$_3$COO$^-$] | A |
| 333 | 1.01 | 452 | 450 | A |
| 334 | 1.03 | 440 | 438 | A |
| 335 | 1.7 | 458 | 456 | C |
| 336 | 0.93 | 448 | 446 | A |
| 337 | 0.9 | 420 | 418 | A |
| 338 | 1.00 | 470 | 468 | A |
| 339 | 0.99 | 432 | 430 | A |
| 340 | 0.98 | 452 | 450 | A |
| 341 | 0.9 | 420 | 418 | A |
| 342 | 1.02 | 486 | 484 | A |
| 343 | 1.72 | 432 | 430 | C |
| 344 | 1.87 | 434 | 432 | C |
| 345 | 1.8 | 935 [2M + 1] | 466 | C |
| 346 | 1 | 430 | 428 | A |
| 347 | 0.9 | 404 | 402 | A |
| 348 | 1.04 | 430 | 428 | A |
| 349 | 0.91 | 404 | 402 | A |
| 350 | 0.98 | 464 | 462 | A |
| 351 | 0.97 | 424 | 422 | A |
| 352 | 1.02 | 490 | 488 | A |
| 353 | 1.74 | 424 | 422 | C |
| 354 | 0.83 | 388 | 386 | A |
| 355 | 1.96 | 465 | 463 | C |
| 356 | 1.01 | 452 | 450 | A |
| 357 | 1.91 | 470 | 468 | |
| 358 | 1.83 | 418 | 416 | C |
| 359 | 1.81 | 450 | 448 | C |
| 360 | 0.74 | 430 | 428 | A |
| 361 | 0.68 | 417 | 415 | A |
| 362 | 1.79 | 427 | 425 | C |
| 363 | 1.84 | 451 | 449 | C |
| 364 | 0.8 | 444 | 442 | A |
| 365 | 1.64 | 413 | 411 | C |
| 366 | 0.75 | 413 | 411 | A |
| 367 | 0.7 | 416 | 414 | A |
| 368 | 0.82 | 455 | 453 | A |
| 369 | 1 | 432 | 430 | A |
| 370 | 0.97 | 442 | 440 | A |
| 371 | 0.96 | 424 | 422 | A |
| 372 | 0.94 | 440 | 438 | A |
| 373 | 1.8 | 451 | 449 | C |
| 374 | 0.94 | 455 | 453 | A |
| 375 | 1.01 | 432 | 430 | A |
| 376 | 0.92 | 448 | 446 | A |
| 377 | 0.95 | 436 | 434 | A |
| 378 | 0.88 | 455 | 453 | A |
| 379 | 0.7 | 438 | 436 | A |
| 380 | 0.78 | 438 | 436 | A |
| 381 | 0.71 | 436 | 434 | A |
| 382 | 0.74 | 438 | 436 | A |
| 383 | 0.85 | 450 | 448 | A |
| 384 | 0.88 | 457 | 455 | A |
| 385 | 0.9 | 455 | 453 | A |
| 386 | 1.55 | 431 | 429 | C |
| 282/387 | 0.93 | 435 | 433 | A |
| 390 | 0.99 | 417 | 415 | E |
| 391 | 1.25 | 411 | 409 | E |
| 392 | 1.01 | 461 | 459 | A |
| 394 | 1.01 | 473 | 471 | A |
| 396 | 1.88 | 473 | 471 | C |
| 398 | 0.99 | 435 | 433 | A |
| 400 | 0.78 | 431 | 429 | A |
| 402 | 0.62 | 417 | 415 | A |
| 403 | 0.9 | 455 | 453 | A |
| 404 | 0.93 | 451 | 449 | A |
| 405 | 0.91 | 451 | 449 | A |
| 406 | 0.75 | 438 | 436 | A |

SFC-MS Methods

The SFC measurement was performed using an Analytical Supercritical fluid chromatography (SFC) system composed by a binary pump for delivering carbon dioxide ($CO_2$) and modifier, an autosampler, a column oven, a diode array detector equipped with a high-pressure flow cell standing up to 400 bars. If configured with a Mass Spectrometer (MS) the flow from the column was brought to the (MS). It is within the knowledge of the skilled person to set the tune parameters (e.g. scanning range, dwell time . . . ) in order to obtain ions allowing the identification of the compound's nominal monoisotopic molecular weight (MW). Data acquisition was performed with appropriate software.

TABLE 4A

Analytical SFC-MS Methods (Flow expressed in mL/min; column temperature (T) in ° C.; Run time in minutes, Backpressure (BPR) in bars.

| Method code | Column | Mobile Phase | Gradient | Flow Col T | Run time BPR |
|---|---|---|---|---|---|
| 1 | Daicel Chiralpak ® AD-H column (5.0 μm, 250 × 4.6 mm) | A: $CO_2$ B: EtOH + 0.2% iPrNH$_2$ | 40% B hold 4 min, to 50% in 1 min hold 2 min | 5 40 | 7 110 |
| 2 | Daicel Chiralpak ® AD-3 column (3.0 μm, 150 × 4.6 mm) | A: $CO_2$ B: EtOH + 0.2% iPrNH2 | 10%-50% B in 6 min, hold 3.5 min | 2.5 40 | 9.5 110 |
| 3 | Daicel Chiralpak ® AD-H column (5.0 μm, 250 × 4.6 mm) | A: $CO_2$ B: (EtOH-iPrOH) + 0.2% iPrNH2 | 35% B hold 4 min, to 50% in 1 min hold 2 min | 5 40 | 7 110 |

TABLE 4A-continued

Analytical SFC-MS Methods (Flow expressed in mL/min; column temperature (T) in ° C.; Run time in minutes, Backpressure (BPR) in bars.

| Method code | Column | Mobile Phase | Gradient | Flow Col T | Run time BPR |
|---|---|---|---|---|---|
| 4 | Daicel Chiralpak ® AD-H column (5.0 μm, 250 × 4.6 mm) | A: $CO_2$<br>B: iPrOH + 0.2% $iPrNH_2$ | 25% B hold 4 min, to 50% in 1 min hold 2 min | 5<br>40 | 7<br>110 |
| 5 | Daicel Chiralpak ® AD-H column (5.0 μm, 250 × 4.6 mm) | A: $CO_2$<br>B: iPrOH + 0.2% $iPrNH_2$ | 30% B hold 4 min, to 50% in 1 min hold 2 min | 5<br>40 | 7<br>110 |
| 6 | Daicel Chiralpak ® AD-H column (5.0 μm, 250 × 4.6 mm) | A: $CO_2$<br>B: iPrOH + 0.2% $iPrNH_2$ | 40% B hold 4 min, to 50% in 1 min hold 2 min | 5<br>40 | 7<br>110 |
| 7 | Daicel Chiralpak ® AD-3 column (3.0 μm, 150 × 4.6 mm) | A: $CO_2$<br>B: iPrOH + 0.2% $iPrNH_2$ | 10%-50% B in 6 min, hold 3.5 min | 2.5<br>40 | 9.5<br>110 |
| 8 | Daicel Chiralpak ® AD-H column (5.0 μm, 250 × 4.6 mm) | A: $CO_2$<br>B: (MeOH-iPrOH) + 0.2% $iPrNH_2$ | 25% B hold 4 min, to 50% in 1 min hold 2 min | 5<br>40 | 7<br>110 |
| 9 | Daicel Chiralpak ® AD-H column (5.0 μm, 250 × 4.6 mm) | A: $CO_2$<br>B: (MeOH-iPrOH) + 0.2% $iPrNH_2$ | 30% B hold 4 min, to 50% in 1 min hold 2 min | 5<br>40 | 7<br>110 |
| 10 | Daicel (AD, OD, OJ, AS,)-H-column (5.0 μm, 250 × 4.6 mm) | A: $CO_2$<br>B: 3 different solvent for B used: (MeOH, EtOH, iPrOH) + 0.2% $iPrNH_2$ | 10%-40% B in 19.4 min, 40-50% in 2.00 min hold 3.6 min | 3<br>30 | 25<br>110 |
| 13 | Daicel AS-H column (5.0 μm, 500 × 4.6 mm) | A: $CO_2$<br>B: 3 different solvent for B used: (MeOH, EtOH, iPrOH) + 0.2% $iPrNH_2$ | 10%-40% B in 19.4 min, 40-50% in 2.00 min hold 3.6 min | 3<br>50 | 25<br>110 |
| 12 | Daicel AS-H column (5.0 μm, 500 × 4.6 mm) | A: $CO_2$<br>B: 3 different solvent for B used: (MeOH, EtOH, iPrOH) + 0.2% $iPrNH_2$ | 20% B hold 17.5 min, 20-50% in 3.00 min hold 4.1 min | 3<br>50 | 25<br>110 |
| 13 | Daicel OJ-H-column (5.0 μm, 250 × 4.6 mm) | A: $CO_2$<br>B: 3 different solvent for B used: MeOH) + 0.2% $iPrNH_2$ | 12% B hold 10 min | 3<br>30 | 10<br>110 |
| 14 | Daicel Chiralpak ® AD-H column (5.0 μm, 250 × 4.6 mm) | A: $CO_2$<br>B: MeOH + 0.2% $iPrNH_2$ | 20% B hold 4 min, to 50% in 1 min hold 2 min | 5<br>40 | 7<br>110 |
| 15 | Daicel Chiralpak ® OD-H column (5.0 μm, 250 × 4.6 mm) | A: $CO_2$<br>B: EtOH + 0.2% $iPrNH_2$ | 30% B hold 4 min, to 50% in 1 min hold 2 min | 5<br>40 | 7<br>110 |
| 16 | Daicel Chiralpak ® OD-3 column (3.0 μm, 150 × 4.6 mm) | A: $CO_2$<br>B: EtOH + 0.2% $iPrNH_2$ | 10%-50% B in 6 min, hold 3.5 min | 2.5<br>40 | 9.5<br>110 |
| 17 | Daicel Chiralpak ® AD3 column (3.0 μm, 150 × 4.6 mm) | A: $CO_2$<br>B: EtOH + 0.2% $iPrNH_2$ | 10%-50% B in 6 min, hold 3.5 min | 2.5<br>40 | 9.5<br>130 |
| 18 | Daicel Chiralpak ® IC3 column (3.0 μm, 150 × 4.6 mm) | A: CO2<br>B: EtOH + 0.2% iPrNH2 | 10%-50% B in 6 min, hold 3.5 min | 2.5<br>40 | 9.5<br>130 |

TABLE 4b

Analytical SFC data - $R_t$ means retention time (in minutes), $[M + H]^+$ means the protonated mass of the compound, method refers to the method used for (SFC)MS analysis of enantiomerically pure compounds.

| Co. No. | $R_t$ (MIN) | $[M + H]^+$ | Method | Elution order |
|---|---|---|---|---|
| 1a | 3.66 | 365 | 14 | Enantiomer 2 |
| 1b | 2.51 | 365 | 14 | Enantiomer 1 |
| 3a | 3 | 365 | 8 | Enantiomer 1 |
| 3b | 2.11 | 365 | 8 | Enantiomer 2 |
| 24a | 1.05 | 445 | 6 | Enantiomer 1 |
| 24b | 1.52 | 445 | 6 | Enantiomer 2 |
| 25a | 4.79 | 441 | 16 | Enantiomer 1 |
| 25b | 5.48 | no response | 16 | Enantiomer 1 |
| 28 | 3.95 | 439 | 2 | Enantiomer 2 |
| 29 | 1.33 | 413 | 15 | Enantiomer 2 |
| 30 | 2.54 | 413 | 15 | Enantiomer 1 |
| 33 | 5.45 | 447 | 7 | Enantiomer 1 |
| 34 | 4.85 | 447 | 7 | Enantiomer 2 |
| 45 | 1.2 | 443 | 4 | Enantiomer 2 |
| 46 | 1.56 | 443 | 4 | Enantiomer 1 |
| 62 | 3.42 | 417 | 2 | |
| 73 | 2.47 | 448 | 5 | Enantiomer 1 |
| 75 | 1.42 | 448 | 5 | Enantiomer 2 |
| 81 | 2.81 | 419 | 2 | Enantiomer 1 |
| 82 | 3.25 | 419 | 2 | Enantiomer 2 |
| 86 | 3.09 | 417 | 2 | Enantiomer 2 |
| 95 | 6.8 | 405 | 7 | Enantiomer 2 |
| 97 | 5.22 | 412 | 13 | N/A |
| 99 | 3.33 | 376 | 3 | Enantiomer 2 |
| 104 | 1.67 | 413 | 1 | Enantiomer 2 |
| 109 | 2.54 | 398 | 1 | N/A |
| 116 | 2.12 | 382 | 9 | Enantiomer 2 |
| 123 | 5.72 | 400 | 10 | N/A |
| 140 | 4.67 | 438 | 2 | Enantiomer 2 |
| 201 | 8.79 | 412 | 11 | Enantiomer 1 |
| 203 | 9.22 | 455 | 12 | Enantiomer 1 |
| 204 | 7.53 | 455 | 12 | Enantiomer 1 |
| 216 | 2.2 | 376 | 3 | Enantiomer 1 |
| 217 | 1.29 | 382 | 9 | Enantiomer 1 |
| 218 | 1.33 | 398 | 1 | Enantiomer 1 |
| 230 | 6.35 | 405 | 7 | Enantiomer 2 |
| 273 | 4.21 | 438 | 2 | Enantiomer 2 |
| 274 | 4.5 | 439 | 2 | |
| 285 | 6.81 | 467 | 18 | Diastereomer 4 |
| 286 | 4.95 | 467 | 18 | Diastereomer 3 |
| 392 | 2.64 | 461 | 17 | Enantiomer 1 |

Nuclear Magnetic Resonance (NMR)

The $^1$H NMR spectrum was recorded either on Bruker DPX-400 spectrometer with standard pulse sequences, operating at 400 MHz or on a Bruker DPX-360 operating at 360 MHz, using DMSO-$d_6$ (deuterated DMSO, dimethyl-d6 sulfoxide) as solvents. Chemical shifts (δ) are reported in parts per million (ppm) relative to tetramethylsilane (TMS), which was used as internal standard.

Co. No. 25a: $^1$H NMR (400 MHz, DMSO-$d_6$ $_{ON}$ 100 CELSIUS DEGREES) δ ppm 1.74-1.93 (m, 4H) 1.97-2.11 (m, 3H) 2.31-2.45 (m, 1H) 4.06-4.23 (m, 1H) 4.61 (br s, 1H) 4.82 (br s, 1H) 7.02 (t, J=54.2 Hz, 1H) 7.50 (s, 1H) 7.78 (dd, J=8.4, 1.8 Hz, 1H) 8.17 (d, J=8.4 Hz, 1H) 8.44 (br s, 1H) 8.47 (d, J=1.1 Hz, 1H) 9.45 (s, 1H);

Co. No. 93: $^1$H NMR (400 MHz, DMSO-$d_6$ $_{ON}$ 100 CELSIUS DEGREES) δ ppm 0.84 (d, J=6.6 Hz, 3H) 0.88-0.98 (m, 4H) 1.45 (qd, J=12.4, 4.4 Hz, 1H) 1.91 (br dd, J=13.4, 2.6 Hz, 1H) 2.06-2.14 (m, 1H) 2.42 (s, 3H) 2.45-2.49 (m, 1H) 3.13 (br t, J=11.6 Hz, 1H) 3.37 (dd, J=12.9, 11.1 Hz, 1H) 3.60 (td, J=10.9, 4.0 Hz, 1H) 4.17 (br s, 2H) 6.79-7.23 (m, 3H) 7.57 (s, 1H) 8.72 (s, 1H);

Co. No. 108: $^1$H NMR (400 MHz, DMSO-$d_6$) δ ppm 0.77 (d, J=6.4 Hz, 3H) 1.34-1.56 (m, 1H) 1.68-2.00 (m, 1H) 2.43 (br s, 1H) 2.76-3.28 (m, 2H) 3.49-3.74 (m, 2H) 3.87 (s, 3H) 4.46-4.76 (m, 1H) 6.81-7.33 (m, 3H) 7.65 (s, 1H) 8.80 (s, 1H);

Co. No. 110: $^1$H NMR (400 MHz, DMSO-$d_6$ $_{ON}$ 100 CELSIUS DEGREES) δ ppm 0.83 (d, J=6.6 Hz, 3H) 1.39-1.50 (m, 1H) 1.85-1.95 (m, 1H) 2.43 (s, 3H) 2.44-2.48 (m, 1H) 3.13 (br t, J=12.3 Hz, 1H) 3.37 (dd, J=13.0, 11.2 Hz, 1H) 3.58 (td, J=10.9, 4.0 Hz, 1H) 3.88 (s, 3H) 4.13 (br s, 2H) 6.58 (s, 1H) 6.82 (s, 1H) 7.01 (t, J=54.2 Hz, 1H) 7.56 (s, 1H) 8.71 (s, 1H);

Co. No. 132: $^1$H NMR (360 MHz, DMSO-$d_6$) δ ppm 0.78 (d, J=6.6 Hz, 3H) 1.38-1.61 (m, 1H) 1.67-2.01 (m, 1H) 2.60 (s, 3H) 2.86-3.30 (m, 2H) 3.49 (br d, J=14.6 Hz, 1H) 3.59-3.72 (m, 2H) 4.48-4.79 (m, 1H) 6.87-7.35 (m, 1H) 7.54-7.89 (m, 3H) 8.79 (s, 1H);

Co. No. 228: $^1$H NMR (400 MHz, DMSO-$d_6$ $_{ON}$ 100 CELSIUS DEGREES) δ ppm 0.85 (d, J=6.6 Hz, 4H) 1.43-1.56 (m, 1H) 1.86-1.99 (m, 1H) 3.19 (td, J=12.9, 2.8 Hz, 1H) 3.42 (dd, J=13.0, 11.2 Hz, 1H) 3.64 (td, J=10.9, 4.0 Hz, 1H) 4.15-4.26 (m, 1H) 4.28-4.38 (m, 1H) 7.01 (t, J=54.2 Hz, 1H) 7.58 (br s, 1H) 7.61 (dd, J=8.4, 1.5 Hz, 1H) 8.11 (d, J=7.9 Hz, 1H) 8.27 (d, J=1.3 Hz, 1H) 8.70 (s, 1H) 9.40 (s, 1H);

Co. No. 281: $^1$H NMR (400 MHz, DMSO-$d_6$ $_{ON}$ 120 CELSIUS DEGREES) δ ppm 0.82 (d, J=6.40 Hz, 3H) 1.46 (qd, J=12.47, 4.40 Hz, 1H) 1.84-1.93 (m, 1H) 2.41-2.53 (m, 1H) 2.84 (s, 3H) 3.07-3.18 (m, 1H) 3.35 (dd, J=12.98, 11.22 Hz, 1H) 3.58 (td, J=10.95, 3.85 Hz, 1H) 3.88-4.33 (m, 2H) 6.85 (s, 1H) 6.98 (t, J=54.36 Hz, 1H) 7.12 (s, 1H) 7.53 (s, 1H) 7.55 (t, J=73.07 Hz, 1H) 7.74 (s, 1H) 8.67 (s, 1H);

Co. No. 295: $^1$H NMR (400 MHz, DMSO-$d_6$ $_{ON}$ 100 CELSIUS DEGREES) δ ppm 1.67-1.87 (m, 4H) 1.89-2.10 (m, 3H) 2.26-2.38 (m, 1H) 3.82 (s, 3H) 4.13 (br d, J=12.10 Hz, 1H) 4.56 (br s, 1H) 4.86 (br s, 1H) 6.55 (d, J=2.64 Hz, 1H) 7.02 (t, J=55.00 Hz, 1H) 7.35 (d, J=3.08 Hz, 1H) 7.41-7.49 (m, 3H) 7.90 (s, 1H) 8.59 (s, 1H);

Co. No. 321: $^1$H NMR (400 MHz, DMSO-$d_6$ $_{ON}$ 100 CELSIUS DEGREES) δ ppm 0.81 (d, J=6.60 Hz, 3H) 1.47 (qd, J=12.43, 4.29 Hz, 1H) 1.85-1.93 (m, 1H) 2.39-2.46 (m, 1H) 2.94 (s, 3H) 3.09-3.18 (m, 1H) 3.33-3.40 (m, 1H) 3.57-3.64 (m, 1H) 3.83-4.52 (m, 2H) 6.82 (m, 1H) 7.00 (m, 1H) 7.43 (s, 1H) 7.46 (s, 1H) 7.55 (s, 1H) 8.69 (s, 1H);

Co. No. 335: $^1$H NMR (400 MHz, DMSO-$d_6$ $_{ON}$ 100 CELSIUS DEGREES) δ ppm 1.74-2.00 (m, 6H) 2.02-2.08 (m, 1H) 2.36-2.41 (m, 1H) 2.42 (s, 3H) 3.84 (s, 3H) 4.08-4.14 (m, 1H) 4.81-4.85 (m, 1H) 5.13-5.17 (m, 1H) 7.05 (t, J=54.40 Hz, 1H) 7.56 (s, 1H) 7.89 (s, 1H) 8.69 (s, 1H);

Co. No. 356: $^1$H NMR (400 MHz, DMSO-$d_6$ $_{ON}$ 100 CELSIUS DEGREES) δ ppm 1.68-1.89 (m, 4H) 1.92-2.04 (m, 3H) 2.30-2.45 (m, 1H) 4.01-4.07 (m, 1H) 4.39-4.84 (m, 2H) 7.01 (t, J=52.80 Hz, 1H) 7.49 (s, 1H) 7.58 (dd, J=8.25, 1.87 Hz, 1H) 7.71 (d, J=8.14 Hz, 1H) 7.83 (d, J=1.54 Hz, 1H) 8.58 (br s, 1H).

Pharmacological Examples

The compounds provided in the present invention are an inhibitors of PDE2, particularly of PDE2A. The results of testing the compounds in several pharmacological assays are shown below.

In Vitro Assay PDE2A

Human recombinant PDE2A (hPDE2A) was expressed in Sf9 cells using a recombinant rPDE10A baculovirus construct. Cells were harvested after 48 h of infection and the hPDE2A protein was purified by metal chelate chromatography on Ni-sepharose 6FF. Tested compounds were dissolved and diluted in 100% DMSO to a concentration 100 fold of the final concentration in the assay. Compound dilutions (0.4 µl) were added in 384 well plates to 20 µl of incubation buffer (50 mM Tris pH 7.8, 8.3 mM MgCl$_2$, 1.7 mM EGTA). 10 µl of hPDE2A enzyme in incubation buffer was added and the reaction was started by addition of 10 µl substrate to a final concentration of 10 µM cGMP and 0.01 µCi $^3$H-cGMP. The reaction was incubated for 45 minutes at room temperature. After incubation, the reaction was stopped with 20 µl of stop solution consisting of 17.8 mg/ml PDE SPA scintillation proximity assay) beads supplemented with 200 mM ZnCl$_2$. After sedimentation of the beads during 30 minutes the radioactivity was measured in a Perkin Elmer Topcount scintillation counter and results were expressed as cpm. For blanc values the enzyme was omitted from the reaction and replaced by incubation buffer. Control values were obtained by addition of a final concentration of 1% DMSO instead of compound. A best fit curve is fitted by a minimum sum of squares method to the plot of % of control value subtracted with blanc value versus compound concentration and the half maximal inhibitory concentration (IC$_{50}$) value is derived from this curve.

In Vitro Assay PDE3A

Human recombinant PDE3A (hPDE3A) was supplied as a partially purified insect cell lysate by Scottish Biomedical, it was cloned from human brain and expressed in Sf9 cells. Tested compounds were dissolved and diluted in 100% DMSO to a concentration 100 fold of the final concentration in the assay. Compound dilutions (0.4 µl) were added in 384 well plates to 20 µl of incubation buffer (50 mM Tris pH 7.8, 8.3 mM MgCl$_2$, 1.7 mM EGTA). 10 µl of hPDE3A enzyme in incubation buffer was added and the reaction was started by addition of 10 µl substrate to a final concentration of 0.4 µM cAMP and 2.4 µCi/ml [$^3$H]-cAMP. The reaction was incubated for 60 min at room temperature. After incubation, the reaction was stopped with 20 µl of stop solution consisting of 17.8 mg/ml PDE SPA (scintillation proximity assay) beads supplemented with 200 mM ZnCl$_2$. After sedimentation of the beads during 30 min the radioactivity was measured in a Perkin Elmer Topcount scintillation counter and results were expressed as cpm. For blanc values the enzyme was omitted from the reaction and replaced by incubation buffer. Control values were obtained by addition of a final concentration of 1% DMSO instead of compound. A best fit curve is fitted by a minimum sum of squares method to the plot of % of control value subtracted with blanc value versus compound concentration and the half maximal inhibitory concentration (IC$_{50}$) value is derived from this curve.

In Vitro Assay PDE10A

Rat recombinant PDE10A (rPDE10A2) was expressed in Sf9 cells using a recombinant rPDE10A baculovirus construct. Cells were harvested after 48 h of infection and the rPDE10A protein was purified by metal chelate chromatography on Ni-sepharose 6FF. Tested compounds were dissolved and diluted in 100% DMSO to a concentration 100 fold of the final concentration in the assay. Human recombinant PDE10A (hPDE2A) was expressed in Sf9 cells using a recombinant hPDE10A baculovirus that was made and amplified in house. Cells were harvested after 72 h of infection and the hPDE10A protein was purified by metal chelate chromatography on Ni-sepharose. Compound dilutions (0.4 µl) were added in 384 well plates to 20 µl of incubation buffer (50 mM Tris pH 7.8, 8.3 mM MgCl$_2$, 1.7 mM EGTA). 10 µl of rPDE10A or hPDE10A enzyme in incubation buffer was added and the reaction was started by addition of 10 µl substrate to a final concentration of 60 nM cAMP and 0.008 µCi $^3$H-cAMP. The reaction was incubated for 60 minutes at room temperature. After incubation, the reaction was stopped with 20 µl of stop solution consisting of 17.8 mg/ml PDE SPA (scintillation proximity assay) beads. After sedimentation of the beads during 30 minutes the radioactivity was measured in a Perkin Elmer Topcount scintillation counter and results were expressed as cpm. For blanc values the enzyme was omitted from the reaction and replaced by incubation buffer. Control values were obtained by addition of a final concentration of 1% DMSO instead of compound. A best fit curve is fitted by a minimum sum of squares method to the plot of % of control value subtracted with blanc value versus compound concentration and the half maximal inhibitory concentration (IC$_{50}$) value is derived from this curve.

TABLE 5

IN VITRO DATA FOR COMPOUNDS OF THE INVENTION. By default, data on inhibition of PDE10A refers to the human clone (also indicated as (h)) unless indicated as (r), referring to the rat clone.

| Co. No. | hPDE2A pIC$_{50}$ | hPDE2A E$_{max}$ | hPDE3B pIC$_{50}$ | hPDE3B E$_{max}$ | hPDE10A2 or rPDE10A2 pIC$_{50}$ | hPDE10A2 or rPDE10A2 E$_{max}$ |
|---|---|---|---|---|---|---|
| 1b | 5.96 | 88 | <5 | 13 | 5.01 | 50 |
| 1a | 9.1 | 100 | 5.68 | 65 | 7.89 | 98 |
| 2b | 7.72 | 100 | <5 | 31 | 6.57 | 95 |
| 2a | 9.23 | 101 | 6.11 | 98 | 8.14 | 101 |
| 3b | 5.25 | 64 | <5 | 14 | <5 | 19 |
| 3a | 8.24 | 97 | 5.46 | 77 | 6.57 | 93 |
| 4 | 8.84 | 100 | 5.24 | 70 | 7.62 | 99 |
| 5 | 9.02 | 100 | 6.23 | 97 | 8.05 | 100 |
| 6 | 8.79 | 99 | 6.17 | 97 | 7.75 | 100 |
| 7 | 9.1 | 100 | 7.12 | 100 | 7.77 | 101 |
| 8 | 8.96 | 100 | 6.56 | 97 | 7.95 | 100 |
| 9 | 7.86 | 101 | 5.37 | 74 | 7.13 | 100 |
| 10 | 8.96 | 100 | 7.14 | 101 | 8.34 | 100 |
| 11 | 7.64 | 100 | 5.32 | 69 | 6.43 | 95 |
| 12 | 7.67 | 101 | 5.96 | 94 | 6.44 | 97 |
| 13 | 7.98 | 100 | <5 | 38 | 6.46 | 95 |
| 14 | 8.22 | 99 | 5.33 | 70 | 7.05 | 99 |
| 15 | 8.49 | 100 | 5.09 | 54 | 7.14 | 97 |
| 16 | 8.21 | 100 | 5.78 | 88 | 7.2 | 98 |
| 17 | 8.31 | 99 | 5.37 | 74 | 7.09 | 97 |

TABLE 5-continued

IN VITRO DATA FOR COMPOUNDS OF THE INVENTION. By default, data on inhibition of PDE10A refers to the human clone (also indicated as (h)) unless indicated as (r), referring to the rat clone.

| Co. No. | hPDE2A pIC$_{50}$ | hPDE2A E$_{max}$ | hPDE3B pIC$_{50}$ | hPDE3B E$_{max}$ | hPDE10A2 or rPDE10A2 pIC$_{50}$ | hPDE10A2 or rPDE10A2 E$_{max}$ |
|---|---|---|---|---|---|---|
| 18 | 8.33 | 100 | 5.19 | 65 | 6.71 | 97 |
| 19 | 7.98 | 101 | 5.51 | 79 | 6.89 | 96 |
| 20 | 7.92 | 101 | 5.37 | 74 | 6.88 | 98 |
| 21 | 8.34 | 99 | 5.82 | 89 | 6.88 | 97 |
| 22 | 8.63 | 100 | 5.82 | 87 | 7.8 | 99 |
| 23 | 9.33 | 101 | 5.98 | 90 | 8.15 | 100 |
| 24a | 5.59 | 80 | <5 | 31 | <5 | 23 |
| 24b | 8.19 | 98 | <5 | 28 | 5.13 | 60 |
| 25a | 9.15 | 100 | 5.04 | 57 | 6.41 | 96 |
| 25b | 5.96 | 92 | <5 | 37 | <5 | 28 |
| 26a | <5 | 21 | <5 | 0 | <5 | 7 |
| 26b | 8.17 | 98 | <5 | 41 | 6.63 | 95 |
| 27 | 9.04 | 100 | <5 | 37 | 5.96 | 88 |
| 28 | 9.02 | 101 | <5 | 17 | 6.35 | 95 |
| 29 | 8.82 | 101 | <5 | 18 | 6.16 | 90 |
| 30 | 5.45 | 77 | <5 | 8 | <5 | 32 |
| 31 | 8.6 | 100 | <5 | 8 | 5.95 | 84 |
| 32 | 8.46 | 100 | <5 | 31 | 5.84 | 81 |
| 33 | 7.83 | 99 | <5 | 25 | 5.21 | 67 |
| 34 | 5.71 | 88 | <5 | 31 | <5 | 28 |
| 35 | 8.17 | 100 | <5 | 1 | 5.59 | 76 |
| 38 | 8.21 | 100 | <5 | 43 | 5.64 | 80 |
| 39 | 8.08 | 98 | <5 | 16 | 5.51 | 75 |
| 40 | 9.45 | 101 | 5.15 | 58 | 6.91 (h) 7.1 (r) | 97 (h) 96 (r) |
| 41 | 7.86 | 99 | <5 | 17 | 5.38 | 72 |
| 42 | 8.94 | 100 | <5 | 48 | 6.5 | 95 |
| 43 | 8.3 | 99 | <5 | 29 | 5.88 | 88 |
| 44 | 8.02 | 100 | <5 | 39 | 5.59 | 79 |
| 45 | <5 | 37 | <5 | 1 | <5 | 24 |
| 46 | 7.82 | 100 | <5 | 5 | 5.65 | 86 |
| 47 | 8.6 | 99 | 5.47 | 80 | 6.19 | 92 |
| 48 | 9.76 | 100 | 7.06 | 99 | 7.36 | 100 |
| 49 | 8.68 | 99 | 5.24 | 42 | 6.29 | 95 |
| 50 | 8.51 | 100 | <5 | 61 | 6.14 | 93 |
| 51 | 8.26 | 101 | <5 | 44 | 5.9 | 86 |
| 52 | 7.86 | 101 | <5 | 22 | 5.52 | 76 |
| 53 | 8.25 | 100 | 5.17 | 62 | 6.11 | 89 |
| 54 | 8.38 | 100 | 5.02 | 51 | 6.18 | 89 |
| 55 | 7.9 | 101 | <5 | 41 | 5.75 | 83 |
| 56 | 7.3 | 101 | <5 | 38 | 5.25 | 63 |
| 57 | 7.56 | 100 | <5 | 21 | 5.5 | 78 |
| 58 | 7.61 | 99 | <5 | 18 | 5.35 | 69 |
| 59 | 8.43 | 98 | 5.07 | 56 | 6.23 | 95 |
| 60 | 9.07 | 100 | 5.96 | 92 | 6.82 | 97 |
| 61 | 8.36 | 101 | <5 | 45 | 6.34 | 92 |
| 63 | 8.14 | 100 | 5.16 | 60 | 6.06 | 89 |
| 64 | 8.8 | 99 | 5.17 | 62 | 6.45 | 96 |
| 65 | 8.9 | 100 | 5.17 | 70 | 6.6 | 95 |
| 66 | 7.76 | 99 | <5 | 48 | 5.64 | 79 |
| 67 | 8.59 | 99 | <5 | 49 | 6.54 | 94 |
| 68 | 8.2 | 99 | 5 | 50 | 5.86 | 85 |
| 69 | 9.39 | 102 | 6.42 | 95 | 7.34 | 100 |
| 70 | 8.76 | 102 | 5.21 | 63 | 6.42 | 95 |
| 71 | 8.73 | 98 | <6 | 32 | 6.47 | 94 |
| 72 | 8.99 | 100 | <6 | 46 | 6.98 | 92 |
| 73 | 8.71 | 101 | 5.58 | 83 | 6.66 | 98 |
| 74 | 7.52 | 101 | <5 | 30 | <5 | 36 |
| 75 | 5.53 | 81 | <5 | 22 | <5 | 27 |
| 76 | 9.64 | 99 | 5.91 | 91 | 7.5 | 101 |
| 77 | 9.34 | 101 | 6.17 | 96 | 7.08 | 98 |
| 78 | 9 | 102 | 5.8 | 87 | 6.98 | 98 |
| 79 | 8.76 | 99 | 6.04 | 93 | 6.72 | 97 |
| 80 | 9.1 | 100 | 5.38 | 71 | 7.09 | 98 |
| 81 | 5.15 | 59 | <5 | 17 | <5 | 1 |
| 82 | 7.47 | 101 | <5 | 9 | <5 | 18 |
| 83 | 9.03 | 100 | 5.1 | 58 | 7.01 | 98 |
| 84 | 8.5 | 101 | 5.13 | 30 | 6.15 | 89 |
| 85 | 8.19 | 100 | 5.11 | 37 | 5.92 | 88 |
| 87 | 6.67 | 98 | <5 | 11 | 5.34 | 69 |
| 88 | 9.68 | 101 | 6.41 | 97 | 8.4 | 99 |

TABLE 5-continued

IN VITRO DATA FOR COMPOUNDS OF THE INVENTION. By default, data on inhibition of PDE10A refers to the human clone (also indicated as (h)) unless indicated as (r), referring to the rat clone.

| Co. No. | hPDE2A pIC$_{50}$ | hPDE2A E$_{max}$ | hPDE3B pIC$_{50}$ | hPDE3B E$_{max}$ | hPDE10A2 or rPDE10A2 pIC$_{50}$ | hPDE10A2 or rPDE10A2 E$_{max}$ |
|---|---|---|---|---|---|---|
| 89 | 9.64 | 104 | 6.84 | 96 | 7.68 (h) 7.92 (r) | 101 (h) 98 (r) |
| 90 | 9.45 | 101 | 6.67 | 98 | 7.71 | 102 |
| 91 | 9.43 | 100 | 6.15 | 61 | 7.65 | 94 |
| 92 | 9.4 | 100 | 5.88 | 88 | 7.61 | 98 |
| 93 | 9.4 | 101 | 5.61 | 84 | 7.44 | 99 |
| 94 | 9.3 | 101 | 6.98 | 99 | 7.93 | 97 |
| 95 | 9.29 | 100 | 5 | 55 | 7.32 | 98 |
| 96 | 9.26 | 100 | 6.4 | 73 | 7.48 | 95 |
| 97 | 9.24 | 101 | 5.89 | 93 | 7.27 (h) 7.46 (r) | 101 (h) 99 (r) |
| 98 | 9.22 | 100 | 6.22 | 94 | 7.4 | 98 |
| 99 | 9.22 | 100 | 5.68 | 87 | 8.02 | 100 |
| 100 | 9.18 | 101 | 6.57 | 99 | 7.79 | 100 |
| 101 | 9.18 | 101 | 5.32 | 70 | 7.24 | 98 |
| 102 | 9.17 | 100 | <6 | 44 | 7.58 | 95 |
| 103 | 9.15 | 99 | 7.06 | 100 | 7.74 | 100 |
| 104 | 9.09 | 100 | 6.29 | 92 | 7.13 | 98 |
| 105 | 9.06 | 101 | 5.87 | 90 | 7.53 | 101 |
| 106 | 9.05 | 100 | 6.41 | 98 | 7.67 | 99 |
| 107 | 9.04 | 100 | 5.38 | 61 | 7.09 | 99 |
| 108 | 9.04 | 100 | 5.57 | 80 | 7.28 | 99 |
| 109 | 9.03 | 101 | 6.34 | 98 | 8.18 | 99 |
| 110 | 9.02 | 101 | 5.58 | 78 | 7.14 | 98 |
| 111 | 9.01 | 100 | 5.98 | 92 | 7.42 | 99 |
| 112 | 9 | 101 | 5.75 | 84 | 7.32 | 99 |
| 113 | 9 | 99 | 5.95 | 88 | 7.42 | 99 |
| 114 | 8.98 | 100 | 7.05 | 98 | 7.34 | 101 |
| 115 | 8.98 | 100 | 5.71 | 87 | 7.11 | 99 |
| 116 | 8.94 | 100 | 6.07 | 97 | 8.01 | 99 |
| 116 | 8.95 | 101 | 5.66 | 82 | 7.1 | 98 |
| 118 | 8.78 | 101 | 6.02 | 92 | 7.13 | 99 |
| 119 | 8.76 | 100 | 7.21 | 101 | 7.11 | 99 |
| 120 | 8.76 | 100 | 6.15 | 95 | 6.7 | 96 |
| 121 | 8.75 | 99 | 6.29 | 95 | 7.23 | 96 |
| 122 | 8.73 | 100 | 5.74 | 86 | 7.13 | 100 |
| 123 | 8.71 | 99 | 5.79 | 87 | 7.04 | 99 |
| 124 | 8.69 | 99 | 6.38 | 98 | 7.44 | 98 |
| 125 | 8.68 | 100 | 6.23 | 96 | 6.23 | 96 |
| 126 | 8.68 | 101 | 5.22 | 65 | 6.95 | 97 |
| 127 | 8.65 | 99 | 6.36 | 94 | 7.59 | 99 |
| 128 | 8.64 | 100 | 6.03 | 90 | 6.81 | 98 |
| 129 | 8.64 | 101 | 5.71 | 85 | 7.04 | 99 |
| 130 | 8.61 | 100 | 5.76 | 87 | 6.87 | 96 |
| 131 | 8.61 | 98 | 5.11 | 61 | 7.39 | 99 |
| 132 | 8.6 | 101 | <5 | 46 | 6.7 | 98 |
| 133 | 8.53 | 100 | 5.79 | 85 | 6.87 | 98 |
| 134 | 8.5 | 101 | 5.65 | 84 | 6.8 | 100 |
| 135 | 8.48 | 100 | 5.58 | 81 | 6.72 | 97 |
| 136 | 8.47 | 101 | <5 | 51 | 6.54 | 97 |
| 137 | 7.55 | 100 | <5 | 35 | 5.87 | 84 |
| 139 | 7.54 | 99 | <5 | 20 | 5.62 | 78 |
| 140 | 7.53 | 100 | 5.05 | 57 | 5.51 | 83 |
| 141 | 7.53 | 100 | <5 | 12 | 5.69 | 81 |
| 142 | 7.52 | 100 | <5 | 35 | 5.59 | 79 |
| 143 | 7.48 | 97 | 5.1 | 58 | 5.62 | 77 |
| 144 | 7.46 | 100 | 5.62 | 86 | 6.33 | 96 |
| 145 | 7.44 | 99 | 5.69 | 86 | 6.19 | 93 |
| 147 | 7.42 | 100 | 5.65 | 81 | 6.06 | 90 |
| 148 | 7.41 | 101 | 5.25 | 67 | 6.04 | 89 |
| 149 | 7.41 | 99 | 5.29 | 66 | 5.74 | 83 |
| 150 | 7.4 | 100 | <5 | 22 | 5.45 | 72 |
| 152 | 7.38 | 99 | <5 | 30 | 5.69 | 80 |
| 153 | 7.36 | 100 | 5.51 | 76 | 5.97 | 89 |
| 154 | 7.29 | 100 | <5 | 50 | 5.56 | 79 |
| 155 | 7.27 | 98 | <5 | 37 | 5.53 | 72 |
| 156 | 7.23 | 100 | <5 | 19 | 5.7 | 81 |
| 157 | 7.22 | 99 | <5 | 33 | 5.59 | 75 |
| 158 | 7.19 | 100 | <5 | 19 | 5.67 | 78 |
| 159 | 7.14 | 100 | <5 | 42 | 5.49 | 75 |
| 160 | 7.14 | 99 | <5 | 34 | 5.99 | 88 |

TABLE 5-continued

IN VITRO DATA FOR COMPOUNDS OF THE INVENTION. By default, data on inhibition of PDE10A refers to the human clone (also indicated as (h)) unless indicated as (r), referring to the rat clone.

| Co. No. | hPDE2A pIC$_{50}$ | hPDE2A E$_{max}$ | hPDE3B pIC$_{50}$ | hPDE3B E$_{max}$ | hPDE10A2 or rPDE10A2 pIC$_{50}$ | hPDE10A2 or rPDE10A2 E$_{max}$ |
|---|---|---|---|---|---|---|
| 161 | 7.13 | 98 | <5 | 11 | 5.51 | 74 |
| 162 | 7.13 | 97 | <5 | 26 | 5.37 | 72 |
| 163 | 7.05 | 98 | <5 | 12 | 5.49 | 74 |
| 164 | 7.05 | 100 | <5 | 22 | 5.71 | 82 |
| 165 | 7.03 | 100 | <5 | 36 | 5.46 | 78 |
| 166 | 7.03 | 98 | <5 | 32 | 5.65 | 81 |
| 167 | 7.01 | 97 | 5.27 | 64 | 5.7 | 81 |
| 168 | 8.4 | 98 | 5.29 | 66 | 7.27 | 99 |
| 169 | 8.43 | 98 | 5.75 | 82 | 6.75 | 98 |
| 170 | 8.34 | 100 | 5.67 | 84 | 5.89 | 84 |
| 171 | 7.93 | 99 | 5.94 | 93 | 6.45 | 97 |
| 172 | 8.34 | 101 | 6.57 | 98 | 7.49 | 100 |
| 173 | 7.86 | 101 | <5 | 31 | 6.52 | 96 |
| 174 | 8.28 | 99 | 5.88 | 85 | 6.24 | 88 |
| 175 | 8.31 | 100 | 5.22 | 71 | 6.85 | 98 |
| 176 | 8.04 | 100 | 5.06 | 56 | 6.05 | 88 |
| 177 | 8.02 | 99 | <5 | 21 | 6.34 | 93 |
| 178 | 7.87 | 101 | 5.13 | 62 | 6.1 | 92 |
| 179 | 7.67 | 100 | <5 | 32 | 6.27 | 90 |
| 180 | 8.3 | 100 | 5.29 | 66 | 6.76 | 97 |
| 181 | 8.34 | 98 | <5 | 52 | 6.51 | 94 |
| 182 | 7.6 | 100 | <5 | 44 | 6.38 | 95 |
| 183 | 7.58 | 99 | <5 | 36 | 5.64 | 79 |
| 184 | 7.55 | 100 | <5 | 17 | 5.56 | 75 |
| 186 | 7.97 | 100 | 5.22 | 69 | 6.47 | 95 |
| 187 | 7.75 | 99 | 5.46 | 74 | 6.37 | 95 |
| 188 | 8.07 | 99 | 5.81 | 87 | 6.68 | 98 |
| 189 | 8.29 | 100 | 5.56 | 80 | 6.73 | 96 |
| 190 | 7.99 | 100 | <5 | 39 | 6.8 | 96 |
| 191 | 7.89 | 100 | 5.41 | 74 | 6.65 | 97 |
| 192 | 8.03 | 99 | 6.14 | 95 | 7.14 | 99 |
| 193 | 8.23 | 100 | 5.46 | 76 | 6.86 | 98 |
| 194 | 7.73 | 99 | 5.34 | 57 | 6.58 | 97 |
| 195 | 8.35 | 98 | 5.25 | 70 | 6.43 | 93 |
| 196 | 7.63 | 99 | 5.31 | 68 | 6.25 | 92 |
| 197 | 7.99 | 98 | <5 | 42 | 6.68 | 96 |
| 198 | 8.25 | 98 | <5 | 35 | 6.38 | 91 |
| 199 | 7.27 | 92 | 5.08 | 62 | 5.23 (h) | 62 (h) |
|  |  |  |  |  | 5.32 (r) | 21 (r) |
| 200 | 7.01 | 91 | <5 | 35 | <5 | 13 |
| 201 | 6.19 | 61 | <5 | 24 | 5.51 (r) | −1 (r) |
| 202 | 5.57 | 30 | <5 | 18 | <5 (h) | 38 (h) |
|  |  |  |  |  | <5 (r) | 4 (r) |
| 203 | 6.02 | 48 | <5 | 41 | <5 (r) | 14 (r) |
| 204 | 6.79 | 88 | 5.13 | 48 | <5 (r) | 13 (r) |
| 205 | 8.94 | 99 | 5.65 | 83 | 7.01 | 98 |
| 206 | 5.78 | 39 | <5 | −1 | <5 | 16 |
| 207 | 5.1 | 21 | <5 | 2 | <5 | −5 |
| 208 | 6.23 | 62 | <5 | 30 | <5 | 4 |
| 209 | 6.14 | 57 | <5 | 25 | <5 | 7 |
| 210 | 6.21 | 56 | <5 | 5 | <5 | 16 |
| 211 | <5 | 3 | <5 | 13 | <5 | 10 |
| 212 | 6.24 | 61 | <5 | 7 | <5 | 8 |
| 213 | 5.63 | 28 | <5 | 11 | <5 | 23 |
| 214 | 5.2 | 9 | <5 | 9 | <5 | 30 |
| 215 | 6.58 | 82 | 5 | 45 | 5.13 | 63 |
| 216 | 6.36 | 98 | <5 | 26 | 5.35 | 67 |
| 217 | 6.25 | 99 | <5 | 37 | 5.32 | 72 |
| 218 | 6.69 | 100 | <5 | 51 | 5.65 | 85 |
| 219 | 6.86 | 100 | <5 | 18 | 5.04 | 45 |
| 220 (•HCl) | 6.01 | 54 | <5 | 7 | <5 | 27 |
| 221 | 5.92 | 45 | <5 | 4 | <5 | 26 |
| 222 | 6.55 | 98 | <5 | 13 | 5.17 | 59 |
| 223 | 6.71 | 98 | <5 | 19 | 5.46 | 71 |
| 226 | 9.06 | 100 | 6.89 | 100 | 7.09 | 100 |
| 227 | 8.66 | 101 | 6.42 | 95 | 7.34 | 98 |
| 228 | 9.65 | 100 | 5.92 | 91 | 7.77 | 100 |
| 229 | 6.25 | 95 | <5 | 18 | <5 | 33 |
| 230 | 5.99 | 93 | <5 | 40 | 5.27 | 65 |
| 231 | 8.87 | 97 | 5.04 | 57 | 7.71 | 100 |

TABLE 5-continued

IN VITRO DATA FOR COMPOUNDS OF THE INVENTION. By default, data on inhibition of PDE10A refers to the human clone (also indicated as (h)) unless indicated as (r), referring to the rat clone.

| Co. No. | hPDE2A $pIC_{50}$ | hPDE2A $E_{max}$ | hPDE3B $pIC_{50}$ | hPDE3B $E_{max}$ | hPDE10A2 or rPDE10A2 $pIC_{50}$ | hPDE10A2 or rPDE10A2 $E_{max}$ |
|---|---|---|---|---|---|---|
| 232 | 6.67 | 99 | <5 | 31 | <5 | 48 |
| 233 | 6.24 | 94 | <5 | 10 | <5 | 26 |
| 234 | 6.29 | 96 | <5 | 22 | 5.06 | 59 |
| 235 | 6.91 | 98 | <5 | 32 | 5.26 | 67 |
| 236 | 6.68 | 100 | <5 | 18 | 5.11 | 58 |
| 237 | 6.73 | 97 | <5 | 20 | 5.09 | 51 |
| 238 | 6.42 | 94 | <5 | 35 | 5 | 48 |
| 239 | 6.72 | 96 | <5 | 16 | <5 | 43 |
| 240 | 5.81 | 90 | <5 | 9 | 5.04 | 51 |
| 241 | 7.68 | 97 | 5.76 | 88 | 6.57 | 94 |
| 242 | 6.87 | 97 | 5.21 | 67 | 5.09 | 56 |
| 243 | 6.88 | 99 | <5 | 13 | 5.44 | 70 |
| 244 | 6.17 | 92 | <5 | 12 | 5.03 | 54 |
| 245 | 6.91 | 99 | 5.23 | 62 | 5.66 | 79 |
| 246 | 6.9 | 98 | <5 | 25 | <5 | 44 |
| 247 | 6.81 | 98 | 5.69 | 85 | 5.54 | 77 |
| 248 | 6.46 | 95 | <5 | 2 | 4.98 | 49 |
| 249 | 6.43 | 95 | <5 | 10 | <5 | 45 |
| 250 | 6.88 | 99 | <5 | 28 | 5.31 | 64 |
| 251 | 6.55 | 98 | <5 | 17 | 5.06 | 53 |
| 252 | 6.15 | 96 | <5 | 17 | 5.17 | 66 |
| 253 | 6.34 | 95 | <5 | 17 | <5 | 39 |
| 254 | 6.97 | 99 | <5 | 25 | 5.42 | 70 |
| 255 | 6.57 | 95 | <5 | 28 | 5.11 | 58 |
| 256 | 6.49 | 97 | <5 | 12 | 5 | 48 |
| 257 | 6.58 | 95 | <5 | 15 | <5 | 45 |
| 258 | 6.82 | 99 | 5.81 | 89 | 5.9 | 90 |
| 259 | 6.37 | 99 | 5.45 | 82 | 5.77 | 92 |
| 260 | 6.86 | 97 | <5 | 23 | 5.53 | 74 |
| 261 | 6.44 | 95 | <5 | 19 | <5 | 45 |
| 262 | 6.81 | 101 | <5 | 37 | 5.49 | 74 |
| 263 | 6.89 | 99 | 5.31 | 65 | 5.29 | 64 |
| 264 | 6.98 | 100 | 4.98 | 47 | 5.48 | 74 |
| 265 | 8.62 | 102 | 5.2 | 55 | 7.43 | 98 |
| 266 | 6.38 | 100 | 5.27 | 74 | 5.58 | 89 |
| 267 | 9.4 | 102 | 7.21 | 100 | 7.95 | 99 |
| 268 | 5.72 | 82 | <5 | 13 | <5 | 39 |
| 269 | 9.15 | 101 | 5.43 | 78 | 6.16 | 93 |
| 270 | 8.63 | 100 | <5 | 29 | 6.57 | 96 |
| 271 | 8.53 | 99 | 5.13 | 61 | 6.79 | 95 |
| 272 | 8.66 | 102 | 5.05 | 54 | 6.1 | 93 |
| 273 | 8.63 | 100 | 6.09 | 96 | 6.01 | 96 |
| 274 | 6.54 | 97 | <5 | 7 | 5.22 | 63 |
| 1a | 9.1 | 100 | 5.68 | 65 | 7.89 | 98 |
| 1b | 5.96 | 88 | <5 | 13 | 5.01 | 50 |
| 2a | 9.23 | 101 | 6.11 | 98 | 8.14 | 101 |
| 2b | 7.72 | 100 | <5 | 31 | 6.57 | 95 |
| 3a | 8.24 | 97 | 5.46 | 77 | 6.57 | 93 |
| 3b | 5.25 | 64 | <5 | 14 | <5 | 19 |
| 4 | 8.84 | 100 | 5.24 | 70 | 7.62 | 99 |
| 5 | 9.02 | 100 | 6.23 | 97 | 8.05 | 100 |
| 6 | 8.79 | 99 | 6.17 | 97 | 7.75 | 100 |
| 7 | 9.1 | 100 | 7.12 | 100 | 7.77 | 101 |
| 8 | 8.96 | 100 | 6.56 | 97 | 7.95 | 100 |
| 9 | 7.86 | 101 | 5.37 | 74 | 7.13 | 100 |
| 10 | 8.96 | 100 | 7.14 | 101 | 8.34 | 100 |
| 11 | 7.64 | 100 | 5.32 | 69 | 6.43 | 95 |
| 12 | 7.67 | 101 | 5.96 | 94 | 6.44 | 97 |
| 13 | 7.98 | 100 | <5 | 38 | 6.46 | 95 |
| 14 | 8.22 | 99 | 5.33 | 70 | 7.05 | 99 |
| 15 | 8.49 | 100 | 5.09 | 54 | 7.14 | 97 |
| 16 | 8.21 | 100 | 5.78 | 88 | 7.2 | 98 |
| 17 | 8.31 | 99 | 5.37 | 74 | 7.09 | 97 |
| 18 | 8.33 | 100 | 5.19 | 65 | 6.71 | 97 |
| 19 | 7.98 | 101 | 5.51 | 79 | 6.89 | 96 |
| 20 | 7.92 | 101 | 5.37 | 74 | 6.88 | 98 |
| 21 | 8.34 | 99 | 5.82 | 89 | 6.88 | 97 |
| 22 | 8.63 | 100 | 5.82 | 87 | 7.8 | 99 |
| 23 | 9.33 | 101 | 5.98 | 90 | 8.15 | 100 |
| 24a | 5.59 | 80 | <5 | 31 | <5 | 23 |
| 24b | 8.19 | 98 | <5 | 28 | 5.13 | 60 |

TABLE 5-continued

IN VITRO DATA FOR COMPOUNDS OF THE INVENTION. By default, data on inhibition of PDE10A refers to the human clone (also indicated as (h)) unless indicated as (r), referring to the rat clone.

| Co. No. | hPDE2A pIC$_{50}$ | hPDE2A E$_{max}$ | hPDE3B pIC$_{50}$ | hPDE3B E$_{max}$ | hPDE10A2 or rPDE10A2 pIC$_{50}$ | hPDE10A2 or rPDE10A2 E$_{max}$ |
|---|---|---|---|---|---|---|
| 25a | 8.97 | 100 | 5.06 | 54 | 6.23 | 94 |
| 25b | 5.96 | 92 | <5 | 37 | <5 | 28 |
| 26a | <5 | 21 | <5 | 0 | <5 | 7 |
| 26b | 8.17 | 98 | <5 | 41 | 6.63 | 95 |
| 27 | 9.04 | 100 | <5 | 37 | 5.96 | 88 |
| 28 | 9.02 | 101 | <5 | 17 | 6.35 | 95 |
| 29 | 8.82 | 101 | <5 | 18 | 6.16 | 90 |
| 30 | 5.45 | 77 | <5 | 8 | <5 | 32 |
| 31 | 8.6 | 100 | <5 | 8 | 5.95 | 84 |
| 32 | 8.46 | 100 | <5 | 31 | 5.84 | 81 |
| 33 | 7.83 | 99 | <5 | 25 | 5.21 | 67 |
| 34 | 5.71 | 88 | <5 | 31 | <5 | 28 |
| 35 | 8.17 | 100 | <5 | 1 | 5.59 | 76 |
| 36 | 8.56 | 100 | 5.4 | 64 | 6.33 | 93 |
| 37 | 7.76 | 100 | 5.05 | 52 | 6.37 | 93 |
| 38 | 8.21 | 100 | <5 | 43 | 5.64 | 80 |
| 39 | 8.08 | 98 | <5 | 16 | 5.51 | 75 |
| 40 | 9.45 | 101 | 5.15 | 58 | 6.91 (h) 7.1 (r) | 97 (h) 96 (r) |
| 41 | 7.86 | 99 | <5 | 17 | 5.38 | 72 |
| 42 | 8.94 | 100 | <5 | 48 | 6.5 | 95 |
| 43 | 8.3 | 99 | <5 | 29 | 5.88 | 88 |
| 44 | 8.02 | 100 | <5 | 39 | 5.59 | 79 |
| 45 | <5 | 37 | <5 | 1 | <5 | 24 |
| 46 | 7.82 | 100 | <5 | 5 | 5.65 | 86 |
| 47 | 8.6 | 99 | 5.47 | 80 | 6.19 | 92 |
| 48 | 9.76 | 100 | 7.06 | 99 | 7.36 | 100 |
| 49 | 8.68 | 99 | 5.24 | 42 | 6.29 | 95 |
| 50 | 8.51 | 100 | <5 | 61 | 6.14 | 93 |
| 51 | 8.26 | 101 | <5 | 44 | 5.9 | 86 |
| 52 | 7.86 | 101 | <5 | 22 | 5.52 | 76 |
| 53 | 8.25 | 100 | 5.17 | 62 | 6.11 | 89 |
| 54 | 8.38 | 100 | 5.02 | 51 | 6.18 | 89 |
| 55 | 7.9 | 101 | <5 | 41 | 5.75 | 83 |
| 56 | 7.3 | 101 | <5 | 38 | 5.25 | 63 |
| 57 | 7.56 | 100 | <5 | 21 | 5.5 | 78 |
| 58 | 7.61 | 99 | <5 | 18 | 5.35 | 69 |
| 59 | 8.43 | 98 | 5.07 | 56 | 6.23 | 95 |
| 60 | 9.07 | 100 | 5.96 | 92 | 6.82 | 97 |
| 61 | 8.36 | 101 | <5 | 45 | 6.34 | 92 |
| 62 | 5.52 | 77 | <5 | 8 | <5 | 36 |
| 63 | 8.14 | 100 | 5.16 | 60 | 6.06 | 89 |
| 64 | 8.8 | 99 | 5.17 | 62 | 6.45 | 96 |
| 65 | 8.9 | 100 | 5.17 | 70 | 6.6 | 95 |
| 66 | 7.76 | 99 | <5 | 48 | 5.64 | 79 |
| 67 | 8.59 | 99 | <5 | 49 | 6.54 | 94 |
| 68 | 8.2 | 99 | 5 | 50 | 5.86 | 85 |
| 69 | 9.39 | 102 | 6.42 | 95 | 7.34 | 100 |
| 70 | 8.71 | 102 | 5.29 | 66 | 6.48 | 93 |
| 71 | 8.73 | 98 | <6 | 32 | 6.47 | 94 |
| 72 | 8.99 | 100 | <6 | 46 | 6.98 | 92 |
| 73 | 8.71 | 101 | 5.58 | 83 | 6.66 | 98 |
| 74 | 7.52 | 101 | <5 | 30 | <5 | 36 |
| 75 | 5.53 | 81 | <5 | 22 | <5 | 27 |
| 76 | 9.64 | 99 | 5.91 | 91 | 7.5 | 101 |
| 77 | 9.34 | 101 | 6.17 | 96 | 7.08 | 98 |
| 78 | 9 | 102 | 5.8 | 87 | 6.98 | 98 |
| 79 | 8.76 | 99 | 6.04 | 93 | 6.72 | 97 |
| 80 | 9.1 | 100 | 5.38 | 71 | 7.09 | 98 |
| 81 | 5.15 | 59 | <5 | 17 | <5 | 1 |
| 82 | 7.47 | 101 | <5 | 9 | <5 | 18 |
| 83 | 9.03 | 100 | 5.1 | 58 | 7.01 | 98 |
| 84 | 8.5 | 101 | 5.13 | 30 | 6.15 | 89 |
| 85 | 8.19 | 100 | 5.11 | 37 | 5.92 | 88 |
| 86 | 7.3 | 100 | <5 | 34 | <5 | 40 |
| 87 | 6.67 | 98 | <5 | 11 | 5.34 | 69 |
| 88 | 9.68 | 101 | 6.41 | 97 | 8.4 | 99 |
| 89 | 9.64 | 104 | 6.84 | 96 | 7.68 (h) 7.92 (r) | 101 (h) 98 (r) |
| 90 | 9.45 | 101 | 6.67 | 98 | 7.71 | 102 |
| 91 | 9.43 | 100 | 6.15 | 61 | 7.65 | 94 |

TABLE 5-continued

IN VITRO DATA FOR COMPOUNDS OF THE INVENTION. By default, data on inhibition of PDE10A refers to the human clone (also indicated as (h)) unless indicated as (r), referring to the rat clone.

| Co. No. | hPDE2A pIC$_{50}$ | hPDE2A E$_{max}$ | hPDE3B pIC$_{50}$ | hPDE3B E$_{max}$ | hPDE10A2 or rPDE10A2 pIC$_{50}$ | hPDE10A2 or rPDE10A2 E$_{max}$ |
|---|---|---|---|---|---|---|
| 92 | 9.4 | 100 | 5.88 | 88 | 7.61 | 98 |
| 93 | 9.34 | 101 | 5.59 | 84 | 7.4 | 99 |
| 94 | 9.3 | 101 | 6.98 | 99 | 7.93 | 97 |
| 95 | 9.29 | 100 | 5 | 55 | 7.32 | 98 |
| 96 | 9.26 | 100 | 6.4 | 73 | 7.48 | 95 |
| 97 | 9.24 | 101 | 5.89 | 93 | 7.27 (h) 7.46 (r) | 101 (h) 99 (r) |
| 98 | 9.22 | 100 | 6.22 | 94 | 7.4 | 98 |
| 99 | 9.22 | 100 | 5.68 | 87 | 8.02 | 100 |
| 100 | 9.18 | 101 | 6.57 | 99 | 7.79 | 100 |
| 101 | 9.18 | 101 | 5.32 | 70 | 7.24 | 98 |
| 102 | 9.17 | 100 | <6 | 44 | 7.58 | 95 |
| 103 | 9.15 | 99 | 7.06 | 100 | 7.74 | 100 |
| 104 | 9.09 | 100 | 6.29 | 92 | 7.13 | 98 |
| 105 | 9.06 | 101 | 5.87 | 90 | 7.53 | 101 |
| 106 | 9.05 | 100 | 6.41 | 98 | 7.67 | 99 |
| 107 | 9.04 | 100 | 5.38 | 61 | 7.09 | 99 |
| 108 | 9.04 | 100 | 5.57 | 80 | 7.28 | 99 |
| 109 | 9.03 | 101 | 6.34 | 98 | 8.18 | 99 |
| 110 | 8.88 | 100 | 5.47 | 76 | 6.95 | 98 |
| 111 | 9.01 | 100 | 5.98 | 92 | 7.42 | 99 |
| 112 | 9 | 101 | 5.75 | 84 | 7.32 | 99 |
| 113 | 9 | 99 | 5.95 | 88 | 7.42 | 99 |
| 114 | 8.98 | 100 | 7.05 | 98 | 7.34 | 101 |
| 115 | 8.98 | 100 | 5.71 | 87 | 7.11 | 99 |
| 117 | 8.94 | 100 | 6.07 | 97 | 8.01 | 99 |
| 116 | 8.95 | 101 | 5.66 | 82 | 7.1 | 98 |
| 118 | 8.78 | 101 | 6.02 | 92 | 7.13 | 99 |
| 119 | 8.76 | 100 | 7.21 | 101 | 7.11 | 99 |
| 120 | 8.76 | 100 | 6.15 | 95 | 6.7 | 96 |
| 121 | 8.75 | 99 | 6.29 | 95 | 7.23 | 96 |
| 122 | 8.73 | 100 | 5.74 | 86 | 7.13 | 100 |
| 123 | 8.71 | 99 | 5.79 | 87 | 7.04 | 99 |
| 124 | 8.69 | 99 | 6.38 | 98 | 7.44 | 98 |
| 125 | 8.68 | 100 | 6.23 | 96 | 6.23 | 96 |
| 126 | 8.68 | 101 | 5.22 | 65 | 6.95 | 97 |
| 127 | 8.65 | 99 | 6.36 | 94 | 7.59 | 99 |
| 128 | 8.64 | 100 | 6.03 | 90 | 6.81 | 98 |
| 129 | 8.64 | 101 | 5.71 | 85 | 7.04 | 99 |
| 130 | 8.61 | 100 | 5.76 | 87 | 6.87 | 96 |
| 131 | 8.61 | 98 | 5.11 | 61 | 7.39 | 99 |
| 132 | 8.6 | 101 | <5 | 46 | 6.7 | 98 |
| 133 | 8.53 | 100 | 5.79 | 85 | 6.87 | 98 |
| 134 | 8.5 | 101 | 5.65 | 84 | 6.8 | 100 |
| 135 | 8.48 | 100 | 5.58 | 81 | 6.72 | 97 |
| 136 | 8.47 | 101 | <5 | 51 | 6.54 | 97 |
| 137 | 7.55 | 100 | <5 | 35 | 5.87 | 84 |
| 138 | 7.55 | 93 | 5.31 | 64 | <5 | 24 |
| 139 | 7.54 | 99 | <5 | 20 | 5.62 | 78 |
| 140 | 7.53 | 100 | 5.05 | 57 | 5.51 | 83 |
| 141 | 7.53 | 100 | <5 | 12 | 5.69 | 81 |
| 142 | 7.52 | 100 | <5 | 35 | 5.59 | 79 |
| 143 | 7.48 | 97 | 5.1 | 58 | 5.62 | 77 |
| 144 | 7.46 | 100 | 5.62 | 86 | 6.33 | 96 |
| 145 | 7.44 | 99 | 5.69 | 86 | 6.19 | 93 |
| 146 | 7.43 | 100 | 5.78 | 85 | 5.48 | 76 |
| 147 | 7.42 | 100 | 5.65 | 81 | 6.06 | 90 |
| 148 | 7.41 | 101 | 5.25 | 67 | 6.04 | 89 |
| 149 | 7.41 | 99 | 5.29 | 66 | 5.74 | 83 |
| 150 | 7.4 | 100 | <5 | 22 | 5.45 | 72 |
| 151 | 7.39 | 100 | <5 | 11 | 5.86 | 85 |
| 152 | 7.38 | 99 | <5 | 30 | 5.69 | 80 |
| 153 | 7.36 | 100 | 5.51 | 76 | 5.97 | 89 |
| 154 | 7.29 | 100 | <5 | 50 | 5.56 | 79 |
| 155 | 7.27 | 98 | <5 | 37 | 5.53 | 72 |
| 156 | 7.23 | 100 | <5 | 19 | 5.7 | 81 |
| 157 | 7.22 | 99 | <5 | 33 | 5.59 | 75 |
| 158 | 7.19 | 100 | <5 | 19 | 5.67 | 78 |
| 159 | 7.14 | 100 | <5 | 42 | 5.49 | 75 |
| 160 | 7.14 | 99 | <5 | 34 | 5.99 | 88 |
| 161 | 7.13 | 98 | <5 | 11 | 5.51 | 74 |

TABLE 5-continued

IN VITRO DATA FOR COMPOUNDS OF THE INVENTION. By default, data on inhibition of PDE10A refers to the human clone (also indicated as (h)) unless indicated as (r), referring to the rat clone.

| Co. No. | hPDE2A pIC$_{50}$ | hPDE2A E$_{max}$ | hPDE3B pIC$_{50}$ | hPDE3B E$_{max}$ | hPDE10A2 or rPDE10A2 pIC$_{50}$ | hPDE10A2 or rPDE10A2 E$_{max}$ |
|---|---|---|---|---|---|---|
| 162 | 7.13 | 97 | <5 | 26 | 5.37 | 72 |
| 163 | 7.05 | 98 | <5 | 12 | 5.49 | 74 |
| 164 | 7.05 | 100 | <5 | 22 | 5.71 | 82 |
| 165 | 7.03 | 100 | <5 | 36 | 5.46 | 78 |
| 166 | 7.03 | 98 | <5 | 32 | 5.65 | 81 |
| 167 | 7.01 | 97 | 5.27 | 64 | 5.7 | 81 |
| 168 | 8.4 | 98 | 5.29 | 66 | 7.27 | 99 |
| 169 | 8.43 | 98 | 5.75 | 82 | 6.75 | 98 |
| 170 | 8.34 | 100 | 5.67 | 84 | 5.89 | 84 |
| 171 | 7.93 | 99 | 5.94 | 93 | 6.45 | 97 |
| 172 | 8.34 | 101 | 6.57 | 98 | 7.49 | 100 |
| 173 | 7.86 | 101 | <5 | 31 | 6.52 | 96 |
| 174 | 8.28 | 99 | 5.88 | 85 | 6.24 | 88 |
| 175 | 8.31 | 100 | 5.22 | 71 | 6.85 | 98 |
| 176 | 8.04 | 100 | 5.06 | 56 | 6.05 | 88 |
| 177 | 8.02 | 99 | <5 | 21 | 6.34 | 93 |
| 178 | 7.87 | 101 | 5.13 | 62 | 6.1 | 92 |
| 179 | 7.67 | 100 | <5 | 32 | 6.27 | 90 |
| 180 | 8.3 | 100 | 5.29 | 66 | 6.76 | 97 |
| 181 | 8.34 | 98 | <5 | 52 | 6.51 | 94 |
| 182 | 7.6 | 100 | <5 | 44 | 6.38 | 95 |
| 183 | 7.58 | 99 | <5 | 36 | 5.64 | 79 |
| 184 | 7.55 | 100 | <5 | 17 | 5.56 | 75 |
| 185 | 7.66 | 98 | 5.48 | 79 | 5.92 | 87 |
| 186 | 7.97 | 100 | 5.22 | 69 | 6.47 | 95 |
| 187 | 7.75 | 99 | 5.46 | 74 | 6.37 | 95 |
| 188 | 8.07 | 99 | 5.81 | 87 | 6.68 | 98 |
| 189 | 8.29 | 100 | 5.56 | 80 | 6.73 | 96 |
| 190 | 7.99 | 100 | <5 | 39 | 6.8 | 96 |
| 191 | 7.89 | 100 | 5.41 | 74 | 6.65 | 97 |
| 192 | 8.03 | 99 | 6.14 | 95 | 7.14 | 99 |
| 193 | 8.23 | 100 | 5.46 | 76 | 6.86 | 98 |
| 194 | 7.73 | 99 | 5.34 | 57 | 6.58 | 97 |
| 195 | 8.35 | 98 | 5.25 | 70 | 6.43 | 93 |
| 196 | 7.63 | 99 | 5.31 | 68 | 6.25 | 92 |
| 197 | 7.99 | 98 | <5 | 42 | 6.68 | 96 |
| 198 | 8.25 | 98 | <5 | 35 | 6.38 | 91 |
| 199 | 7.27 | 92 | 5.08 | 62 | 5.23 (h) | 62 (h) |
| | | | | | 5.32 (r) | 21 (r) |
| 200 | 7.01 | 91 | <5 | 35 | <5 | 13 |
| 201 | 6.19 | 61 | <5 | 24 | 5.51 (r) | −1 (r) |
| 202 | 5.57 | 30 | <5 | 18 | <5 (h) | 38 (h) |
| | | | | | <5 (r) | 4 (r) |
| 203 | 6.02 | 48 | <5 | 41 | <5 (r) | 14 (r) |
| 204 | 6.79 | 88 | 5.13 | 48 | <5 (r) | 13 (r) |
| 205 | 8.94 | 99 | 5.65 | 83 | 7.01 | 98 |
| 206 | 5.78 | 39 | <5 | −1 | <5 | 16 |
| 207 | 5.1 | 21 | <5 | 2 | <5 | −5 |
| 208 | 6.23 | 62 | <5 | 30 | <5 | 4 |
| 209 | 6.14 | 57 | <5 | 25 | <5 | 7 |
| 210 | 6.21 | 56 | <5 | 5 | <5 | 16 |
| 211 | <5 | 3 | <5 | 13 | <5 | 10 |
| 212 | 6.24 | 61 | <5 | 7 | <5 | 8 |
| 213 | 5.63 | 28 | <5 | 11 | <5 | 23 |
| 214 | 5.2 | 9 | <5 | 9 | <5 | 30 |
| 215 | 6.58 | 82 | 5 | 45 | 5.13 | 63 |
| 216 | 6.36 | 98 | <5 | 26 | 5.35 | 67 |
| 217 | 6.25 | 99 | <5 | 37 | 5.32 | 72 |
| 218 | 6.69 | 100 | <5 | 51 | 5.65 | 85 |
| 219 | 6.86 | 100 | <5 | 18 | 5.04 | 45 |
| 220 | 6.52 | 54 | <5 | 8 | <5 | 41 |
| 220 (•HCl) | 6.52 | 54 | <5 | 8 | <5 | 41 |
| 221 | 5.92 | 45 | <5 | 4 | <5 | 26 |
| 222 | 6.55 | 98 | <5 | 13 | 5.17 | 59 |
| 223 | 6.71 | 98 | <5 | 19 | 5.46 | 71 |
| 224 | 8.52 | 100 | 5.98 | 87 | 7.15 | 99 |
| 225 | 7.94 | 99 | 5.75 | 83 | 7.03 | 98 |
| 226 | 9.06 | 100 | 6.89 | 100 | 7.09 | 100 |
| 227 | 8.66 | 101 | 6.42 | 95 | 7.34 | 98 |
| 228 | 9.65 | 100 | 5.92 | 91 | 7.77 | 100 |

TABLE 5-continued

IN VITRO DATA FOR COMPOUNDS OF THE INVENTION. By default, data on inhibition of PDE10A refers to the human clone (also indicated as (h)) unless indicated as (r), referring to the rat clone.

| Co. No. | hPDE2A $pIC_{50}$ | hPDE2A $E_{max}$ | hPDE3B $pIC_{50}$ | hPDE3B $E_{max}$ | hPDE10A2 or rPDE10A2 $pIC_{50}$ | hPDE10A2 or rPDE10A2 $E_{max}$ |
|---|---|---|---|---|---|---|
| 229 | 6.25 | 95 | <5 | 18 | <5 | 33 |
| 230 | 5.99 | 93 | <5 | 40 | 5.27 | 65 |
| 231 | 8.87 | 97 | 5.04 | 57 | 7.71 | 100 |
| 232 | 6.67 | 99 | <5 | 31 | <5 | 48 |
| 233 | 6.24 | 94 | <5 | 10 | <5 | 26 |
| 234 | 6.29 | 96 | <5 | 22 | 5.06 | 59 |
| 235 | 6.91 | 98 | <5 | 32 | 5.26 | 67 |
| 236 | 6.68 | 100 | <5 | 18 | 5.11 | 58 |
| 237 | 6.73 | 97 | <5 | 20 | 5.09 | 51 |
| 238 | 6.42 | 94 | <5 | 35 | 5 | 48 |
| 239 | 6.72 | 96 | <5 | 16 | <5 | 43 |
| 240 | 5.81 | 90 | <5 | 9 | 5.04 | 51 |
| 241 | 7.68 | 97 | 5.76 | 88 | 6.57 | 94 |
| 242 | 6.87 | 97 | 5.21 | 67 | 5.09 | 56 |
| 243 | 6.88 | 99 | <5 | 13 | 5.44 | 70 |
| 244 | 6.17 | 92 | <5 | 12 | 5.03 | 54 |
| 245 | 6.91 | 99 | 5.23 | 62 | 5.66 | 79 |
| 246 | 6.9 | 98 | <5 | 25 | <5 | 44 |
| 247 | 6.81 | 98 | 5.69 | 85 | 5.54 | 77 |
| 248 | 6.46 | 95 | <5 | 2 | 4.98 | 49 |
| 249 | 6.43 | 95 | <5 | 10 | <5 | 45 |
| 250 | 6.88 | 99 | <5 | 28 | 5.31 | 64 |
| 251 | 6.55 | 98 | <5 | 17 | 5.06 | 53 |
| 252 | 6.15 | 96 | <5 | 17 | 5.17 | 66 |
| 253 | 6.34 | 95 | <5 | 17 | <5 | 39 |
| 254 | 6.97 | 99 | <5 | 25 | 5.42 | 70 |
| 255 | 6.57 | 95 | <5 | 28 | 5.11 | 58 |
| 256 | 6.49 | 97 | <5 | 12 | 5 | 48 |
| 257 | 6.58 | 95 | <5 | 15 | <5 | 45 |
| 258 | 6.82 | 99 | 5.81 | 89 | 5.9 | 90 |
| 259 | 6.37 | 99 | 5.45 | 82 | 5.77 | 92 |
| 260 | 6.86 | 97 | <5 | 23 | 5.53 | 74 |
| 261 | 6.44 | 95 | <5 | 19 | <5 | 45 |
| 262 | 6.81 | 101 | <5 | 37 | 5.49 | 74 |
| 263 | 6.89 | 99 | 5.31 | 65 | 5.29 | 64 |
| 264 | 6.98 | 100 | 4.98 | 47 | 5.48 | 74 |
| 265 | 8.62 | 102 | 5.2 | 55 | 7.43 | 98 |
| 266 | 6.38 | 100 | 5.27 | 74 | 5.58 | 89 |
| 267 | 9.4 | 102 | 7.21 | 100 | 7.95 | 99 |
| 268 | 5.72 | 82 | <5 | 13 | <5 | 39 |
| 269 | 9.15 | 101 | 5.43 | 78 | 6.16 | 93 |
| 270 | 8.63 | 100 | <5 | 29 | 6.57 | 96 |
| 271 | 8.53 | 99 | 5.13 | 61 | 6.79 | 95 |
| 272 | 8.66 | 102 | 5.05 | 54 | 6.1 | 93 |
| 273 | 8.63 | 100 | 6.09 | 96 | 6.01 | 96 |
| 274 | 6.54 | 97 | <5 | 7 | 5.22 | 63 |
| 275 | 8.55 | 100 | 6.01 | 92 | 7.54 | 100 |
| 276 | 8.65 | 100 | 5.89 | 93 | 6.78 | 98 |
| 277 | 7.12 | 99 | <5 | 14 | <5 | 27 |
| 278 | 9.03 | 99 | 6.15 | 97 | 6.84 | 99 |
| 279 | 8.65 | 99 | 5.55 | 86 | 6.5 | 96 |
| 280 | 8.6 | 100 | 6.03 | 96 | 6.61 | 99 |
| 281 | 8.78 | 100 | 5.65 | 87 | 6.96 | 99 |
| 282 | 8.54 | 100 | 5.77 | 88 | 6.56 | 98 |
| 283 | 8.07 | 100 | <5 | 38 | 6.75 | 98 |
| 284 | 8.77 | 101 | 5.9 | 89 | 7.26 | 98 |
| 285 | 5.16 | 65 | <5 | 21 | <5 | 37 |
| 286 | 8.16 | 101 | <5 | 14 | 5.65 | 79 |
| 287 | 8.42 | 100 | 5.2 | 61 | 6.76 | 98 |
| 288 | 8.57 | 101 | <5 | 44 | 6.38 | 93 |
| 289 | 8.62 | 100 | 6.75 | 98 | 7.2 | 99 |
| 290 | 8.23 | 98 | 5.16 | 53 | 5.85 | 89 |
| 291 | 8.57 | 101 | 5.58 | 86 | 6.29 | 95 |
| 292 | 8.6 | 100 | 5.33 | 73 | 6.14 | 94 |
| 293 | 7.95 | 100 | 5.46 | 80 | 5.99 | 90 |
| 294 | 7.97 | 99 | <5 | 14 | 5.68 | 81 |
| 295 | 9.31 | 101 | 6.01 | 94 | 6.61 | 98 |
| 296 | 9.34 | 99 | 6.1 | 93 | 6.92 | 100 |
| 297 | 8.63 | 97 | 5.23 | 62 | 6.23 | 96 |
| 298 | 7.73 | 99 | <5 | 25 | <5 | 47 |
| 299 | 8.11 | 99 | <5 | 40 | 5.67 | 84 |

TABLE 5-continued

IN VITRO DATA FOR COMPOUNDS OF THE INVENTION. By default, data on inhibition of PDE10A refers to the human clone (also indicated as (h)) unless indicated as (r), referring to the rat clone.

| Co. No. | hPDE2A $pIC_{50}$ | hPDE2A $E_{max}$ | hPDE3B $pIC_{50}$ | hPDE3B $E_{max}$ | hPDE10A2 or rPDE10A2 $pIC_{50}$ | hPDE10A2 or rPDE10A2 $E_{max}$ |
|---|---|---|---|---|---|---|
| 300 | 8.19 | 100 | 5.7 | 88 | 5.54 | 80 |
| 301 | 8.09 | 100 | 5.2 | 62 | 5.9 | 89 |
| 302 | 8.19 | 101 | 5.1 | 59 | 6.05 | 93 |
| 303 | 8.15 | 99 | 5.18 | 57 | 6.27 | 95 |
| 304 | 7.4 | 100 | 5.04 | 48 | <5 | 45 |
| 305 | 7.06 | 100 | <5 | 7 | 5.15 | 57 |
| 306 | 7.35 | 100 | 5.35 | 71 | 5.44 | 74 |
| 307 | 8.04 | 99 | 5.83 | 88 | 6.22 | 97 |
| 308 | 7.76 | 98 | 5.34 | 72 | 5.17 | 66 |
| 309 | 8.53 | 100 | 5.12 | 53 | 5.82 | 86 |
| 310 | 8.85 | 100 | 5.41 | 78 | 6.4 | 95 |
| 311 | 8.96 | 96 | 5.13 | 62 | 6.37 | 96 |
| 312 | 7.66 | 99 | <5 | 37 | 6.21 | 93 |
| 313 | 8.87 | 97 | 5.22 | 61 | 5.91 | 86 |
| 314 | 8.24 | 100 | 5.45 | 73 | 6.03 | 91 |
| 315 | 6.95 | 98 | <5 | 20 | 5.01 | 47 |
| 316 | 6.59 | 94 | <5 | 5 | <5 | 14 |
| 317 | 7.07 | 99 | <5 | 15 | <5 | 34 |
| 318 | 5.82 | 89 | <5 | 11 | <5 | 13 |
| 319 | 8.95 | 100 | 5.99 | 95 | 6.58 | 99 |
| 320 | 7.27 | 100 | <5 | 47 | 5.15 | 62 |
| 321 | 8.66 | 101 | 5.09 | 45 | 6.51 | 97 |
| 322 | 9.3 | 100 | 6.32 | 95 | 7.73 | 99 |
| 323 | 8.41 | 100 | 6.14 | 95 | 6.65 | 97 |
| 324 | 9.07 | 100 | 6.58 | 97 | 7.18 | 100 |
| 325 | 8.94 | 100 | 6.51 | 98 | 7.19 | 98 |
| 326 | 8.67 | 100 | 6.59 | 97 | 7.22 | 99 |
| 327 | 9.38 | 101 | 7.11 | 99 | 7.69 | 100 |
| 328 | 9.2 | 100 | 5.83 | 90 | 7.21 | 100 |
| 329 | 9.26 | 100 | 6.69 | 95 | 7.67 | 100 |
| 331 | 9.32 | 98 | 7.3 | 99 | 7.84 | 100 |
| 332 | 8.32 | 99 | 5.92 | 90 | 7.51 | 98 |
| 333 | 8.09 | 99 | 5.16 | 63 | 6.15 | 93 |
| 334 | 8.61 | 100 | 5.63 | 84 | 7 | 98 |
| 335 | 9.02 | 102 | 5.14 | 52 | 7.06 | 98 |
| 336 | 7.73 | 101 | 5.49 | 78 | 5.72 | 87 |
| 337 | 6.78 | 99 | <5 | 43 | 5.34 | 71 |
| 338 | 7.04 | 99 | 5.26 | 62 | 5.51 | 70 |
| 339 | 8.18 | 101 | 5.32 | 69 | 6.21 | 95 |
| 340 | 7.15 | 100 | 5.37 | 69 | 5.48 | 72 |
| 341 | 6.85 | 97 | <5 | 33 | 5.3 | 63 |
| 342 | 7.49 | 100 | 5.35 | 69 | 5.57 | 77 |
| 343 | 7.17 | 102 | <5 | 44 | 5.34 | 68 |
| 344 | 7.53 | 99 | 5.14 | 61 | 5.59 | 80 |
| 345 | 7.12 | 99 | 5.08 | 48 | 5.43 | 72 |
| 346 | 8.28 | 100 | 5.22 | 68 | 6.14 | 92 |
| 347 | 8.27 | 101 | 5.14 | 63 | 6 | 91 |
| 348 | 7.47 | 99 | 5.35 | 70 | 5.89 | 92 |
| 349 | 7.65 | 102 | 5.32 | 64 | 5.75 | 86 |
| 350 | 7.6 | 100 | 5.31 | 74 | 5.68 | 85 |
| 351 | 7.29 | 99 | 5.2 | 69 | 5.67 | 83 |
| 352 | 8.12 | 100 | 5.74 | 89 | 6.32 | 99 |
| 353 | 8.47 | 99 | 5.32 | 69 | 6.01 | 94 |
| 354 | 7.05 | 100 | 5.01 | 45 | 5.35 | 70 |
| 355 | 9.03 | 99 | 6.14 | 98 | 6.63 | 98 |
| 356 | 8.27 | 99 | 5.23 | 65 | 6.03 | 92 |
| 357 | 7.11 | 98 | <5 | 34 | 5.47 | 73 |
| 358 | 7.57 | 102 | <5 | 40 | 5.1 | 58 |
| 359 | 7.92 | 99 | 5.4 | 71 | 5.67 | 86 |
| 360 | 7.39 | 97 | 5.07 | 50 | 5.16 | 55 |
| 361 | 8.56 | 100 | <5 | 37 | 6.45 | 92 |
| 362 | 8.77 | 99 | 6.06 | 88 | 6.1 | 93 |
| 363 | 9.56 | 99 | 6.21 | 97 | 6.75 | 98 |
| 364 | 8.41 | 101 | 5.5 | 75 | 5.74 | 85 |
| 365 | 7.2 | 99 | <5 | 24 | <5 | 33 |
| 366 | 7.99 | 99 | <5 | 22 | 5.24 | 64 |
| 367 | 6.36 | 97 | <5 | 21 | <5 | 44 |
| 368 | 8.21 | 101 | 5.19 | 61 | 6.6 | 99 |
| 369 | 8.31 | 100 | 5.43 | 72 | 6.14 | 93 |
| 370 | 7.47 | 100 | 5.84 | 87 | 6.18 | 94 |
| 371 | 7.86 | 101 | 6.41 | 96 | 6.41 | 98 |

TABLE 5-continued

IN VITRO DATA FOR COMPOUNDS OF THE INVENTION. By default,
data on inhibition of PDE10A refers to the human clone (also indicated
as (h)) unless indicated as (r), referring to the rat clone.

| Co. No. | hPDE2A pIC$_{50}$ | hPDE2A E$_{max}$ | hPDE3B pIC$_{50}$ | hPDE3B E$_{max}$ | hPDE10A2 or rPDE10A2 pIC$_{50}$ | hPDE10A2 or rPDE10A2 E$_{max}$ |
|---|---|---|---|---|---|---|
| 372 | 8.99 | 100 | 5.87 | 90 | 6.6 | 96 |
| 373 | 8.57 | 100 | 6.27 | 97 | 6.5 | 99 |
| 374 | 9.13 | 100 | 6.13 | 97 | 6.74 | 98 |
| 375 | 8.45 | 101 | 5.35 | 73 | 6.09 | 94 |
| 376 | 8.37 | 101 | 5.47 | 79 | 6.51 | 97 |
| 377 | 7.75 | 99 | 5.01 | 47 | 5.89 | 89 |
| 378 | 8.77 | 99 | 6.12 | 96 | 6.39 | 97 |
| 379 | 7.95 | 102 | 5.28 | 67 | 5.79 | 87 |
| 380 | 8.26 | 101 | 5.4 | 72 | 6.44 | 96 |
| 381 | 8.12 | 99 | 5 | 48 | 5.88 | 88 |
| 382 | 7.99 | 99 | <5 | 37 | 5.4 | 75 |
| 386 | 8.62 | 98 | 5.6 | 79 | 6.26 | 93 |
| 387 | 8.54 | 100 | 5.77 | 88 | 6.56 | 98 |
| 390 | 8.68 | 98 | 5.59 | 84 | 7.21 | 99 |
| 391 | 8.62 | 99 | 5.65 | 81 | 7.2 | 97 |
| 392 | 8.95 | 99 | 6.35 | 97 | 6.58 | 93 |
| 394 | 8.03 | 99 | <5 | 27 | 5.65 | 76 |
| 396 | 7.82 | 98 | <5 | 56 | 5.83 | 84 |
| 398 | 8.31 | 99 | 5.28 | 67 | 6.23 | 95 |
| 400 | 7.65 | 99 | <5 | 16 | <5 | 41 |
| 402 | 7.58 | 100 | <5 | 28 | 5.83 | 87 |

PDE2 Occupancy by Test Compounds

Methods

Occupancy of PDE2A was evaluated by ex-vivo autoradiography using [$^3$H]B-17a (described in WO2013/000924) as radioligand (compound 12 in Buijnsters et al., (2014). Structure-Based Design of a Potent, Selective, and Brain Penetrating PDE2 Inhibitor with Demonstrated Target Engagement. ACS Med Chem Lett. 5(9):1049-53.)

Male Wistar rats (200-250 g) were treated by oral administration of vehicle or increasing doses of [$^3$H]B-17a and killed one h after. Brains were immediately removed from the skull and rapidly frozen in dry-ice cooled 2-methylbutane (−40° C.). Twenty μm-thick striatal sections were cut using a Leica CM 3050 cryostat-microtome (van Hopplynus, Belgium), thaw-mounted on microscope slides (SuperFrost Plus Slides, LaboNord, France) and stored at −20° C. until use.

After thawing, sections were dried under a cold stream of air and incubated for one minute with 30 nM [$^3$H]B-17a in Tris-HCl (50 mM, pH7.4) containing 0.3% BSA. Brain sections from drug-treated and vehicle-treated animals were incubated in parallel. Non-specific binding was measured on cerebellar sections, a brain area which does not contain the PDE2A enzyme. After incubation, the excess of [$^3$H]B-17a was washed off in ice-cold buffer 2 times 10 minutes, followed by a quick dip in distilled water. The sections were then dried under a stream of cold air.

Brain sections were loaded in a β-imager (Biospace, Paris) for 4 h and radioactivity emerging from delineated brain area was quantified using the Beta vision program (Biospace, Paris). Specific binding was determined as the difference between total binding in the striatum and non-specific binding in the cerebellum. Percentage receptor occupancy of the drug administered to the animal corresponded to 100% minus the percentage receptor labeled in the treated animal. For the determination of ED$_{50}$-values, the percentage of receptor occupancy was plotted against dose and the sigmoidal log dose-effect curve of best fit was calculated by non-linear regression analysis, using the GraphPad Prism program. ED$_{50}$s (the drug dose producing 50% receptor occupancy) with 95% confidence limits were calculated from the dose-response curves.

TABLE 6

| Co. No. | PDE2 Occupancy at 10 mg/kg | Route PDE2 Occupancy at 10 mg/kg | PDE Occupancy ED$_{50}$ | Route Occupancy ED$_{50}$ |
|---|---|---|---|---|
| 1a | 37 | PO | | |
| 2b | 3 | SC | | |
| 2a | 70 | SC | | |
| 3a | 0 | PO | | |
| 4 | 9 | PO | | |
| 6 | 67 | PO | | |
| 13 | 2 | PO | | |
| 18 | 4 | PO | | |
| 22 | 18 | PO | | |
| 24b | 30 | PO | | |
| 25a | 0 | SC | | |
| 25b | 66 | SC | 4 | PO |
| 27 | −9 | PO | | |
| 28 | 34 | PO | | |
| 29 | 49 | SC | 25 | PO |
| 30 | 31 | SC | | |
| 32 | 0 | SC | | |
| 33 | −6 | PO | | |
| 35 | −7 | PO | | |
| 36 | −3 | PO | | |
| 37 | 32 | PO | 45.2 | PO |
| 38 | −13 | PO | | |
| 39 | 1 | PO | | |
| 41 | −8 | PO | | |
| 42 | 8 | PO | | |
| 43 | 54 | PO | | |
| 46 | 2 | PO | | |
| 47 | −9 | PO | | |
| 48 | 5 | PO | | |
| 49 | 96 | SC | | |
| 50 | 12 | SC | | |
| 51 | −30 | PO | | |
| 52 | 20 | PO | | |
| | 2 | PO | | |

TABLE 6-continued

| Co. No. | PDE2 Occupancy at 10 mg/kg | Route PDE2 Occupancy at 10 mg/kg | PDE Occupancy ED$_{50}$ | Route Occupancy ED$_{50}$ |
|---|---|---|---|---|
| 53 | 22 | PO | | |
| 54 | 39 | PO | | |
| 59 | 7 | PO | | |
| 60 | 32 | PO | | |
| 64 | 7 | PO | | |
| 65 | −23 | PO | | |
|  | −9 | PO | | |
| 66 | −14 | PO | | |
| 68 | 31 | SC | | |
| 69 | 0 | PO | | |
| 70 | 65 | SC | 6.4 | PO |
| 71 | 49 | SC | | |
| 72 | 0 | PO | | |
| 73 | 0 | PO | | |
| 74 | 14 | SC | | |
| 76 | 17 | PO | | |
| 77 | 54 | PO | 5.67 | PO |
|  | 54 | PO | | |
| 78 | 77 | SC | | |
| 79 | 15 | PO | | |
|  | 0 | PO | | |
| 80 | 52 | SC | 8.63 | PO |
| 82 | 28 | PO | | |
| 83 | 82 | PO | | |
| 84 | 45 | PO | 14.13 | PO |
| 85 | 1 | SC | | |
| 89 | 88 | SC | | |
| 90 | 73 | SC | | |
| 91 | −7 | PO | | |
| 93 | 85 | PO | 7.8 | PO |
| 95 | 27 | SC | | |
| 96 | 1 | PO | | |
| 97 | 92 | PO | | |
| 99 | 1 | PO | | |
| 101 | 43 | SC | | |
| 102 | −4 | PO | | |
| 103 | 42 | SC | | |
| 106 | −0 | PO | | |
| 107 | 29 | PO | | |
| 108 | 65 | PO | 4.8 | PO |
| 109 | 43 | PO | | |
| 110 | 75 | PO | 8.3 | PO |
| 115 | 23 | PO | | |
| 117 | 8 | PO | | |
| 116 | 3 | SC | | |
| 120 | 12 | PO | | |
| 121 | −15 | PO | | |
| 122 | 0 | PO | | |
| 123 | 4 | PO | | |
| 125 | −16 | PO | | |
| 126 | 31 | PO | | |
| 127 | 34 | PO | | |
|  | 53 | SC | | |
| 129 | 21 | PO | | |
| 130 | 0 | PO | | |
| 131 | −0 | PO | | |
| 132 | 76 | SC | 5 | PO |
| 133 | −19 | PO | | |
| 134 | 21 | PO | | |
| 139 | −11 | PO | | |
| 169 | 3 | PO | | |
| 170 | 1 | PO | | |
| 184 | −2 | PO | | |
| 186 | 8 | SC | | |
| 187 | 0 | SC | | |
| 188 | 2 | SC | | |
| 189 | 9 | PO | | |
| 190 | 1 | PO | | |
| 191 | −18 | PO | | |
| 192 | −13 | PO | | |
| 193 | −11 | PO | | |
|  | −3 | SC | | |
| 195 | −7 | PO | | |
|  | −13 | SC | | |
| 196 | 0 | PO | | |
| 197 | 8 | PO | | |
| 220 | −8 | PO | >80 | PO |
| 223 | 19 | PO | | |
| 224 | −6 | PO | | |
| 225 | −6 | PO | | |
| 227 | 18 | SC | | |
| 228 | 92 | SC | 1.5 | PO |
| 231 | −13 | SC | | |
| 267 | 59 | PO | 11 | PO |
| 269 | 22 | PO | 24.2 | PO |
| 270 | 6 | PO | | |
| 272 | 3 | PO | | |
| 273 | 65 | SC | | |
| 275 | 23 | PO | | |
| 277 | −4 | PO | | |
| 278 | 30 | PO | | |
| 281 | 57 | PO | 4.2 | PO |
| 282 | 47 | PO | 11.8 | PO |
|  | 47 | PO | | |
| 283 | −12 | PO | | |
| 284 | 16 | PO | | |
| 286 | 5 | PO | | |
| 287 | 43 | PO | | |
| 290 | −3 | PO | | |
| 291 | 38 | PO | | |
| 292 | 23 | PO | | |
| 293 | 6 | PO | | |
| 294 | 17 | PO | | |
| 295 | 71 | PO | 5.63 | PO |
| 296 | 88 | PO | | |
| 297 | −2 | PO | | |
| 299 | 31 | PO | | |
| 300 | −11 | PO | | |
| 301 | −7 | PO | | |
| 302 | 1 | PO | | |
| 303 | 17 | PO | | |
| 307 | 8 | PO | | |
| 308 | 18 | PO | | |
| 309 | 12 | PO | | |
| 310 | 52 | PO | 9.6 | PO |
| 311 | −1 | PO | | |
| 312 | −16 | PO | | |
| 313 | 28 | PO | | |
| 314 | 5 | PO | | |
| 319 | 37 | PO | | |
| 321 | 73 | PO | 3.37 | PO |
| 328 | −18 | PO | | |
| 332 | 8 | PO | | |
| 334 | 17 | PO | | |
| 335 | 88 | PO | 0.985 | PO |
| 339 | −1 | PO | | |
| 346 | 19 | PO | | |
| 347 | 11 | PO | | |
| 352 | 16 | PO | | |
| 353 | 15 | PO | | |
| 356 | 51 | PO | 5.55 | PO |
| 362 | 3 | PO | | |
| 363 | −11 | PO | | |
| 364 | −5 | PO | | |
| 366 | 18 | PO | | |
| 368 | 11 | PO | | |
| 369 | 9 | PO | | |
| 386 | 23 | PO | | |
| 387 | 47 | PO | 11.8 | PO |
|  | 47 | PO | | |
| 391 | 3 | PO | | |
| 392 | 46 | PO | | |
| 398 | 29 | PO | | |

PO = oral;
SC = subcutaneous

Effect of Compound 110 on Synaptic Transmission
Critical Reagents

Sucrose dissection buffer contained (in mM) sucrose (150), NaCl (40), KCl (4), NaH$_2$PO$_4$.H$_2$O (0.3), MgCl.6H$_2$O (7), NaHCO$_3$ (26), CaCl$_2$.2H$_2$O (0.5), D-glucose (10), equilibrated with 95% $O_2$ and 5% $CO_2$ gas mixture. Artificial cerebrospinal fluid (ACSF) used during equilibration and recording contained (in mM): NaCl (124), KCl (2.7), $NaH_2PO_4.H_2O$ (1.25), $MgSO_4.7H_2O$ (1.3), $NaHCO_3$ (26), $CaCl_2.2H_2O$ (2), D-glucose (10), Ascorbic acid (2), equilibrated with 95% $O_2$ and 5% $CO_2$ gas mixture. CNQX and Kynurenic acid were prepared in ACSF at a 50 µM and 1 mM concentration respectively. Test compounds were prepared fresh from stock solution (with DMSO) in ACSF and with a final DMSO concentration that did not exceed 0.1%. All reagents were from Sigma-Aldrich, unless otherwise indicated.

Animals (Species, Weight, and Gender)

Animals used were male Sprague-Dawley rats with a weight range between 145 and 200 g provided by Charles River Germany.

Preparation of Hippocampal Slices

Horizontal brain slices (300 µm) were obtained from the mid- to ventral hippocampus of male Sprague-Dawley rats anesthetized with isofluorane according to standard protocol. Slices were cut using a vibrating tissue slicer (Leica VT1200S) in cold (4° C.) sucrose dissection buffer at a speed of 0.1 mm/s. After cut, slices were placed for equilibration at 35° C. for 20 min and then allowed to recover at RT for at least one hour in artificial cerebrospinal fluid (ACSF). Three to four slices were prepared from one brain.

Test System

All data were recorded with a MEA set-up commercially available from MultiChannel Systems MCS GmbH (Reutlingen, Germany) composed of a 4-channel stimulus generator and a 60-channels amplifier head-stage connected to a 60-channels A/D card. Software for stimulation, recordings and analysis are the ones commercially available from Multi Channel Systems: MC Stim (II 2.0.0 release) and MC Rack (3.8.1.0 release), respectively. All of the experiments were carried out with 3-dimensional MEA (Ayanda Biosystems, S.A., CH-1015 Lausanne, Switzerland) that consist of 60 tip-shaped and 60-µm-high electrodes spaced by 100 µm. The MEA electrodes are made of platinum with 600 kΩ<impedance <900 kΩ.

Experimental Design

The effect of test compounds on synaptic transmission was investigated by recording the extracellular field potentials in hippocampal slices. It is well established that synaptic transmission a can generate a deflection of the extracellular field potential that reflects the synchronized synaptic activity in the population of neurons surrounding the recording electrode.

Extracellular field potential recordings. After recovery, brain slices were mounted on MEA chip under microscope and locating the 60 recording electrodes on the mossy fiber synapse (Dentate Gyms—CA3) region of the hippocampus. ACSF solutions were continuously perfused at a rate of 2 mL/min. The temperature of the MEA chamber was maintained at 32±0.1° C. with a Peltier element located in the MEA amplifier headstage. All data were recorded with a MEA set-up commercially available from MultiChannel Systems MCS GmbH (Reutlingen, Germany). Two adjacent electrodes of the chip were selected to stimulate the mossy fibres in the hilar region of the dentate gyrus and the fEPSP was recorded the terminal zone area of the CA3 region of the hippocampus. Field extracellular post-synaptic potentials (fEPSPs) were evoked by stimulation of the mossy fibre input with two consecutive electrical pulses separated by 30 ms and repeated every 60 s (pulse width 100 µs, and current stimulation strength (µA) 40% relative maximum amplitude). Control experiments were performed simultaneously from slices that were randomly assigned to be treated with vehicle (DMSO). N represents the number of slices and usually 3-4 slices were used per animal. Evoked-responses at post-synaptic neurons level (fEPSP) are recorded if they satisfy certain quality criteria including: correct location, stable baseline (fluctuation within +/−10% during ten consecutive minutes, amplitude >100 µV. The fEPSP from selected electrodes were sampled at 5 kHz and recorded on the hard disk of a PC for offline analysis. In parallel, fEPSP amplitudes of selected electrodes were compiled online (with MC Rack program) to monitor and to follow the quality of the experiment. Data are plotted in a spreadsheet file for off-line analysis.

Weak Long Term Potentiation (LTP) was evoked by a single high frequency stimulus (HFS) to produce a less than maximal potentiation of the fEPSP.

Figure 1A:
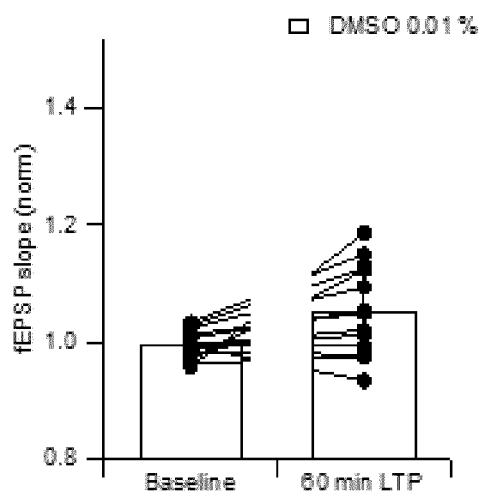
Figure 1A:
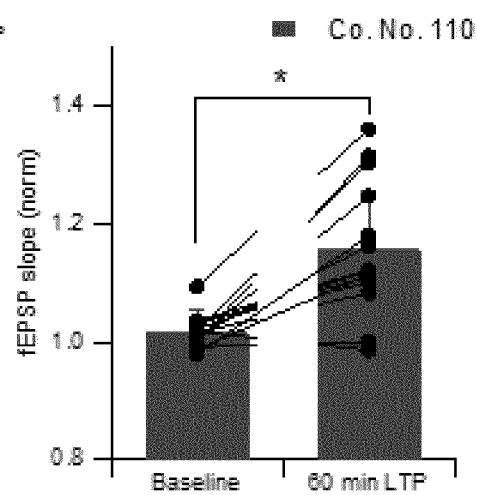

The results of this test are shown in FIG. 1 for the effect of compound 110 a PDE2 inhibitor on the facilitation on induction of LTP with a weak Long Term Potentiation protocol.

Effect of Compounds 70, 25a and 220 (Free Base) on Synaptic Transmission

Critical Reagents

Sucrose dissection buffer contained (in mM), NaCl (124), KCl (4.4), $NaH_2PO_4.H_2O$ (1.2), $MgCl.6H_2O$ (2), $NaHCO_3$ (26), $CaCl_2.2H_2O$ (2), D-glucose (10), equilibrated with 95% $O_2$ and 5% $CO_2$ gas mixture. Artificial cerebrospinal fluid (ACSF) used during equilibration and recording contained (in mM): NaCl (124), KCl (4.4), $NaH_2PO_4.H_2O$ (1.2), $MgSO_4.7H_2O$ (2), $NaHCO_3$ (26), $CaCl_2.2H_2O$ (2), D-glucose (10), Ascorbic acid (2), equilibrated with 95% $O_2$ and 5% $CO_2$ gas mixture. Compound 1, 2, and 3 were prepared fresh from stock solution (with DMSO) in ACSF and with a final DMSO concentration that did not exceed 0.1%. All reagents were from Sigma-Aldrich, unless otherwise indicated.

Animals (Species, Weight, and Gender)

Animals used were male Sprague-Dawley rats with a weight range between 145 and 200 g provided by Charles River Germany.

Preparation of Hippocampal Slices

Rats were anesthetized with isoflurane and decapitated acutely. The brain was placed next to an agarose block and was cut horizontally, with the blade advancing from anterior to posterior. Slices were cut at a thickness of 350 µm using a vibrating tissue slicer (Leica VT1200S) in cold (4° C.) carbogenated artificial cerebrospinal fluid (ACSF) at a speed of 0.08 mm/s and 0.75 mm vibration amplitude. After cutting, slices were equilibrated at 35° C. for 20 minutes and then allowed to recover at room temperature for at least one hour in ACSF. Normally, six to eight slices were prepared from each brain and three to four were used per experiment.

Test System

All data were recorded with a Slicemaster set-up commercially available from Scientifica (UK) composed of a 4 recording stations. Plamtinum stimulation electrode coated with isonel was placed in the rat hippocampal CA3 area. Recording microelectrodes (resistance around 5 MΩ) were filled with ACSF and placed within rat hippocampal CA1. Placement of stimulating and recording electrodes was confirmed by applying a current stimulation every 20 s. A pre-recording of 20 min was applied to see if the responses from the slices were stabilized. The current stimulation was applied by a current isolator A365 (World Precision Instruments). Data were acquired using pClamp 10 interfaced to a Digidata 1440A data acquisition board (Molecular Devices, Sunnyvale, Calif., USA) at a sampling rate of 10 kHz, low-pass filtered at 1 kHz, and high-pass filtered at 3 Hz. One hundred μs stimuli ranging from 0-100 μA were used to evoke fEPSPs, and the magnitude of the fEPSP was determined by measuring the peak negative amplitude or the 20-80% slope of the rising phase. Data was analyzed offline using custom made algorithms in IGORpro (Wavemetrics).

Experimental Design

The effect of compounds 70, 25a and 220 (free base) on synaptic transmission was investigated by recording the extracellular field potentials in hippocampal slices. It is well established that synaptic transmission a can generate a deflection of the extracellular field potential that reflects the synchronized synaptic activity in the population of neurons surrounding the recording electrode.
Extracellular Field Potential Recordings.

After recovery, slices were continuously perfused with oxygenated ACSF (2.5 mL/min). Solution was preheated in the water bath before being pumped into the recording chamber. Recordings were performed at 32° C. fEPSPs from four independent brain slices were recorded simultaneously. N represents the number of slices and usually 3-4 slices were used per animal. Evoked-responses at post-synaptic neurons level (fEPSP) are recorded if they satisfy certain quality criteria including: correct location, stable baseline (fluctuation within +/−10% during ten consecutive minutes, amplitude >100 μV. The fEPSP from selected electrodes were sampled at 5 kHz and recorded on the hard disk of a PC for offline analysis. In parallel, fEPSP amplitudes were compiled online (with pclamp) to monitor and to follow the quality of the experiment. Data are plotted in a spreadsheet file for off-line analysis.

Figure 2:
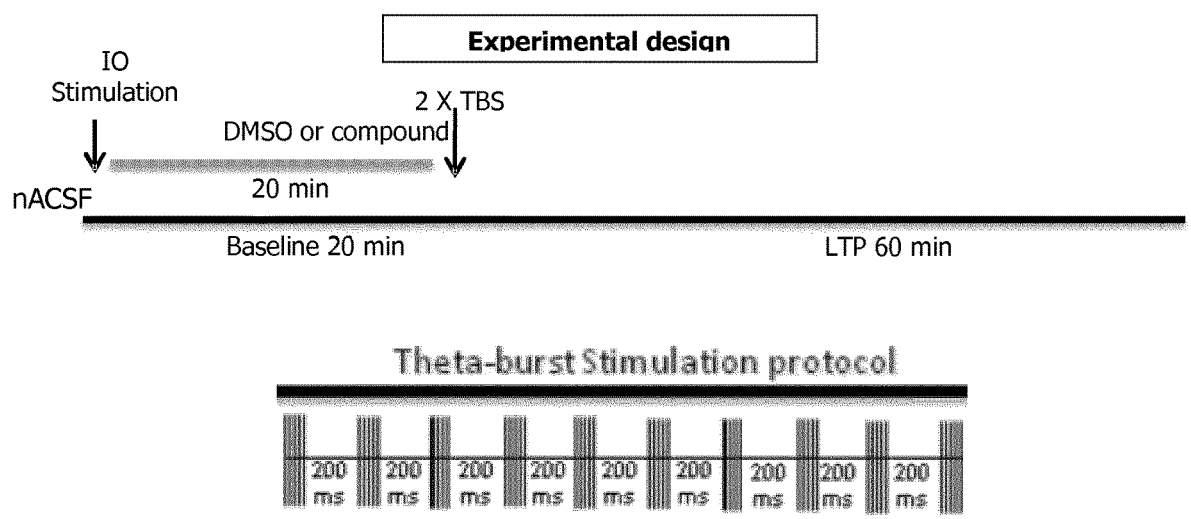
FIG. 2 shows the experimental design for theta-burst stimulation.

Input-output curves were generated and the stimulation strength was set to 50% of the range between the minimum and maximum fEPSP (as defined by either the stimulation strength sufficient to produce a population spike or a plateau in the amplitude of the fEPSP). For LTP experiments, slices were then stimulated every 60 s for a 20 min baseline period (vehicle with or without compound) and immediately followed by the theta-burst stimulation (shown as in FIG. 2). After the theta-burst stimulation, slices were then stimulated every 60 s for 60 min to measure the level of LTP.

Figure 3:
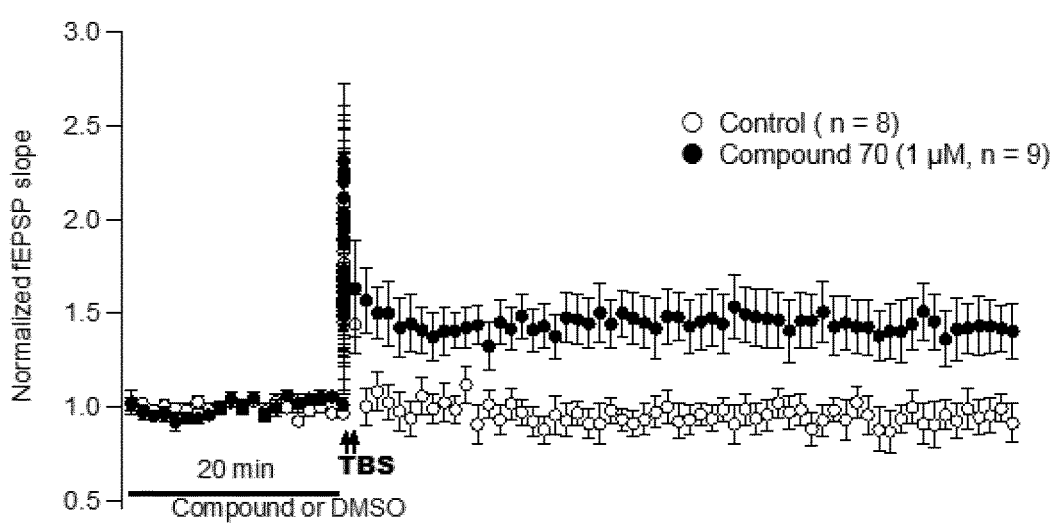
FIG. 3 shows the effect of compound 70 on weak HFS-induction of long term potentiation (LTP) at the mossy fiber synapse.
Figure 4:
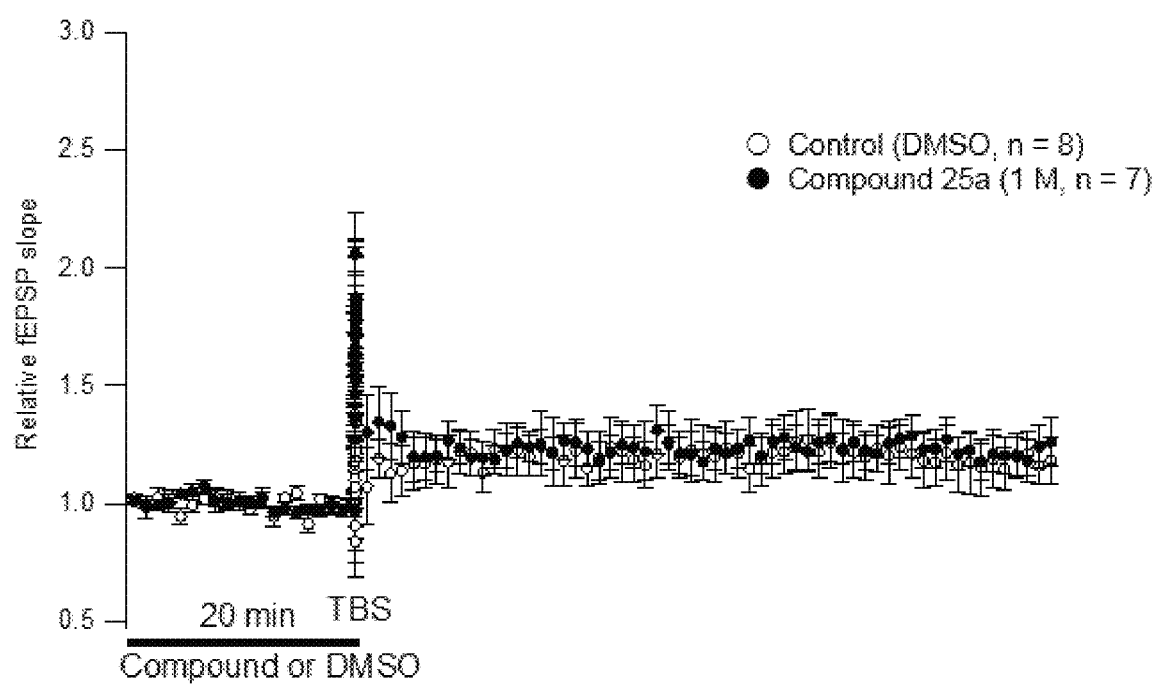
FIG. 4 shows the effect of compound 25a on weak HFS-induction of long term potentiation (LTP) at the mossy fiber synapse.
Figure 5:
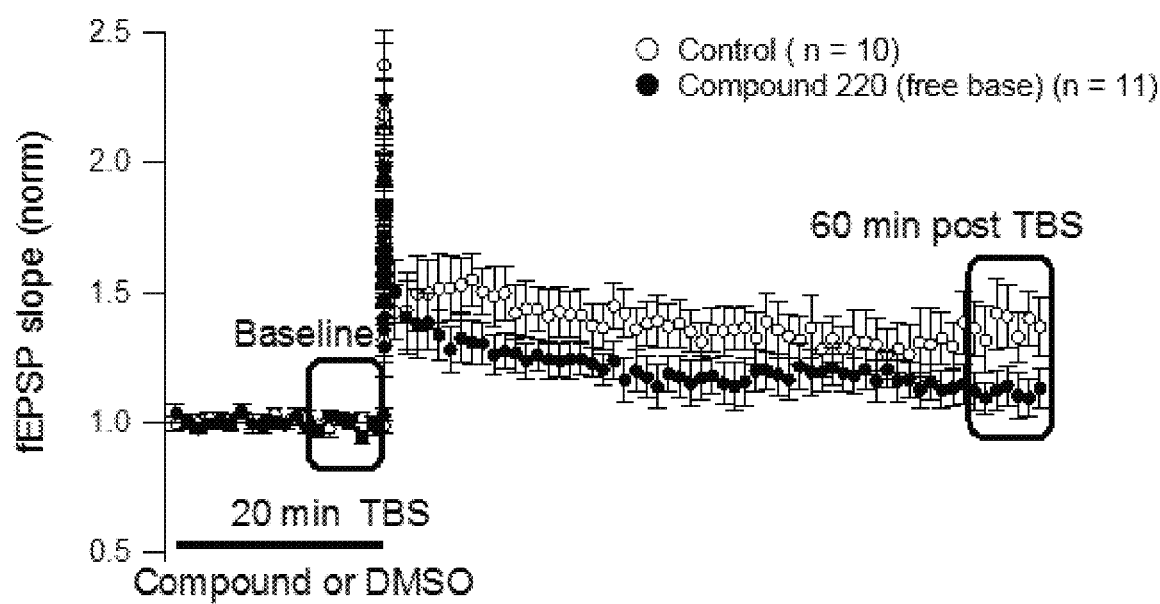
FIG. 5 shows the effect of compound 220 on weak HFS-induction of long term potentiation (LTP) at the mossy fiber synapse.
Figure 6:
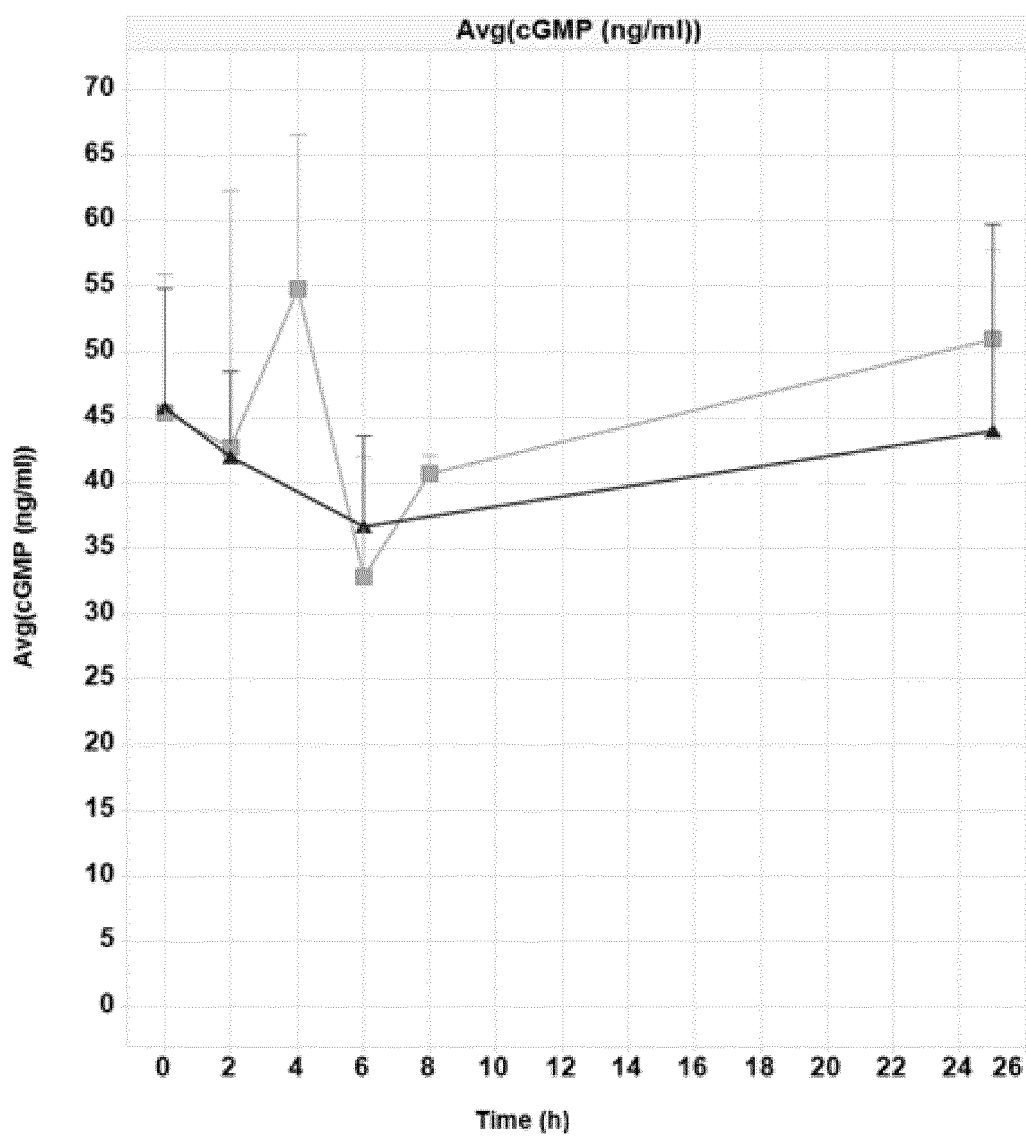
FIGS. 6 to 15 (compounds 220, 110, 93, 32, 70, 25a, 281, 295, 356, and 335, respectively) show measurement of cGMP levels in CSF in Marshall Beagle dogs.
Figure 7:
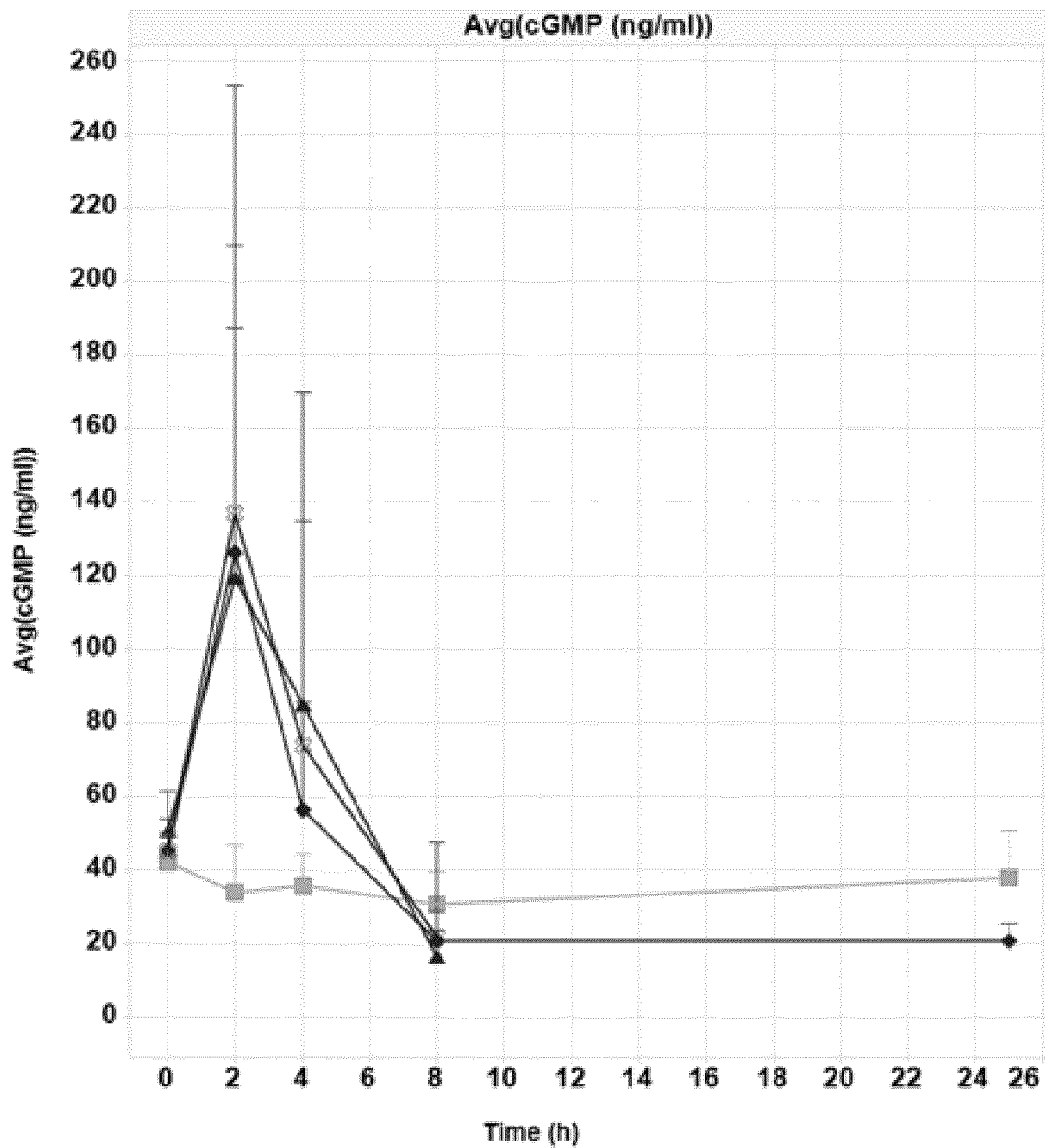
Figure 8:
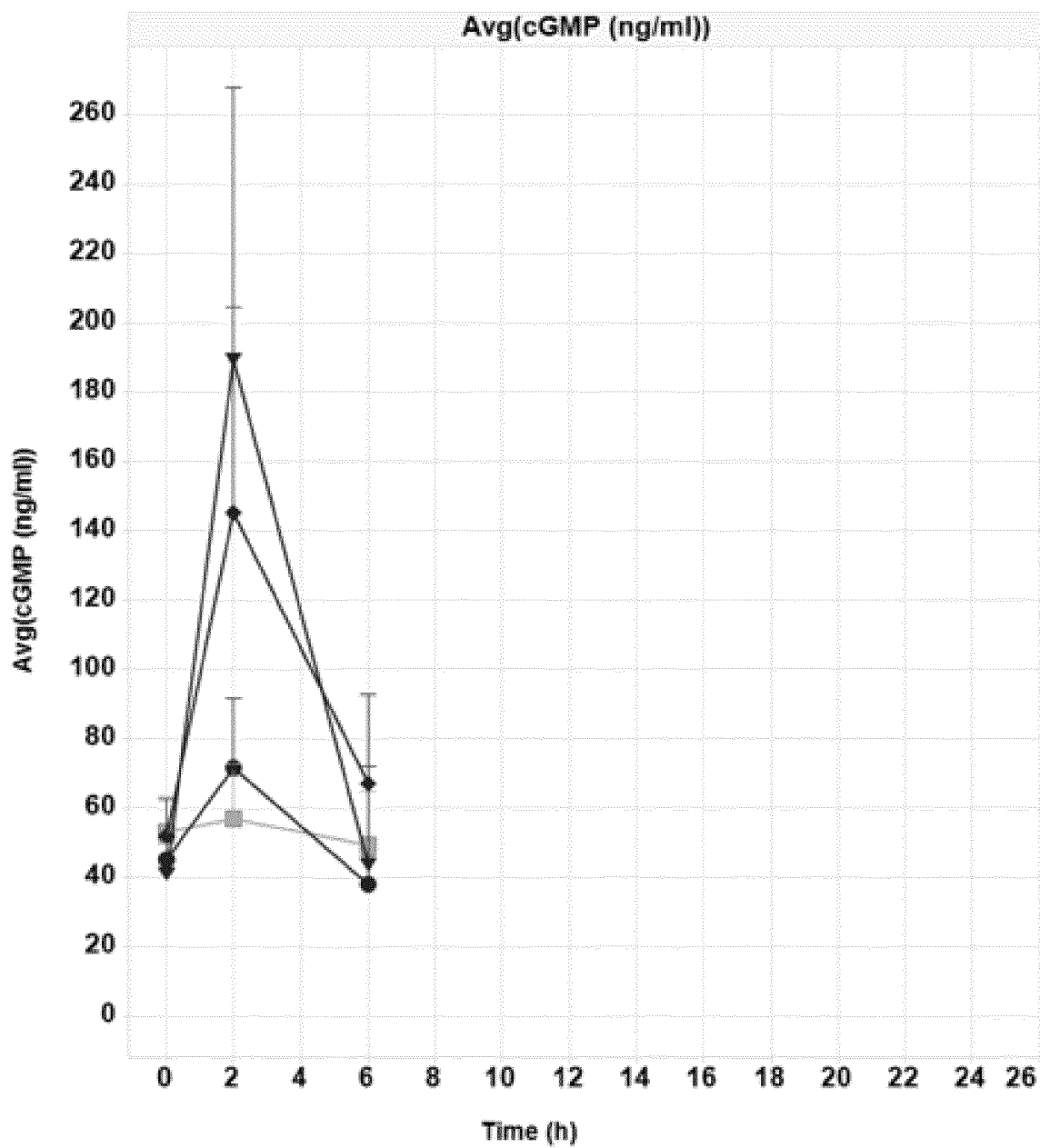
Figure 9:
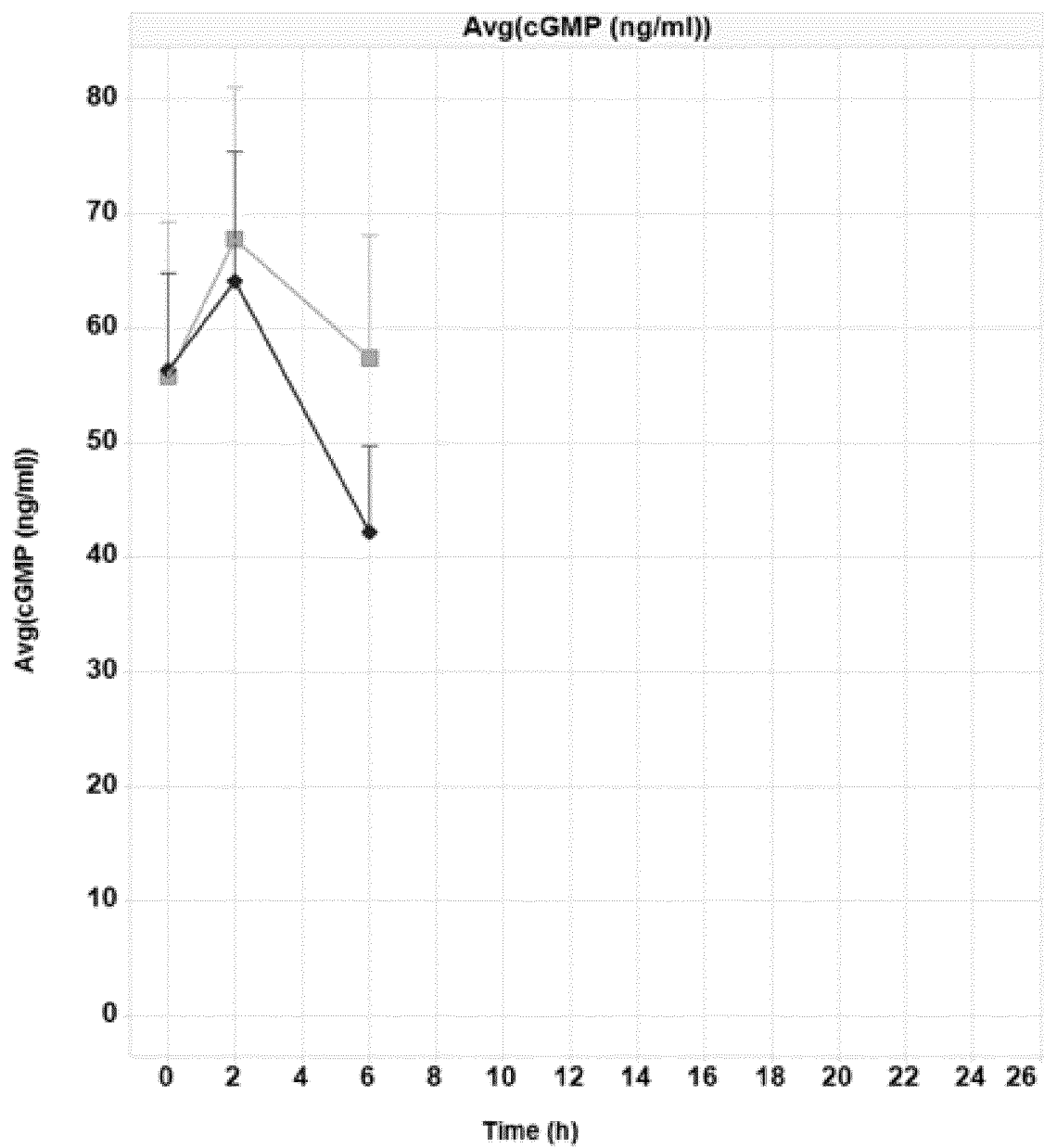
Figure 10:
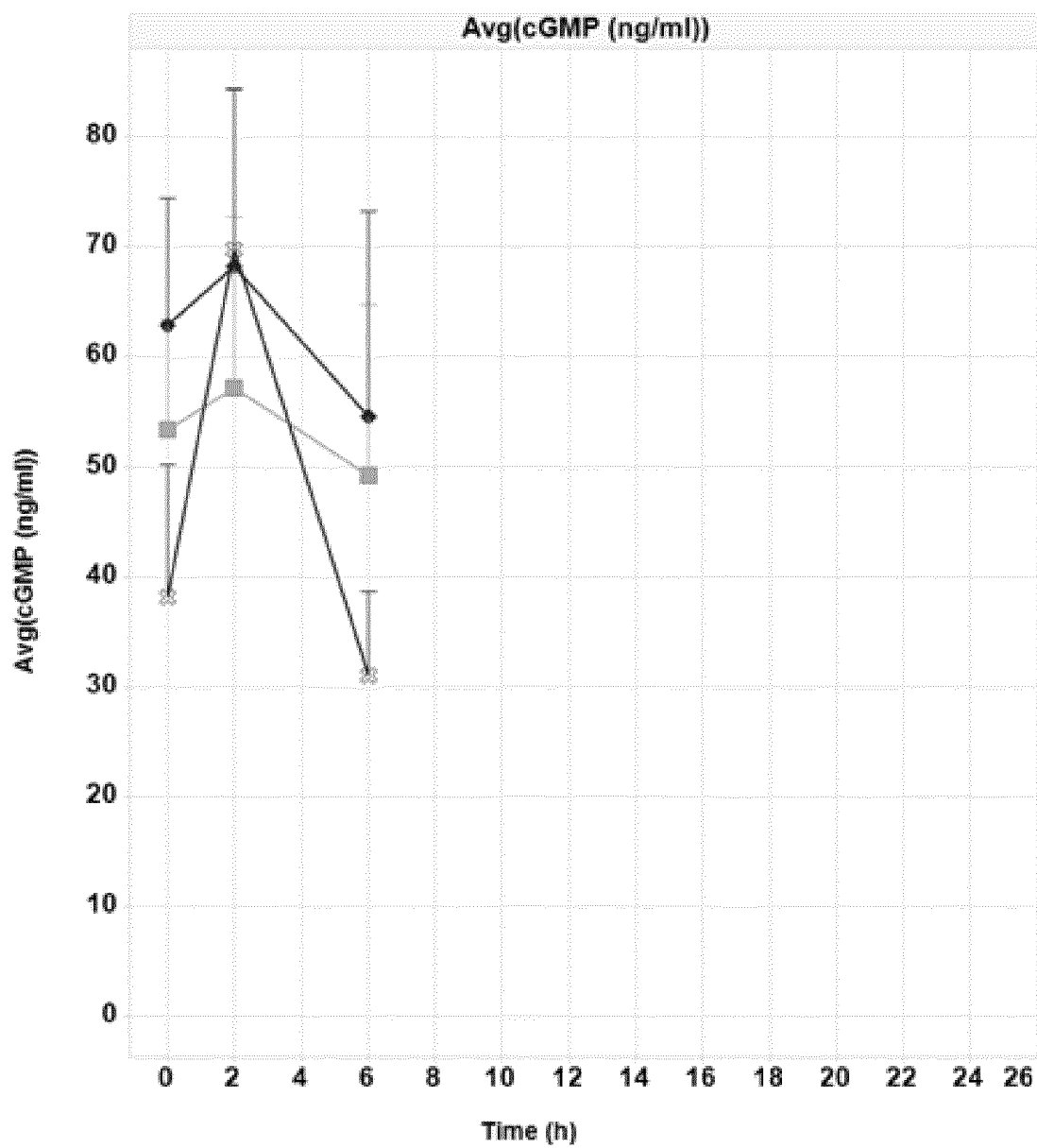
Figure 11:
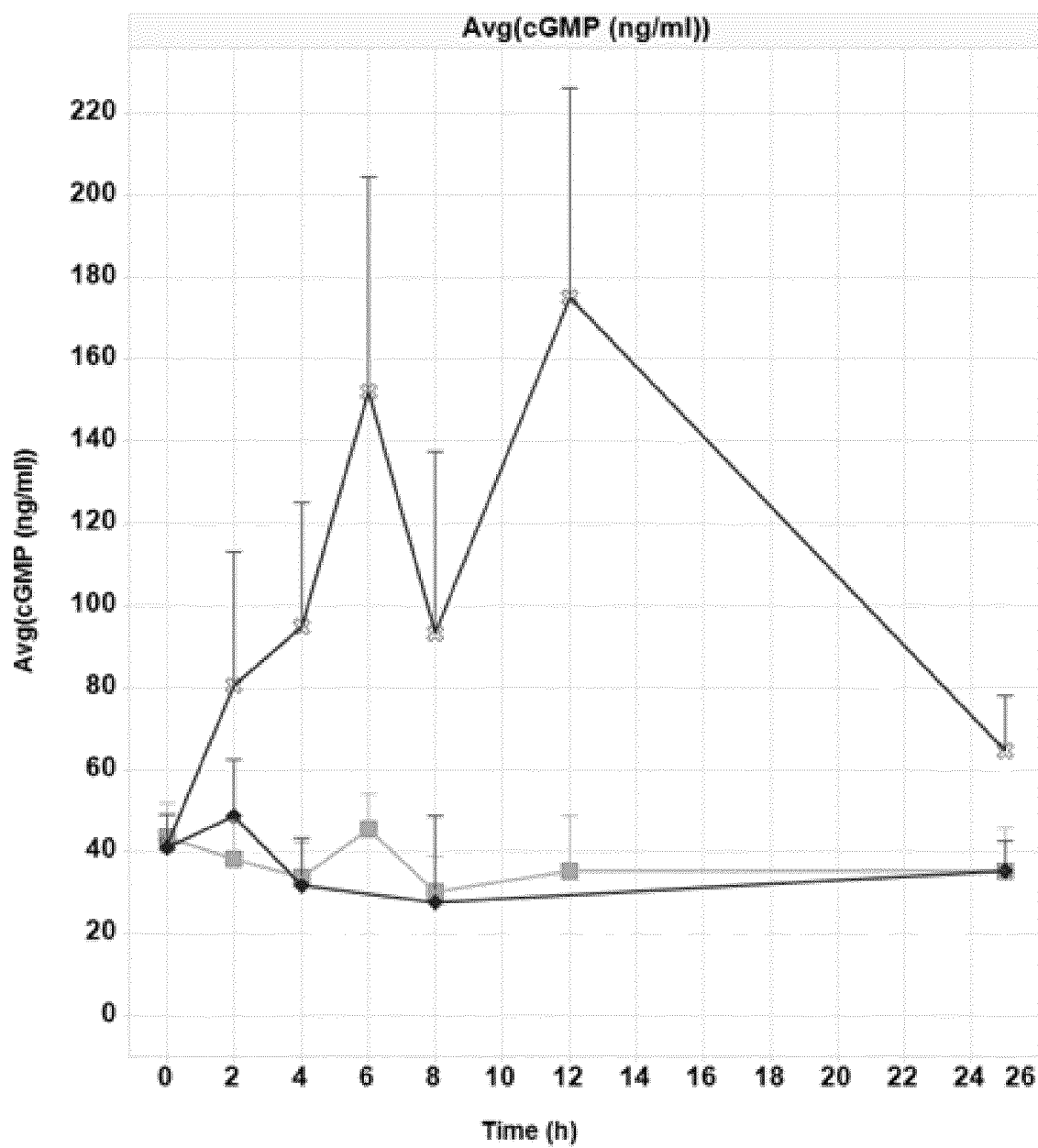
Figure 12:
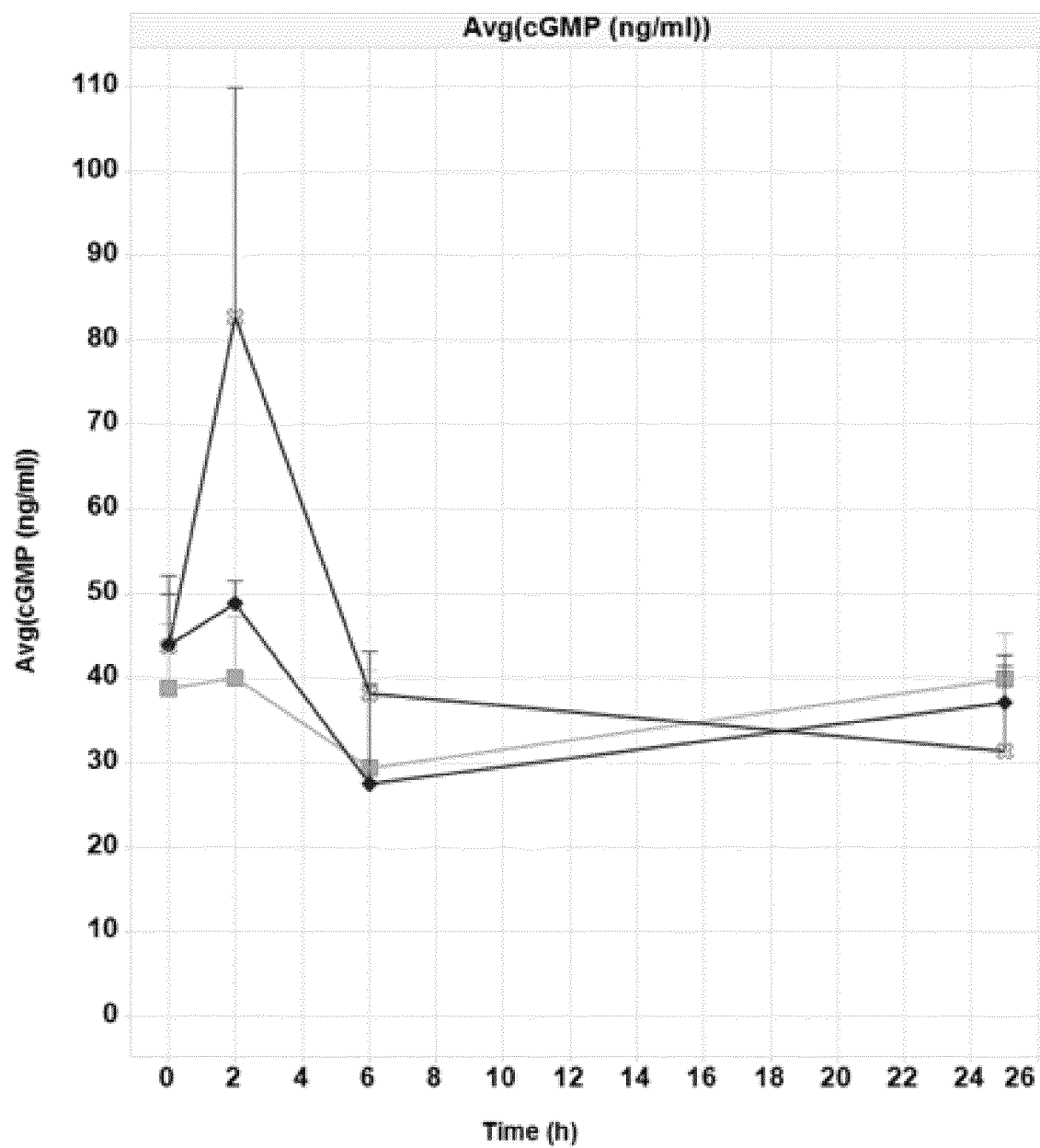
Figure 13:
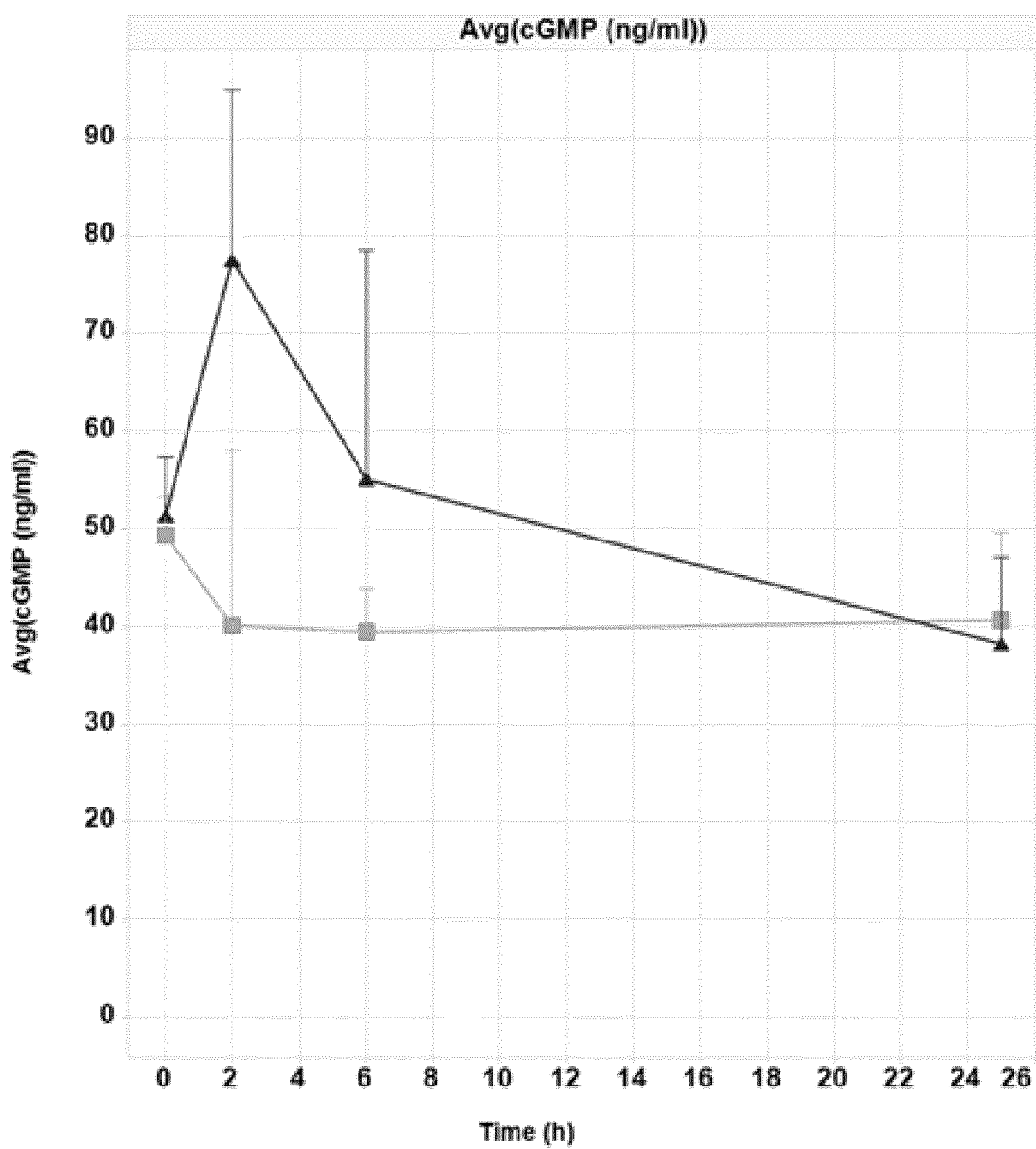
Figure 14:
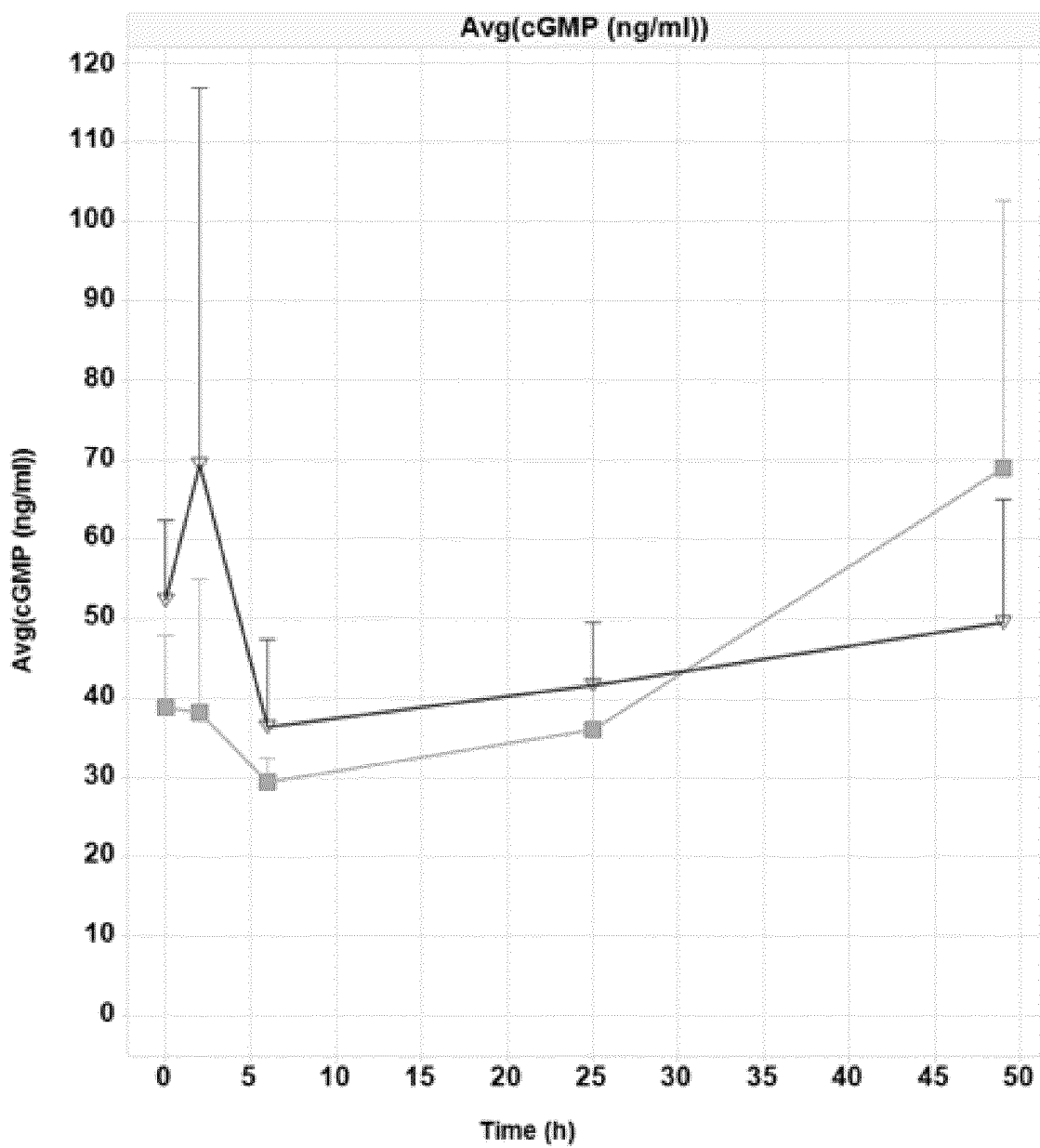
Figure 15:
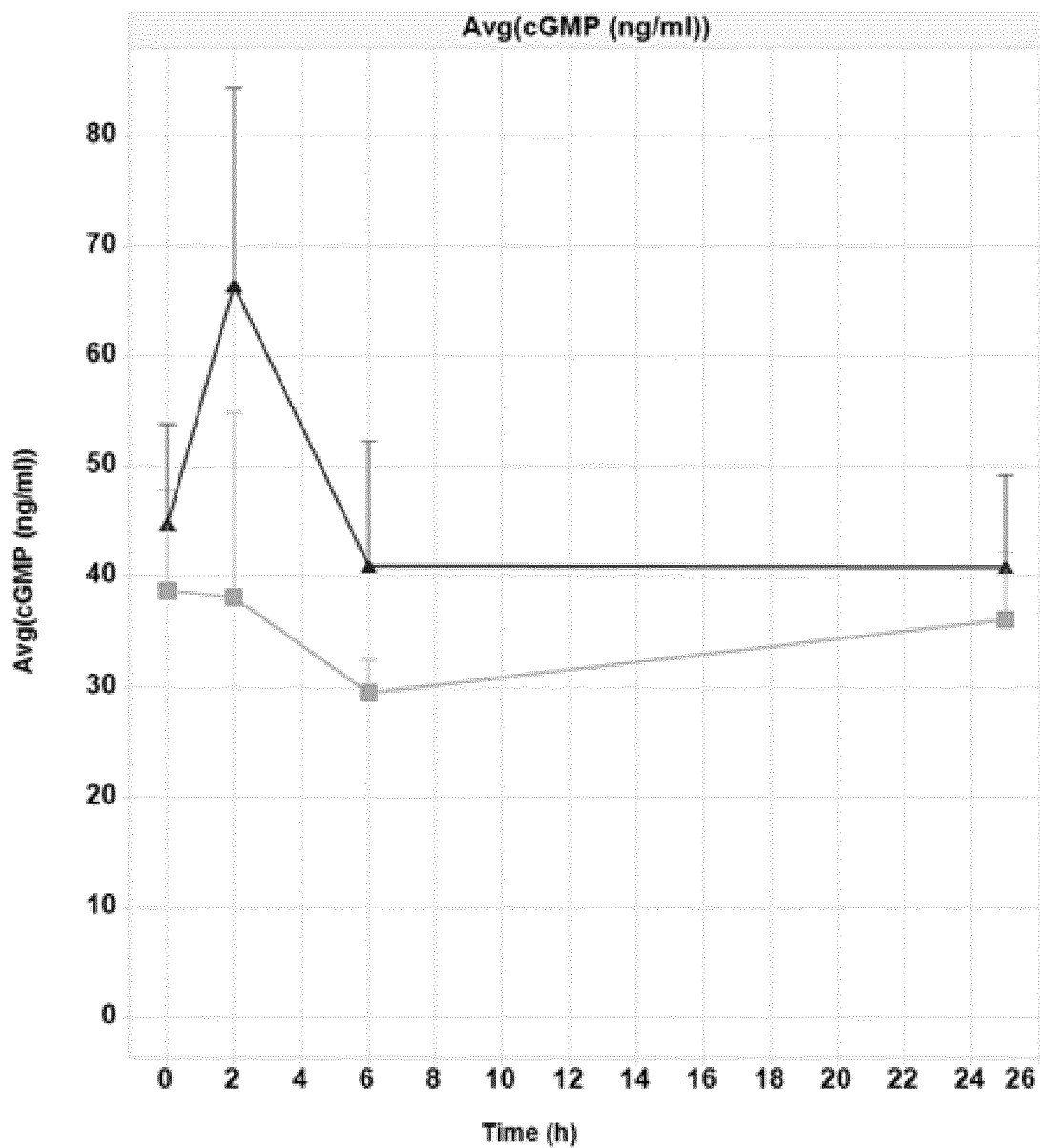

The results of this test are shown in FIG. 3 for the effect of compound 70, FIG. 4 for the effect of compound 25a and FIG. 5 for the effect of compound 220 (free base) on the facilitation on induction of LTP with a weak Long Term Potentiation protocol.
Single Dose PK/PD PDE2i Dog Study For these studies male and female Marshall Beagle dogs (1-6 y) were used: 2 males and 2 females per treatment group. Cerebrospinal fluid (CSF) was sampled from the lateral ventricle via a needle guide cannula in instrumented conscious animals.

Baseline CSF and blood samples were taken 2 to 5 days before dosing. The dogs are fasted overnight and the next morning dosed on an empty stomach (orally by gavage). At predetermined time points after dosing blood and/or CSF was collected for the measurement of compound levels and cGMP. Analysis of cGMP was done by LC-MS/MS: 25 μl CSF was diluted with 125 μl artificial CSF (STIL (20 ng/ml)), centrifugated and 25 μl was injected. The systems used were: a Shimadzu SIL-30 UPLC-system (Hypercarb (50 mm×1 mm (3 μm)) column, basic (10 mM ammonium carbonate) aqueous-acetonitrile gradient (5% to 98% in 5.5 minutes) at a flow-rate of 250 μl/min) and an API Sciex 5500 system equipped with an ESI source (selective MRM transition (m/z 346.1→152.1 (75 msec dwelltime)). The results of this study are summarized in FIGS. 6-15.
PDE2 Inhibition Enhanced Synaptic Plasticity in the Hippocampal Schaffer Collateral-CA1 Circuit in Anesthetized Rats: Case Study with Compound 110
Introduction Synaptic plasticity is a fundamental mechanism to many neurobiological functions. Long-term potentiation (LTP), a long-lasting highly localized increase in synaptic strength in the hippocampus as well as in the cortex, is a synaptic substrate for memory and learning (Cooke and Bliss, Curr Opin Investig Drugs. 2005; 6(1):25-34). The increase and decrease of synaptic strength depends on the activity of presynaptic and postsynaptic neurons, on how networks in the brain operate in setting up sensory representation of multiple items in memory and producing motor response. Different features of these synaptic modifications, in intact brain, are crucial to the operation of different types of networks and the operation of several different brain circuits. Therefore, LTP is expected to be compromised in aging psychiatric and neurodegenerative disorders such as Alzheimer's disease (Bergado and Almaguer, Neural Plast. 2002; 9(4):217-32; Rowan et al., Biochem Soc Trans. 2005; 33: 563-7). In animals, the procedure carried out under anesthesia in intact highly interconnected brain regions, provides a powerful tool to investigate lasting changes in effective connectivity and plasticity in hippocampal-cortex circuits following a tetanic electrical stimulation with low and high frequency delivered in single or paired pulses (Albensi et al., Exp Neurol. 2007; 204A: 1-13). The studies help expand understanding of the neural circuits underlying development of impaired synaptic strength i.e. determine the direct-circuit path and the role of specific biological target harboured by specific inter-regional network connections in mediating synaptic weakening. The procedure allows for testing pharmacological agents aimed at restoring pathological neuroplasticity e.g. reverse deficits in LTP and network connectivity by increasing synaptic efficacy, which is expected to have beneficial effects on related cognitive and learning ability (Cooke and Bliss, 2005; Albensi et al., 2007).

Phosphodiesterases (PDEs) are a class of enzymes responsible for metabolic inactivation of secondary messengers 3',5'-cyclic adenosine monophosphate (cAMP) and 3',5'-cyclic guanosine monophosphate (cGMP) (Francis et al. Physiol Rev. 2011, 9: 651-90). Up to 11 families of PDEs were categorized based on their structural, enzymatic and distribution (Omori and Kotera Circ Res. 2007; 100:309-27). The role of PDEs in the augmentation of cyclic nucleotide signalling makes these enzymes attractive targets for regulating excitability and enhancing the effects of neuronal communication. In the brain, PDE2 is mainly expressed in cortex, hippocampus and striatum where it controls the hydrolysis of cAMP. Over the last few years, research groups have focused on the development of PDE2 inhibitors as a way to modify intracellular second messengers cGMP and cAMP to exert action on plasticity and cognitive processes (Duinen et al., Curr Pharm Des. 2015; 21:3813-28; Gomez and Breitenbucher, Bioorg Med Chem Lett. 2013; 23: 6522-7; Xu et al., Neurobiol Aging. 2015; 36:955-70; Barco et al., Expert Opin Ther Targets 2003; 7: 101-114).

In the present study, it was investigated whether PDE2 inhibition, using compound 110, leads to alterations in excitability or in the ability to express synaptic potentiation at the hippocampal Shaffer collateral-CA1 synapses in urethane-anesthetized Sprague Dawley rats.

Material and Methods

Animals

The present experiments were conducted in strict accordance with the guidelines of the Association for Assessment and Accreditation of Laboratory Animal Care International (AAALAC), and with the European Communities Council Directive of 24 Nov. 1986 (86/609/EEC) and were approved by local ethical committee. Sprague Dawley rats, weighing 170-200 g at the time of surgery, were group-housed in ventilated cages located on a 12-h light/dark cycle (lights on at 07:00 AM) after their arrival to animal facilities maintained under controlled environmental conditions.

Surgery and Electrophysiology

Figure 16A:
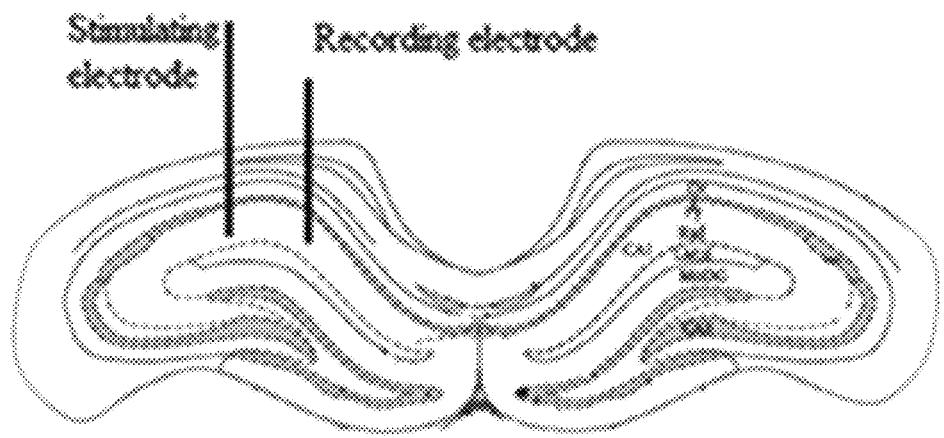
FIG. 16a shows a schematic representation of the location of the bipolar stimulating electrode in the Schaffer Collateral path and of the monopolar recording electrode in the stratum *radiatum* of the Cornu Ammonis CA1 area of the hippocampus.

Rats were anesthetized with an intra-peritoneal injection of urethane 1.5 g/kg body weight. Animals were placed in a stereotactic frame for the insertion of electrodes and their body temperature was constantly monitored through a rectal probe and maintained at 37° C. with a heating pad. Supplementary administration of urethane (0.2-0.5 g/kg) was given when necessary to ensure full anaesthesia. Two small holes (1 mm diameter) were drilled in the skull at the position of left hippocampus structures for stimulating and recording electrodes. A bipolar stimulating electrode; a pair of twisted tungsten wires (75 μm) with tips horizontally separated 0.125 μm apart, were positioned at Schaffer collateral-commissural (SC) pathway (AP −3.4, ML −2.5, DV −1.9 to 2.4), and a tungsten recording electrode are positioned at the Stratum *Radiatum* of the Cornu Ammonis (CA1) area of the dorsal hippocampus (AP −4.2, ML −4.0, DV −2.5 to 3.4) (FIG. 16a). The dura was pierced through both holes, and the stimulating and recording electrodes were lowered very slowly (0.2 mm/min) through the cortex and upper layers of the hippocampus into the mPP and the DG of the dorsal hippocampus. During surgery, all efforts were made to minimize animal suffering.

The field excitatory postsynaptic potential (fEPSP) slope is used as a measure of excitatory synaptic transmission. Single monophasic square 0.1 or 0.2 ms wave pulses generated by a constant current unit (MC, Germany) were applied for instance to the SC and evoked responses are generated in the CA1. Extracellular field potentials are amplified; band pass filtered between 1 Hz and 2 kHz, digitized and analyzed using custom made software. The electrodes were lowered until a negative deflecting fEPSP with the maximum response is observed. A minimum of 30 min is allowed to ensure stabilization excitability before measurements. Next, monophasic constant current pulses with stimulus intensities ranging from 1 to 12 Volts were delivered to generate Input/Output (I/O) curves and determine the maximum fEPSP slopes, and then stimulus intensity that produced 50% of the maximum response (i.e., test pulse) was used in subsequent experiments.

LTP induction: After the determination of I/O curves, test stimulation was then applied every 30 s before and after tetanic stimulation. For each time point measured during the experiments, five records of evoked responses at the frequency of 0.033 Hz were averaged. Baseline activity was measured every 5 min for at least 1 h to ensure stable baseline. The last 30 min of the baseline recording (6 time points), immediately after drug application was averaged and used as control for LTP induction. Tetanisation was induced using a high-frequency stimulation (HFS) 200-Hz protocol consisting of square pulses (0.2 ms stimulus duration, 10 bursts of 20 stimuli, 2 s inter-burst interval) at a stimulus intensity that evoked a fEPSP slope that was approximately 50% of the maximal response. fEPSP were recorded during 120 min after HFS to determine possible changes in the synaptic response of SC-CA1 neurons. LTP measurements were derived from field EPSP ratios of the normalized slope average obtained 120 min following HFS divided by the normalized slope average collected 30 min prior to HFS. Slope of putative fEPSP were measured between the end of stimulus artefact and the trough of the negative peak. In 80% interval between these points, a linear fit least square analysis was used to calculate the EPSP slope.

Histology

At the end of the electrophysiological study, electrical stimulation of 500 μA for 30 sec was delivered to produce a lesion at the end tip of the stimulation and recording electrodes and brains were harvested for histological verification of electrodes placement. Brain sections (20 μm) were examined using a light microscope. Animals with incorrect electrode placement were excluded from the study.

Compound 110 was dissolved in 20% Cyclodextrine (CD)+1HCl. For subcutaneous administration, Compound 110 was dissolved in 20% CD+1HCl to achieve final concentrations of 2 and 4 mg/ml.

Statistic

For each animal, the stable baseline (pre-tetanus) responses over 30 min were averaged and the mean was normalized as being 100%, and the post-tetanus response data were expressed relative by the baseline average. Comparison of the effects of vehicle and compound 110 after tetanus was performed on 30 min intervals using One-way analysis of variance (ANOVA) and least significant difference (LSD) post-hoc analysis was applied for group comparisons.

Results

Figure 16B:
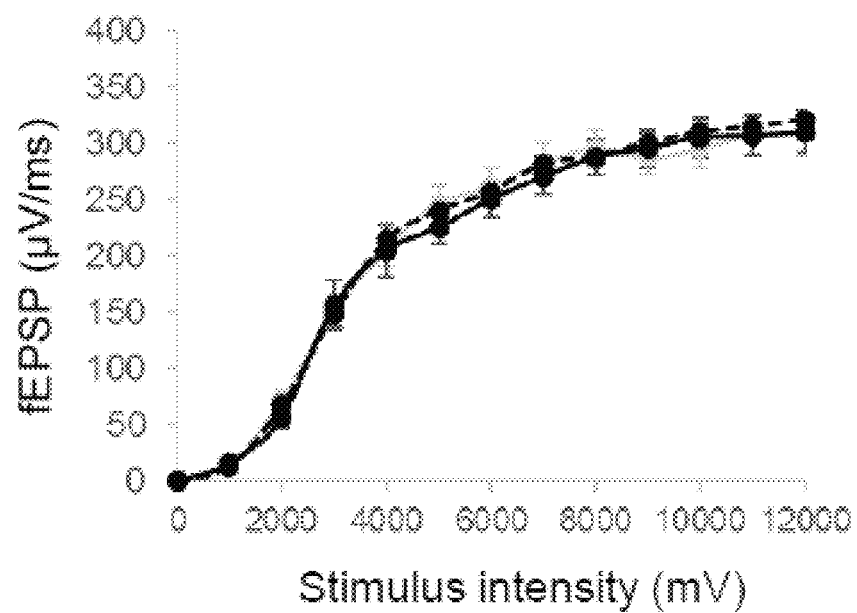
FIG. 16b shows a summary of I/O curves generated by applying stimuli f increasing intensity and measuring the initial slopes of the resulting fEPSP revealed no difference in basic excitability of the SC-CA1 pathway.
Figure 16:
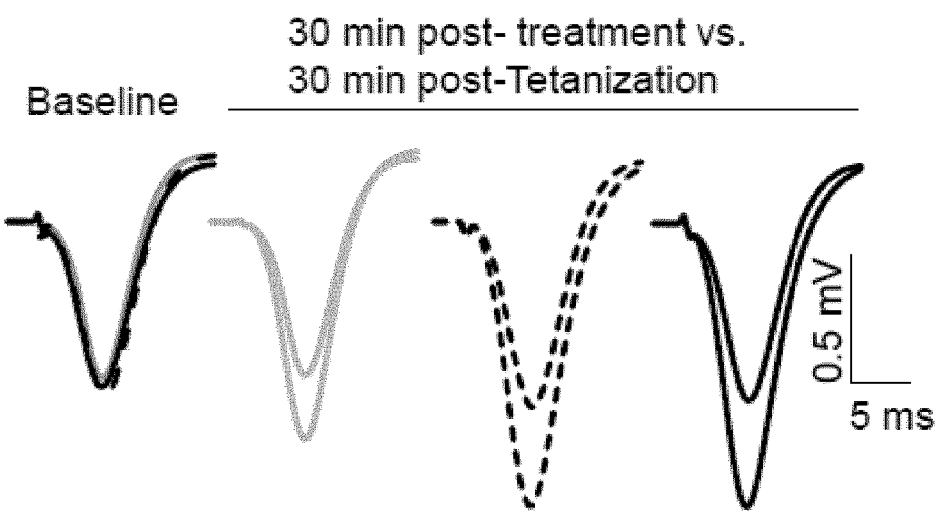
FIG. 16 shows the acute effects of compound 110 on synaptic function in vivo at the Schaffer Collateral (SC)-CA1 synapse.
Figure 16D:
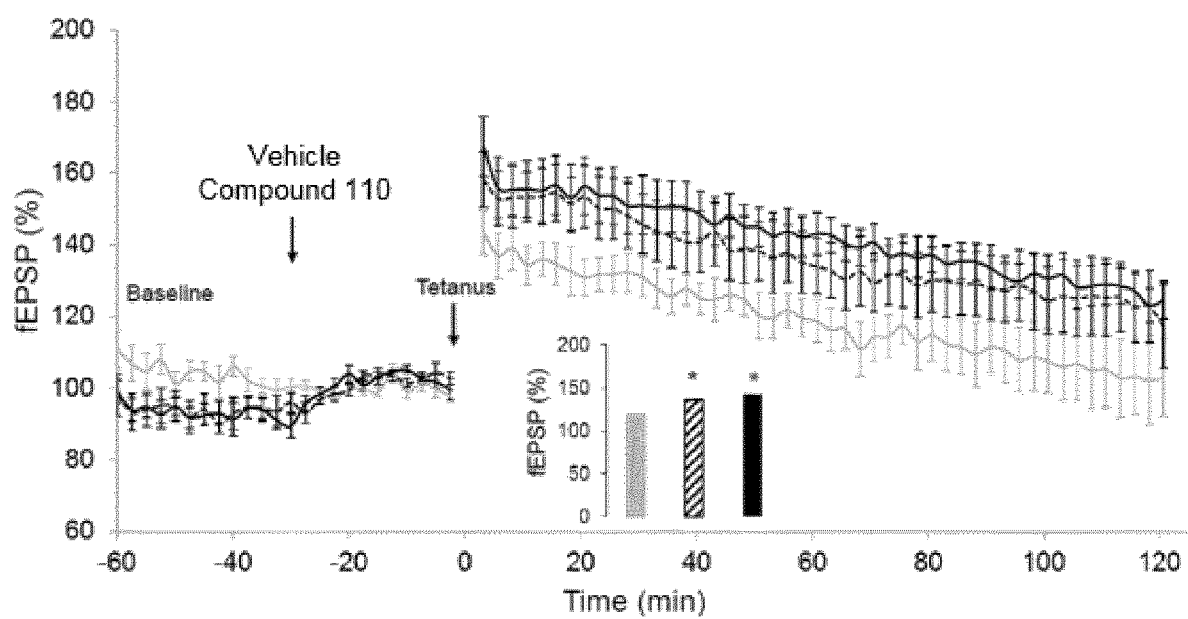
FIG. 16d shows the time course of fEPSP slope after 30 min of baseline recording, 30 min after the administration of compound 110, and tetanic HFS protocol was applied and slope of fEPSP was recorded for other 2 hours. Note that compound 110 at the dose of 20 and 40 mg/kg enhanced basal synaptic transmission prior the tetanic HFS protocol and the slope of the fEPSPs throughout the 2-hours post-HFS protocol (Inset plot)
Figure 16E:
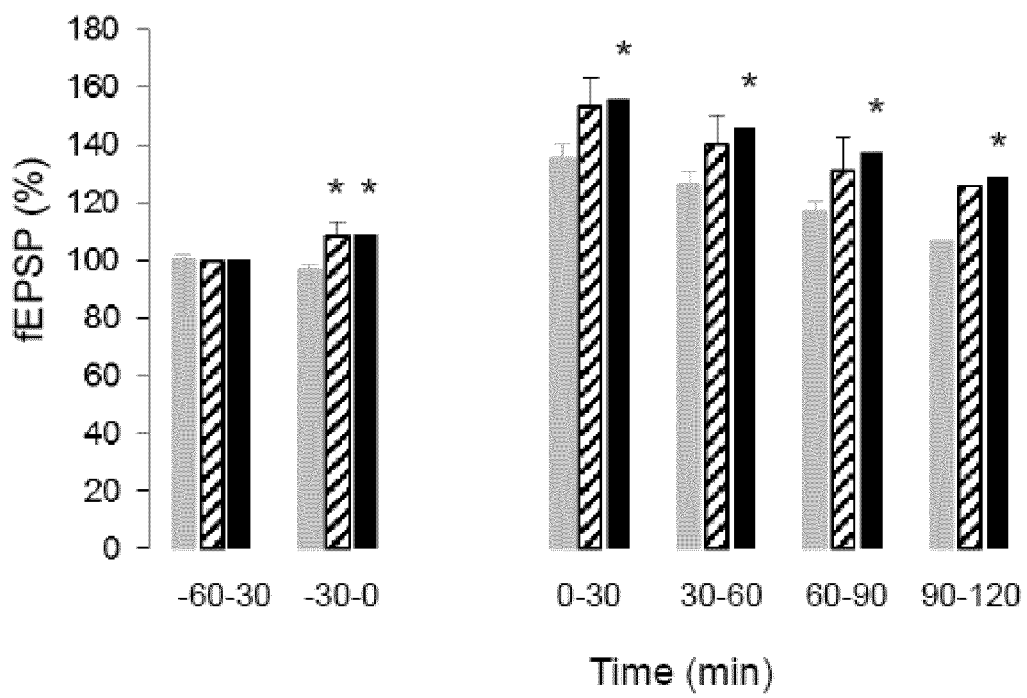
FIG. 16e shows that when fEPSPs were averaged in 30 min periods, compound 110 (40 mg/kg) enhanced the magnitude of synaptic transmission and the difference with the vehicle-treated group remained significant. Values are expressed as a percentage of the values recorded before HFS and results are presented as means±SEM. One-way analysis of variance (ANOVA) and least significant difference (LSD) post-hoc analysis tests were applied for group comparisons.

No differences in the slope of the SC-CA1 path fEPSPs were found across the I/O of the study groups, suggesting that the excitability of CA1 cells was similar in all animals (FIG. 16b, c). Basal synaptic transmission was enhanced as significant changes were found between Compound 110 (20 and 40 mg/kg) and vehicle-treated control during baseline pre-tetanus (+8 and 9%, respectively) (FIG. 16d, e). During the LTP induction paradigm, subcutaneous administration of compound 110 (20 and 40 mg/kg) enhanced an enduring (>2 h) synaptic potentiation (137±8% and 142±5% as compared to vehicle level 119±4%, respectively) (FIG. 16d, Inset plot). At 0-30 min after completion of the tetanization, fEPSP slopes were 153±5% and 155±4% as compared to vehicle level 139±1%, $p<0.05$). In subsequent 30 min intervals, analysis of stimulus-response curves revealed a significant lasting increase in the fEPSP with the dose 40 mg/kg (30-60 min: 146±6%, 60-90 min: 137±5% and 90-120 min: 129±5% as compared to vehicle levels 125±6, 116±9 and 106±13%, $p<0.05$, respectively). Overall, Compound 110 facilitates basal synaptic transmission and LTP in vivo Reasonable variations are not to be regarded as a departure from the scope of the invention. It will be obvious that the thus described invention may be varied in many ways by those skilled in the art.

The invention claimed is:
1. A compound having the Formula (I)

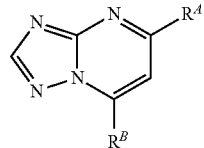

(I)

or a stereoisomeric form thereof, wherein
$R^A$ is selected from the group consisting of H, CH$_3$, CN, and CHF$_2$;
$R^B$ is a radical selected from the group consisting of (a), (b) and (c):

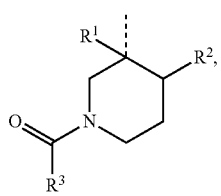

(a)

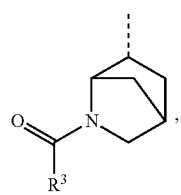

(b)

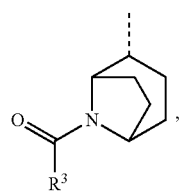

(c)

wherein
$R^1$ is H, F or CH$_3$;
$R^2$ is H or C$_{1-4}$alkyl, in particular methyl or n-butyl; with the proviso that when $R^2$ is H, then $R^1$ is F or CH$_3$;
$R^3$ is Ar, Het, or Ar-C$_{2-4}$alkenyl; wherein
Ar represents phenyl or naphthyl, each optionally substituted with 1, 2 or 3 substituents, each independently selected from the group consisting of halo; CN; NR$^{2A}$R$^{2B}$ wherein R$^{2A}$ and R$^{2B}$ are each independently selected from H and CH$_3$; OH; C$_{1-6}$alkyl optionally substituted with 1, 2 or 3 independently selected halo substituents; C$_{1-6}$alkyl substituted with CN; C$_{3-6}$cycloalkyl; C$_{1-6}$alkyloxy optionally substituted with 1, 2 or 3 independently selected halo substituents; and pyrazolyl;
Het represents
(i) a 5-membered heteroaryl selected from the group consisting of 1H-pyrrolyl; thienyl; furanyl; 1H-pyrazolyl; 1H-imidazolyl; 1,2-oxazolyl; 1,3-oxazolyl; and thiazolyl; each of which may be optionally substituted with 1, 2 or 3 substituents each independently selected from the group consisting of halo; C$_{1-4}$alkyl optionally substituted with 1, 2, or 3 independently selected halo substituents; NR$^{3A}$R$^{3B}$ wherein R$^{3A}$ and R$^{3B}$ are each independently selected from H and CH$_3$; and furan-2-yl; or
(ii) a 6-membered heteroaryl selected from the group consisting of pyridyl, pyrimidinyl, pyrazinyl, and pyridazinyl; each of which may be optionally substituted with 1, 2 or 3 substituents each independently selected from the group consisting of halo; OH; CN; NR$^{4A}$R$^{4B}$ wherein R$^{4A}$ and R$^{4B}$ are each independently selected from H and CH$_3$; C$_{1-4}$alkyl optionally substituted with 1, 2 or 3 independently selected halo substituents; C$_{1-4}$alkyl substituted with OH; C$_{3-6}$cycloalkyl; C$_{3-6}$cycloalkyloxy; C$_{1-4}$alkyloxy optionally substituted with 1, 2 or 3 independently selected halo substituents; and C$_{1-4}$alkyloxyC$_{1-4}$alkyl; or
(iii) a 8- to 10-membered bicyclic partially unsaturated heterocyclyl selected from the group consisting of 2,3-dihydro-1-benzofuranyl; 2H-chromenyl; 3,4-dihydro-2H-chromenyl; 2,3-dihydro-1H-indolyl optionally substituted at the 1-position with C$_{1-4}$alkyl, methyl sulfonyl, 1-acetyl, or fluoroacetyl; 2,2-difluoro-1,3-benzodioxolyl; 1,3-benzodioxolyl optionally substituted with a methyl substituent; 3,4-dihydro-2H-1,4-benzoxazinyl optionally substituted with C$_{1-4}$alkyl; 5,6,7,8-tetrahydroimidazo[1,2-a]pyridinyl; 5,6,7,8-tetrahydroquinolinyl optionally substituted with a halo substituent; and 2,3-dihydropyrazolo[5,1-b][1,3]oxazolyl; or
(iv) a 9- to 10-membered bicyclic heteroaryl selected from the group consisting of 1-benzofuranyl; 1-benzothiophenyl; 1H-indolyl; 1,3-benzoxazolyl; 1,3-benzothiazolyl; indolizinyl; 1H-benzimidazolyl; imidazo[1,2-a]pyridinyl; pyrazolo[1,5-a]pyridinyl; 1H-thieno[2,3-c]pyrazolyl; imidazo[2,1-b]thiazolyl; pyrrolo[2,3-c]pyridinyl; thieno[3,2-b]pyridinyl; quinolinyl; isoquinolinyl; quinoxalinyl; 1,8-naphthyridinyl; and 1,6-naphthyridinyl; each of which may be optionally substituted with 1 or 2 substituents each independently selected from the group consisting of halo; OH; NR$^{5A}$R$^{5B}$ wherein R$^{5A}$ and R$^{5B}$ are each independently selected from H and CH$_3$; C$_{1-4}$alkyl optionally substituted with 1, 2 or 3 independently selected halo substituents; and C$_{1-4}$alkyloxy optionally substituted with 1, 2 or 3 independently selected halo substituents;
with the proviso that the compound is not

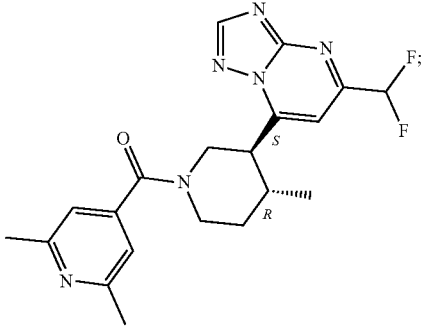

or an N-oxide, or a pharmaceutically acceptable salt or a solvate thereof.

2. The compound according to claim 1, wherein
R³ is Ar or Het; wherein
Ar represents phenyl optionally substituted with 1, 2 or 3 substituents, each independently selected from the group consisting of halo; CN; OH; $C_{1-6}$alkyl optionally substituted with 1, 2 or 3 independently selected halo substituents; $C_{1-6}$alkyl substituted with CN; $C_{3-6}$cycloalkyl; and $C_{1-6}$alkyloxy optionally substituted with 1, 2 or 3 independently selected halo substituents;
Het represents
(i) a 5-membered heteroaryl selected from the group consisting of 1H-pyrrolyl; thienyl; furanyl; 1H-pyrazolyl; 1H-imidazolyl; 1,2-oxazolyl; 1,3-oxazolyl; and thiazolyl; each of which may be optionally substituted with 1, 2 or 3 substituents each independently selected from the group consisting of halo; $C_{1-4}$alkyl optionally substituted with 1, 2, or 3 independently selected halo substituents; $NR^{3a}R^{3b}$ wherein $R^{3a}$ and $R^{3b}$ are each independently selected from H and $CH_3$; and furan-2-yl; or
(ii) a 6-membered heteroaryl selected from the group consisting of pyridyl, pyrimidinyl, pyrazinyl, and pyridazinyl; each of which may be optionally substituted with 1, 2 or 3 substituents each independently selected from the group consisting of halo; OH; CN; $NR^{4a}R^{4b}$ wherein $R^{4a}$ and $R^{4b}$ are each independently selected from H and $CH_3$; $C_{1-4}$alkyl optionally substituted with 1, 2 or 3 independently selected halo substituents; $C_{3-6}$cycloalkyl; $C_{3-6}$cycloalkyloxy; and $C_{1-4}$alkyloxy optionally substituted with 1, 2 or 3 independently selected halo substituents; or
(iii) a 8- to 10-membered bicyclic partially unsaturated heterocyclyl selected from the group consisting of 2,3-dihydro-1-benzofuranyl; 2H-chromenyl; 3,4-dihydro-2H-chromenyl; 2,3-dihydro-1H-indolyl optionally substituted at the 1-position with $C_{1-4}$alkyl, methylsulfonyl, 1-acetyl, or fluoroacetyl; 2,2,-difluoro-1,3-benzodioxolyl; 1,3-benzodioxolyl optionally substituted with a methyl substituent; 5,6,7,8-tetrahydroimidazo[1,2-a]pyridinyl; 5,6,7,8-tetrahydroquinolinyl optionally substituted with a halo substituent; and 2,3-dihydropyrazolo[5,1-b][1,3]oxazolyl; or
(iv) a 9- to 10-membered bicyclic heteroaryl selected from the group consisting of 1-benzofuranyl; 1-benzothiophenyl; 1H-indolyl; 1,3-benzoxazolyl; 1,3-benzothiazolyl; indolizinyl; 1H-benzimidazolyl; imidazo[1,2-a]pyridinyl; pyrazolo[1,5-a]pyridinyl; 1H-thieno[2,3-c]pyrazolyl; thieno[3,2-b]pyridinyl; quinolinyl; 1,8-naphthyridinyl; and 1,6-naphthyridinyl; each of which may be optionally substituted with 1 or 2 substituents each independently selected from the group consisting of halo; OH; $NR^{3a}R^{3b}$ wherein $R^{3a}$ and $R^{3b}$ are each independently selected from H and $CH_3$; $C_{1-4}$alkyl optionally substituted with 1, 2 or 3 independently selected halo substituents; and Ci-4alkyloxy optionally substituted with 1, 2 or 3 independently selected halo substituents;
or a pharmaceutically acceptable salt or a solvate thereof.

3. The compound according to claim 1, wherein $R^A$ is $CH_3$ or $CHF_2$.

4. The compound according to claim 1, wherein $R^B$ is (a) or (c).

5. The compound according to claim 1, wherein $R^3$ is Het.

6. The compound according to claim 5, wherein $R^3$ is
(i) a 6-membered heteroaryl selected from the group consisting of pyridyl, pyrimidinyl, pyrazinyl, and pyridazinyl; each of which may be optionally substituted with 1, 2 or 3 substituents each independently selected from the group consisting of halo; OH; CN; $NR^{4a}R^{4b}$ wherein $R^{4a}$ and $R^{4b}$ are each independently selected from H and $CH_3$; $C_{1-4}$alkyl optionally substituted with 1, 2 or 3 independently selected halo substituents; $C_{3-6}$cycloalkyl; $C_{3-6}$cycloalkyloxy; and $C_{1-4}$alkyloxy optionally substituted with 1, 2 or 3 independently selected halo substituents; or (ii) a 9- to 10-membered bicyclic heteroaryl selected from the group consisting of 1-benzofuranyl; 1-benzothiophenyl; 1H-indolyl; 1,3-benzoxazolyl; 1,3-benzothiazolyl; indolizinyl; 1H-benzimidazolyl; imidazo[1,2-a]pyridinyl; pyrazolo[1,5-a]pyridinyl; 1H-thieno[2,3-c]pyrazolyl; thieno[3,2-b]pyridinyl; quinolinyl; 1,8-naphthyridinyl; and 1,6-naphthyridinyl; each of which may be optionally substituted with 1 or 2 substituents each independently selected from the group consisting of halo; OH; $NR^{3a}R^{3b}$ wherein $R^{3a}$ and $R^{3b}$ are each independently selected from H and $CH_3$; $C_{1-4}$alkyl optionally substituted with 1, 2 or 3 independently selected halo substituents; and $C_{1-4}$alkyloxy optionally substituted with 1, 2 or 3 independently selected halo substituents.

7. The compound according to claim 1, having the Formula (I-a) or (I-b)

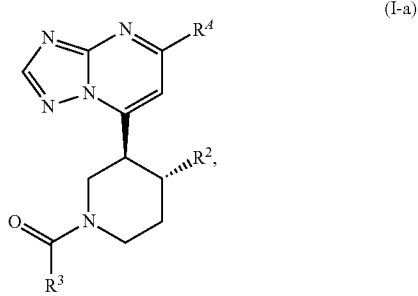

(I-a)

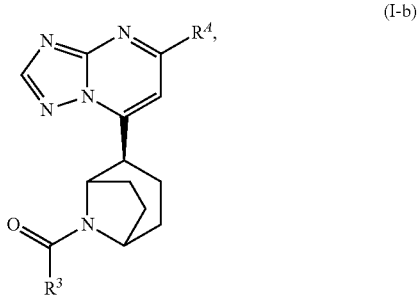

(I-b)

wherein $R^A$, $R^2$ and $R^3$ are as defined in claim 1.

8. A pharmaceutical composition comprising a therapeutically effective amount of a compound according to claim 1 and a pharmaceutically acceptable carrier.

9. A method of treating:
(i) psychotic disorders selected from the group of schizophrenia; schizophreniform disorder; schizoaffective disorder; delusional disorder; substance-induced psychotic disorder; personality disorders of the paranoid type; and personality disorder of the schizoid type;
(ii) anxiety disorders selected from the group of panic disorder; agoraphobia; specific phobia; social phobia; obsessive-compulsive disorder; post-traumatic stress disorder; acute stress disorder; and generalized anxiety disorder;

(iii) movement disorders selected from the group of Huntington's disease and dyskinesia; Parkinson's disease; restless leg syndrome and essential tremor; Tourette's syndrome and other tic disorders;
(iv) substance-related disorders selected from the group of alcohol abuse; alcohol dependence; alcohol withdrawal; alcohol withdrawal delirium; alcohol-induced psychotic disorder; amphetamine dependence; amphetamine withdrawal; cocaine dependence; cocaine withdrawal; nicotine dependence; nicotine withdrawal; opioid dependence and opioid withdrawal;
(v) mood disorders selected from depression; mania; bipolar I disorder, bipolar II disorder; cyclothymic disorder; dysthymic disorder; major depressive disorder; treatment-resistant depression; and substance-induced mood disorder;
(vi) neurodegenerative disorders selected from the group of Parkinson's disease; Huntington's disease; dementia; Alzheimer's disease; multi-infarct dementia; AIDS-related dementia or frontotemperal dementia;
(vii) disorders or conditions comprising as a symptom a deficiency in attention and/or cognition selected from the group of dementia associated with Alzheimer's disease; multi-infarct dementia; dementia due to Lewy body disease; alcoholic dementia or substance-induced persisting dementia; dementia associated with intracranial tumours or cerebral trauma; dementia associated with Huntington's disease; dementia associated with Parkinson's disease; AIDS-related dementia; dementia due to Pick's disease; dementia due to Creutzfeldt-Jakob disease; delirium; amnestic disorder; post-traumatic stress disorder; stroke; progressive supranuclear palsy; mental retardation; a learning disorder; attention-deficit/hyperactivity disorder (ADHD); mild cognitive impairment; Asperger's syndrome; age-related cognitive impairment; and cognitive impairment related to perception, concentration, learning or memory; and
(viii) disorders related to memory acquisition and consolidation selected from memory disorders; comprising administering to a subject in need thereof, a therapeutically effective amount of a compound according to claim 1.

10. A process for preparing a pharmaceutical composition, characterized in that a pharmaceutically acceptable carrier is intimately mixed with a therapeutically effective amount of a compound according to claim 1.

11. A method of treating:
(i) psychotic disorders selected from the group of schizophrenia; schizophreniform disorder; schizoaffective disorder; delusional disorder; substance-induced psychotic disorder; personality disorders of the paranoid type; and personality disorder of the schizoid type;
(ii) anxiety disorders selected from the group of panic disorder; agoraphobia; specific phobia; social phobia; obsessive-compulsive disorder; post-traumatic stress disorder; acute stress disorder; and generalized anxiety disorder;
(iii) movement disorders selected from the group of Huntington's disease and dyskinesia; Parkinson's disease; restless leg syndrome and essential tremor; Tourette's syndrome and other tic disorders;
(iv) substance-related disorders selected from the group of alcohol abuse; alcohol dependence; alcohol withdrawal; alcohol withdrawal delirium; alcohol-induced psychotic disorder; amphetamine dependence; amphetamine withdrawal; cocaine dependence; cocaine withdrawal; nicotine dependence; nicotine withdrawal; opioid dependence and opioid withdrawal;
(v) mood disorders selected from depression; mania; bipolar I disorder, bipolar II disorder; cyclothymic disorder; dysthymic disorder; major depressive disorder; treatment-resistant depression; and substance-induced mood disorder;
(vi) neurodegenerative disorders selected from the group of Parkinson's disease; Huntington's disease; dementia; Alzheimer's disease; multi-infarct dementia; AIDS-related dementia or frontotemperal dementia; and
(vii) disorders or conditions comprising as a symptom a deficiency in attention and/or cognition selected from the group of dementia associated with Alzheimer's disease; multi-infarct dementia; dementia due to Lewy body disease; alcoholic dementia or substance-induced persisting dementia; dementia associated with intracranial tumours or cerebral trauma; dementia associated with Huntington's disease; dementia associated with Parkinson's disease; AIDS-related dementia; dementia due to Pick's disease; dementia due to Creutzfeldt-Jakob disease; delirium; amnestic disorder; post-traumatic stress disorder; stroke; progressive supranuclear palsy; mental retardation; a learning disorder; attention-deficit/hyperactivity disorder (ADHD); mild cognitive impairment; Asperger's syndrome; age-related cognitive impairment; and cognitive impairment related to perception, concentration, learning or memory; and
(viii) disorders related to memory acquisition and consolidation selected from memory disorders; comprising administering to a subject in need thereof, a therapeutically effective amount of a pharmaceutical composition according to claim 8.

12. A method of treating:
(i) psychotic disorders selected from the group of schizophrenia; schizophreniform disorder; schizoaffective disorder; delusional disorder; substance-induced psychotic disorder; personality disorders of the paranoid type; and personality disorder of the schizoid type;
(ii) anxiety disorders selected from the group of panic disorder; agoraphobia; specific phobia; social phobia; obsessive-compulsive disorder; post-traumatic stress disorder; acute stress disorder; and generalized anxiety disorder;
(iii) movement disorders selected from the group of Huntington's disease and dyskinesia; Parkinson's disease; restless leg syndrome and essential tremor; Tourette's syndrome and other tic disorders;
(iv) substance-related disorders selected from the group of alcohol abuse; alcohol dependence; alcohol withdrawal; alcohol withdrawal delirium; alcohol-induced psychotic disorder; amphetamine dependence; amphetamine withdrawal; cocaine dependence; cocaine withdrawal; nicotine dependence; nicotine withdrawal; opioid dependence and opioid withdrawal;
(v) mood disorders selected from depression; mania; bipolar I disorder, bipolar II disorder; cyclothymic disorder; dysthymic disorder; major depressive disorder; treatment-resistant depression; and substance-induced mood disorder;
(vi) neurodegenerative disorders are selected from the group of Parkinson's disease; Huntington's disease; dementia; Alzheimer's disease; multi-infarct dementia; AIDS-related dementia or frontotemperal dementia; and (vii) disorders or conditions comprising as a symptom a deficiency in attention and/or cognition selected from the group of dementia associated with Alzheimer's disease; multi-infarct dementia; dementia due to Lewy body disease; alcoholic dementia or substance-induced persisting dementia; dementia associated with intracranial tumours or cerebral trauma; dementia associated with Huntington's disease; dementia associated with Parkinson's disease; AIDS-related dementia; dementia due to Pick's disease; dementia due to Creutzfeldt-Jakob disease; delirium; amnestic disorder; post-traumatic stress disorder; stroke; progressive supranuclear palsy; mental retardation; a learning disorder; attention-deficit/hyperactivity disorder (ADHD); mild cognitive impairment; Asperger's syndrome; age-related cognitive impairment and cognitive impairment related to perception, concentration, learning or memory; and (viii) disorders related to memory acquisition and consolidation selected from memory disorders; comprising administering to a subject in need thereof, a therapeutically effective amount of a compound according to claim 1 in combination with an additional pharmaceutical agent.

13. The compound according to claim 7, selected from the group consisting of:

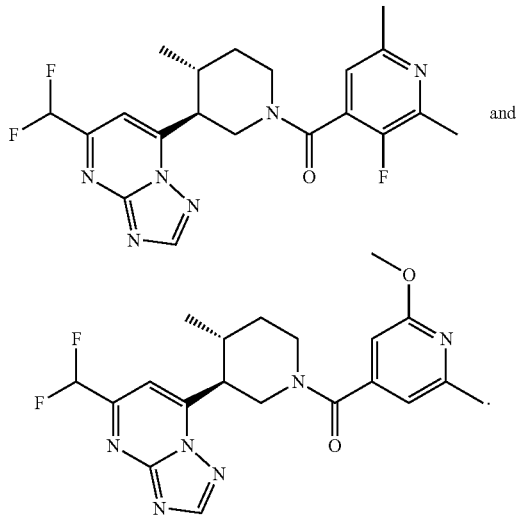

* * * * *